US007635765B2

(12) United States Patent
Farnet et al.

(10) Patent No.: US 7,635,765 B2
(45) Date of Patent: Dec. 22, 2009

(54) GENE ENCODING A NONRIBOSOMAL PEPTIDE SYNTHETASE FOR THE PRODUCTION OF RAMOPLANIN

(75) Inventors: Chris M. Farnet, Outremont (CA); Emmanuel Zazopoulos, Outremont (CA); Alfredo Staffa, St-Léonard (CA)

(73) Assignee: Thallion Pharmaceuticals, Inc., Montreal (CA)

( * ) Notice: Subject to any disclaimer, the term of this patent is extended or adjusted under 35 U.S.C. 154(b) by 107 days.

(21) Appl. No.: 11/205,109

(22) Filed: Aug. 17, 2005

(65) Prior Publication Data

US 2005/0287641 A1  Dec. 29, 2005

Related U.S. Application Data

(60) Division of application No. 09/976,059, filed on Oct. 15, 2001, now Pat. No. 7,078,185, application No. 11/205,109, and a continuation-in-part of application No. 09/910,813, filed on Jul. 24, 2001, now abandoned.

(60) Provisional application No. 60/239,924, filed on Oct. 13, 2000, provisional application No. 60/283,296, filed on Apr. 12, 2001.

(51) Int. Cl.
*C07H 21/04* (2006.01)
*C07K 14/00* (2006.01)
(52) U.S. Cl. .................. 536/23.1; 536/23.2; 435/69.1; 435/320.1; 435/252.3; 435/254.11; 435/325; 435/419; 530/350
(58) Field of Classification Search .............. 435/69.1, 435/320.1, 252.3, 254.11, 325, 419; 536/23.2, 536/23.1; 530/350
See application file for complete search history.

(56) References Cited

U.S. PATENT DOCUMENTS

| | | | |
|---|---|---|---|
| 4,303,646 | A | 12/1981 | Cavalleri et al. |
| 4,427,656 | A | 1/1984 | Cavalleri et al. |
| 4,551,433 | A | 11/1985 | DeBoer |
| 5,017,478 | A | 5/1991 | Cashion et al. |
| 7,078,185 | B2 * | 7/2006 | Farnet et al. ............ 435/69.1 |

OTHER PUBLICATIONS

Ciabatti R. et al., J. Antibiot (Tokyo), (1989)vol. 42, No. 2, pp. 254-267 "Ramoplanin (A-16686), a new glycolipodepsipeptide antibiotic. III. Structure elucidation".
Gastaldo I. et al., J. Ind. Microbiol. (1992), vol. 11, No. 1, pp. 13-18 "Isolation, structure determination and biological activity of A-16686 factors A'1, A'2 and A'3 glycodepsipeptide antibiotics".
Konz D. & Marahiel MA, Chem. Biol. (1999) vol. 6, pp. R39-R48 "How do peptide synthetases generate structural diversity?".
Quadri LE et al., Chem. Biol. (1998) vol. 5, No. 11, pp. 631-645 "Identification of a Mycobacterium tuberculosis gene cluster encoding the biosynthetic enzymes for assembly of the virulence-conferring siderophore mycobactin".
Chung S. K. et al., The Journal of Antibiotics (1986) pp. 642-651 "Biosynthetic Studies of Aridicin Antibiotics—1. Labeling patterns and overall pathways".
Nicas T. et al., Biotechnology of Antibiotics, Marcel Dekker, Inc. (1997) pp. 363-392 "Vancomycin and other glycopeptides".
Bateman Alex et al. Nucleic Acid Research (2000) vol. 28, No. 1, pp. 263-266 "The Pfam protein families database".
Ullah JH et al., J. Mol Biol. (1998)vol. 284, No. 1, pp. 125-136 "The crystal structure of the L1 metallo-beta-lactamase from Stenotrophomonas maltophilia at 1.7 A resolution".
Stryer, Biochemistry 3rd edition (1998), W.H. Freeman and Co., New York, pp. 752-754.
Casey & Davidson, Nucl. Acid. Res. (1977) vol. 4, No. 5, pp. 1539-1552 "Rates of formation and thermal stabilities of RNA:DNA and DNA:RNA duplexes at high concentrations of formamide".
Edge MD, Nature (1981) vol. 20, No. 292, pp. 756-762 "Total synthesis of a human leukocyte interferon gene".
Namblar KP et al., Science (1984) vol. 23, No. 233, pp. 1299-1301 "Total synthesis and cloning of a gene coding for the ribonuclease S protein".
Jay E. et al., J. Biol. Chem. (1984) vol. 259, No. 10, pp. 6311-6317 "Chemical Synthesis of a Biologically Active Gene for Human Immune Interferon-γ".
Malpartida F. and Hopwood DA, Nature (1984) vol. 6, No. 309, pp. 462-464 "Molecular cloning of the whole biosynthestic pathway of a *Streptomyces* antibitic and its expression in a heterologous host".
Kao CM et al., Science (1994) vol. 22, No. 265, pp. 509-512 "Engineered biosyntesis of complete macrolactone in a heterologous host".
Hopwood DA et al., Methods Enzymol. (1987) vol. 153, pp. 116-166 "Plasmid and phage vectors for gene cloning and analysis in *Streptomyces*".
Vara J. et al., J. Bacteriol. (1989) vol. 171, No. 11, pp. 5872-5881 "Cloning of genes governing the deoxysugar portion of the erythromycin biosynthesis pathway in *Saccharopolyspora erythraea*".
Guilfoile P. & Hutchinson R., Proc. Natl. Acad. Sci. USA (1991) vol. 88, pp. 8553-8557 "A bacterial analog of the mdr gene of mammalian tumor cells in present in *Streptomyces peucetius*, the producer of daunorubicin and doxorubicin".
Shen B. and Hutchinson R., J. Biol. Chem. (1994) vol. 269, No. 48, pp. 30726-30733 "Triple hydroxylation of tetracenomycin A2 to tetracenomycin C in *Streptomyces glausescens*".
Pieper R. et al., Nature (1995) vol. 16, No. 378, pp. 263-266 "Cell-free synthesis of polyketides by recombinant erythromycin polyketide synthases".
Pieper R. et al., J. Am. Chem. Soc. (1995) vol. 117, pp. 11373-11374 "Remarkably broad substrate specofoty of a modular polyketide synthase in a cell-free system".
Wiesmann KE et al., Chem. Biol. (1995) vol. 2, No. 9, pp. 583-589 "Polyketide synthesis in vitro on a modular polyketide synthase".

(Continued)

*Primary Examiner*—Chih-Min Kam

(57) ABSTRACT

The present invention relates to isolated genetic sequences encoding nonribosomal peptide synthetase (NRPS) proteins which direct the biosynthesis of the antibiotic ramoplanin in microorganisms such as *Actinoplanes* sp. The isolated gene sequences serve as substrates for bioengineering of antibiotic structures.

25 Claims, 16 Drawing Sheets

OTHER PUBLICATIONS

Stutzman-Engwall K. and Hutchison R., Proc. Ntl. Acad. Sci. USA (1989) vol. 86, pp. 3135-3139 "Multigene families for anthracycline antibiotic production in *Streptomyces peucetius*".

Motamedi H. and Hutchinson R., Proc. Ntl. Acad. Sci. USA (1987) vol. 84, pp. 4445-4449 "Cloning and heterologous expression of a gene cluster for the biosynthesis of tetracenomycin C, the anthracycline antitumor antibiotic of *Streptomyces glaucescens*".

Grimm A. et al., Gene (1994) vol. 151, pp. 1-10 "Characterization of the *Streptomyces peucetius* ATCC 29050 genes encoding doxorubin polyketide synthase".

van Wageningen AMA et al., Chem. Biol. (1997) vol. 5, pp. 155-162 "Sequencing and analysis of genes involved in the biosynthesis of a vancomycin group of antibiotic".

Hofmann K. et al., Nucleic Acids Research (1999) vol. 27, No. 1, pp. 215-219 "The PROSITE database, its status in 1999".

Osoegawa K. et al., Genomics (1998) vol. 15, No. 52, pp. 1-8 "An improved approached for construction of bacterial artificial chromosome librairies".

Huang Z. et al., Nucl. Acids Res. (1996) vol. 24, No. 21, pp. 4202-4209 "Large DNA fragment sizing by flow cytometry: application to the characterization of P1 artificial chromosomes (PAC) clones".

Quadri LE et al., Biochemistry (1998) vol. 10, No. 37, pp 1585-1595 "Characterization of Sfp, a *Bacillus subtills* phosphopantheinyl transferase for peptidyl carrier protein domains in peptide synthetases".

Nakano MM et al., Mol. Gen. Genet. (1992) vol. 232, No. 2, pp. 313-321 "Isolation and characterization of sfp: a gene that functions in the production of the lipopeptide biosurfactant, surfactin, in *Bacillus subtilis*".

Kunkel T. et al., Proc. Natl. Acad. Sci. USA (1985) vol. 82, pp. 448-492 "Rapid and efficient site-specofoc mutagenesis without phenotypic selection".

Carreras CW and Khosia C, Biochemistry (1998) vol. 24, No. 37, pp. 2084-2088 "Purification and in vitro reconstitution of the essential protein components of an aromatic polyketide synthase".

Hosoda J. et al, Agric. Biol. Chem. (1977) vol. 41, No. 10, pp. 2007-2012 "Incorporation of 14C-Amino Acids into Nocardin A by growing cells".

Nielsen PE et al., Science (1991) vol. 6, No. 254, pp. 1497-1500 "Sequence-selective recognition of DNA by strand displacement with a thymine-substituted polyamide".

Southern EM, J. Mol. Biol. (1975) vol. 5, No. 98, pp. 503-517 "Detection of specific sequences among DNA fragments seperated by gel electrophoresis".

Dunn AR et al., Cell (1977) vol. 12, No. 1, pp. 23-36 "A novel method to map transcripts: evidence for homology between an adenovirus mRNA and discrete multiple regions of the viral genome".

Altschul SF et al., J. Mol. Biol. (1990) vol. 5, 215, pp. 403-410 "Basic local alignment search tool".

Fleishmann RD et al., Science (1995) vol. 28, No. 269, pp. 496-512 "Whole-genome random sequencing and assembly of *Haemophilus influenza* Rd."

Altschul S. et al., Nucleic Acids Res. (1997) vol. 25, No. 17, pp. 3389-3402 "Grapped BLAST and PSI-BLAST: a new generation of protein database search programs".

Hammond J. S. et al., J. Chem. Soc., Chem Commun. (1982), pp. 344-346 "On the biosynthesis of the antibiotic vancomycin".

Stachelhaus T. et al., Chem. Biol. (1999) vol. 6, No. 8, pp. 493-505 "The specificity-conferring code of adenylation domains in nonribosomal peptide synthetases".

Challis G. et al., Chem. Biol. (2000) vol. 7, pp. 211-224 "Predictive, structure-based model of amino acid recognition by non-ribosomal peptide synthetase sdenylaiton domains".

Stachelhaus T. et al., Science (1995) vol. 269, pp. 482-485 "Rational Design of peptide antibiotics by targeted replacement of bacterial and fungal domains".

Schneider A. et al., Mol. Gen. Genet. (1998) vol. 257, pp. 308-318 "Targeted alteration of the substrate specificity of peptide synthetases by rational module swapping".

De Ferra F. et al., J. Biol. Chem. (1998) vol. 272, No. 40, pp. 25304-25309 "Engineering of peptide synthetases".

Guenzi E. et al., J. BIol. Chem. (1998) vol. 273, No. 49, pp. 32857-32863 "Characterization of the syringomycin synthetase gene cluster".

Weber G. et al., Curr. Genet. (1994) vol. 26, pp. 120-125 "The peptide synthetase catalyzing cyclosporine production in Tolypocladium niveum is encoded by a giant 45.8-kilobase open reading frame".

Scott-Craig J. et al., J. Biol. Chem.(1992) vol. 267, pp. 26044-26049 "The cyclic peptide synthetase catalyzing HC-toxin production in the filamentous fungus cochiobolus carbonum is encoded by a 15.7-Kilobase open reading frame".

Pfeifer E. et al., Biochem. (1995) vol. 34, pp 7450-7459 "Characterization fo Tyrocidine Synthetase 1 (TY1): Requirement of Post-translational modification for peptide biosynthesis".

Stein T. et al., Biochem. (1995) vol. 34, pp. 4633-4642 "Gramicidin S synthetase 1 (Phenylalanine Racemase), a prototype of amino acid racemases containing the cofactor 4'-Phosphopantetheine".

Stachelhaus et al., Journal of Biol. Chem. (1998) vol. 273, pp. 22773-22781 "Peptide bond formation in nonribosomal peptide biosynthesis".

* cited by examiner

```
Orf12         --------------------ERRRLLDEWN-ATAAPSSDTVLARFEEQAARTPEAPAVVC
Orf13|M1      --------------------ERSRLLVEWNDTARPVVESSVPALFAKRVAATPDATAVVG
Orf13|M2      ------------------------NATAVPAQPALVPELFTAQAARTPTWPALVT
Orf13|M3      --------------------DRLLTAWNEAREPAPP-VTLPDLFDRQARRTPEAVALTA
Orf13|M4      --------------------EIERVVHSWNDTARPVVESSVPALFAEQVAAAPDATAVVG
Orf13|M5      --------------------ERSRLLVEWNDTARPVVESSVPALFAEQVAAAPDAVAVVG
Orf13|M7      -------------------------TVPELVAAQVARRPGAVALRS
Orf14|M1      ------------------------NDTAAPAPAGLVPDLFAAQAARTPDAVAVAG
Orf14|M2      ------------------------NDTARRVRQASVPELFAERVAAAPGAPAVAA
Orf14|M3      --------------------EESRLMLAAGEEPAPALPEITVAALVAEQCARTPGAVAVTG
Orf14|M4      ------------------------NETRRAVTRASVPELFAKQVAATPDAIAVAG
Orf14|M5      --------------------ERRLVLTGWNDTTAAVPAVAVPELIERRAAAEPEAGAVWC
Orf14|M6      --------------------ERREVLRTPNATARDVAAATLPAIVGEWARTTPGATAVTA
Orf14|M7      --------------------EREAVLSGGNGGTAPVPVTTVPALFAEQARRTPGAVAALS
Orf14|M8      --------------------ERSRLLVEWNDTARPVVESSVPALFAERVAAAPDAVAVVG
Orf17         ----------------------------RTLTGLFAEQVAARPTAVAVSD
GrsA_Adomain  MLNSSKSILIHAQNKNGTHEEEQYLFAVNNTKAEYPRDKTIHQLFEEQVSKRPNNVAIVC
                                                          *    *

A1                                    A2
Orf12         GDVTVTYAEIEAGANRLARVLRARGAGPESVVALCLPRGPEVVTGILAAWKAGAAYLPVD
Orf13|M1      EGVSWSYREIDRRSDVLARRLVAAGVGVESPVVVALERSPEVLSAFLAVAKAGGVFVPVD
Orf13|M2      AGAEMSYAELEERSNRLARWLAGRGVGADDRVALMMRRGPELMVAILAVLKAGAAYLPVD
Orf13|M3      DGVSLTYREISERANRIARLLTSRGIGPESLVGVVLPRSADLVVALLGVLQAGAAYVPVD
Orf13|M4      EGVSWSYREIDARSDALARSLVAAGVGVESPVVVALERSPEVLSAFLAVAKAGGVFVPVD
Orf13|M5      EGVSWTYREIDARSDALARSLVAAGVGVESPVVVALERSPEVLSAFLAVAKAGGVFVPVD
Orf13|M7      EDGEITYAEIDARAGRLAAVLRRRGIGPESRVAVLLPRGVEQVVAFLAVVRAGGTYLPID
Orf14|M1      PDRRLTYAEIDERSGRLARWLIRRGVAADTRVALVLERSAELPVAILAVLKAGGAYLPID
Orf14|M2      GDLRWTYADIDARSDALARSLVAAGVTAESPVVVALERSADVLTAFLAVAKAGGVFVPVD
Orf14|M3      PDASLTYAEIDERAARIARWLRRHGAGPGAAVCVLMERSAELVAVLLGVMRAGAAYVPVD
Orf14|M4      EGVSWSYREIDVRSDALARSLVAAGVGIESPVVVALDRSPEVPTAFLAVAKAGGVFVPVD
Orf14|M5      GDTHLRYGEINARANRLARLLVERGAGPESIVAVCLERSADLVVTLLAVLKTGAAYLPID
Orf14|M6      ENDRLTYAEIDARANRLARSLIARGVGPGAVVGMLLPRSPGLVVAMLAIVKAGGAYLPLD
Orf14|M7      EGMSLTYADIAARVNRLARHLVSLGAGPETVVGIAMSRGLDMLVAVLAVGQAGAAYVPVD
Orf14|M8      EGVSWSYREIDRRSDVLARSLVAAGVGLESPVVVALERSADVLTAFLAVAKAGGVFVPVD
Orf17         DRGRHTYREIDEWSGRLARGLRKAGVRDGDAVGVCLDRSAELVAVLLAVLKAGAAYVPLD
GrsA_Adomain  ENEQLTYHELNVKANQLARIFIEKGIGKDTLVGIMMEKSIDLFIGILAVLKAGGAYVPID
                *  :*       :*    :     *      * :  :.  .*.  ::*...::*:*

Orf12         TELPAERVAYLLGDSAAAVRLG--TAETLAALPDGP---------------AADVDVHA
Orf13|M1      LSWPQARVDAVVADCAARVAVA--DRPMSGLTVVSAGL------------GGDSAVVSA
Orf13|M2      PDLPRDRVDYLLADAAPAFVLA--ERATAPWVPVA---------------GGIPVLVDA
Orf13|M3      ADYPAERIGYILGDAGAVCVLT--VDATAGAVPPG---------------VPKLVLDH
Orf13|M4      LSWPQARIDAVVADCAARVAVA--DRPMSGLTVVPA------------------
Orf13|M5      LSWPQARVDAVVADCGARIAVA--DRPMSGLTVVSAGL------------GGDSAVVSG
Orf13|M7      PAYPRDRVDYLVRDAEPACLLT--VAGHRAAAPAAP--------------AVVELDD
Orf14|M1      PAQPPRRIADIVADAAPALVLA--QASTADVVADASPALVLAPASDGVPTGAVPVHLLDS
Orf14|M2      LSWPRARVDAVIADCAAWIAVA--DRPMTGLTVVPAN-------------------
Orf14|M3      PAYPAERIRFVVTDARAACVVS--ESASAGLVPDG---------------VPCLAIDD
Orf14|M4      LSWPQARVDAVIADCAARVAVA--DRPMTGLTVVPA------------------
Orf14|M5      PGYPAGRIAYMLADARPALLVTSPAVASGDSLPDGG--------------AQRIVLGD
Orf14|M6      PGYPAPRLARMVEDAAPALLLA--TAGTADAVPAGP--------------QRLLLDD
Orf14|M7      PSYPDERKEFMLTDAGAAYVLT--LASDADRVPPGTP-------------AAAVVLDE
Orf14|M8      LSWPQTRIDAVIAD-S--------RPVLVLDSVDLP-----------------
Orf17         AAYPADRIAYTVGDAGLAVVVT--TSADFPDV-DG---------------VRLLAPES
GrsA_Adomain  IEYPKERIQYILDDSQARMLLT--QKHLVHLIHNIQFN------------GQVEIFEE
                 *     *       : *
```

Figure 3A

```
                                                                A3
Orf12         PEIARE-----SP----SPLRLEPLPDQLAYVIYTSGSTGLSKGVGVSHGGLANYVGWAS
Orf13|M1      DLTADRAVVLPSRPVP---------GAAVYRMYTSGSTGRPKGVVTTHQNLVDLAT---
Orf13|M2      PAVAAEVAAHSGEAVTDRDRRAALRGGHLAYVIYTSGSTGRPKGVLITHDGLANLTL-DH
Orf13|M3      PETVTALAACDTAPLGEAERAGELLPEHPAYVIYTSGSTGTPKGVLIPHRNVVELFAATR
Orf13|M4      DQVGDSAVVLPAGPVP---------GAAVYRMYTSGSTGRPKGVVTTHQNLVDLAT---
Orf13|M5      DLTADRAVVLPAGPVP---------GAAVYRMYTSGSTGRPKGVVTTHQNLVDLAT---
Orf13|M7      PATAAEIADAEPEPP------VAVRPTHSAYLIYTSGSTGRPKGVVVTHRGVAALVATQA
Orf14|M1      PAVRDEVAQCPAGAVTDADRRGVLLGGHAAYVIYTSGSTGRPKGVVVSHDAFANLVL-DQ
Orf14|M2      -RAGDPAVALPPRPLP---------GAAAYRMYTSGSTGRPKGVVTTHQNVVDLVT---
Orf14|M3      P----AAAAEPAEPGDDPGDAAGPRPDDPAYIIYTSGSTGTPKGVVVSHRNVVALLTATR
Orf14|M4      DAAGDPAAELPPRPLP---------GAEVYRMYTSGSTGRPKGVVTTHQNLVDLAT---
Orf14|M5      PDTAAALDGLAGTDLLVSERRGVTHPAHPAYVIYTSGSTGRPKGVVVPHGALTNFVAAMS
Orf14|M6      PGTAAELARLDGDPIRDEERTHPLRPGHPAYLMFTSGSTGRPKGVLVPHAGIDRMVR-RS
Orf14|M7      PVTAARIAGLDPADLTDADRVAPLLPAHRAYVIYTSGSTGRPKGVAVEHRTVVNLLSWAA
Orf14|M8      ----AAEADLPRVPA----------GAGVYRMYTSGSTGRPKGVVTTHQNLVDLAT---
Orf17         ------LAEAGDDPGIPLATPAG--PERPAYVIYTSGSTGRPKGVVVPHANVSALLDATR
GrsA_Adomain  DTIKIREGTNLHVPSK---------STDLAYVIYTSGTTGNPKGTMLEHKGISNLKVFFE
                                          .*  ::***:**  **.    *    .

A4
Orf12         VLYGGLSAP---LHSSLAFDLTVTSVFVPLVCGGSVVVSAAGGGRGLASLLAAGDG--FS
Orf13|M1      -DTCWGPTPRVLFHAPHAFDASSYEIWVPLLNGGTVVVAPQRSID-ATVLKDLIRAHDLT
Orf13|M2      GRFGLGPGARVAQFASPGFDMFVDEWSMALLAGAALTFVPPERRL-GADLAAFLAEYGVT
Orf13|M3      GSFHFGEGDVWSWFHSVAFDFSVWELWGALLHGGRVVMVPFAVSRSPRDFWELLVRERVT
Orf13|M4      -DTCWGPTPRVLFHAPHAFDASSYEIWVPLLNGGTVVVAPRRSID-ATVLRDLIRGHELT
Orf13|M5      -DTCWGPTPRVLFHAPHAFDASSYEIWVPLLNGGTVVVAPRRSID-ATVLRDLIGAHELT
Orf13|M7      ERLAVTGESRVLQFASVGFDASIWEMVMALCAGATLVVAPADDLLPGPALAATLSGHAVT
Orf14|M1      RRLGIGPGSRVAQFASPGFDMFVDEWSMALLAGAALVIVPPERRL-GADLAAFLTERGVT
Orf14|M2      -DRCWGPTPRVLFHAPHAFDASVSFELWVPLLTGGTVVVAPGESID-TGVLRQLIRAHELT
Orf14|M3      PLFGFAGDEVWSWFHSVAFDFSVWELWGALTHGGRVVVVPYAVSRSPRDFWELVVREGVT
Orf14|M4      -DTCWGPTPRVLFHAPHAFDASSYEIWVPLLNGGTVVVAPGRSID-AAVLGELIRAHELT
Orf14|M5      DRLALGAGDRLLAVTTVAFDIHVLELYVPLVGGAGVVVAEDAVVRDPAAVAALLDRHAVT
Orf14|M6      TCLQLAPDDVLPHLSSVSFDAAITFEIWGALLNGATLAVAPAETLS-VAELRAFLADRGAT
Orf14|M7      GRFGGADFARTLAATSLNFDVSVFEIFGPLVSGGSIEIVTDLLALADPASPAWEA----S
Orf14|M8      -DTCWGSTPRVLFHAPHAFDASSYEIWVPLLNGGTVVVAPRRSID-ATVLRDLVRGHELT
Orf17         EEYALGPGDVWTFFHSAAFDFSVWEIWGCLLTGGHLVVVPYWVSRSPEQFHDLLAERGVT
GrsA_Adomain  NSLNVTEKDRIGQFASISFDASVWEMFMALLTGASLYIILKDTINDFVKFEQYINQKEIT
                                 **   *  *.:.

A5
Orf12         LVKVVPGHLRLLAELVPAGEMAAVG----SLVAGGEVLAGGDVREWLSRVPGS--VVVNE
Orf13|M1      HVHVTA---GLLRVL---DPSCFAG--LTEVLTGDAVSAEAVRRVKDANPGL--RVRQL
Orf13|M2      HATLPP---AVVGTIPDGVLPPSF-----VLDVGGDVLPGDLARR--WLRDGR--VLFNS
Orf13|M3      VLSQTP---SAFYQLAAAA-DDTPD-ALRVVVFGGEALDPGRLAGWRERRPDG-PRLVNM
Orf13|M4      HVHVTA---GLLRVL---DPSCFAG--LTEVLTGDAVSAEAVRRVREANPGL--RVRQL
Orf13|M5      HVHVTA---GLLRVL---DPSCFAG--LTEVLTGDAVSAEAVRRVKDANPGL--RVRQL
Orf13|M7      HATLPP---AVLAASAPGDLAPLA-----VLVSAGEALGPDLVR---QFAPGR--ALVNA
Orf14|M1      HATLPP---AVVATLPEESLPRSF-----VLDIGGDALPDDLARR--WLRDGR--WLGNS
Orf14|M2      HVHVTA---GLLRVLAE-DPSCFAG--LTEVLTGDVVPAEAVRRVLDANPGV--RVRQL
Orf14|M3      VLSQTP---SAFAQLMAAAGDDDRD-ALRFVVFGGEALDPGRLAGWLARRPDK-PRLVNM
Orf14|M4      HVHVTA---GLLRVL---DPSCFAG--LTEVLTGDAVSAEAVRRVMEANPGL--RVRQL
Orf14|M5      IVQATP---ALWQALLAGHADAVRD---VRLLVGGEALPPALAG--RMAAAGR--GVTNL
Orf14|M6      KLFLTT---GLLHEVIDADVTALAG--LKAVYTGDVLSPAHCRSLLDRVPGL--ELYNA
Orf14|M7      LVSGVP---SAFSRVLDRGDIAART---RSVVLAGEALTADVVNATRAALPGV--RVANI
Orf14|M8      HVHVTA---GLLRVL---DPSCFAG--LTEVLTGDAVSAEAVRRVKEANPGL--RVRQL
Orf17         VLNQTP---SSFTQLVAADRGAERDLAVRLVIFGGEPLDARTVLPWLDRRPEARCRLVNM
GrsA_Adomain  VITLPP---TYVVHLDPERILSIQT-----LITAGSATSPSLVNKWKEKVT-----YINA
                                              .*.                     :
```

Figure 3A cont'd

```
                       A5                                                              A6
Orf12         YGPTETVVGCSVFSVAAGDVVGD--VVPVGRPVANTRLFVLDEGLRPVPAGVAGELYVAG
Orf13|M1      YGPTEVTLCATQHLLD-DG-------VPIGRPLDNTRVYVLDDLLQPVPVGVTGELYVAG
Orf13|M2      YGPTETTVNAATWR-AEAGDWGS--VAPIGTPVPNLRAYVLDGWLRPVPVGADGELYVSG
Orf13|M3      YGITETTVHVTHQDLAPAD-TTG--S-PIGRGIPGLSVYVLDEALRPVPPGVAGEVYVAG
Orf13|M4      YGPTEVTLCATQHLLV-DG-------VPIGRPLDNTRVYVLDDLLQPVPVGVTGELYVAG
Orf13|M5      YGPTEVTLCATQHLLD-DG-------VPIGRPLDNTRVYVLDDLLRPVPTGVVGELYVAG
Orf13|M7      YGPTETTVCATASAPLGPEDPPH-----IGAPVADSRVYVLDDALTPVPPGVTGELYVSG
Orf14|M1      YGPTETTVNAATWR-CEPGTWEG--ATPIGRPVANLRAYVLDGRLRPVPVGVEGELYVSG
Orf14|M2      YGPTEVTLCATQHVVREPSPV-----LPIGRPLDNTRVYVLDGLLQPVPVGVTGELYIAG
Orf14|M3      YGITETTVHTTYQHIAPG--TTG--S-VIGRGLPGFGLYVLDEALRPVPAGVPGEVYARG
Orf14|M4      YGPTEVTLCATQQVLDGTG-------VPIGRPLDNTRVYVLDDLLQPVPVGVTGELYVAG
Orf14|M5      YGPTEVTVWATVADLGA-SPAG---PVPIGTPLRNTRAFVLDDALRPVPPGVPGELYLAG
Orf14|M6      YGPTENTTITTLHR-VRPEDLDAGTGVPIGVPISDTRVYVLDDALRPVPVGVAGELYTSG
Orf14|M7      YGPTEATVYSTAWHTDR-DVTGG--AAPIGRPVTNTRAYVLDDRLTPVPPGVVGELYLAG
Orf14|M8      YGPTEVTLCATQHLLD-DG-------VPIGRPLDNTRVYVLDDLLRPVPTGVVGELYVAG
Orf17         FGITETTVHVTAVDVTRAAALAG--SRSVGRPLPGWAVRVLDEQRREVPPGVPGEIYVGG
GrsA_Adomain  YGPTETTICATTWVATKETIGHS---VPIGAPIQNTQIYIVDENLQLKSVGEAGELCIGG
              :* **    :                  :*   :    ::*       . *  **:  *

A6                      A7              A8
Orf12         SQVARGYVGRSGLTASRFVACPFG-VGERMYRTGDVVRLAG-GDLVFVGRVDEQVKIRGY
Orf13|M1      AGVARGYAGMPGLTAERFVADPFNT-GGRLYRTGDLVRWTDDGVLHFAGRADDQVKIRGY
Orf13|M2      AGLARGYLNRAGLTAERFVACPFEP-GERMYRTGDVVRWTAEGRLVFAGRSDDQVKIRGF
Orf13|M3      RQLARAYLGRAALTGTRFVACPFLPAGERMYRTGDRARWSR-GRLQFAGRTDDQVQIRGF
Orf13|M4      AGLARGYAGMPGLTAERFVADPFSV-GGRLYRTGDLVRWTDDGVLHFAGRADDQVKIRGY
Orf13|M5      SGLARGYAGMPGLTAERFVADPFNT-GGRLYRTGDLVRWADDGVLHFAGRADDQVKIRGY
Orf13|M7      ASLARGYAGRAALTAERFVACPFAP-GERMYRTGDRARWDAAGRLTFAGRADDQVKIRGF
Orf14|M1      AGLARGYLNRAGLTAGSFVACPFEP-GERMYRTGDIVRWDARGRLVYAGRADDQAKIRGF
Orf14|M2      AGVARGYADMPGTTAERFVADPFTA-GGRLYRTGDLVRWTGEGELVFAGRADDQVKIRGY
Orf14|M3      PQVARGYIGRPGLTAERFVASPFAP-GERMYRTGDVARWTADGRLVFAGRSDDQIKIRGF
Orf14|M4      AGLARGYAGMPGLTAERFVADPFSS-GGRLYRTGDLVRWTDDGVLHFAGRADDQVKIRGY
Orf14|M5      DQLARGYHGRAGLTAERFVADPFG-RGERMYRTGDRVRWTRGGSLEFLGRVDDQVKIRGF
Orf14|M6      IGLAHGYAGRPAPTAERFVACPFAP-GERMYRTGDLVRWTADGRLLFAGRADNQVKIRGF
Orf14|M7      AQLARGYLGRPGLTGERFVACPFGPGGERMYRTGDRVRWNADGDLVFAGRADDQVKIRGF
Orf14|M8      SGLARGYAGMPGLTAERFVADPFSV-GGRLYRTGDLVRWTDDGVLHFAGRADDQVKIRGY
Orf17         AGVAIGYLNRPELTAERFVTG---PDGRRWYRSGDHGRLLPDGTLEHLGRLDDQVKLRGF
GrsA_Adomain  EGLARGYWKRPELTSQKFVDNPFVP-GEKLYKTGDQARWLSDGNIEYLGRIDNQVKIRGH
              : .*   .   *.  **        *  :  *::** *    * :   ** *:* ::**.

A8                       A9
Orf12         RVEPDEVRLVVAGHPRVAGAAVVARPDAVGE---RQLVAYVVAAGEPAG---LAESVRAH
Orf13|M1      RVEPGEVEAVLAQHPDVSQVAVVVREDTPGD---KRLVAYVVGG----------DIEAY
Orf13|M2      RIEPGEVEAVLAAGPGVSQAAVIVREDVPGD---KRLVAYVVGG----D----VEALRSY
Orf13|M3      RIEPGEVQAVVAAHPEIAAAAVVVREDVPGD---PRLTAYVVPAGPRTAPAAVAETVRRF
Orf13|M4      RVEPGEVEAVLAQHPDVSQVAVVVREDTPGD---KRLVAYVVGG-----------DVEAY
Orf13|M5      RVEPGEVEAVLAQHPDVSQVAVVVREDTPGD---KRLVAYVVGG-----------DVEAY
Orf13|M7      RVEPGEVAAVLGEHPAVARAAVVARTDGPQG---ARLVAYLVAADP--AGPDLAAAVRAY
Orf14|M1      RVEPGEVEAVLAAGPGVNQVAVIVREDVPGD---KRLVAYVVGG----D----VETLRSY
Orf14|M2      RVEPGEVEAVLAALPGVSQAAVIVREDVPGD---KRLVAYLVAAPE------TVEAARAH
Orf14|M3      RIEPGEVEAVLAAGPGVSQSAVIVREDVPGD---KRLVAYVVGG---------DAETLRSH
Orf14|M4      RVEPGEVEAVLAAHPDVAQVAVVVREDTPGD---KRLVAYVVGG-----------DVEAY
Orf14|M5      RIELGEVEAALAAFGPVARAAAAVREDVPGD---RRLVGYVVPAAGEPE--PDPAAVRAH
Orf14|M6      RVEPGELETVLSGHPAVARAAVVLAREDTPGA---KRLVAYVVPARPDEDGDALAESVRAY
Orf14|M7      RIEPGEVQAVVARQAGVARAVVLARSDSPGD---ARLVAYVVPADRDADRRALAATVRSD
Orf14|M8      RVEPGEVEAVLAQHPDVSQVAVVVREDAPGD---KRLVAYVVGG-----------DVEAY
Orf17         RIELDEIRGVLTECAGVAAAAVVIRRSTPDDPATARLDAYVVAEAG------ATPPVAEH
GrsA_Adomain  RVELEEVESILLKHMYISETAVSVHKDHQEQ---PYLCAYFVSEKHIP-----LEQLRQF
              *:*  *:    :   :           .  : .           *  .:*.*
```

Figure 3A cont'd (2)

```
                                                                      A10
Orf12            VAERLPEYMVPAAVVTLDEIPLTV NGKVDR AALPEP---------------
Orf13|M1         GQERLPGYMVPSAFVHLDALPLTS NQKVDR AALPAPSMESG-----------
Orf13|M2         AQQRLPGYMVPSAFVELDRLPLTV NGKLDR RALPVPDLARG-----------
Orf13|M3         AADRLPAYMLPSAVVVLDALPLTD HGKLDR RALPAPQHT-------------
Orf13|M4         AQERLPGYLVPSAFVHLDALPLTS NQKVDR AALPAPSVESGV----------
Orf13|M5         AQERLPGYMVPSAFVQLDALPLTS NQKVDR AALPAPSMESG-----------
Orf13|M7         AAATLPAHLLPAAFVPLDRLPLTT NGKLDR AALPEPETGAG-----------
Orf14|M1         AQQRLPGYLVPSAIVALAELPLTP SAKVDR RALPVPD---------------
Orf14|M2         AEQRLPSYLVPSAFVQLDALPLTG NQKVDR AALPAP----------------
Orf14|M3         AQQRLPGYLVPSAFVELDRLPLTV NGKLDR RALPVPD---------------
Orf14|M4         AQERLPGYLVPSAFVHLDALPLTS NQKVDR AALPAPSVESG-----------
Orf14|M5         VAAQLPAYMVPSAVVVLPDLPLTA NGKLDR KALPAPDYGAASAGRAPADE--
Orf14|M6         AARQVPDYLMPAATVVLPDLPLTS SGKVDR AALPAPDVPGG-----------
Orf14|M7         TARELPAYLVPAAVVVLDELPVTA NGKLDR RALPAPGL--------------
Orf14|M8         AQERLPGYMVPSAFVHLEALPLTA NQKVDR AALPAPE---------------
Orf17            AARMLPAYMCPATFTFLDALPMTP NGKVDK AALPEP----------------
GrsA_Adomain     SSEELPTYMIPSYFIQLDKMPLTS NGKIDR KQLPEPDLTFGMRVDYEAPRNE
                   :*  ::  *:       *  :*:*    *:*:  **  *
```

Figure 3A cont'd (3)

|  |  | 235 | 236 | 239 | 278 | 299 | 301 | 322 | 330 |  |
|---|---|---|---|---|---|---|---|---|---|---|
| Orf13\|M1\|HPG | | D | A | Y | H | L | G | L | L | |
| Orf13\|M4\|HPG | | D | A | Y | H | L | G | L | L | |
| Orf13\|M5\|HPG | | D | A | Y | H | L | G | L | L | |
| Orf14\|M2\|HPG | | D | A | F | H | L | G | L | L | HPG |
| Orf14\|M4\|HPG | | D | A | Y | H | L | G | L | L | |
| Orf14\|M8\|HPG | | D | A | Y | H | L | G | L | L | |
| emb\|CAB38518.1\|Cda1\|M6\|HPG | | D | V | Y | H | L | G | L | L | |
| emb\|CAA11795.1\|CepB\|M2\|HPG | | D | A | V | H | L | G | L | L | |
| emb\|CAA11795.1\|CepB\|M1\|HPG | | D | I | F | H | L | G | L | L | |
| | | | | | | | | | | |
| Orf13\|M3\|Thr | | D | F | W | S | V | G | M | V | |
| Orf14\|M3\|Thr | | D | F | W | S | V | G | M | V | |
| Orf17\|M1\|Thr | | D | F | W | N | I | G | M | V | Thr |
| gb\|AAC38442.1\|AcmB\|M1\|Thr | | D | F | W | N | V | G | M | V | |
| emb\|CAB38518.1\|Cda1\|M2\|Thr | | D | F | W | N | V | G | M | V | |
| emb\|CAA09819.1\|FenD\|M2\|Thr | | D | F | W | N | I | G | M | V | |
| | | | | | | | | | | |
| Orf13\|M2\|Orn | | D | M | D | T | D | G | S | V | |
| Orf14\|M1\|Orn | | D | M | D | T | D | G | S | V | |
| gb\|AAC06347.1\|BacB\|M1\|Lys | | D | A | E | S | I | G | S | V | Orn |
| gb\|AAC82550.1\|FxbC\|M1\|5hOrn | | D | M | E | N | L | G | L | I | |
| gb\|AAC82550.1\|FxbC\|M3\|5hOrn | | D | M | E | N | L | G | L | I | |
| | | | | | | | | | | |
| Orf12\|M1\|Asn | | D | L | T | K | V | G | E | V | |
| emb\|CAB38517.1\|Cda2\|M3\|Asn | | D | L | T | K | V | G | E | V | Asn |
| gb\|AAC06348.1\|BacC\|M5\|Asn | | D | L | T | K | I | G | E | V | |
| gb\|AAC45930.1\|TycC\|M1\|Asn | | D | L | T | K | I | G | E | V | |
| | | | | | | | | | | |
| Orf13\|M7\|Phe | | D | A | W | T | V | A | A | V | |
| emb\|CAA33603.1\|GrsA\|M1\|Phe | | D | A | W | T | I | A | A | I | Phe |
| gb\|AAC45929.1\|TycB\|M3\|Phe | | D | A | W | T | I | A | G | V | |
| gb\|AAC06348.1\|BacC\|M2\|Phe | | D | A | F | T | V | A | A | V | |
| | | | | | | | | | | |
| Orf14\|M5\|Gly | | D | I | L | Q | L | G | L | V | |
| emb\|CAB38517.1\|Cda2\|M2\|Gly | | D | I | L | Q | L | G | L | I | Gly |
| emb\|CAB15186.1\|DhbF\|M1\|Gly | | D | I | L | Q | L | G | L | I | |
| gb\|AAF17280.1\|NosC\|M2\|Gly | | D | I | L | Q | L | G | L | I | |
| | | | | | | | | | | |
| Orf14\|M6\|Leu | | D | A | F | F | Y | G | A | T | |
| emb\|CAA82227.1\|CssA\|M2\|Leu | | D | A | W | L | Y | G | A | V | Leu |
| emb\|CAA82227.1\|CssA\|M3\|Leu | | D | A | W | L | Y | G | A | V | |
| gb\|AAC06346.1\|BacA\|M3\|Leu | | D | A | W | F | L | G | N | V | |
| | | | | | | | | | | |
| Orf14\|M7\|(Ala) | | D | V | F | S | V | A | I | V | |
| gb\|AAC06348.1\|BacC\|M2\|Phe | | D | A | F | T | V | A | A | V | (Ala) |
| gb\|AAC83656.1\|PchE\|M1\|Cys | | D | L | F | N | L | S | L | I | |
| emb\|CAA82227.1\|CssA\|M11\|Ala | | D | V | F | I | Y | A | A | I | |

Figure 3B

```
Orf26                          ---------------------------------MVIDAATQPTVPDAFRAQ
gb|AAB52538.1|acyl_CoA_L|Mb     ---------------------------------MAMSVRSLPAALRAC
emb|CAB05426.1|fadD29|Mt        MKTNSSFHAAGEVATQPAWGTGEQAAQPLNGSTSRFAMSESSLADLLQKA
gb|AAG02359.1|blmVI|M1|Sv       ---------------------------------MSRPAGIVDIARRH
gb|AAC44128.1|safB|M1|Mx        -------------------MACRPDSLHASAVTSRRRMRHTLVELLQER
gb|AAF08795.1|MycA|M1|Bs        ---------------------------------MYTSQFQTLVDVIRNR
                                                                 :

Orf26                          AIARPGEPALVVLPG--DPDAEPVTLTYAELDRRAAARAAWLAARFPAGE
gb|AAB52538.1|acyl_CoA_L|Mb     ACLQPHDPAFTFMDYEQDWDGVAITLTWSQLYRRTLNVARELSRCGSTGD
emb|CAB05426.1|fadD29|Mt        ASQYPNRAAYKFIDYDTDPAGFTETVTWWQVHRRAMIVAEELWIYASSGD
gb|AAG02359.1|blmVI|M1|Sv       AERTPARPAYAFLP---DGETESVRFSFADIDRRARAVAAVLQDRGLAGE
gb|AAC44128.1|safB|M1|Mx        ALSEPRHEAFTFLG---EAGVPAVRVDYSSMDVLARAIAARLQADGRVGE
gb|AAF08795.1|MycA|M1|Bs        SNIS--DRGIRFIE----SDKIETFVSYRQLFDEAQGFLGYLQHIGIQPK
                                  :        . .:        .  :  .:     :     *     .

AL1
Orf26                          R-ILIALPTGAHFVELYLACLYAGLVAVPAPPPGGS--SGASERTVGIAA
gb|AAB52538.1|acyl_CoA_L|Mb     R-VVISAPQGLEYVVAFLGALQAGRIAVPISVPQGG---VTDERSDSVLS
emb|CAB05426.1|fadD29|Mt        R-VAILAPQGLEYIIAFMGVLQAGLIAVPIPVPQFG---IHDERISSALR
gb|AAG02359.1|blmVI|M1|Sv       R-VLVAYPSGPEYVQAFLGCLYAGVVAVPQDEPR-S--GPSAERLAGIRA
gb|AAC44128.1|safB|M1|Mx        R-ALLLYAPGPEYVAAFFGCLYAGVVAVPVYPPDTARLERSLLRLRTVAR
gb|AAF08795.1|MycA|M1|Bs        QEIVFQIQENKSFVVAFWACLLGGMIPVPVSIGEDNDHKLKVWRIWNILN
                                :  .   . .::   : . .** .* .: .**       *

Orf26                          DCSPALAVVN----ADDAAPLTA------VLRERGLSGLPVGALPPLAAE
gb|AAB52538.1|acyl_CoA_L|Mb     DSSPVAILTTS---SAVDDVVQ---HVARRPGESPPSIIEVDLLDLDAPN
emb|CAB05426.1|fadD29|Mt        DSAPSIILTTS---SVIDEVTTYAPHACAAQGQSAPIVVAVDALDLSSSR
gb|AAG02359.1|blmVI|M1|Sv       DARPALALTA----GAPEAGLA-----------GLATLDVAGVPDSAAG
gb|AAC44128.1|safB|M1|Mx        DSRASVVLTTSFLQGLAGAMFEL------APELGELSWVATDGIALEEAG
gb|AAF08795.1|MycA|M1|Bs        NPFLLASETVLDKMKKFAADHD-------LQDFHHQLIEKSDIIQDRIYD
                                :          .                                     :

AL2
Orf26                          AIRPPRGPRPDSLAVLQYSSGSTGSPKGVMLSHRAVLANLRAFDRSSGHN
gb|AAB52538.1|acyl_CoA_L|Mb     GYTFKEDE-YPSTAYLQYTSGSTRTPAGVVMSHQNVRVNFEQLMSGYFAD
emb|CAB05426.1|fadD29|Mt        ALDPTRFE-RPSTAYLQYTSGSTRAPAGVVLSHKNVITNCVQLMSDYIGD
gb|AAG02359.1|blmVI|M1|Sv       AWTDPVAG-PDALAFLQYTSGSTRRPRGVMVGHGNLLANERCIAAACGHD
gb|AAC44128.1|safB|M1|Mx        AWKPPGLS-GDSVAFLQYTSGSTADPKGVVLTHRNLMHNLSVIHERFQLN
gb|AAF08795.1|MycA|M1|Bs        HPASQYEPEADELAFIQFSSGSTGDPKGVMLTHHNLIHNTCAIRNALAID
                                 * :*::****     * **::  *    : .*      :       :

AL3
Orf26                          SDDVF------GSWLPLHHDMGLHAMLTAGLLNGAGVVLMSPTAFVRRPA
gb|AAB52538.1|acyl_CoA_L|Mb     TDGIPPPNSALVSWLPFYHDMGLVIGICAPILGGYPAVLTSPVSFLQRPA
emb|CAB05426.1|fadD29|Mt        SEKVP---STEVSWLPFYHDMGLMLGIILPMINQDTAVLMSPMAFLQRPA
gb|AAG02359.1|blmVI|M1|Sv       RDSTF------VGWAPFFHDMGLVANLLQPLYLGSLSVLMPPMAFLQRPA
gb|AAC44128.1|safB|M1|Mx        RGSRG------VIWLPPYHDMGLIGGVLTPIFGGLPVDLMSPLSFLQEPL
gb|AAF08795.1|MycA|M1|Bs        LKDTL------LSWMPLTHDMGLIACHLVPALAGINQNLMPTELFIRRPI
                                           * * ***** .    .  *  .    *::.*
```

Figure 3C

```
                                              AL4
Orf26                          DWLRMMDRYRVTI SAAPNFAYDL CVRAVRDEQIAGLDLSRIRTLYNGSEP
gb|AAB52538.1|acyl_CoA_L|Mb    RWMHLMASDFHAF SAAPNFAFEL AARRTTDDDMAGRDLGNILTILSGSER
emb|CAB05426.1|fadD29|Mt       RWMQLLAKHRAQI SSAPNFGFEL AVRRTSDDDMAGLDLGHVRTIVTGAER
gb|AAG02359.1|blmVI|M1|Sv      RWLRAVSRYRAHT SGGPNFAYDL CVDRVGEDERAGLDLSGWKVAYNGAEP
gb|AAC44128.1|safB|M1|Mx       RWLKTLSERRGTC SGGPNFAYEL CVRKISDEQKAGLDLSSWELAFCGAEP
gb|AAF08795.1|MycA|M1|Bs       LWMKKAHEHKASI LSSPNFGYNY FLKFLKDNKSYDWDLSHIRVIANGAEP
                                 *::          .·***·::            ::.  .  **.    *:*

AL5
Orf26                          VNPATVRAFTERFAPFGLHTHAVN PCYGMAEFTA YVSTKVFEAPAVFLPA
gb|AAB52538.1|acyl_CoA_L|Mb    VQAATIKRFADRFARFNLQERVIR PSYGLAEATV YVATSKPGQPPETVDF
emb|CAB05426.1|fadD29|Mt       VNVATLRRFTERFAPFNLSETAIR PSYGLAEATV YVATAGPGRAPKSVCF
gb|AAG02359.1|blmVI|M1|Sv      VRADTVRRFTDRFAPHGFTPGAHF PTYGLAEATL LVATGPKGVPPRTLTA
gb|AAC44128.1|safB|M1|Mx       IRPDTLEAFSKAFEPCGFRREAFY PCYGLAEGTL IVTGVSKGRAARVEHF
gb|AAF08795.1|MycA|M1|Bs       ILPELCDEFLTRCAAFNMKRSAIL NVYGLAEASV GATFSNIGERFVPVYL
                                 :       *       .:   .    **:**   :    .:

Orf26                          DPRALEDAASPALRPADP-AAAREIP---GVGRV-PDFEVLIVDPDGLRP
gb|AAB52538.1|acyl_CoA_L|Mb    DTESLSAGH---AKPCAGGG-ATSLIS----YMLPRSPIVRIVDSDTCIE
emb|CAB05426.1|fadD29|Mt       DYQQLSVGQ---AKRAENGSEGANLVS----YGAPRASTVRIVDPETRME
gb|AAG02359.1|blmVI|M1|Sv      DRAALRAGR---LRPAGPGEAGLELV---GNGTAGLDTTLRIVDPATARE
gb|AAC44128.1|safB|M1|Mx       QREALEAHR--AVAASSPGEAARDTVRHVSCGTVVPDEQILVVDPETRTA
gb|AAF08795.1|MycA|M1|Bs       HRDHLNLGE----RAVEVSKEDQNCASFVEVGKPIDYCQIRICN-EANEG
                                 .    *          .            :      :::

AL6
Orf26                          LPEGRVGEIWLRGPGAGAGYWGRTELNPGIFDARPAGDG---QDG WVRT
gb|AAB52538.1|acyl_CoA_L|Mb    CPDGTVGEIWVHGDNVGNGYWQKPDESERTFGGKIVTPSPGTPEG WLRT
emb|CAB05426.1|fadD29|Mt       NPAGTVGEIWVQGDNVGLGYWRNPQQTEATFRARLVTPSPGTSEG WLRT
gb|AAG02359.1|blmVI|M1|Sv      CPPGEVGEVWVRGPGVARGYFGRPRESAPLLAARLPGG-----EG YLRT
gb|AAC44128.1|safB|M1|Mx       LPPGHIGEIWVRGPSVAQGYWLRPEETARTFQARLAGG----TEA WLRT
gb|AAF08795.1|MycA|M1|Bs       LEDGFIGHIQIKGENVTQGYYNNPESTNRALTP----------DG WVKT
                                * :*.:  ::*  .. **:  ..   . :             :::*

AL6              AL7
Orf26          GDLG ALTGGELFLT GRLKELLIVHGRNLAPHDLR REARAAHDAVDHQIGA
gb|AAB52538.1  GDSG FVTDKMFII GRIKDLLIVYGRNHSPDDIR ETIQEITRGR----CA
emb|CAB05426.1 GDLG VIFEGELFIT GRIKELLVVDGANHYPEDIR ATIQEITGGR----VV
gb|AAG02359.1  GDLG ALHDGELFLT GRHKDLIVIRGQNHHPDLR RTAEQAHPALRPTCAA
gb|AAC44128.1  GDLG FLHDGELFVS GRRKDLLVIRGRNYYPQDLR LTVERSHPALRPGCAA
gb|AAF08795.1  GDLG FIRKGNLVVT GREKDIIFVNGKNVYPHDIR RVAIELEDIDLG-RVA
                ** *  :  *::.: ** *:::.: *  *.*:*

Orf26                          AFGVPAP--DERIVLVQEVHPRTPLDELPR-----VASAVSRRLTVSFGV
gb|AAB52538.1|acyl_CoA_L|Mb    AISVPGDRRTEKLVAIIELKKRGDSDQDAMARLGAIKREVTSALSSSHGL
emb|CAB05426.1|fadD29|Mt       AIAVPDDR-TEKLVTIIELMKRGRTDEEEKNRLRTVKREVASAISRSHRL
gb|AAG02359.1|blmVI|M1|Sv      AFAVPGDG-AERLVLVCELTSYRAVDPAA------VAEAVRAALAARHGV
gb|AAC44128.1|safB|M1|Mx       VFSVSVGA-SEEVVVVQEVDRRYPGGDWPD-----VIAAIRRDISEQHAL
gb|AAF08795.1|MycA|M1|Bs       ACGVYDQETRSREIVLFAVYKKSADRFAP------LVKDIKKHLYQRGGW
                                . .*      .. :: :                    :   :   :
```

Figure 3C cont'd

```
                                               AL8
Orf26                         PVRNVLLVRRGTVRRTTSGKIRFTAVRERFLAGGITALHAELEPALRPVQ
gb|AAB52538.1|acyl_CoA_L|Mb    SVADLVLVAPGSIPITTSGKVRFGACVEQYRQDQFARLDA----------
emb|CAB05426.1|fadD29|Mt       RVADVVMVAPGSIPVTTSGKVRFSASVERYLHHEFSRLDAMA--------
gb|AAG02359.1|blmVI|M1|Sv      APHTLVVLRRGQIPKTTSGKVRFGHCRTAYLDGTLPVHTAVRLP------
gb|AAC44128.1|safB|M1|Mx       RVHAVVLIKSGSLLKTSSGKVQFGATREAYLEGQLDTVSADAAQEPVGE-
gb|AAF08795.1|MycA|M1|Bs       SIKEILPIR--KLPKTTSGKVKHYELAEQYESGKFALESTKIKEFLEG--
                                 ::  :      : *:***::*     :          :        :

Orf26                         AGAGR
gb|AAB52538.1|acyl_CoA_L|Mb   -----
emb|CAB05426.1|fadD29|Mt      -----
gb|AAG02359.1|blmVI|M1|Sv     -----
gb|AAC44128.1|safB|M1|Mx      -----
gb|AAF08795.1|MycA|M1|Bs      -----
```

Figure 3C cont'd (2)

```
pfam00753   LVEDDDGAALIDTGFTAPAAKALLRLLKDG--GKKIDAIILTHAHADHIGGVPELLER
1SML        LVQTPDGAVLLDGGMPQMASHLLDNMKARGVTPRDLRLILLSHAHADHAGPVAELKRR
ORF 10      VMQTEQAAVVTDP-FISTDNRHGDRYTLDDL-PDHIDLVLITHGHQDHIVLETLLQLR
            :::  :.*.: *  :                .: ::::*.****   . * *
```

Figure 5A

```
pfam00067   DPE--RFLDEN-GKFKKSYAFLPFGAGPRNCLGERLARMELFLFLATLLQRFELE
ORF 10      DPVLYRYIRDHVGQVD-----MAFL-G-MECDGAPLNWLYKGLLTKPVNKKMSAS
            **   *:: :: *:..     :.* * :* *  *   *: .: :::. .
```

Figure 5B

SEQUENCE LISTING

```
<160> NUMBER OF SEQ ID NOS: 46

<210> SEQ ID NO 1
<211> LENGTH: 88421
<212> TYPE: DNA
<213> ORGANISM: Actinoplanes sp.
<220> FEATURE:
<221> NAME/KEY: misc_feature
<222> LOCATION: (2077)..(3078)
<223> OTHER INFORMATION: ORF 1; positive strandedness
<220> FEATURE:
<221> NAME/KEY: misc_feature
<222> LOCATION: (3118)..(4032)
<223> OTHER INFORMATION: ORF 2; positive strandedness
<220> FEATURE:
<221> NAME/KEY: misc_feature
<222> LOCATION: (4038)..(5048)
<223> OTHER INFORMATION: ORF 3; positive strandedness
<220> FEATURE:
<221> NAME/KEY: misc_feature
<222> LOCATION: (6665)..(5814)
<223> OTHER INFORMATION: ORF 4; negative strandedness
<220> FEATURE:
<221> NAME/KEY: misc_feature
<222> LOCATION: (7703)..(6693)
<223> OTHER INFORMATION: ORF 5; negative strandedness
<220> FEATURE:
<221> NAME/KEY: misc_feature
<222> LOCATION: (9464)..(8130)
<223> OTHER INFORMATION: ORF 6; negative strandedness
<220> FEATURE:
<221> NAME/KEY: misc_feature
<222> LOCATION: (9691)..(10761)
<223> OTHER INFORMATION: ORF 7; positive strandedness
<220> FEATURE:
<221> NAME/KEY: misc_feature
<222> LOCATION: (12751)..(10829)
<223> OTHER INFORMATION: ORF 8; negative strandedness
<220> FEATURE:
<221> NAME/KEY: misc_feature
<222> LOCATION: (13617)..(12802)
<223> OTHER INFORMATION: ORF 9; negative strandedness
<220> FEATURE:
<221> NAME/KEY: misc_feature
<222> LOCATION: (15203)..(13614)
<223> OTHER INFORMATION: ORF 10; negative strandedness
<220> FEATURE:
<221> NAME/KEY: misc_feature
<222> LOCATION: (15591)..(15863)
<223> OTHER INFORMATION: ORF 11; positive strandedness
```

```
<220> FEATURE:
<221> NAME/KEY: misc_feature
<222> LOCATION: (15880)..(19035)
<223> OTHER INFORMATION: ORF 12; positive strandedness
<220> FEATURE:
<221> NAME/KEY: misc_feature
<222> LOCATION: (19032)..(39713)
<223> OTHER INFORMATION: ORF 13; positive strandedness
<220> FEATURE:
<221> NAME/KEY: misc_feature
<222> LOCATION: (39713)..(65800)
<223> OTHER INFORMATION: ORF 14; positive strandedness
<220> FEATURE:
<221> NAME/KEY: misc_feature
<222> LOCATION: (65826)..(66530)
<223> OTHER INFORMATION: ORF 15; positive strandedness
<220> FEATURE:
<221> NAME/KEY: misc_feature
<222> LOCATION: (66546)..(67370)
<223> OTHER INFORMATION: ORF 16; positive strandedness
<220> FEATURE:
<221> NAME/KEY: misc_feature
<222> LOCATION: (67384)..(70059)
<223> OTHER INFORMATION: ORF 17; positive strandedness
<220> FEATURE:
<221> NAME/KEY: misc_feature
<222> LOCATION: (70099)..(70662)
<223> OTHER INFORMATION: ORF 18; positive strandedness
<220> FEATURE:
<221> NAME/KEY: misc_feature
<222> LOCATION: (70659)..(71906)
<223> OTHER INFORMATION: ORF 19; positive strandedness
<220> FEATURE:
<221> NAME/KEY: misc_feature
<222> LOCATION: (73439)..(71964)
<223> OTHER INFORMATION: ORF 20; negative strandedness
<220> FEATURE:
<221> NAME/KEY: misc_feature
<222> LOCATION: (74216)..(73563)
<223> OTHER INFORMATION: ORF 21; negative strandedness
<220> FEATURE:
<221> NAME/KEY: misc_feature
<222> LOCATION: (75424)..(74213)
<223> OTHER INFORMATION: ORF 22; negative strandedness
<220> FEATURE:
<221> NAME/KEY: misc_feature
<222> LOCATION: (75535)..(76464)
<223> OTHER INFORMATION: ORF 23; positive strandedness
<220> FEATURE:
<221> NAME/KEY: misc_feature
<222> LOCATION: (78110)..(76449)
<223> OTHER INFORMATION: ORF 24; negative strandedness
<220> FEATURE:
<221> NAME/KEY: misc_feature
<222> LOCATION: (79864)..(78107)
<223> OTHER INFORMATION: ORF 25; negative strandedness
<220> FEATURE:
<221> NAME/KEY: misc_feature
<222> LOCATION: (81624)..(79861)
<223> OTHER INFORMATION: ORF 26; negative strandedness
<220> FEATURE:
<221> NAME/KEY: misc_feature
<222> LOCATION: (81909)..(81682)
<223> OTHER INFORMATION: ORF 27; negative strandedness
<220> FEATURE:
<221> NAME/KEY: misc_feature
<222> LOCATION: (82346)..(82062)
<223> OTHER INFORMATION: ORF 28; negative strandedness
<220> FEATURE:
<221> NAME/KEY: misc_feature
<222> LOCATION: (82587)..(84446)
<223> OTHER INFORMATION: ORF 29; positive strandedness
<220> FEATURE:
<221> NAME/KEY: misc_feature
<222> LOCATION: (84481)..(85548)
<223> OTHER INFORMATION: ORF 30; positive strandedness
```

```
<220> FEATURE:
<221> NAME/KEY: misc_feature
<222> LOCATION: (85556)..(86845)
<223> OTHER INFORMATION: ORF 31; positive strandedness
<220> FEATURE:
<221> NAME/KEY: misc_feature
<222> LOCATION: (87372)..(86803)
<223> OTHER INFORMATION: ORF 32; negative strandedness
<220> FEATURE:
<221> NAME/KEY: misc_feature
<222> LOCATION: (87494)..(88420)
<223> OTHER INFORMATION: ORF 33; positive strandedness; N-terminus only

<400> SEQUENCE: 1
```

| | | | | | |
|---|---|---|---|---|---|
| ggcgaactgc | ttgtcctcgc | tcggcggcag | gctgttccac | ctgtccttct | cggccatcgg | 60 |
| cacgatcacc | tcgttgaaga | gggggttgcc | gagccgggag | acctgcacct | gcgggccgac | 120 |
| ggtcacatcg | ccggaggagg | agccgtcgcg | gacctgaacc | tgacggcgac | tggccgaggt | 180 |
| ccacaccccg | atgaccgcgc | ccgcgtcacg | tccgcgcacc | cgcttcttgc | cgtcacggcg | 240 |
| caccatgtgt | acgggatct | gcagcgcgat | gctgtgcacg | ttggtcttgt | cggtggcgtt | 300 |
| gaccgccttg | ccggcgtagt | tgaacaggtt | ctgcccgacc | aggtgcttgt | cctggaacgg | 360 |
| gcgcagcgtg | ccgaggtcga | agatggcgcc | cagatcgacg | aagaaggcgt | cggcgcgctg | 420 |
| gccggcgaag | accttctcgc | cggtcttcag | cttgtgcacg | gcgtcggcgg | cgaggccgtc | 480 |
| gtagtcggcg | atcgacacct | tgccgacgtt | gcacggcggg | cagggcagct | tgctcgccag | 540 |
| caccgtgctc | ttgccgtgct | tgtcgacctt | cgtcaccgag | tagaactggc | ggcgattcca | 600 |
| gttctcgctg | tcgagcgact | cgatcgggcc | ggtgttgtag | aggaacgtct | tgttgttgcg | 660 |
| cagctcggtg | cggaaccgga | actggtaggt | gatctcggcg | cgggcgtcac | cgtccgagtc | 720 |
| gatgtggatc | tcgtagacga | cgtcgtcgcc | gaactcgaag | aagttcgggc | cgctcgccgg | 780 |
| cagctgcaac | ggcacgtagt | tggcgatcag | ggtgaccgtg | tcgggctcgt | cggggctgac | 840 |
| gaaggcgtac | aggtcggagc | tgtcggccac | cgggtccttg | ctgatctcgg | gtgcttcgcg | 900 |
| gtgtgaagac | atgtcatgcc | ctcccggcgg | ccttgatcag | gctcgcgacg | agcttcttgt | 960 |
| cggtgatcgt | cttgagctgc | tcgcccgaga | agacgtcgat | cgtgcccttc | ttggcgtccc | 1020 |
| ggatggagac | gacgatcggg | gagccgtcac | cggtgggctc | gttctcgccg | gcgaggctca | 1080 |
| gcccggcgac | cgaggcggcc | gatacgccga | cgccggtcgc | ggcgagggcg | aggacccggc | 1140 |
| gacgggaaag | ccacggacgt | gctgccgggg | cgcgatagcg | agtgcgactc | atgctcgacc | 1200 |
| tttcgtcttt | cttacggtcg | gtggtgcgag | gactggaacg | ggcgttgcgt | gtcgacgccc | 1260 |
| gtcagtacgt | gatccaccgg | cctgcggttc | aaagacgaat | tggagcgctc | ccaacgggac | 1320 |
| gactcgagcc | gcgccggggc | gggcacggca | ccggccgtgc | ccgccccgcg | tgcgcggtca | 1380 |
| ccgccagttg | gcgtgatccg | cggcggcggc | gcggtcgcgc | tcgtcggcgg | cccggcggcc | 1440 |
| cttgtcgacc | tcgcgcatcg | accagccgat | cgcgacggcg | gccaggtagg | cgagggtgcc | 1500 |
| gagcaccgcc | acgcccggga | agccgccggt | cacccagcag | gccaggaaca | cggccaggcc | 1560 |
| accggcgccg | atgcccgccg | cccacgagga | cggcagccgg | cggatcgccg | agccgaccag | 1620 |
| cacggccagg | cccagcgacg | cgatcgggct | cggctcctgc | ggcaggtcgg | cgaagtggga | 1680 |
| gacgagcacg | gcgatcaggc | cgaggcccac | gcccgccgcc | gcggtcatcg | ccgggttgat | 1740 |
| ccggcggggcc | agggccaggc | cggtcatcag | cacggcgacg | atcgtgtcga | agaccgcgta | 1800 |
| accggcgccc | cagctgtcgg | agagcatgta | gacggtgaac | gcgatgccgg | ccagcgcgat | 1860 |
| cagcccgaac | accacgtcga | aggcgacacc | ggcccgcggg | gccggccttg | ctgaagtagt | 1920 |

```
catgccgccc acgctaggaa atcggcccgt ccggcgaacc ggtcgaaagt acggtcggcg   1980
ccgcggcgaa ccctgctttg gaccgatgct cgcgacgggg tgcttcccg agggtgatgg    2040
catgcgtttc taccacgagg tgcgccgatg atctggatga gctggcgcca gttccgctgg   2100
caggccctgg ccggtgccgt cgccctggtg ccgttggtgg cctacttgat cgtcacgagc   2160
ctggacatcc ggcgcgccca cgaccgctat caggcgcagt gcgcgtccat cggcaactgc   2220
gccgaggcga tgctccagtt ccagaacgac ttccgcaccc gctgctgct gctcgccatc    2280
ctgctggccg cgatccccgg catcctcggg gtgttctggg gcgcgccgct ggtggcccgc   2340
gagctcgaga ccggcacgca ccgcctggtc tggaaccaga cgtcacccg cgccggtgg     2400
ctggcggtca aggtgctgtt cgtcggtgtc gccgcgatgg ccgtggccac gctcgtcagc   2460
acgctgctga cctgggcgag cagcccggtc gacgcggtgt cgcaggaccg gttcggcgcg   2520
ctggtgttcg acgccgcaa catcgtgccg gtcgcgtacg ccgccttcgc cctcgtcctc    2580
ggcacggtga tcgccctgct cgtgcgccgc accatcccgg ccatggcgct caccatgctc   2640
gtcttcgccg tcgtgcagtt caccgtgccg gcgctggccc ggccgcacct gatggcgccg   2700
gagacccaga cccggcagat gacgttgcag gagttcggcg aggtgcgcgg cttcggcgac   2760
gagcccacgg tcaacgggct gagcatccgg ggcgcgtggg tgaccagcac cagcccgctg   2820
ctcaccgccg acgggacccg gctcgacaag gccacgtacc gcaaatgcgt gaccgacccc   2880
ccggccgtct cgggcggagc tcccggcgtc ggcggcaccg tcgcctgcct ggccgacctc   2940
gatctgcacg tcgaggtggc ctaccagccc aacgaccggt actggacctt ccagtggatc   3000
gagtcggccc tctacctggc gctcggtgga ctgctcctcg ccgtgggcct gtggcgcatc   3060
cgccgccacg tcatctgatc gtcccccccgt ccgcacggat tcgaaggata gaaagacatg   3120
ccacacgagg attcctcgcc cgttctgcag gcggagggct tgaccaaacg ctacggtcgg   3180
cgcaccgccc tgcaggactg caacctgacc attccgcgcg gccgggtgat cggcctggtc   3240
ggcccgaacg gcgccggcaa gtcgacgctg ctccagctgg cctgcgggct gatcacgccg   3300
tcggagggct cgctgcgcgt gctcggcgag acgccggccg cgaacgccgg ccacctcgcc   3360
aaggtcggct tcgtcgcaca ggacaccccg gtctacagca acttcacggt cggcgaccac   3420
ctgaagatgg gtgccaagct caacccgacg tgggaccagg cgctcgccga gcgccgcgtc   3480
gcgcaggtcg ggctcaacca cggccagaag gcgggccggc tctccggcgg tcagcgcgcc   3540
cagctcgccc tgacgcttgc cgccgccaag cgcccggaac tgctgatgtt cgacgagccg   3600
gccgccgcgc tcgacccgct ggcccgcgac ggcttcctgc agaacctgct cgagttcgtc   3660
accgagctcg acgccagcgc gatcctgtcg tcgcacctgc tcggcgacgt cgagcgcgtc   3720
tgcaactacc tgatcgtgct ctgcgcctcc cgggtgcagg tcgccggcga cgttcccgac   3780
ctgctcaaca cgcactaccg catcgtcgcg ccccgcggcg agctggacca tccgccggcc   3840
ggcctcgagg tcatccgggc gcagcacgcc gaccggtaca ccaccgccgt cgtgcgcggc   3900
gacggcagcc ggccgagcac ctggacgatc gagcccatcc agctcgagga gctcgtgctg   3960
gcgtacatga cgcgggcgat gggcgtcacc ggcgagccgc tgatggccgc gtccggggag   4020
gtcgtccgtt gatctggatg agctggcggc agttccgcgg tcaggccgtc gtcggggtcg   4080
tcgtgctggc cctgctcgcc gcatacctgg tctacctcgg cgtcgacatc cgcggcgcct   4140
acgacgacta tcgggcgcag tgccccgcgg gcggcgactg cgccgggccc ctgggccagt   4200
tcagcctcga ctacgagaac acgttgctct atctggccgg cgtgctggcg ctggtgcccg   4260
gcctgctcgg catgttctgg ggcgcgcccc tgatcacccg ggagctggag aacggcaccc   4320
```

| | |
|---|---|
| agcgcctggt gtggaaccag agcgtgaccc gccgccgatg gctgctgatc aagctactcg | 4380 |
| tcgtgggctt ggcctgcatg gtggtggccg gggtgccgag cctgctgctg acctgggccg | 4440 |
| ccgcgccggt cgacaatgtg gccgacaacc ggttcagcac ggtgatgttc ggagcccggt | 4500 |
| tcctgccgcc gatcgcctac gccgccttcg cgttcgtgct cggcacgctc atcggcctgc | 4560 |
| tggtccgccg gacggtgccg gcgatggcgc tcacgctcgt ggcgttcgtg atcttccagt | 4620 |
| tcctggtgcc gaacctggtg cgcccccacc tcatgccggc caagcacctg gtcaagccga | 4680 |
| tgacggtgag cgccatcaac gaggccaagt cgctgggcag catcaccggc gcgccggtgc | 4740 |
| tgaacggcct gtcgatctcg cagggctgga tcaccgacgt cagcgcgctc aagaccgccg | 4800 |
| acggccggtc gctggacgcg aagacgttcg acaactgcta catgaacgcg cccaagaccg | 4860 |
| gtgcgaccga gggcccgtac ggtgacgtcg cggtctgcct ggccaagctg gacctgcacg | 4920 |
| tcgacatcgc ctaccagccg tggaaccggt actgggcctt ccagttcctc gaatcggggt | 4980 |
| tctatgtgct gctcagcggc ctgctgatcg gcgccgcgt gtggcgcgtc cagcggcggc | 5040 |
| ccagctgaga tgagcgcgca cagcaccgtg accgagccgg gcgcactcgt ccgtggcacc | 5100 |
| cgggaagccg gggcggcgg cgagcgtcgt gccgcggtgg ccgccctggt catcggcggg | 5160 |
| gcggcggtgc ggtaccgcac ggtgctggtg gcgctgggaa gcccgccgac cgacagcgac | 5220 |
| gaagcagttc tcgggctggt ctccctgcac atcgcgcagg gacgcgacgc accggtccat | 5280 |
| ctgtacggcc aggactacat gggcatgctc gaggcccacc tggccgcacc gctggtccgg | 5340 |
| gcgttcggcg ccggggtggt gccggtccgt gcgccgctgc tcgtcctgtt cgcgctgttc | 5400 |
| ctggtcgtca tgtaccagct cacccggaga ctgtggtcgc cgggcgtcgc ggtggcgacg | 5460 |
| gtgctggtgc tcggtctcgg cgccgaccgc gtgctgagcg ccgagttgac ggccggcggc | 5520 |
| gggtacccgg agatcgccgt tctcggcgcg ctcctgttcc tcctcgcggt gcggatcggc | 5580 |
| cgcggggagg tccgccgccc ggtgctcgcc ctggccgaat tcgggcttgc gctgggcctc | 5640 |
| ggcgtgtcga tggtggccaa cctctgcccg ggcgaccgct gcggcactac gagtttctgg | 5700 |
| tggccgccga tctgtctcgc gctgctcgcg gtgacggccg ggccggcggt gcgtgcgctg | 5760 |
| cggcgcgccg ttccggagcc ggcggcgatc cggtcgcgcc cgccgacgcg cggtcagggg | 5820 |
| ctggcggcga tgcggtcgcg cccgtcgacg ccgcgctgga gcatgccggt gagcgcggcg | 5880 |
| agcgcctccg cgcggcccgg atgggcctcc agctcgcgca gcgccgagat ggtcgccgcc | 5940 |
| agctcggcgg acaggtcgtc gagcacgtcg gcgaccgcgc cggcgttggc ggccaggatc | 6000 |
| tccgtccaca gtgccgcgcg accgcccgcg atccgcgtgg tgtcccgcac gccctggccg | 6060 |
| gccaggccca gctgggccgg ggtgccgtcc agcatccgcg cggccagcag gccggccacc | 6120 |
| aggtgcggca cgtgcgagac gagggccacc gcccggtcgt gctcctcggc gctcatcagc | 6180 |
| accggcgtgg cgccgcaggc cgaaaccacg gccagggccc cgtcgacggc ggcggtgctg | 6240 |
| cttcgccggc cggggagag cacccagggc cgcccctcga acagcgagcc ccgggccgcg | 6300 |
| tgcggtccgg agcgttcgct gccggcgagg ggatgcccgc cgacgtggga ggaggcgtcg | 6360 |
| cagccgagca cctcgatctg ccgggagggc agcactttca cgctcgccgc atcggtgtgc | 6420 |
| acccgggccg ttccccgccg ctggaggtcg gccagcacgg gagcgacggc cgccggcggc | 6480 |
| accgcgatca cggcgacgtc cacccggtg cgcggctcgc ccgcgatgcc cgcgccgagc | 6540 |
| gccgccgcgg cgcgcgcggc ggcgggatcg gcgtccagca ggtgaacggt gatgtcacgt | 6600 |
| tgggtgagag cgaggccgac cgaggtcccg atcagcccgg tgccgacgac gaccgcgctg | 6660 |
| cgcacaaggg ctcccatcgc cgcattcgct gttcaggccg cgttcttctc gagtgtttcg | 6720 |

-continued

```
gcgaattcca accactcttg tgaacaacgc cgggccacgt tcgccaggac gtacgtgcaa     6780
tgcgacggaa ccgcgtcgag catgtctttc cactcatcat cttgaaccgt gcgggcaaga     6840
acccatcgca aaagattgcg gccggattcg gtaaatcgca gcgacgggtc gttcttcaag     6900
ccttgaagta ttgaccgcac ggtcggctcg agcagccgaa tcgtgttttc cttgtcgaag     6960
gaaatgtcgt cgcggtgacc gcccgtgcgg cggggccgg gcagcgggtc ctcgccgcgc      7020
tgcaggcgat tgcgcacgtc acgcgcggtc gagggcgata cgccggcgtt cttggcgatc     7080
tcccgcaggg aggcgtcggg ctgttgctga atgtagctga cggccttcag tcggccctcg     7140
gaattgtcca gcgggcgcac ccggccgtcc ggccgacgc gggtgcgcga gccctgcccg      7200
atgtcgccgg agagctcgag gcgccggcgt atgttgccca cggtgcgggc gctgagtccg     7260
ctggaggccg ctattgtgcg gtctgaccag gacggatgcg actcgatgat ccgttccgcg     7320
gcgcgcgtgc ggtccgctgt ggacagtggc aggccgtgcg cgatgttcgc cttgacgccg     7380
aggacgaatg cctcctgctc gctgcccctcg aacatcgcgg ccttgatcag ctcgtcgccg    7440
cgcagccggg ccgcgcccag ccggtgcgcg ccgtcgatga cccgcatgct gcgcggtgc     7500 acgatgatcg gcgcagttc ggcgtcgagg ctggccagca tctgggtgtg ccgcggatcc      7560
tcgccggcca gccggggtga atcgagcatt ccagtgaat ccacaggtag ccactcgacg      7620
cgcatcattg acgagtgtt catctgtgtt tcgtcgtgcc gatccggctc gtggcgcgct      7680
gacgcgatgt gcaatgactc cataccaacc cccgaatggc tggactccga tgaccgctgg    7740
acacgatgca ccgcaggtct caacgagatg ctttgacgac cgtcggccgg ctcggccgtc    7800
gtggccgagt gcgcttgtgc agcgggcttt caatgtccga cactaatcga ggcggcgctg    7860
gctcgccaag ctcgtaagag gttctctgac gcattttaa gctgtcttca cggtgaagtt     7920
tatcgatccc acggtgggtc ggtgggcgtc gagcgggatc tgatcgccac gatgcgtcat    7980
cgtgtccgtg ccgttcgtac tggtcaaccg ggagatctcg ggggtgccac ggtggacgtg    8040
ccggccgggt ccgggccgcc ccggccgagg gcgccgggga cgggttcggc cctatttctg    8100
caagttgcag actgtgcgat tcgggtgggt cacggccgga gtgccgcgat ctcggtcgtg    8160
atgaagcccg ccagccgctt gacaccctcg tcgatctcct ccggggtgag gtagctgatc    8220
gacaggcgga tgccctgttc gccgccgccg gccgggtaga agtacgacat cggcgtccag    8280
atcaccccgt ggtcctcggc gcttcgggac agggcggcgt tgtcggcggt gaagggcacg    8340
ttcacggcga ggaagaagcc gccgctcggg cggttccagc gcacgcccgt gcgtgcgcgg    8400
aaggacgccg gaaggtgctc ctcgagccgg tcgagggtgc gccgcatcgc cgcgccgtag    8460
tgcgccgagc tctccgcact cgcctcggcc gcggtgccgc cggccgcgag cagcatcccg    8520
gccacggcgg cctggctcag cggcgaggtg ttcaccgtga ccatgctctt caccttcgcc    8580
agctcgtcgg cgagcaggcc ggcgccgccc gcggcgtccg acaccggctg gtcggcgatc    8640
gcgaagccca cgcgcgcgcc cggaaagagc gtcttggaga cgatccgag gtggacgacg     8700 tgccggcccg ggtcgagggc cttgagggag ggaagctgct gccccgggct gacgagccgg    8760
tacgggctgt cctcgatcac cagcaggccg agctcgccgg cgaggtcgag cagggcgtgg    8820
cgggcctcca gcggcatcgt ggcgcccgac gggttggtgt ggtcgggcac gacatagaag    8880
gcgcggggac gccggccccg gctcagctcc gcgtggaccg cgcgggccag gtcctcggga    8940
tggaagccgt cctcgcgctc ggcgacgggc accgggtcga tgtcgagcag ccgcgcggcg    9000
ccggtgatgc cgacgtagca cgggctcgcc acgaacagcg cgtcgcgctc gtcccggatc    9060
agcgcgcgca gcgccagcag catcgcctcc tgcgcgccga ccgtcacgac gatggactcc    9120
```

```
ggagccacgt cgatgccctc gtcgcgccgc agccactgcg cgatcacctc gcggatgcgg   9180
ccggccgccg ggccgtactg gaagacggcg tccctgatct ccgcgggcga gcggccctgg   9240
ccggcgaggt gctcgagata ccgcggatg ccgcggaaga tctgctcgac gtcgaagaac   9300
ccgtcgaacg ggcggccggg cgcgaacgag acggctcgcg gatagcgggc ggtcacctcg   9360
ttgaggaagt tcatggtgtc cagcagcggg tcggacaggc tctggtgcag gtcctcgcgc   9420
cgcaggacgc ggccggtgcc cggagcctcg cgcaggatgc tcatcatggt ctcctcggtc   9480
gtcgcgaagc cctgactgtg gcaccgcatt ccgcaccgat caatcgaagc cacggcggtg   9540
accgcacacc tgtgcaactg ccgcgaacgc acggttggac accgtcggtg agctgcgttg   9600
gtggacggtt cggccgacgt ccatagtggt ccggggctc gctcggccgc ctcgccggcg   9660
cctccaggcc gccagcgaaa ggacgccgcc gtgaccgcca ccgccctcct gcccctgacc   9720
ctcgcggact acgaacagct ggcccaagcg cgaatggagc cccggtgtg ggacttcatc   9780
gccggcggcg cggggaagga gctgacgctg ccgcgaaca ccgccgcctt cgcaccgccg   9840
cggctgcggc cacgggtgct gaccggcgcg ggcgcgccgg acacgggcac gacgatcctc   9900
ggacggcggt gggcggcgcc gatcggcgtc gccccgctcg gctatcacac gctcgtcgac   9960
ccggcgggcg aggtcgccac cgccgcggcg gccggcgcgg ccgggctgcc gctcgtggtg  10020
agcacgttct ccgggcggac cgtggaggac atcgccgcgg ccaccaccgc gccgcgctgg  10080
ttgcaggtct attgcttccg cgaccgggcg gtcaccgccg cgctcgtcac gagggccgtc  10140
cgcgccggct tcgaggcgct ggtgctcacc gtcgacgcgc cgcggctggg ccgccgcctg  10200
cgggacatcc gcaacgactt ccgcctgccg cccggcgtgg cgccggcaaa cctcaccggc  10260
gacggcttcg cgtcgcccag cgggcacgcg ctcggcgcgt tcgacgccgc gatggactgg  10320
accgtcgttg cctggctgcg ggagctcagc gggctgccgg tgctgctcaa gggcgtgctg  10380
accgccgacg gtgcccggcg ggcgctcgac gcgggtgcgg acgggatcgt cgtctccaac  10440
cacggcggcc ggcagctcga cggcgtgccg gcgacgctcg acgtgctgcc cgaggtggtg  10500
gcggccgtgg ccgggcgctg cccggtcctg ctcgacggcg gcgtgcggcg cggccgcgac  10560
gtcctgctgt cgctggccct cggcgccgac gcggtcctgg taggccgccc ggtgctgtac  10620
ggcctcgcgg tcggcggcac ggccggcgtg cggcacgtgc tcgacatcct cgcggggag  10680
ctgaccgacg acatggccct ggcgggcgtg gcctcgcccg cggacgccgg cgcggacctg  10740
gcgggcccgg tcgcgccgta gaggcggtcc atacgactgc ggcggccggg aatacccggc  10800
cgccgcaacg tcgtcctcca gggacatctc aggacggcac ggccggctgg cgctcctcgg  10860
tgcgctggcc ggcgaactgg gtccggtaca gctcggcgta caggccaccg tgcgcgatca  10920
gctcgtcgtg ggtgccgcgc tcgacgacgc ggccgtcgtc gatgacgagg atctggtcgg  10980
cgtccaggat cgtggcgagc cggtgggcga tgacgagcga cgtacgcccg gcgagcgccg  11040
tgtccagggc ccgctggatc gccgcctccg attcggagtc cagatgggcg gtggcctcgt  11100
cgagcaccac caccggggc gatttgagca gcaggcgggc cagggcgagg cgctgcttct  11160
cgccgcccga gagccggtag ccgcgatcgc cgaccaccgt gtccagcccg tcgggcagcg  11220
aggacaccat ctcccagatg cgggccgcct cgcaggccgc gacgaggtcg cgctcgccgg  11280
cgtcgggacg gccgtagagc aggttggccc ggatggtgtc gtggaacagg tgcgcgtcct  11340
gcgtgaccac gccgatggac tcgctcagcg agcgcagggt gaggtcgcgg acgtcgtggc  11400
cggcgatccg gaccgtgccc gaggtggtgt cgtagaggcg cggcaccagg tgggtgatcg  11460
tggtcttgcc ggcgcccgac gggccgacca gggcggtgag cttgccggcc ggggcgagaa  11520
```

```
agctgatccc gttgagcacc ggccgctccg cggtgccgtc ggaggaccgc tgggccacgg   11580
tctccaacga ggccagcgag acctcgtccg cgcccggata gcggaacacg acgttgtcga   11640
actcgatgtc cggcgccgcc gagcggcccg gctcggcggc cggcagggcg cgggcgcccg   11700
ggcgctcctt gacgagcggg tcgaggtcga gcacctcgaa gacccggtcg aagctcacca   11760
gcgcggtgac gacgtccacc tggatgttgg tgagctggtt caccgggccg tacagctgcg   11820
ccagcagggc gaccatggcg acaagggtgc cgatgccgag cgtgccgtcg atgaccaggg   11880
cgccgccgaa gccgtagacc atggccgtgg tcaccgtggt cagcagcgtg gcgatgatga   11940
acagcagccg tgcgtgcacg cccatcgaga tggcgatgtc acgcacccgc gcggcccgcc   12000
cggcgaaggc ggtctcctcg ctctccggcc ggccgtagag cttgaccagc atggcgccgg   12060
agacgttgaa ccgctcgttc atcatcgagc ccagctccgc gtcgacctgc atgccgccgc   12120
gggccagccg ctccagccgg cccgcgatga gcttgccggg caggaagaac agcgggatga   12180
gcaccagcgc caccagcgcg atcgcccagg agaggtagaa catcgcgccg atgaccagca   12240
cgacggtcag gaccgtggag accgtctgcg tgatcatcga ggtcatggcc tgctcggcgc   12300
cgaccacgtc ggtgttgagc cggctcacca gcgaccccgt ctgcgcccgg gtgaagaacg   12360
ccagcggctg gcgcatgacg tgggcgaaca ccttggtgcg caggtcgtag atgagaccct   12420
gcccgacgcg cccggaggcc agcgtctgca cgtggatcgc cgccacgttg accagggcga   12480
ggccggccac caccagcgac agcccgacca ccacgtccag gcggccggcc acgatgccgc   12540
ggtcgatgat ctgcttgagc agcagcgggt tggcgaccgt gagcgcggcg tcgaccacgg   12600
tcatcagcag ggcgacggcc agggaccagc ggtgtttctt cgcgtacggg aggatgcgcc   12660
gcaccgtgcc gggcctgacc ttctgcatcg gtatgaggcc gtcgacgcgc agcccgatga   12720
cgcccagatc cgggccgtcg atggttgcca cggaaccttc tctctcgcgg tagcgggtgc   12780
gccggtcgtg ccggcgcgtc cctagtggga gtcgaggaac tcgaggatcg cggcgttcac   12840
cgcgtccggc cgttccagat agccgaggtg cccgcagcgg gatatctcga ccaggtcgca   12900
gtcggggatc gcctcggcca cctcggcggc caggtgcggc ggcgtgatga ggtcgtcggc   12960
gaacgagatc acccggcagg gcgcggtgac cgagcgcagg gcggcgcgcc ggtcaccggt   13020
cagctcggcc caggcctgcc cgccggccga gacgcccgtg ccggagagct cgaagatgtc   13080
gagccactcg cgcacggcca cgtcgtcgtt gagcgtcgcc ggggagaaca tcttgaagac   13140
cgcggtcgcg gcctcgtacg cggcgggcag cgtgaccccg ctctccagca ggtcgatgtc   13200
ggcctggttc tgcgccgcgc gggccgcgtc gggccgggcc agggtcgcga tcaggaccgc   13260
gcagcgcacc agctcggat ggtcgacggc cagctcctgg gcgatcatcg cgcccagcga   13320
ggtgccgacg atccggcagg gcgcgagatc gagggcctcg atgagaccgc gggtgtcggc   13380
ggtcatgtcg gcgagggagt acttgccggc gggcacgtcc gagggcggga tgccacggct   13440
gtcgaagacg acggtggaat atcccgcctc gtgcaacgcg ggcgtctggt gcaccgtcca   13500
ggtctggccg gccgagcccg atcccatgat catgagaacg ggctcgccgg ctccggagcg   13560
gcgatacgcc aggcggaccc cgttggtggt gacgaaaccg gagcccgcgg cgctcaccag   13620
cgccactcgc gcttgttgaa caggtgctcg gcggtgaagc cccggtccgc gcaccacgcg   13680
aggaactcgt cgatctgctt gagctggtag gtgtcctcgt tgtaggtcgt cgccatgacg   13740
tggccctgcc aggactcctc gcccatggcg tagatgtatc cggcggtggc gccgagctcg   13800
gtcatgatcg cgccggcctg ctccgcgttc gatccggaca gccgccgtga ggcgctcatc   13860
ttcttgttga ccggcttggt cagcagtccc ttgtagagcc agttgagcgg cgcgccgtcg   13920
```

```
cactccatgc cgaggaacgc catgtcgacc tggccgacgt ggtcgcggat gtagcggtag   13980
agcaccgggt cgatgcccga cgagtcggcg ccgatgaaga tggtgcgccc ggccatccgc   14040
acgaagtacg tcgacttccc gcggatgtcc agatcggcgt gctcgcccag gaacggcgtg   14100
gcggtgaccg tgccgcccgg gaacggcacc tcgtcgaact cctcgacctc gacgacggtg   14160
aaaccgatcc ggcgcaggta cagcgcgatc gacgggtccg ggaggttgcc gcggctggtg   14220
cgcggcacga caacggtgcc gatccggccg cgcagctgca gcagggtctc gagcacgatg   14280
tggtcctggt gcccgtgcgt gatgagcacc aggtcgatgt ggtcgggcag gtcgtcgagc   14340
gtgtaccggt cgccgtggcg gttgtcgtg ctgatgaacg ggtcggtgac caccgccgcc    14400
tgctcggtct gcatcaccac gcaggcgtga ccgtagtagc ggacccggcc gccggactcg   14460
atgtgccggt cgggcgacag gctcggctcg tcggtgagca gggcatccag cgcggccgcg   14520
ccggcgtcgt cgagctccag cgcctcgcgc aggcggttga gcgaggtggg ccgcacgcgg   14580
gcgtcgaaga gctcggtcag cccgggatgc cgcaggggca gcggaaggtc gagcacgcca   14640
gcccggggaa gccgcggtgt gctgaggatg aacgggcgct ccacccgtc gtcgagcgag    14700
agctgcaccg actgccgccg ctcgtcgtag gccgggctgc ggtagagcag cggctcgagg   14760
aagtgcagcg agggctggtt gctggtgtcg tacgcgatct ccaccagccc gttgagcgcg   14820
gccggcagcc gggggtagag cggcgtcagg tcgtagccga ccgcgttctc gcggatcagg   14880
tcctcggcct cggccaccgc ggcggcgaag ccgagcatgt cggcccgctc gttcttgatc   14940
gtcttgagca gctcggcgac ctcgtcgctg cgggattcct cgacggcgac gaagtagccg   15000
ccgcgcatct tcgggttcgt gctcgccgcc acgtgcaccg gcggcgactg caggtacgac   15060
tcgagcagag gcacctgcag gaacgccagg ttcatggagg ccggcaccgg tgccaccgtg   15120
tgcagccacg cgtagaaacg gtcgacgagc ggttcggcga tgacgttgga gcgcaggtat   15180
ctcggctgat cggcgttgcc catgtgaacc tctccatcct gatggcgggt gcgcccggag   15240
cgggcacgat cgggcgggag ggaatgcggc ctcggtacgg ccggcgcggc aaacggcgcg   15300
tccgtccctc cggcgtgggc gcggtccact atggcatcgg cccaggagcc ggtacagcgt   15360
gcacgtgcgc ggcccgatcg cgtcgaacgc cctgtacaac cggcggtgcg acgcagtcga   15420
acagcggtga acgaccgagg cggcggcggc ccgttgatcg gccgcccgag cgcccgcata   15480
gtgaatcgcc ggaggggcct tggagagccg gcccgccgtt cccggccatc gccgggcgcc   15540
cgccctcaca aaccgatcgc ccggcgccgc cgggtcgcac ggaggtgccc atgtccgaga   15600
ccgacctgtc cgccgcccgg cacacgcccg agcagatccg ctcctggctg atcgaccgga   15660
tcgcctacta cgtgatgctg ccgacccagg agatcgagcc ggacgtgtcc ctggccgagt   15720
acggcctgga ctcggtgtac gcgttcgcgc tctgcggcga gatcgaggac acgctcggca   15780
tcccgatcga gccgaccctg ctgtgggacg tcgacaccgt cgccacccTc accgcccacc   15840
tcgccgaccg cgtcaaccga taagccggag gtgaccgtcg tgcccacccc tgacctgcgc   15900
ccgctcacgc ccgcccagct cgccgtctgg cacgcgcagc agctcgcccc gcacagcccc   15960
gtctatcagg tcgcgagtt cgtcgagatc gacggcgagt gcgacccga tctcctggtg     16020
gcggcgttgc gtcaggtcat gggcgaggcc gagagcgccc ggctgcggtt ccgcgtgatc   16080
gacggtacgc cgtggcagta cgtcgccgag acggcgacg acccgatcca ggtcgtgac    16140
ctcggcgcgg ccgcggaccc gcgccgccg gcgctgggcc gcatggcggc cgacctcgac   16200
cggcccggcg acctgcgcga cggcccgctc gtcgagcacc acgtctacct gctcggcgag   16260
ggccgggtca tctggtacca ccgcgcgcac cacatcgtct gcgacggcgg cagcctcggc   16320
```

```
attgtcgcct cccgggtggc cggcgtctat tccgcgctcg cggccggtgg tgacgtccgg   16380
ccgggtgcgc tgccgccgct gtcggtgttg ctgtcgccg  ccgacgccta cgagcgctcc   16440
ggcgaccgcg accgggaccg cgagcactgg cgctccgcgc tggcgggcct gcccgccgag   16500
ctgctcgcgg gcgcgggccg gccgcggccg ctgcccggac cgccggtgcg ccacgagcac   16560
gacctctccg cggcggaggc gggccggctg cgcgcggggg cgcggcggct gcggaccagc   16620
gtggcgcagg ccggcatcgc ggccgcgcc  ctctaccagc accggctcac cggcgcccgg   16680
gacgtgctgg tggcggtgcc cgtcgccggc cgcaccaccc gcccggagtt cgacgtgccc   16740
ggcatgacgt cgaacgtggt gccggtgcgc ctcgcggtca cgcccgccac gaccgtcggc   16800
gagctgctgc gcgacgtcgc ccgtggtgtc cgcgacggcc tgcggcacca gcggtacccg   16860
tacccgaaca tcgtggacga cctcggcctg gccgaccgtg ccgcgctgcg cccggtgacc   16920
gtcaacgccc tggcgctggg acggccgctg cgcttcggct cggcggtggg tgtgcgctcc   16980
ggcctgtcgg cgggcccggt ggacgacgtc accatcggcc tctacgaaaa ggtcagcggc   17040
ggcggcatgc agacgatcgc cgagctgaac cccgggcgca cggaccgccc ggacgcggcg   17100
gaggtctccc gctggttccg tacgctgctg cgcgggctgg ccgagagcga cgccggcgac   17160
ccggtggccc gcatcgacat cgtcgacgag cccgagcgcc gccggctgct ggacgagtgg   17220
aacgccaccg cggcgccgtc gagcgacacc gtcctcgcgc gtttcgagga gcaggcggcg   17280
cgtacgcccg aggcgcccgc cgtcgtctgc ggcgacgtga cggtcaccta cgccgagctg   17340
gaggccggcg ccaaccggct cgcccgcgtc cttcgcgcgc gcggcgccgg accggagtcg   17400
gtcgtggccc tctgcctgcc ccgcggcccc gaggtcgtga ccggcatcct cgccgcctgg   17460
aaggcgggcg ccgcctacct gccggtcgac accgaactgc cggccgagcg cgtcgcctat   17520
ctgctcggcg acagcgccgc cgccgtccgc ctcggcaccg ccgagacgct cgccgccctc   17580
ccggacggcc ccgccgccga cgtcgacgtc cacgcaccgg agatcgcccg ggaatcgccc   17640
tcgcccctgc ggctcgagcc cttgccggat cagttggcgt atgtgattta tacgtcgggt   17700
tcgacggggt tgagcaaggg tgtcggtgtt tcgcatggtg ggttggcgaa ttatgtgggt   17760
tgggcgtcgg ttttgtatgg gggtttgtcg gcgccgttgc attcttcgtt ggcttttgat   17820
ttgacggtga cgagtgtttt tgtgccgttg gtgtgtggtg gttcggtggt ggtgtcggcg   17880
gccggtggtg gtcggggttt ggcgtcgttg ttggcggctg gtgatggttt ttcgttggtg   17940
aaggtggtgc cgggtcattt gcgttttgctg gcggagttgg tgccggcggg tgagatggcg   18000
gcggtgggtt cgttggtggc cggtggtgag gttttggccg gtggtgatgt gcgtgagtgg   18060
ttgtcgcggg tgccgggttc ggtggtggtg aatgagtacg ggccgacgga gaccgtggtg   18120
ggttgttcgg ttttctcggt ggccgcgggt gatgtggttg gtgatgtggt gccggttggc   18180
cggccggtgg cgaatacgcg tttgtttgtt ttggatgagg gtttgcggcc ggttccggct   18240
ggggtggcgg gtgagttgta tgtggctggt tcgcaggtgg cgcggggtta tgtgggtcgt   18300
tctggtttga cggcttcgcg ttttgtggcg tgtccgttcg gtgtgggtga gcggatgtat   18360
cgcacgggtg atgtggtgcg gttggccggt ggtgatctgg tgtttgtggg ccgggtcgat   18420
gagcaggtga agattcgtgg ttatcgggtg gagccggatg aggtgcggtt ggtggtggcg   18480
gggcatccgc gggtagcggg tgcggcggtg gtggctcggc cggatgcggt gggtgagcgg   18540
cagttggtgg cctatgtggt cgctgccggt gagccggccg ggttggcgga gtcggtacgc   18600
gcccacgtcg ccgagcgcct gcccgaatac atggtcccgg ccgccgtcgt gaccctcgac   18660
gagatcccgc tgaccgtgaa cggcaaggtc gaccgcgccg ccctgcccga gcccggcccc   18720
```

```
gtcgccaccg gcaacgccga ccgcgagccc acgaccgagc gcgaatcgct gctctgcggc   18780
gccttcgccg acgtgctcgg catcgagcgg gtcggcgtcg acgacgactt cttcagcctc   18840
ggcggccatt ccctgctcgc caccagcctg gtgagccggg tacgcctcgt gctcggtgag   18900
gaactgccca tcgaggagct cttcgccacg cccacccccg ccgagctggc ggcctggctg   18960
caacgcaacg cggaccggcc gcaaccggcc cggccggcgc tgcgcccgat gcacgaaagg   19020
gaaacgaccg catgaccccg atgtcgtacg cccagcgccg tctctggttc cagctgcggg   19080
tcgagggccc cgacgccacg tacaacagtc ccgccgtcct gcgcctcacc ggcgagctcg   19140
acaccgccgc cctggagcac gcgctgcgcg acgtcctcga acggcacgag gtcctgcgca   19200
cggtctatcc cgacgtcggc ggcgagccgc ggcagcgcgt ggttcgcccg gacgacatgg   19260
tgtgggagct gcccacgacc cgggtgtccg gtgccgcgc gggcgacgac cggctcgtca   19320
cgctcgacga gctgccctgg gaccgcccgg tgctcgacct gccgtcgccc gcaccggccg   19380
gccgggaacc ggacgcgag atcaccgtcg acgagctgcc cggcgcgatc gcccgggtgg   19440
cggcccaccc cttcgacctc tccatcgaga tcccggtgcg ggcgcggctg ttcgccctgg   19500
gcccgcggca ccacgtcctc gtcgtcgtgc tccaccacat cgccaccgac ggcagctccg   19560
gcgggccgtt cgcccgcgac ctcgccgccg cctaccgcgc ccgccgcacc ggaacggcgc   19620
cccagtgggg acccccttccg gtgcagtacg ccgactacgc ggcctggcag caggaactgc   19680
tcggcgccga ggacgacccc gacagcgtca tctcgcggca gctcgcccac tggcaggagc   19740
ggctggccgg catgccggtc gagctggatc tgccggccga ccgtccgcgg cccgccgaac   19800
ccgggcacgg cgggcacacc aaggcgctga gcctgccccc ggccgtgcac cgaggactgg   19860
ccacgctggc ccggcggcgc cgcgccacgc ttcaaatggt cgtgcagacc ggcgtcgcga   19920
tcctgctgtc caagctcggc gccggccgcg acgtcccgct cggcatcccg gtcgccgggc   19980
gcaccgacgc cgcgctcgac gacctgatcg gtttcttcgt caacaccttg gtcgtacgcg   20040
ccgacctgtc cggcgacccc acggtggccg acgcgctggg ccgggtgcgc ggaggcgcgg   20100
tggccgccct ggccgaccag gacgtgccct cgacaaaact cgtcgagcgg ctggcgccgg   20160
cccgcgtgct cgggcggcac ccgctgttcc aggtcatggt cgcgccgctc gacgacggga   20220
cgccgatcga cctggacggg gtgcgaggcg agccgctcac catcggccgc tccggtgcca   20280
agttcgacgt cgaggtgatg accggagagg tacgcgcggc ggacggcgcg ccggccggca   20340
tccgcggaat cctgacgctc tcggccgacc tgttcgacga ggcgacggcc ggccggatgg   20400
ccgccgggct ggtgcgggtg ctgaccgcga tggccgaggc cccggagcgg cggctctccg   20460
gcatcgaggt gctgtcgccc ggggagcggt cgcggctgct ggtggagtgg aacgacacgg   20520
ctcgtccggt ggtggagtcg tcggtgccgg cgttgttcgc gaagcgggtg gcggccacgc   20580
cggacgcgac ggcggtggtg ggcgagggtg tgtcgtggtc ctatcgcgaa ctcgatcgtc   20640
gctcggatgt gctggcgcgg cgtctggtgg cggcgggtgt gggtgtggag tcgccggtgg   20700
tggtggcgtt ggagcggtcg ccggaggtgc tgtccgcgtt tttggcggtg gcgaaggccg   20760
gtggtgtgtt tgttccggtg gatttgtcgt ggccgcaggc gcgtgtcgat gcggtggttg   20820
ctgactgtgc cgcgcgggtg gcggtggctg accggccgat gagcgggctg acggtcgtgt   20880
ccgccggcct gggcggggat tcggccgtcg tgtccgccga cctgaccgcg gatcgggccg   20940
ttgtgttgcc gtctcgcccg gtgccgggtg cggcggtcta ccggatgtac acctccggct   21000
cgacgggccg cccaagggt gtggtgacca cccaccagaa cctggtggat ctggcgaccg   21060
acacgtgttg gggtccgacc ccgcgggtgc tgttccacgc cccgcacgcc ttcgacgcgt   21120
```

```
cgtcgtacga aatctgggtg cctctgttga atggcggcac ggtcgtggtc gccccgcagc   21180
gcagcatcga cgccaccgtc ctgaaggatc tgatccgcgc gcatgatttg acgcacgtgc   21240
acgtcaccgc gggcctgctg cgggtgctgg acccgtcgtg cttcgcgggc ctgaccgagg   21300
tgctcacggg tggcgatgcg gtgtcggcgg aggcggtgcg ccgggtcaaa gacgcgaacc   21360
cgggtctgcg ggtgcggcag ctgtacggcc cgaccgaggt gacgctgtgc gcgacgcagc   21420
atctgctgga tgacggggtg ccgatcgggc ggccgttgga caacaccgc gtgtatgtcc    21480 tggacgactt gctgcagccg gtgccggtcg gtgtgaccgg cgagctgtat gtggccggtg   21540
ccggcgtggc gcgtggctat gcgggcatgc ccgggttgac ggccgagcga tttgtcgccg   21600
acccgttcaa caccggcggt cgcctctacc gcacgggtga tctggtgcgg tggaccgatg   21660
acggtgtgct gcatttcgcc ggccgagccg atgatcaggt gaagatccgc ggctatcggg   21720
tggagccggg cgaggttgaa gcggttctgg ctcaacatcc cgatgtcagc caggtcgcgg   21780
tggtcgtccg ggaggacacc ccaggcgaca agcgtcttgt cgcgtatgtc gtcggcggtg   21840
acatcgaggc gtatggccag gagcgccttc ccggttacat ggtcccgtcg gcattcgtac   21900
atctggatgc gttgccgctg accagcaacc agaaggtgga tcgggccgca ctgcccgcgc   21960
cgtccatgga gtccggcgcc ggtcgagctc ccgcggatgc ccgcgaggag ttggtgtgtg   22020
ccgcgttcgc cgaggtgctc ggcctggatc gggtcggtgt cgacgacgac ttcttcgctc   22080
tcggcggtca ctcgctgctt gccgtctccc ttgtggagga tttgcggcag cgtggcctgc   22140
acgtctccgt tcgcgcgctc ttcgccacgc cgacccccgc ggcgctggcc gtctcgaccg   22200
tggcggcccc gatcgaggtg ccgcccaacc tcatccccca gggcggcgcc cgggaactga   22260
cccccgacat gctgccccctg gtcgacctga ccggcgagga gctggccacc atcgtggccg   22320
cggtgcccgg cggcgctgcc aacatcgccg acatctaccc cctagccccg ctgcaagagg   22380
gcatcttctt ccaccacctc atgaccgagg gcgacaccgc cgacgtctac gcgctgccgt   22440
acctgctgcg cgttggcacg cgtgagcagc tcgacgcctt cctcggggct ttgcagcagg   22500
tggtggaccg ccacgacgtc taccgcacgg ccatcgcctg gcagaacctg cgcgagcccg   22560
tccaggtcgt gcaccgccac gccaccctgc ccgtcaccga agtcaccccc gaccaactgc   22620
acgccgccgc caccggcggc cggctcccgc tcgaccacgc accccctgctc agcgtccaca   22680 tcgcacccga acccgacggc ggctggctcg ccctactgcg catgcaccac ctcgtgcagg   22740
accacaccgc cctcgacatc gtcctcgacg agatccgcac catcctcgcc ggcgcaaccg   22800
accacctccc cccgcccgta ccgttccgca atttcgtggc gcgctcgcgg cgtggtgccg   22860
ccgaggccgc gcaccgcgac tacttcaccg gcctgctcgg cgacgtcacc gagaccaccg   22920
ccccgtacgg cctcaccgac gtgcacggtg agcactccgg cgtgcgccgg ggccggctcg   22980
ccgtgtccgc cgggctcgcc ggccgggtgc gggagaccgc tcgcgaccgg ggcgtcagcc   23040
ccgccaccct cttccacctg gcctgggcgc gcgtgctcgc cgccgtctcg ggccgcgacg   23100
acgtcgtctt cggcaccgtg ctgctgggcc ggatggatgc cggcccgggc gccgaccggg   23160
tgccgggcct tttcatgaac accctgccgg ttcgcgtacg cctcggcggc cgcaccgtcg   23220
acgaggcgct gcacgggatg cgcgcccagc tcgccgacct gctcacccac gagcacgccc   23280
cgctggtgct cgcgcagcag tcggccgcc tgccggcgg cagcccccctg ttcacctcgc    23340 tgttcaacta ccggcacaac gcgaccgaca tcgagcgctc cggaacgggc atcgacggcg   23400
tcgaggcgct gcccaccggc gacccgtcga actatccgct cgacgtctcg gtcaaccaga   23460
gcccgctcgg cttcgagctc gtcgtcgagg ccaccgagcc ggccgacccg gaccagctct   23520
```

```
gccggctcct gcacgcctgc ctcgacgacc tgatcgccgc cctcgacgag cagcccggcc    23580
gcgcgctcgg caccctcgac gtcgtcgccg gacgggagcg cgacctcctc ctggacggct    23640
ggaacgccac ggcggtcccg gcccagccgg ccctggtgcc ggagctcttc acggcgcagg    23700
cggcgcggac acccacctgg ccggcgctgg tgacggccgg cgcggagatg tcctacgccg    23760
agctcgagga gcggtccaac cggctggcgc gctggctggc cgggcgcggg gtgggcgccg    23820
acgaccgggt ggccctgatg atgcgccgcg gcccggagct gatggtggcg atcctggccg    23880
tgctcaaggc gggcgcggcg tatctgcccg tggatccgga cctgccccgc gaccgggtgg    23940
actacctgct cgcggacgcg gccccggcgt tcgtgctggc cgagcgggcc accgcgccgt    24000
gggtgccggt ggccggtggg attccggtgc tggtcgtgga cgcgccggcc gtcgccgccg    24060
aggtggcgg ccactcggc gaggccgtca ccgaccggga ccggcgcgcc gcctgcgcg    24120
gcggccacct cgcctacgtc atctacacct cgggatccac cgggcggccc aagggcgtgc    24180
tgatcacgca cgacgcctc gccaatctca cgctcgacca cggccggttc ggcctcggtc    24240
cgggtgcccg ggtggcgcag ttcgcctcgc ccggcttcga catgttcgtc gacgagtggt    24300
cgatggcgct gctggccggc gccgcgctga ccttcgtgcc gccggagcgg cgactgggcg    24360
ccgacctggc cgcgttcctc gccgagtacg gcgtgacgca cgcgacgctg ccgcccgcgg    24420
tcgtgggcac gatcccggac ggtgtgctgc cgccgtcgtt cgtgctcgac gtcggcggcg    24480
acgtgctgcc gggcgacctc gcgcgccggt ggctgcgcga cggccgggtg ctgttcaact    24540
cgtacgccc gacggagacc acggtcaacg cggcgacgtg gcgggccgag gccggtgact    24600
ggggaagcgt ggcgccgatc ggcacgcccg tgccgaatct gcgggcgtac gtgctcgacg    24660
gctggctgcg cccggtgccg gtgggcgccg acggcgagct gtacgtctcg ggcgccggac    24720
tcgcccgcgg ctatctgaac cgggccggcc tgaccgcgga gcggttcgtg gcgtgcccgt    24780
tcgagccggg ggagcggatg taccgcaccg gcgacgtggt gcggtggacc gccgaggggc    24840
gcctggtgtt cgccggtcgc tcggacgacc aggtcaagat ccgcggattc cggatcgagc    24900
ccggcgaggt ggaggccgtg ctggccgccg gaccgggtgt gagccaggcc gcggtgatcg    24960
tgcgtgagga cgtgccgggt gacaagcgct tggtggcgta cgtcgtgggc ggtgacgtcg    25020
aagctctccg gtcgtacgcg cagcagcggt tgccgggtta catggtgccg tcggcttttcg    25080
tggagctgga ccggttgccc ttgacggtga acggcaagct cgaccgccgg ccctgccgg    25140
tgcccgacct cgccccgcgg cacgggatcc gccggcccgc cggcacgccg cgcgagcagc    25200
tgttgtgcgc gggcttcgcg gccgtcctgg gcgtggacga cgtcggcgcc gacgacgact    25260
tcttcgcgct cggcggtcat tcgctgttgg tggtttctct ggtggagtgg ctgcgccgtc    25320
gtggggtctc ggtgccggtg cggcgcttgt tcaccacgcc gaccccggcc gggctggccg    25380
aggcggtcgg tgatggtgcc gtggtggtgc cgccgaacct gattccggaa ggtgcggccg    25440
agctgacccc ggagatggtg ccgctggccg atctgacgtc cgaggagctg gcgatcgtcg    25500
tcgcatcggt gccgggcggt gcggccaatg tggccgatgt gtatccgttg gcgccgttgc    25560
aggagggcat cttcttcccc gtagccacag gcccccagtg ctacgccacg gtggggagtt    25620
cactcccgga cgatggcggt tctgccccctt gcagcaggtt tcgccgtcga tgtgtatcga    25680
cgagtgtggt gtgcagggg ctgcgtgagc cggtgcaggt ggtgtggcgg cacgcgcggc    25740
tgcccgtcga ggaggtcgtg ctgcacgagg gggccgaccc ggtcgagcag atgatggcgc    25800
tcgccggcgg ttgatggac ctcacccggg cgccgctcat cgacgtccac atcgccgccg    25860
gccccggcgg cgaccgctgg ctggccgtgc tgcgcatcca ccacctcgtg caggaccaca    25920
```

```
ccgccctgga gacgctgctc gacgagctgc agtcctttct ggagggccgc ggtggcgagc   25980
ttgccgagcc ggtgccgttc cgcgagttcg tggcgcaggc gcggctcggt gtgccgcgcg   26040
aggagcacga gcggtatttc gcggagttgc tcggcgacat caccgagacc accgcgccgt   26100
acgacctgac cgacgtgcac ggcgacggca ccggatacga ccacgcgcg ctgccgctgg    26160 acgccaccgt cgcggcccgc gtccgggagg cggcccgaac cctcggcgtc agcccggcga   26220
cgctcttcca cctcgcgtgg gcgcgggtgc tcggcacgct ggccgggcgc gacgacgtcg   26280
tcttcggcac cgtcctgttc ggacggatga actcgggtgc cggcgccgac cgggtctccg   26340
gcctgttcat caacacgctg ccggtgcggg tgcggctcgg cgcgcccacc ggcgacgccc   26400
tcggcgacct ccgcgaccag ctcgccgagc tgctcgtgca cgagcacgcc tccctcgcct   26460
ccgcgcagaa ggcgagcggc ctgccgcgcg ggagcccccct gttcacgtcg atcttcaact  26520
accggcacaa ccaggtgagc gccgaacggg agaccgccgc gctgcccggc atccgcgtcc   26580
tcgcggcccg cgactccacg aactatccgc tcaccgtcgc ggtggacgac gacgggcacg   26640
gcttcacgct cgtggtcgag gtcgcgtcca cagtcgacgc cgcgggcgtc tgcgaactgc   26700
tgcacaccgc cgtggacaac ctcatcgcgg ccctcaccga ccggccgggc gggccgctgg   26760
ccgaggtcga catcctcgaa cgcggtctgc gggaccgcct gctgaccgcc tggaacgagg   26820
cccgggagcc cgcaccgccg gtgaccctgc ccgacctgtt cgaccggcag gcccgccgca   26880
cgcccgaggc ggtcgcgctc accgcggacg gcgtctcgct gacctaccgc gagctgtcgg   26940
agcgcgccaa ccggatcgcc cggctgctca cctcccgggg gatcgcccg gagtcgctcg    27000 tcggtgtcgt cctgccccgc tcggccgacc tggtcgttgc gctgctcggc gttctccagg   27060
ccggcgcggc ctacgtgccg gtcgacgccg actacccggc cgagcggatc gggtacatcc   27120
tcggcgacgc gggcgcggtt tgcgtgctca cagtggacgc gaccgcgggc gccgttcctc   27180
ccggcgtacc gaaactggtg ctggaccacc cggaaaccgt gaccgcgctg gcggcgtgtg   27240
acacggcacc gctcggcgag gccgagcggg ccggcgaact gctgccggag caccccgcct   27300
acgtcatcta cacctccggc tccaccggca cgcccaaggg cgtgctcatc ccgcaccgca   27360
acgtggtcga gctcttcgcc gccacccgcg gctcgttcca cttcggcgag ggtgacgtgt   27420
ggtcgtggtt ccactcggtc gccttcgact tctcggtctg ggagctgtgg ggcgcgctgc   27480
tgcacggcgg ccgcgtggtc atggtgccgt tcgccgtctc ccgctcaccg cgggatttct   27540
gggaactgct cgtgcgcgag cgggtcaccg tgctcagcca gacgccgtcc gccttctacc   27600
agctcgccgc ggccgccgac gacacgccgg acgcgctgcg cgtggtggtc ttcggcggcg   27660
aggccctcga cccgggacgg ctcgccggat ggcgggaacg gcgcccggac ggaccgcgcc   27720
tggtcaacat gtacggcatc accgagacga cggtccacgt cacccaccag gacctcgcac   27780
cggccgacac caccggcagc cccatcggac gcggcatacc gggcctgtcc gtctacgtcc   27840
tcgacgaggc gctgcggccg gtgccgcccg ggtcgccgg cgaggtgtac gtggccggtc    27900
gccagctggc ccgggcctac ctcggccgcg ccgcgctgac cggcacccgc ttcgtcgcct   27960
gccccttcct cccggccggg aacggatgt accgcaccgg cgaccgtgcc cgctggagcc    28020
gcggccggtt gcagttcgcc gggcgcaccg acgaccaggt gcagatccgc ggcttccgca   28080
tcgaaccggg cgaggtgcag gccgtcgtcg ccgcccaccc tgagatcgcc gcggcggccg   28140
tcgtcgtgcg cgaggacgtg cccggcgacc cgcgcctgac cgcctacgtg gtgccggccg   28200
gcccgcgcac cgcgccggcg gccgtcgcgg aaaccgtgcg gcgcttcgcc gccgaccggc   28260
tgccggccta catgcttccc tccgcggtcg tcgtgctgga cgccctgccg ctgaccgacc   28320
```

```
acggcaagct cgaccggcgc gcccttcccg caccgcagca cacgggcgcc gcgagcggcc    28380
gggcgccggc caccgtggcc gaggaggtgc tgtgcgccgc cttcgccgag gtgctgggcg    28440
tcgagcgggt cggtgtcgac gacgacttct tcgccctcgg cggccactcg ctgctcatcg    28500
tctcgctcgt cgagcgcgtc cgccgcgccg gcctggcgat cccggtccgc gccctgttcc    28560
gcagcgccac cccggccggg ctggccgcgc tcgcccggcc gtaccgggtc gacatcccgc    28620
ccaacctcgt cccggacggc gcccgcgaga tcaccccgga catgctgacc ctggccgcgc    28680
tcaccgaggc cgagatcgcc acggtgctcg cgaccgtgcc cggcggggcg gtgaacgtgg    28740
ccgacatcta tccgctggcc ccgctccagg agggcatctt cttccaccac ctcatggcgg    28800
acgccggccg ggccgacgcc tacgcgatgc cgtacgtgct gcacctggac acggcggagc    28860
ggctggacgt cctcctcggc gccctccagc gggtgatcga ccgtaacgac atctaccgca    28920
ccggcgtggt ctcggccggc ctgcgcgaac cggtgcaggt ggtgtggcgg tcggccgtcc    28980
tgcccgtcga ggaggtggcg ctggacgcg gccacgaccc ggtcgagcag ttgctcgccg    29040
ccgccggcga ggagttcgac ctgacccggg cgccgctgat ccgggcgcac gtggcggcgc    29100
atccggacgg cggccggctg ctcctgctgc gcatccacca cctcgtgcag gaccacacga    29160
cgttcgacgt ggtgctgggc gagctgcggg ccttcctcga gggccgcggc ggcgagcttg    29220
ccgagccggt gccgttccgc gagttcgtgg cgcaggcgcg gctcggtgtg ccgcgcgagg    29280
agcacgagcg gtatttcgcg gagttgctcg gcgacgtcac cgagaccacc gcgccgtacg    29340
gcctgaccga cgtgcacggc gacggctccc gggccgtcca ggtctcgctg ccggtcgccg    29400
aggccctcgc cgtccgcgtc cgcgaggtgg cccggacact cggcgtcagc ccggccaccg    29460
tcttccacct ggcctgggcg cgcgtgctga cgtcatcgc gggccgcgac gacgtggtgt    29520
tcggaaccat cctcttcgga cggatgaact cgggcgccgc cgccgaacgc gtgcccggcc    29580
tgttcatcaa cacgctgccg gtgcgggtgc gactgaacgg cacgagcgtg ggggaggcgc    29640
tgaccgccct gcgcgaccag atggccgagc tgatggcgca cgagcacgcg ccgctcgcgc    29700
tggcgcagcg ggccggcggc gtgcccgcgg gcagtccgct gttcacgtcg ctgttcaact    29760
atcggcacaa cgtcgcgggc ggcggcgacg gcggagcgct cgagggcgtc acgccggtgc    29820
tgcaccgcga caccacgaac tatcccgtgg tggtctcggt cgacgacgac ggcacgagct    29880
tcgacctggt ggtggaggcg gtcgcgcccg cggaggcggg tcgcgtcggg cggctcatgc    29940
acgaatgcct ggccgagctg gtgggcgccc tggccggtgc gccggagacg cccctgtccc    30000
gcgtgcgggt gatcgacgag gccgagatcg aacgggtcgt tcacagctgg aacgacacgg    30060
ctcgcccggt agtggagtcg tcggtgccgg cgttgttcgc cgagcaggtg gcggctgcgc    30120
cggatgcgac ggcggtggtg ggcgagggtg tgtcgtggtc ttatcgcgag cttgatgcgc    30180
gatcggatgc gctggcccgg agcctggtgg cggccggtgt gggtgtggag tcgccggtgg    30240
tggtggcgtt ggagcggtct cccgaggtgc tgtccgcgtt cctggcggtg gcgaaggccg    30300
ggggcgtgtt tgttccggtg gacctttcgt ggccgcaggc gcgtatcgat gcggtggttg    30360
ctgactgtgc cgcgcgggtt gcggtggctg accggccgat gagcgggctg acggtcgtgc    30420
cggccgacca ggtcggggat tcggctgtcg tcctgccggc cggtccggtg ccgggtgcgg    30480
cggtctaccg gatgtacacc tccggctcca cgggccggcc caagggtgtg gtgaccaccg    30540
accagaacct cgtggatttg gcgaccgaca cgtgttgggg tccgaccccg cgggtgttgt    30600
tccatgcccc gcacgcgttt gatgcgtcgt cgtatgagat ctgggtgccg ttgttgaatg    30660
gcggcacggt cgtggtcgct ccgcagcgca gcatcgacgc gacggtcttg agggacctga    30720
```

```
tccgcgggca tgagttgacg cacgtgcatg tgaccgccgg tctgttgcgg gtgctggacc    30780
cgtcgtgttt tgcggggctg accgaggttt tgaccggcgg ggatgcggtg tcggcggagg    30840
cggtgcgccg ggtccgggaa gcgaacccgg gtctgcgggt gcggcagctt tatggcccga    30900
ccgaggtgac cttgtgcgcg acgcagcatc tgctggtcga cggggtgccg atcgggcggc    30960
cgttggacaa cacccgcgtg tatgtcctgg atgacttgct gcagccggtc ccggtcggtg    31020
tgactggcga gctgtatgtg gccggggccg gcttggcgcg tggctatgcg ggcatgcccg    31080
ggttgacggc cgagcggttc gtcgccgacc cgttctcggt tggtggtcgc ctctaccgca    31140
cgggtgatct ggtccgctgg actgacgacg gggtgctgca tttcgccggg cgggccgatg    31200
atcaggtgaa gattcgtggc tatcgggtgg agccgggcga ggttgaagcg gtcctggctc    31260
aacaccccga cgtcagccag gtggcagtgg tcgtccgcga ggacacgcca ggggataagc    31320
ggctggtcgc ctatgtcgtc ggcggtgacg tcgaggcgta tgcgcaggag cgccttccgg    31380
gctacctggt cccgtcggca ttcgtacatc tggatgcgct gccgctgacc agcaaccaga    31440
aggtcgaccg ggccgcactg cccgcgccgt ccgtggagtc cggcgtcggg cgggcgcccg    31500
ccgacgcgcg tgaagagctg atgtgtgccg cgttcgctga ggtgctcgac ctggatcggg    31560
tcggtgtcga cgacgacttc ttcgctttgg gtgggcattc gctgttggtg gtgcggttgg    31620
tgggccgtat tcggcaggtg ttcggggtgg aggtgtcggc tcggctggtc ttcgatgcgc    31680
ggactccggc cggtgtggtg gcccgcttgt ccgagggcgg cacggcccgg gaggccgtac    31740
gggcgcgggt gcgtccggcg cgggtgccgt tgtcgttcgc gcaacgccgg ttgtggttcc    31800
tgtcccagct ggagggtccg agcgcgacct acaacatccc ggtggcgctg cggctggacg    31860
gtcctctgga tcgcgatgct ctaacggcgg cgttgcacga tgtggtggcc cggcacgagg    31920
tgttgcgtac cgtcttcacc gtcgccgacg gcgagccgtg gcaacagatc ctcgacgatc    31980
cgcaggtctc cgttccggtc gtcgaggtca cgcccgaccg gctgcccgag gcggtggccg    32040
tcgccgcggg gcaccggttc gacctcggcc gggaactgcc gctgcgggcg gtcctgctgg    32100
cgaccggcga cgacgtgcac gtgctggtgc tcgtggtgca tcacattgcc gccgacggct    32160
ggtcgatgcg gccgctcgcc cgggacttgg cggccgccta cgcggccagg atcgacgcga    32220
cggcgccggc cctcggcgcg ctgccggtgc agtacgccga ctacgccctc tggcagcgcg    32280
acgtgctcgg ttccgagcac gacccggaca gcgtcatctc ccaacaggtt gcctattggc    32340
ggcggcagct ggccggcgta ccggaggaat tggatctgcc ggtggaccgg gcgcgcccgg    32400
ccgaggcatc gcatcgcggc cacaccgtgg agttcgccgt gccccggcc gtgcaccacc    32460
aactcgccga actcgcccgc cgcaacggcg tcaccgtctt catgaccgtg caaaccgccc    32520
tcgccgtcct cctgtccaaa ctcggcgccg gcaccgacat ccccatcggc gtcgccgtcg    32580
ccggacgcac cgaccccacc ctcgacaacc tcatcggctt cttcgtcaac accctcgtcc    32640
tacgcaccga cctgaccggc aaccccacca tcaccgacct gctgcaccgc acccgcgaca    32700
ccacccctgca cgccttcacc caccaagacg tcccccttcga aaaactcgtc gaagacctcg    32760
cacccacccg ctccctcgcc cgccacccca tcttccaggt catgatgacc ctgcagagcg    32820
cgtcggcgga cgaagagccg ctggcgctcg ccgggctgcg ggtcaccgac ctcccggccg    32880
gggagacacc cgccaaggtg gacctcgacc tgacgctgca cgaggtggcg ggccgagacg    32940
gcatgcacgc cacgctcctc ggcgcggccg acctcttcga gcaggagacg tgcgcgcccc    33000
tcgccgaccg gttgctgcga acccctggaag ccatggcggc ggccccggac gaccgcctcg    33060
accggatcga ggtgctgtcg ccgggggagc ggtcgcggct gctggtggag tggaacgaca    33120
```

```
cggctcgtcc ggtggtggag tcgtcggtgc ggcgttgtt cgccgagcag gtggcggctg    33180
cgccggacgc ggtcgcggtg gtgggcgagg gtgtgtcgtg gacctatcgc gagcttgatg    33240
cgcggtcgga tgcgttggcg cggagcctgg tggcggcggg tgtgggtgtg gagtcgccgg    33300
tggtggtggc gttggagcgg tctccggagg tgctgtccgc gttttttggcg gtggcgaagg   33360
ccggggggcgt gtttgttccg gtggatttgt cgtggccgca ggcgcgtgtc gatgcggtgg   33420
ttgcggactg cggcgcgcgg attgcggtgg ctgaccggcc gatgagcggg ctgacggtcg    33480
tgtccgccgg cctgggcggg gattcggccg tcgtgtccgg cgacctgacc gcggatcggg    33540
ccgttgtgtt gccggccggt ccggtgccgg gtgcggcggt ctaccgcatg tacacctcgg    33600
gttccacggg tcggcccaag ggtgtggtga ccacccacca gaacctcgtg gatttggcga    33660
ccgacacgtg ttggggtccg accccgcggg tgcttttcca cgccccgcac gccttcgacg    33720
cgtcgtcgta tgagatttgg gtgccgttgt tgaatggcgg cacggtcgtg gtggctccgc    33780
ggcgcagcat cgacgcgacg gtcttgaggg acctgatcgg cgcgcatgag ttgacgcacg    33840
tgcatgtgac cgcgggcttg ttgcgggtgc tggacccgtc gtgcttcgcg ggcctgaccg    33900
aggtgctcac ggggcggggat gcggtgtcgg ccgaggcggt gcgccgcgtc aaagacgcga   33960
atccgggtct gcgggtgcgg cagctgtacg gcccgaccga ggtgaccttg tgcgccacgc    34020
agcatctgct ggatgacggg gtgccgatcg ggcggccgtt ggacaacacc cgcgtctacg    34080
ttctcgacga cctcctgcgg ccggtcccga caggtgtggt gggggagctg tatgtggccg    34140
ggtcgggtct ggcgcgcgggc tatgcgggca tgcccgggtt gacggccgag cgattcgtcg   34200
ccgacccatt caacaccggc ggtcgcctct accgcacggg tgatctggtg cggtgggccg    34260
acgatggtgt gctgcatttc gctgggcggg ccgatgatca ggtgaagatt cgtggctatc    34320
gggtggagcc gggcgaggtt gaagcggtcc tggctcaaca ccccgacgtc agccaggtag    34380
cagtggtcgt ccgcgaggac accccaggcg acaagcgcct ggtcgcctac gtcgtcggcg    34440
gggatgtcga ggcgtatgcg caggagcgcc ttccgggcta catggttccg tcggctttcg    34500
tgcagttgga tgcgctgccg ctgaccagca accagaaggt cgaccgggcc gctctcccgg    34560
cgccatccat ggagtctggc gccggccggg caccecgccga cgcgcgtgaa gagctgatgt   34620
gtgccgcgtt cgccgaggtg ctcgacctgg atcgggtcgg tgtcgacgac gacttcttcg    34680
ccctcggcgg gcattcgctg ctcgccgtct ccctcgtgga gaatctgcgc cgccacggcg    34740
ttcacatctc cgttcgggcc ctcttcgcca ccccacgcc ggccgcgctg gccgcctcgg    34800
cgggaaccgc cgtcccggac gtgccgccca acctcatccc ccagggcggc gcccaggaac    34860
tgaccccga catgctgccc ctggtcgacc tgaccggcga ggaactggcc accatcgtgg    34920
ccgcggtgcc cggcggcgct cccaacatcg ccgacatcta cccctagcc ccgctgcaag    34980
agggcatctt cttccaccac ctcatgaccg agggcgatgc caccgacgtc tacctcctgc    35040
cgcggattct cggcttcggc ggccgtcccg agctggacg cttcctcggg gccctgcagc    35100
aggtggtgga ccgccacgac gtctatcgca cggccatcgc ctggcagaac ctgcgcgagc    35160
ccgtccaggt cgtgcaccgc cacgccaccc tgccccgtcac cgaagtcacc cccgaccagc    35220
tgcacgccgc cgccaccggc ggccggctcc cgctcgacca cgcacccctg ctcagcgtcc    35280
acatcgcacc cgaacccgac ggcggctggc tcgccctgct ccgcatgcac cacctcgtgc    35340
aggaccacac cgccctcgac atcgtcctcg acgagatccg caccatcctc gccggcgcaa    35400
ccgaccacct ccccccgccc gtaccgttcc gcgacttcgt ggcgcaggcc cgcctcggcg    35460
tctcccgcgc ggagcaggag cgctacttcg ccggcctgct cggcgacgtc accgagacca    35520
```

```
ccgccccgta cggcctggcc gacgtgacga acgacggcac cgcatcggtg cgggccgagg    35580
tcgagctcga cgcggccctg gcggcccggc tgcgcgacct cgcccgcgac cggggcgtca    35640
gcccggcgac ggtcttccat ctggcctggg cgcgcgtgct ggcggcggtg ccgaccggg     35700 aggacgtcgt cttcggcacc gtcctgttcg gacggatggc ctccggcgcc cggcgggtgc    35760
ccggcctctt catgaacacc ctgccggttc gcgtacgcct gtccggaacc gccgccgagg    35820
ctctgggaca ggtgcgcgac cggctcgccg agctgatggc gcacgagcac gcgccgctcg    35880
cgctggccca gcaggcgagc ggcctgcccg ccgggagccc gctgttcacg tcgttgttca    35940
actaccgcta tgcccggccg ccggccgcca cgccggacga tccgctggcg ggggtgcgca    36000
cgctgttcgc gtgggaacgc aacaactacc cggtcaccgt gtcgatcgac gacgacggca    36060
ccggattcgc ggtcacggtc gacgtcgtgg cgccggccga cgccgacgag gtcgtccgcc    36120
tgctccgcac gaccctgacc cgcctggccg ccgccctcga acgcactccc gagatgccgg    36180
tggccgacgt gcggcccggc cgcgtgtccc ggcccgccgc cggccgcgcg gtgctcgtgc    36240
cggtcccggc cggcgagcgg gcgaccggcg cgggccgggc tccggccacg gcgtacgagg    36300
agctgatctg ccaggcgtac gcccaggtgc tggaggttga ccgggtggcg gccgacgacg    36360
acttcttcgc cctgggcggc aactcgctgc tcgccacgcg gctggtcagc cggatccgct    36420
cggcgctggg cgtggaggtc accatccgcg cgctcttcga gacgctcacc ccgcaacggc    36480
tggccgcccg gctgacccgc gcctcggcac ccgggcgggt cgcacccgcg ccgaggacac    36540
ggccggagcg gattccgctg tccttcgcgc aacggcgcct gtggttcctg ggcgagctgg    36600
agggcagcag cgccacctac agcaacacga ccgcgctgcg gctctccggc gagctcgacc    36660
cggccgcgct caccgcggcg ctgcacgacg tgatcggccg gcacgaggtg ctgcgcacgg    36720
tgatcccggc cgaggacggc cggccgtacc agctggttct cccgcccgag gaggcacggc    36780
cggcggtgga gatcgtcgag gtcgctcccg gcgagcttgg cgcggccgtc gacgaggtgg    36840
ccggttacgc gttcgacctc gccgccgaga taccggtccg cgcccggctg atccggctgg    36900
gcgcgaccga ccacgtcctc gtcctggtga tccaccacat cgccaccgac ggatggtcga    36960
tggcgccgct cgcccgcgac ctcgccgccg cctacgaggc ccggctggcc ggccgggcac    37020
cgcgctggga gccgctgccg ctgcagtacg ccgactacgc gctctggcag gaggagttgc    37080
tgggcgcggc cggtgacccg gagagcctgc gcgagcgcca gctcgcctac tggcgcgaca    37140
ccctggccgg gatgccgccg gagatcccgc ttccggccga ccgttcccgc ccgccggtgg    37200
cctcgcaccg cggcggcgag gtgccgatcg ccataccgc cgacctgcac cgccgcctgg    37260
ccgagctggc cgtcgccgag cgggccaccc tcttcatggt tctgcaggcc ggcttcgcgg    37320
cgctgctgag ccggctgggt gccggcaccg acgtcccgat cggcaccgcc ctcgccggcc    37380
gcaccgacga cgcccctcga cgagctggtcg gcttcttcgt caacatgctt gtgctgcgca    37440
ccgacgtgtc cggcgacccc gggttcggca cgctgctgcg ccgggtgcgc gagaccggcc    37500
tcgccgcgta cgcccatcag gacgttccct tcgaccaggt cgtcgaggag ctggtgaccg    37560
agcgttccct ggcccggcat ccgctgttcc aggtggcgct gaccgtgcag aacgcgccgg    37620
gcgcgcggcc gcggctggcc ggcctcgaag tcggcaccga ccgatcgag cacggcatcg    37680 cccgctacga cctcacgctc accgtgaccg agcggcgcga cgagcacggc gcgccggacg    37740
gcctggaggg gcatctcgag ttcagccgcg acctgttcga cgcgccgacc gtcgcgaccc    37800
tcggcgaccg gctgatccgg ctcctcaccg ccgcggtggc cgaccggag ctgccgctga    37860 gccggatcga tctgatggcc cccgcggagc gccgcaacgt gctcgagggc tggagcaccg    37920
```

```
cccggcgcga cgtgccggcg gccaccgtgc cggagctggt ggccgcgcag gtggcccggc    37980
gcccgggtgc ggtcgcgctg cggtcggagg acggcgagat cacgtacgcc gagctggacg    38040
cgcgcgccgg gcggctggcc gcggtgctgc gccgccgcgg gatcgggccg gagtcgcggg    38100
tggccgtgct gttgccgcgc ggcgtcgagc aggtggtcgc cttcctcgcc gtggtgcggg    38160
ccggcggcac ctatctgccg atcgatcccg cgtacccgcg cgaccgcgtc gactacctcg    38220
tccgggacgc ggagccggcg tgcctgctga ccgtcgccgg gcatcgcgcg gcggcgccgg    38280
cggcaccggc ggtggtcgag ctggacgacc cggcgaccgc ggccgagatc gccgatgccg    38340
aaccggagcc gccggtcgcg gtgcggccca cccactccgc ctacctgatc tacacctcgg    38400
gctcgaccgg gcggcccaag ggcgtcgtgg tcacccaccg gggtgtggcc gcgctcgtgg    38460
ccacccaggc cgagcggctc gcggtgaccg gcgagagccg cgtcctgcag ttcgccagcg    38520
tgggcttcga cgcctcgatc tgggagatgg tgatggccct gtgcgccggc gccaccctgg    38580
tcgtcgcccc ggccgacgac ctgctgcccg gccggccct ggccgccacg ctgtccgggc     38640
acgcggtgac ccacgcgacc ctgccgccgg ccgtgctcgc cgcgtccgcg cccggcgatc    38700
tcgcgccgct cgccgtgctg gtctcggccg gtgaggcgct cgggccggac ctcgtccggc    38760
agttcgcgcc cggccgcgcg ctggtgaacg cgtacgggcc gaccgagacc acggtgtgcg    38820
ccacggcgtc cgccccgctc ggccggagg atccccgca catcggcgcc cggtcgccg      38880
attcccgggt ctacgtgctc gacgacgcgc tcaccccggt gccgcccggg gtcaccggcg    38940
agctgtacgt ctcgggggcg tcgctggccc gcggatatgc cggtcgcgcg gccctcaccg    39000
cggaacgctt cgtggcctgc ccgttcgcgc cgggtgagcg gatgtaccgg accggggacc    39060
gggcccgctg ggacgcggcc ggccggctca cgttcgccgg gcgcgccgac gaccaggtca    39120
agatccgcgg gttccgggtg aaccgggtg aggtggccgc ggtgctcggc gaacacccgg     39180
cggtcgcccg ggcggcggtc gtggcgcgca cggacgggcc gcaggcgcg cggctggtgg     39240
cgtacctcgt cgccgccgac ccggccgggc ccgacctggc cgctgcggtg cgcgcgtacg    39300
ccgccgcgac cctgcccgcg cacctgcttc cggccgcgtt cgtgccgctc gaccgcctgc    39360
ccctgaccac gaacggcaag ctggaccggg ccgcgctgcc cgaaccggag accggcgccg    39420
ggcgcgagcc gtccggcccc gtcgaacggc tgctctgcga ggcgttcgcc gacgtgctcg    39480
gcctcgaccg ggtcggcgcc gacggccact tcttcgacct gggcggccat tcgctgctcg    39540
ccacccggct gctcagccgg ctccgctcgg ccgcgggcat cgacgtcccg gtccgggtgc    39600
ttttcgagaa ccccactccc gccgggctcg ccgcctgggt ggagacccac gccggatccc    39660
gccggaagtc ccggccggcg ctgccggcga tgcgtcacca aaggagtcc tgatgatccc     39720
cctgtcgttc gcgcagcgcc gcctgtggtt cctcggccgg ctcgaggggc cctccgccac    39780
ctacaacatc ccgctcgtgc tgggcctgac cggcaccgtc gacgccgccg ccctcgaaac    39840
cgccctgcgc gacgtgctgg agcggcacga ggtgctgcgt accgtctatc cggacgccgg    39900
cggcgagccg caccagcgga tcctgccgct cggcgagacc ggcttcggcc tgcgggtcgc    39960
cgaggtgacg gacggcgagc tggacgcggc cgtcgcggac gccaccgggc acgccttcga    40020
cctcgcgacc gagatcccgg tccgggcctc gctgctcacc gtcgagccgg ccggcacgt    40080
cctggcgctg gtgctgcacc acatcgcggc cgacggctgg tcgatggggc cgctgctgcg    40140
cgacctgtcc accgcgtaca cggcccggct ggccggcggg gaaccggcct ggtcgccgct    40200
gccggtccag tacgcggact acgcgctgtg gcagcaggag gtgctcggcg ccggtgacga    40260
cccggagagc ctcctgcgcg agcaggtcgg ctattggcgg tcggcgctcg ccggagcccc    40320
```

```
cgaggagctg cgcctgccgg ccgaccaccg gcgcccgccc gtgtcgtcgt cccgggcgca   40380
catggccgag ttcgccgtgc cggccgccgc ccacggcgac ctgaccgccc tcacccgcga   40440
gctcggcgcc acgctcttca tggccgtgca cgcggcgacc gccatggtgc tttccgggct   40500
gggcgcgggc gacgacctgc cgatcggcac ggtggtggcc ggccgcaccg acgccggcct   40560
cgacgacctc gtcggctgct tcgtcaacaa cctggtgatc cgggccgacc tgaccggcga   40620
cccgaccttc gcggacctgc tgcggcaggt ccgcagcgg ccctcgacg cgtacggcca   40680
ccaggacgtg ccgttcgaga agctcgtcga ggagctcgcg ccgtcgcggt cgctgagccg   40740
ccacccgctg ttccaggtgg ccgtcgccgt ggagaccgac gacctgatcg gcggtcgcgg   40800
cggcggtccc gccctgcggc tgccggcct cggcatcgag gtgctgcccg gcgagccctc   40860
cgctcgcgac ctcgacctcg acctggtggt gcgcgagacg ttcgacgccg agggacgccc   40920
cgccggtctc accggggcac tgatcggcgc ggccggcctg ttcgacgccg cgtcggtgga   40980
gcggctggcc gcgctgctgg cccgcgcgct cgaggcgctg gccgccgacc cgcgcacgcg   41040
cgccggcgac ctcgacctgc tctccccggc ggaccgccgg ctgatcctgc gcggctggaa   41100
cgacaccgcg gctccggcgc cggccggact ggtgccggac ctgttcgccg cccaggccgc   41160
gcgcaccccg gacgcggtcg cggtcgccgg gcccgaccgg gagctgacct atgccgagct   41220
ggacgagcgc tccggccgcc tcgcgcgctg gctgatccgg cgcggggtcg ccgccgacac   41280
ccgggtcgcg ctggtgctgg agcgctccgc ggagctgccg gtggcgatcc tcgccgtgct   41340
caaggccgg ggcgcgtatc tgccgatcga tccggcgcag ccgccgcgcc gcatcgccga   41400
catcgtggcc gacgccgccc cggcgctcgt gctggcccag gcgtccaccg ccgacgtcgt   41460
ggccgacgcg tctccggcgc tcgtgctggc cccggcgtcc gacggtgtgc ccaccggcgc   41520
cgtgcccgtg cacctgctcg actcgcccgc cgtgcgtgac gaggtcgcgc agtgcccggc   41580
cggggccgtg accgacgccg accggcgggg cgtcctgctc ggcggtcacg cggcctacgt   41640
catctacacc tcgggatcga ccggacgccc caagggtgtc gtcgtttcgc acgacgcgtt   41700
cgcgaacctc gtcctggacc agcgccggct cggcatcggg ccgggcagcc gggtggcgca   41760
gttcgcctcg ccgggcttcg acatgttcgt cgacgagtgg tcgatggcgc tgctcgccgg   41820
cgccgccctc gtgatcgtgc cgccggagcg ccggctcggc gcggacctcg ccgcgttcct   41880
caccgagcgc ggggtcaccc acgccacgct gccgccggcg gtggtggcga cgctgccgga   41940
ggagtcgctg ccacgctcgt tcgtgctgga catcggcgc gacgcgctgc cggacgacct   42000
ggcccgccgg tggctgcgcg acggccggtg gctgggcaac tcgtacgcc cgacggagac   42060
cacggtcaac gcggcgacgt ggcgctgcga gcccggcacc tgggagggcg cgaccccgat   42120
cggccggccg gtcgccaacc tgcgggcgta cgtgctcgac ggccgcctgc ggccggtgcc   42180
ggtgggcgtg gagggcgagc tgtacgtctc gggcgccggc ctcgcccgcg gctatctgaa   42240
ccgggccggc ctgaccgccg gcagcttcgt ggcctgcccg ttcgagccgg gggagcggat   42300
gtaccgcacc ggcgacatcg tgcgctggga cgcgcggggc cgcctcgtct acgccggccg   42360
cgccgacgac caggcgaaga tccgcggttt ccgggtcgag ccgggcgagg tggaggccgt   42420
gctggccgcc ggtccgggcg tgaaccaggt cgcggtgatc gtgcgtgagg acgtgccggg   42480
tgacaagcgc ttggtggcgt acgtcgtggg cggcgacgtg gagaccctcc ggtcgtacgc   42540
gcagcagcgg ttgcccggat acctcgtgcc gtccgcgatc gtcgcgctgg ccgagctgcc   42600
gctgacaccg agcgccaagg tggaccggcg ggctctgccg gtgccggact acggccggga   42660
cgccggtggt gggcgggcgc cggccaacgc tcgcgaggaa gtgttgtgcc gggcgttcgc   42720
```

```
cgaggtgctc ggcgtcgagc gggtgggtgt ggaggacgat ttcttcgcgc tgggtggtca   42780
ttcgctgctg gtggtctcgc tggtggagcg gctgcgccgg caggggatct cggtgccggt   42840
gcgggcgttg ttcaccacgc cgaccccggc cgggctggcc gaggcggtcg gtgatggtgc   42900
cgtggtggtg ccgccgaacc tgattcccga gggtgcggcg gagctgaccc cggagatgct   42960
gccgctggcc gatctgaccg ccgacgaact tgctgttgtc gtggattcgg tgcctggtgg   43020
tgcggcgaac atcgcggatg tgtatccgtt ggcgccgttg caggagggca ttttcttcca   43080
tcacatgatg gccgaccggg attcggcgga cgtgtatgtg acgccgacgg tggtggagtt   43140
cgactcccgg gaccggttgg acggcttcct ggccgccttg cagcaggtcg tcgaccgtac   43200
ggatgtgtat cggacgagtg tggtgtggca ggggctgcgc gagccggtgc aggtggtgtg   43260
gcggcacgcg cgcctgcccg tcgacgaggt ggtgctgcgg gacgacctcg acccggtcga   43320
gcagctgaac gcgctcggca cggcctggat ggacctgtcc gaggcgccgc tggtgcaggc   43380
cgtcgtcgcc gcccgcccg gcgatccgca gcgctggctc gccgtgctgc gcatccacca   43440
cctcgtgcag gaccacaccg ccctcgacat cctcctcgag gagctggcgg cgtacctggc   43500
cggccgcggc ggcgacctgc ccgagccggt gccgttccgc gagttcgtcg cgcacacccg   43560
cctcggcgtg ccccgcgagg agcacgagcg ctacttcgcc gggttgctcg gcgacgtcac   43620
cgagaccacc gcgccgtacg ggctcctcga cgtgcacagc ggcggtctcg cctcggcgca   43680
ggcccacctg cggctggacg gcccgctcgg ccggcgcgtg gccgccttcg cccgggaaca   43740
cggcgtcagc ccggcgacgc tcttccacct cgcgtgggcg cgggtgctcg gcacgctggc   43800
cgggcgtgac gacgtcgtct tcggcacggt cctgttcggg cggatgaact cgggcgccgg   43860
cgccgaccgg gttcccggcc tgttcatcaa cacgctgccg gtgcgggtgc ggctcggcgc   43920
gcccgtcggc gacgccctcg acggcctgcg tgaccagctc atcgagctca tcgcccacga   43980
gcacgcgccg ctggccgtgg cccagcaggc cgcgaacctc ttcggccggc cgctcttcac   44040
ctccatcttc aactatcggt acgcccgggg ggccgagccg gccggcgccg cgctcgacgg   44100
catccgcctg ctctccgccc gcgacctcac caactatccg ctggcggtgg ccgtcgacgc   44160
ggagggcgac acgttctcgc tcaccgtcga cgcggtggcg ccggccgacc ccgtgcaggt   44220
cggcgagctg ctcgtcaccg cgctgcgcaa cctgacccgg accgccgaga acgcccccgg   44280
aacgccgctg gccgcggtcg gcgtgctggg cgaggacgag ctgagccggg tcgtctccgg   44340
ctggaacgac accgcccgcc gggtccggca ggcgtcggtg cccgagctct cgcggagcg   44400 ggtggcggcc gcgcccggcg cgccggccgt cgccgccggg gacctgcgct ggacgtacgc   44460
ggacctcgac gcccgttccg acgcgctcgc gcggagcctg gtggcggccg gggtgaccgc   44520
ggagtcgccg gtcgtcgtcg ccctcgagcg ctccgcggac gtgctgaccg cgttcctcgc   44580
cgtcgcgaag gccggcggtg tcttcgtccc ggtggacctc tcctggcccc gggcccgcgt   44640
cgacgcggtg atcgccgact gcgccgcctg atcgcggtg gccgaccggc cgatgaccgg   44700
cctgaccgtc gtgcccgcca accgggccgg cgatcccgcg gtcgcgctgc cgccccgccc   44760
cctgccgggc gcggcggcct accggatgta cacctccggc tccacgggcc ggcccaaggg   44820
cgtggtgacg acccatcaga acgtcgtcga cctggtcacc gaccggtgct ggggcccgac   44880
gccgcgggtc ctgttccacg ccccgcacgc cttcgacgcc tcctcgttcg agtctctggt   44940
gccgctgctg accggcggca cggtcgtggt cgcaccgggg gagagcatcg acaccggtgt   45000
gctgcggcag ctgatccggg cccacgagct gaccacgtg cacgtcaccg cgggcctgtt   45060
gcgcgtgctg gccgaggacc cgtcgtgctt cgccgggctc accgaggtgc tcaccggcgg   45120
```

-continued

```
cgacgtggtc ccggccgagg cggtgcgccg cgtgctggac gccaatcccg gcgtgcgggt    45180
gcggcagctg tacggcccga ccgaggtgac gctctgcgcc acccagcacg tggtgcgcga    45240
gcccagcccg gtgctgccca tcgggcggcc gctcgacaac acccgcgtct acgtgctcga    45300
cgggcttctc cagccggtcc cggtcggtgt caccggcgag ctgtacatcg ccggcgccgg    45360
cgtggcccgg ggctacgccg acatgccggg caccaccgcc gagcggttcg tcgccgaccc    45420
gttcaccgcc ggcggccgcc tctaccgcac cggtgacctg gtccgctgga ccggcgaggg    45480
cgagctggtg ttcgccggcc gggccgacga ccaggtgaag atcccgcggct accgcgtcga    45540 gccgggcgag gtggaggcgg tcctcgccgc gttgccgggc gtcagccagg cggcggtcat    45600
cgtccgcgag gacgtacccg cgacaagcg gctggtggcc tacctggtcg cggcgccgga    45660
gacggtcgag gccgcccgcg cccacgccga gcagcggctt ccgtcctatc tcgtcccgtc    45720
cgcgttcgtg cagctggacg cgctgccgct gaccggcaac cagaaggtcg accgggcggc    45780
gctgccggca ccgctggggt tcgaagccgg tgccggccgg gcgccggcgg acgcccgcga    45840
ggagctggtc ggcgccgcct tcgccgaggt gctcgacctc ggccgggtgg gccccgacga    45900
cgacttcttc gcgctcggcg ggcactcgct gctcgccctc gcgctggtgg agcgcctgcg    45960
ccggcagggc ctgggcgtct cggtgcgtgc cgtcttcgac gcacgcaccc ccgcggcgct    46020
gacccgccgc ggcgacggcg gtgccgacga ccggccggcg ctgcgggccg gtgcgcggcc    46080
cgcgcggctg ccgctttcct acgcgcagcg ccggctgtgg ttcctggccc agctggaagg    46140
accgagcgcc acctacaaca tcccggtcgc gctgcgcctg gagggcgacc tcgaccggga    46200
tgccctgacc gccgccctgc gcgacgtggt ggcccggcac gaggtgctgc gcacggtgtt    46260
cacggtcgcc gacggcgagc cgtggcaaca catcctcgac cccgcgcggg ccgagcccgc    46320
gttgccggtc gtggacgtgc cggccggccg ggtcgaggag gcggtcgccg aagcggccgc    46380
gtacgccttc gacctggccc gggagatccc gctgcgtgcc gtgctgctcg cccccggcga    46440
cggcacccac gtgctcgtgc tggtgctgca ccacatcgcg gccgacggct ggtcgatgcg    46500
gccgctggcc cgcgacctgg cgaccgccta cgccgcgcgg cggcgggggc aggcgcccga    46560
gtcggagacc ctgccccgtcc agtacgccga ctacgccctc tggcagcgtg acctgctggg    46620
ctccgacagc gacccggcga gcctgatctc ccggcagatc gcccactggc gcagcggct    46680 cgacggcgtg ccggaggagc tggacctgcc cgccgaccgg ccgcggcccg ccgcggcctc    46740
gcaccgcggc cacctgcaca cgcgcggaga tcccggccgac gtgcaccgga gcctgcgccg    46800
ggtcgccgcc gaccacggcg cgaccgtctt catgaccctg caggccgccg tggcggtcct    46860
gctgtcgcgg ctcggcgcgg gcaccgacgt cccgatcggc accgtcgtcg ccggccgcgc    46920 cgaccggggcg ctggagaacc tggtcggctt cttcgtcaac acgctcgtgc tgcgcaccga    46980
cctgaccggc gacccgcggc tgaccgacgt gctcggccag gtgcgcgagc tgaccctgcg    47040
ggcgctggcc caccaggacg tcccgttcga gaagctggtc gaggagctca ccccggcccg    47100
ctcgctcgcc cggcaccccc tgttccaggt catggtcacc ctggacggcg gcgggccgga    47160
cggcgccgag ctgccgggcc tggcgatgtc ggtcgtgccg accggcgccg ttccggccaa    47220
gttcgacctc gacctcacgt tcaccgagac cttcgacgcc gcggggagc cggccggcct    47280 gcgcgtcgac ctcatcgcgg cggccgacct cttcgacgcg gcacggccg cccggctcgc    47340 cggctacctg agccgcgttc tcggcgtgct cgcggccgat ccggcgcgcc gcctggccga    47400
ggtcgacccg ctgaggcgg aggagagccg gctcatgctc gccgccggtg aggagcccgc    47460
gccggccctg cccgagatca ccgtcgcggc gctcgtcgcc gagcagtgcg cccgcacgcc    47520
```

```
gggtgcggtc gcggtgaccg gaccggacgc gagcctgacc tacgccgagc tcgacgagcg    47580
ggcggcccgg atcgcccgct ggctgcgccg ccacggtgcc gggcccggcg cggccgtgtg    47640
cgtcctgatg gaacggtcgg cggagctggt cgccgtgctg ctcggcgtga tgcgcgcggg    47700
tgcggcgtac gtgccggtcg accccgccta tccggccgag cggatccggt tcgtcgtcac    47760
cgacgcccgg gccgcctgcg tggtgagcga gtcggcctcg gccggcctcg tcccggacgg    47820
ggtgccgtgc ctggcgatcg acgacccggc cgccgccgcg gaaccggccg agcccggcga    47880
cgacccgggc gacgcggccg ggccgcggcc ggacgatccg gcgtacatca tctacacctc    47940
cggatcgacc ggcaccccca agggcgtcgt ggtctcgcac cgcaacgtcg tggcgctgct    48000
gaccgccacc cggccgctgt tcggcttcgc cggcgacgag gtgtggtcgt ggttccactc    48060
ggtcgcgttc gacttctcgg tgtgggagct gtggggcgcg ctcacccacg gcggccgggt    48120
cgtcgtcgtg ccctacgcgg tgtcccgctc gccgcgcgac ttctgggagc tcgtcgtccg    48180
cgagggcgtc accgtgctga gccagacacc gtcggccttc gcgcagctca tggccgcggc    48240
gggggacgac gaccgggacg cgctgcggtt cgtcgtcttc ggcggcgagg ccctcgaccc    48300
gggccggctg gccggctggc tggcccgccg cccggacaag ccgcgcctgg tcaacatgta    48360
cggcatcacc gagacgaccg tgcacaccac gtaccagcac atcgcgcccg gcacgacggg    48420
cagccgtcatc ggccgcggac tgcccggctt cggcctctac gtgctggacg aggcgctgcg    48480
cccggtgccg gccggcgtgc ccggcgaggt gtacgcccgc ggcccgcagg tggcccgcgg    48540
ctacatcggc cgccccggcc tgaccgcgga gcggttcgtc gcctcgccct tcgcgcccgg    48600
cgagcggatg taccgcaccg gcgacgtggc ccgctggacc gccgacggcc gcctggtgtt    48660
cgccggtcgc tcggacgacc agatcaagat ccgcggtttc cggatcgagc ccggcgaggt    48720
ggaggccgtg ctggccgccg gtccgggcgt gagccaggcc gcggtgatcg tgcgtgagga    48780
cgtgccgggt gacaagcgct tggtggcgta cgtcgtgggc ggcgacgcgg agaccctccg    48840
gtcgcatgcc cagcagcggt tgccgggtta tctggtgccg tcggcgttcg tggagctgga    48900
ccggttgccg ttgacggtca acggcaagct cgatcgccgg gctctgccgg tgccggacta    48960
cggccgggac gccggtggtg ggcgggcgcc ggccaacgct cgcgaggagg tgttgtgccg    49020
ggcgttcgcc gaggtgctcg gcgtcgagcg ggtgggtgtg gaggacgatt tcttcgcgct    49080
gggtggtcat tcgctgctgg tggtctcgct ggtggagcgg ctgcgccggc aggggatctc    49140
ggtgccggtg cgggcgttgt tcaccacgcc gacccccggcc gggctggccg aggcggtcgg    49200
tgatggtgcc gtggtggtgc cgccgaacct gattcccgag gacgcggcgg agctgacccc    49260
ggagatgctg ccgctggccg atctgaccgc cgacgaactt gctgttgtcg tggcgtcggt    49320
gcccggtggt gcggcgaaca tcgcggatgt gtatccgttg gcgccgttgc aggagggcat    49380
tttcttccat cacatgatgg ccgaccggga ttcggcggac gtgtatgtga cgccgacggt    49440
ggtcgagttc gactcccggg accggttgga cggcttcctg gccgccttgc agcaggtcgt    49500
cgaccgcacc gatgtctacc gcaccagcgt ggtgtggcag gggctgcgcg agccggtgca    49560
ggtggtgtgg cggcacgcgc gcctgccgat cgacgaggtc gagctgcacg agggcaccga    49620
tccggccgag cagctgatcg cgctcgccac cgagcgggtg gacctcgacc gcgcgccgct    49680
gatccgcacg acgaccgcgg ccgtgccgg atcggccgg tggctcgcgc ttctgcgcat    49740
ccaccacctc gtgcaggacc acaccaccct ggacgtgctg ctcggcgagc tgcgggcctt    49800
cctcgagggc cgcggcgacg agcttcccga gccggtgccg ttccgcgagt tcgtggcgca    49860
ggcgcggctc ggtgtgccgc gcgaggagca cgagcggtac ttcgcggagt tgctcggcga    49920
```

```
cgtcaccgag accaccgcgc cgtacggcct gaccgaggtg cacggcgacg gttcggccgc   49980
cgtgcacagc cggcgcgagg tggacgacga cctcgccgcg cgcctccacc ggctggcccg   50040
gtcgctcggc gtcagcccgg cggcgctctt ccacctcgcg tgggcgcggg tgctcggcgc   50100
cgtgtcgggc cgggacgacg tcgtcttcgg cacggtcctg ttcggcggc tgaactccgg   50160
cgccgccgcc gaccgcgtgc agggcttgtt catcaacacg ctcccggtgc gcgtgcggct   50220
cgccgccggc agcacccgcg acgccctgac cgggctgcgg gaccagctgg ccgggctgct   50280
ggtgcacgag cacgcgccgc tcgcgctggc gcagcgcgcg ccggcatca ccgacggcag   50340
cccgctgttc gcgtcgatct tcaactaccg ccacaaccag gacgacccgg cggcgtcggc   50400
cgggctcgag ggcatccgca cggtctacag cgccgagcac accaactacc gctcgacgc   50460
ctcgatcgac gtcaccggcg accgcttcgc catcaccgtg aacgcggtgg cgcccgcgga   50520
cgccgcgcgg atcgctgagc tgatgcacac ctgcctcggc cacctcgcgg acgtgctcga   50580
agacgcgccg gagacgccgc tgtcgtgggt cagcccgctg agcgcggagg atctcggccg   50640
catcgtgggc gactggaacg agacgcggcg cgcggtcacc cgcgcgtccg tgccggagct   50700
gttcgccaag caggtggccg ccacgccgga cgcgatcgcg gtggcgggcg agggtgtgtc   50760
gtggtcctat cgcgagctcg atgtgcgctc ggatgcgctg gcccggagtc tggtggcggc   50820
cggtgtgggt atcgagtcgc cggtggtggt ggcgctcgat cggtctccgg aggtgccgac   50880
ggcgttcctc gcggtggcga aggccggcgg tgtgttcgtc ccggtggact tgtcgtggcc   50940
ccaggcgcgt gtcgatgcgg tgatcgccga ctgcgccgcg cgggtggcgg tggccgaccg   51000
gccgatgacc gggctgacgg ttgtgcccgc cgacgcggcc ggcgacccgg ctgccgagtt   51060
gccgccccgc cccttgccgg gtgcggaggt ctaccggatg tacacctccg gctcgacggg   51120
ccggcccaag ggtgtggtga ccacccacca gaacctggtg gatctggcga ccgacacgtg   51180
ttggggtccg accccgcggg tgcttttcca cgccccgcac gccttcgacg cgtcgtcgta   51240
cgagatctgg gtgccgttgc tgaatggcgg cacggtcgtg gtcgcgccgg ggcggagcat   51300
cgatgccgcc gtgctcggcg agctgatccg ggcgcatgag ttgacgcacg tgcacgtcac   51360
cgcgggcctg ctgcgggtgc tggacccgtc gtgcttcgcg gggctgaccg aggtgctcac   51420
gggcggcgat gcggtgtcgg ccgaggcggt gcgccgggtg atggaggcga acccgggcct   51480
gcgggtacgt cagctgtacg gcccgaccga ggtgacgctg tgcgccacgc agcaggtgct   51540
cgatggcacg ggcgtgccga tcgggcggcc gttggacaac acccgcgtgt atgtcctgga   51600
tgacttgctg cagccggtcc cggtcggtgt gaccggcgag ctgtatgtgg ccggtgccgg   51660
cttggcgcgc ggctatgcgg gcatgcccgg gttgacggcc gagcggttcg tcgccgaccc   51720
gttcagcagc ggcggtcgcc tctaccgcac gggtgatctg gtgcggtgga ccgatgacgg   51780
tgtgctggtg ttcgcgggcc gggccgatga tcaggtgaag attcgtggct atcgggtgga   51840
gccgggcgag gtcgaggctg tcttggccgc gcatccggac gtggctcagg tggcagtggt   51900
cgtccgggag gacaccccag gggataagcg gctggtcgcc tacgtcgtcg gcggcgatgt   51960
cgaggcgtat gcgcaggagc gccttccggg ctacctggtc ccgtcggcct tcgtccatct   52020
ggacgcgctg ccgctgacca gcaaccagaa ggtcgaccgg ccgcactgc ccgcgccgtc   52080
cgtggagtcc ggcgcgggcc gggcgcccgc cgacgcgcgt gaagagctga tgtgtgccgc   52140
gtttgccgag gtgctcgacc tggatcgggt cggtgtcgac gacgacttct tcgctttggg   52200
tgggcattcg ctgttggtgg tgcggttggt gggccgtatt cggcaggtgt tcggggtgga   52260
ggtgtcggct cggctggtct tcgatgcgcg gactccggcc ggtgtggtgg cccgcttgtc   52320
```

```
cgagggcggc acggcccggg aggcggtgcg ggcgcgggtg cgtcccgcgc gggtgccgtt    52380
gtcgttcgcg caacgccggt tgtggttcct gtcccagctg gacggcacga gcacgaccta    52440
caacatcccg gtcgcgctgc aactcgacgg cccgctcgat cgggacgcct tcaccgcggc    52500
actgcacgat gtggtcgccc ggcacgaggt gctgcgtacc gtcttcaccg tcgccgatgg    52560
cgagccgtgg caacacatcc tcgacacgcg gtcggtgagc gtccccgtca tcgaggtgcc    52620
cgccgacggg cttccggagg cggtggccgc ggcggccgcg cacaccttcg acctgagccg    52680
ggagatcccg ctccgggcgg tgctgctcgc caccggcgcc gaccggcacg tgctggtgct    52740
ggtcgtgcat cacatcgccg ccgacggctg gtcgatgcag cccctcgccc gggacctcgc    52800
cgtcgcctac gccgcccgga tccggggcga ggcgccggcc tggaccgccc tgcccgtcca    52860
gtacgccgac tacgccctgt ggcagcgcga cgtgctcggc tccgagcacg acccggacag    52920
cgccatctcc cagcaggtcg cccattggcg gcgacagctc gccggagccc ccgacgagct    52980
accgctgccc gccgaccacc ccgtccccgc cgaggccacc taccgcggcc acccgtgga    53040 gttcaccgtg cccccggccg tgcaccacca actcgccgaa ctcgcccgcc gcaacggcgt    53100
caccgtcttc atgaccgtgc aaaccgccct cgccgtcctc ctgtccaaac tcggcgccgg    53160
caccgacatc cccatcggcg tcgccgtcgc cggacgcacc gaccccaccc tcgacaacct    53220
catcggcttc ttcgtcaaca ccctcgtcct acgcaccgac ctgaccggca accccaccat    53280
caccgacctg ctgcaccgca cccgcgacac caccctgcac gccttcaccc accaagacgt    53340 cccccttcgaa aaactcgtcg aagacctcgc acccacccgc tccctcgccc gccacccct    53400 cttccaggtc atgatgaccc tgcagagcac cgggcgggcc ggcgaggcgg ccgagctgcc    53460
cggcctggag acggcggtgc tgtcgccggg cggcgtcgcc gccaaggtcg acctcgacct    53520
gagcctgagc gaggcgtacg acgacgacgg ccgcccggcg ggtctcgccg gaacgctcgt    53580
cgcggcggcc gacctgttcg agcacggcac cgccgagcgg atcgccggtt acctcgcgcg    53640
gctgctcgcc gtgctgcccg ccgatcccgg cgcccggctc ggcgacgtgg acctgctcga    53700
cggcgaggag cggcggctgg tcctcaccgg ctggaacgac acgacggcgg ccgtgccggc    53760
ggtggcggtg cccgagctga tcgagcggcg tgccgccgcc gaaccggagg ccggcgccgt    53820
ctggtgcggc gacacgcacc tgcggtacgg cgagctgaac gcccgcgcga accgcctcgc    53880
ccggctgctc gtggagcgcg gggcgggacc cgagtcgatc gtcgcggtct gcctggaacg    53940
ctcggccgac ctcgtcgtca cgctgctggc cgtgctgaag accggggccg cctacctgcc    54000
gatcgatccc ggatatccgg ccggccggat cgcctacatg ctcgccgacg cccgcccgc    54060 gctgctcgtc acgagcccgg cggtcgcctc cggtgacagc ctcccggacg gtggcgcgca    54120
acggatcgtc ctcggcgatc cggacaccgc ggcggccctc gacggcctcg ccggcaccga    54180
cctgctcgtc tcggagcggc gcggcgtcac gcacccggca catccggcgt acgtcatcta    54240
cacctccggg tcgaccgggc gccccaaggg tgtcgtcgtg ccgcacgggg ccctcacgaa    54300
tttcgtggcg gcgatgagcg accggctcgc gctgggcgcc ggcgaccggc tgctcgcggt    54360
caccacggtc gccttcgaca tccacgtcct ggagctctac gtgccgctgg tcggcggcgc    54420
cggagtggtc gtcgccgagg acgccgtggt gcgcgacccg gccgcggtcg ccgcgctcct    54480
cgaccggcac gccgtgacga tcgtgcaggc caccccggcg ctgtggcagg cgctgctcgc    54540
cgggcacgcc gacgccgtcc gcgacgtgcg gctgctcgtc ggcggcgagg cgctgccgcc    54600
cgcgctcgcc ggccggatgg ccgcggccgg tcgcggtgtc accaacctgt acggcccgac    54660
cgaggtcacc gtgtgggcga ccgtcgccga cctcggcgcg agcccggccg gccggtgcc    54720
```

-continued

```
gatcggcacg cccctgcgca acacccgcgc cttcgttctc gacgacgcgc tgcgcccggt    54780
gccgccgggc gtgccgggcg agctctacct cgccggcgat cagctcgcgc ggggctacca    54840
cggccgggcc ggcctgaccg ccgagcgctt cgtggccgac ccgttcggcc gcggtgagcg    54900
gatgtaccgc accggcgacc gggtccggtg gacccgcggc ggcagcctgg agttcctggg    54960
ccgcgtcgac gaccaggtca agatccgcgg tttccggatc gagctgggcg aggtcgaggc    55020
ggcgcttgcc gcgttcgggc cggtggcccg ggcggccgcc gccgtccgcg aggacgtgcc    55080
gggcgaccgc cggctcgtcg gctatgtcgt gccggccgcc ggcgagccgg agcccgaccc    55140
ggcggcggtc cgcgcgcacg tcgccgccca gctgcccgcc tacatggtcc cgtcggcggt    55200
cgtggtcctg cccgacctgc cgctgaccgc gaacggcaag ctcgaccgca aggcgctgcc    55260
ggcacccgac tacggcgccg cctccgcggg ccgggcaccg gccgacgagc gcgaggcgct    55320
catctgcgcg gtgttcgccg agacgctcgg cgtgaccgac gtcgcagccg atgccgactt    55380
cttcgccctg ggcggccatt cgctgctggc cgtgtcgctg gtcgaacggt tgcgcgagca    55440
cggcatcgcg gttccggtcc gcgccctgtt ccagtcgggc accccgagg gcctggccgc    55500 cgcggccccgc gccgagggcc cggacagagc ggccgtgccg gccaacggca tcccggacgg    55560
cgccaccgcg ctcacgccgg cgatgctcac cctcgtcgac ctcgacgccg aggagatcgc    55620
ccgggtggtc gccgccgtgc ccggcggggc cgcgaacgtg gccgacgtct atccgctcgc    55680
gccgctgcag gaggggctgc tcttccacag cctgatggac ggcggcgacg acgtgtacgt    55740
gctgccggcc gtcctcggat tcgattcgcg gtcccgcctc gacgcgttcc tggccgcgct    55800
gcaacacgtg atcgaccggc acgacacgta ccggaccgcg gtggtgcacg acggcctgcg    55860
cgagccggtg caggtggtct ggcgccgggc cacgctgccg gtcgaggagg tgaccctgac    55920
cgcgggcgcc gacccggtgc aggaactgct cgccaccgcg ccggtcgagt tcgcgctcga    55980
ccgggccccg ctgctgcggg tgcgctgcgc ggcccggccg gacggcggcg gatggctggc    56040
gctgctccag atccaccacc tcgtccagga ccacgccacg ctcgacgcga tgctcgccga    56100
gatccaggcc ttcctcgccg gccgcggcgg cgagctcgcc gcgcccgagc cgttccgcgg    56160
ctacgtcgcc cgggcccggc tcgccggcgc gccggccgag caccgggcgt acttctcccg    56220
gctgctcggt gacgtcaccg agagcaccgc cccgtacggg ctgaccgacg cgcgggacgc    56280
gcggccgacc ggaaaggccc atcgcgaggt cgaccggcgg ctggccgccc gcgtgcgggc    56340
cacggcgagc gagctgggcg tgagcccggc gaccgtgttc catctcgcct gggcgcgggt    56400
gctgggcacg cttccggcc gcgacgacgt cgtcttcggc accgtcctgc tgggacggct    56460
cggcgccggc gcccggtccg ggcgagccct cggcccgttc atcaacaccc tgccggtgcg    56520
ggtgcgcctc gccgccgccg gcagccgcga gacgctggcc gggctgcgcg ccagctggc    56580 cgagctgatc ggtcacgagc acgccccgct gacgctggca caggccgcga gcggcgtgcc    56640
cggcgggacg ccgctgttca cctcgatcct caactaccgg caggggccgc cgccggcga    56700 cgacaccggc gacgaggaga tcgagggcat cgagctgctc tccaccgagg aacgcagcaa    56760
ctacccggtg gccgtctccg tcgacgacga cggttcgggc ttccggctca ccgtcgacgc    56820
ggcccagccg gccgcaccgg accgcgtcgc cgagctgctg cacacctgcc tgcaccggct    56880
caccgacgcg ctcgcgggca cgcccgacgt ggagccggcg cggatcgacg tgctcggcga    56940
ggcggagcgc cgggaggttc tccggacgcc gaacgccacg gccgcgacg tggcggcggc    57000 gacgctgccc gcgatcgtcg gcgagtgggc gggaccacg cccggcgcga ccgcggtcac    57060
cgccgagaac gaccggctca cgtacgccga gctggacgct cgcgccaacc gcctggcccg    57120
```

```
ctcgctgatc gcccgcgggg tcggtcccgg tgccgtcgtc ggcatgctcc tgccccgctc   57180
gccgggcctg gtggtggcga tgctggcgat cgtcaaggcc ggcggcgcct acctgccgct   57240
cgatcccggc tatccggcgc cccggctggc ccggatggtc gaggacgccg cgccggcgct   57300
gctgctggcc acggccggca ccgcggacgc cgtgcccgcc gggccgcagc gactgctgct   57360
ggacgacccc ggcaccgcgg cggagctggc ccggctggac ggcgacccga tccgcgacga   57420
ggagcgcacc caccccgctg cgccccgggca cccggcgtac ctgatgttca cctccggatc   57480
gacgggacgc ccgaagggcg tgctggtgcc gcacgccggc atcgaccgca tggtccgccg   57540
ctccacctgc cttcagctgg caccggacga cgtcctgccg cacctctcgt cggtgtcgtt   57600
cgacgcggcc accttcgaga tctggggcgc gctgctcaac ggcgccaccc tcgccgtcgc   57660
accggcggag acgctctcgg tggccgagct gcgggccttc ctcgcggacc ggggcgccac   57720
caagctgttc ctcaccaccg gcctgctgca cgaggtgatc gacgccgacg tgaccgccct   57780
cgccggcctg aaggcggtct acaccggcgg tgacgtgctc tccccggcgc actgccggtc   57840
gcttctcgac cgggtgcccg gcctcgagct ctacaacgcc tacggcccga ccgagaacac   57900
caccatcacc acccttcatc gcgtacgccc ggaggacctc gacgcgggca cgggcgtacc   57960
gatcggcgtg cccatctccg acacccgggt gtacgtgctc gacgacgcgc tgcggccggt   58020
gcccgtgggg gtcgccggtg agctctacac ctccggcatc gggctggcgc acggctacgc   58080
cggacgaccg gcgccgaccg cggagcgctt cgtggcgtgc ccgttcgcac ccggtgagcg   58140
gatgtaccgc accggcgacc tggtgcgctg gaccgccgac gggcgcctgc tgttcgccgg   58200
ccgcgccgac aaccaggtca agatccgggg cttccgggtg gagccgggcg agctcgagac   58260
ggtcctgtcc ggacatccgg ccgtggcacg ggccgcggtg ctggcgcgcg aggacacgcc   58320
cggcgccaag cggctggtcg catacgtcgt gccggcccgg ccggacgagg acggggacgc   58380
gctggccgag tccgtgcgcg cctacgccgc ccggcaggtg cccgactatc tgatgcccgc   58440
cgcgacggtg gtgctcccgg acctgccgtt gaccagcagc ggcaaggtcg accgggccgc   58500
gctgccggcg ccggacgtgc cgggcggggcc gggccgcgcc gccggcacgc tcaccgagga   58560
gatcctctgc ggcgtcttcg cccaggtgct cgggctgccc acggtcggcg tcgacgacga   58620
cttcttcgcc agcggcggcc attcgctgct ggccacccgg ctggtcagcc ggctgcgtgc   58680
cgtcttcggg gccgagctgc cgatccgggc cgtcttcgag gcgccgacgc cggccacgct   58740
ggccacccgg ctcggcgcat ccgcgccgcg cgactcgcg ctcggcgaac gcgcccggcc   58800
ggagaacgtg cccctgtcgt acgcccagcg gcggctgtgg ttcctcgacc gctggagggg   58860
acaggacggc acctacacca tcccgctcac cgtgcggctc gacgggccgg tcgaccgggc   58920
ggcgctcgcg gcggccctgc gcgacgtcct ggagcgccac gaggtgctgc ggaccgtctt   58980
cccgctcgtg gacggcgaac ccgtccagcg ggtgctgccg gtgcacgaca ccggcttcac   59040
gctcggcggc ggtgacgtcg cggccgccga cctcggcgcc gcggtcgccg aggccacggc   59100
cggcaccttc gatctggccg ccgagatccc ggtgcgcgcc tggctgttcc gcgccgggcc   59160
cgaggaccac accctcgtgc tgctggtgca ccacgtcgcc ggcgacggct ggtcgatgac   59220
gccgctggcc cgcgacatcg ccaccgccta cgacagccgc cgcgagagcc gggcgccgca   59280
atgggagccg ctgccccgtgc agtacgccga ctacgcgctc tggcagcgcg aactgctcgg   59340
cgccgaggac gatccggaga gtttgctgtc gcggcagctg gcctactggc gggacgcgct   59400
cgacggcgta ccggaggagc tggacctccc ggccgaccgg ccgcgccgg ccgaggccac   59460
gcaccgggga cacgaggtgc ccgtgcgggt gccggccgag gtgcaccggc gcctggccga   59520
```

```
gctggcccgg tccgagggcg tgaccgtgtt catggtgctg caggccgcct tcggcacgct   59580
gctgtcccgc ctcggcgccg gcgccgacat cccgatcggc acggcggtcg ccggccgcac   59640
cgaccaggcc ctcgacgagc tcgtcgggtt cttcgtcaac acgctggtga tccgggccga   59700
cctgtccggc gaccccacct tccggagct gctcggccgg gtgcgcgcca ccggcctgtc   59760
cgcctacgag caccaggacg tcccgttcga gcggctcgtc gaggtgctgg caccggcccg   59820
atcgctcgcc cggcacccgc tcttccaggt catgctcacg ctgcagaaca ccggccgcgc   59880
ggacgccggc gaccaggccg tcccgccggc cgccggatcg gccgcggcca agttcgacct   59940
cgagatcagc atcgcggaga cgttcgccgc cgatggcgag ccggccgggc tcagcggcgt   60000
tctcatcgcc gccgccgacc tgttcgagcc ggccaccgcg gccgcgttcg ccgaacggct   60060
ggcccgcgtg ctggccgcgg ccggcgccga tccgcggctg cgggtcagcc aggtcgacat   60120
cctcagcgcc gaggagcgcg aggccgtcct gtccggcggc aacggcggca ccgcgccggt   60180
tcccgtcacc accgtcccgg cgctcttcgc cgagcaggcc cgccgacccc gggcgcggt   60240 ggcggcgctg agcgaggga tgtcgctcac ctacgccgat ctcgccgccc gcgtgaaccg   60300
gctcgcccgg cacctggtga gcctcggcgc cggaccggag accgtcgtcg gtatcgccat   60360
gagccgcggc ctcgacatgc tggtggcggt cctcgcggtc gggcaggccg gcgccgccta   60420
cctgcccgtc gacccgtcct acccggacga gcgcaaggag ttcatgctca ccgacgccgg   60480
cgccgcgtat gtgctcacct tggcctcgga cgccgaccgc gtgccgccgg aaccccggc   60540 cgccgccgtg gtcctggacg agcccgtgac ggccgcgcgg atcgccgggc tcgatccggc   60600
cgacctgacc gacgccgacc gggtggcgcc gctgctgccg gcccaccggg cgtacgtcat   60660
ctacacctcc ggatccaccg gccggcccaa gggtgtcgcc gtcgagcacc gcaccgtggt   60720
caacctgctg tcctgggcgg ccgggcggtt cggcggcgcc gacttcgccc ggacgctcgc   60780
cgccacctcg ctcaacttcg acgtctcggt cttcgagatc ttcgggccgc tggtgtccgg   60840
cggcagcatc gagatcgtca ccgacctgct cgccctggcc gacccggcct ccccggcctg   60900
ggaggccagc ctggtcagcg gcgtgccgtc ggcgttctcg cgggtcctcg accggggcga   60960
catcgccgcg cgcacccgca gcgtggtgct ggccggcgag gcgctgaccg ccgacgtggt   61020
gaacgccacc cgtgccgccc tgcccggtgt ccgggtggcc aacatctacg gccgaccga   61080 ggcgaccgtc tactcgaccg cctggcacac cgaccgggac gtgaccggcg cgccgcgcc   61140 gatcgggcgg ccggtcacca acacccgcgc ctacgtcctc gacgaccgtc tcacgccggt   61200
gccgccgggc gtggtgggcg agctctacct ggccggcgcc cagctggccc gcggctatct   61260
gggccggccc ggcctgaccg gcgagcgctt cgtggcctgc ccgttcggcc cgggcgggga   61320
gcgcatgtac cgcaccggcg accgggtccg gtggaacgcc gacggcgacc tggtcttcgc   61380
cggccgggcc gacgaccagg tcaagatccg cggcttccgt atcgagccgg gcgaggtgca   61440
ggccgtcgtg gcgcgccagg ccggcgtggc ccgggcggtg gtgctggccc ggagcgactc   61500
gcccggcgac gcccgcctgg tcgcgtacgt cgtgccggcc gaccgggacg ccgaccgccg   61560
ggcgctggcc gccaccgtcc gctcggacac cgcgcgcgag ctgccggcgt acctggtgcc   61620
ggcggccgtg gtggtcctcg acgagctgcc cgtcacggcc aacggcaagc tcgatcgccg   61680
tgcgctgccc gcgcccggcc tggccgaggc gggcagcggc cgcgggccgg tcacccaccg   61740
cgaggaggtg ctctgcgagg tcttcgccca ggtgctcggc ctgccctcgg tcggcgtgga   61800
cgacgacttc ttcgcgctcg gcgggcactc cctgctggcc gtctcgctgg tggagcagct   61860
gcgccgccgc ggcgtgacgg tcggggtgcg cgcgctcttc cagacgccca cggtcgccgg   61920
```

```
cctggccgag gcggccgcgc ccaccacggt cgccgttccg cccaacctca tccccgagga   61980
cgcgcggcac atcacgcccg gcctgctgcc gctcgtggag ctggagcagg ccgagatcga   62040
ccaggtcgtg gccactgtgg acggcggcgc cgccaacgtg gccgacatct atccgctcgc   62100
gccgctccag cagggcatgc tcttccacca cctcatggcc ggcgacgacg gcgaggacgt   62160
ctacatcatg cccgcggtcg tggagttcga ctcggcggac cgcttcggcg ccttcgtcga   62220
cgccctccag cacgtgatcg accgcaacga cgtctaccgc accggcgtgg tctgggacgg   62280
cctgcgcgag ccggtgcagg tggtctggcg ccgggcgccc ctgcccgtga ccgaggtgac   62340
gctcgatccg gccggcggcg atcccgccgc ccagctgcac gccgccgccg cgcccggat    62400
ggacctgaac cgggcgcccc tgctcgacct ccacgtggcc gcccggcccg aggacggcca   62460
acggctggcc ctgctgcggg ttcaccacat ggtgcaggac cacatggggc tcgaggtgct   62520
cctcggcgag gtgcaggcgt tcctggccgg ccgcggcgac gagcttcccg atccgctgcc   62580
gttccgcgac ttcgtggcgc agacccgcgc cggggtgccg gaggccgagc accggcggtt   62640
cttcgccggg ctgctgggcg acgtcaccga gcccaccgcg ccgtacggcc tgctcgacgt   62700
gcaccgcgac ggcgtcggcc tggtgcgcca ggaacgcccg ctcgacggtg aggtggtggc   62760
ccggctccgc gccgtggccc gccggctcgg ggtgagcccg gcgaccgtca tgcacgtcgc   62820
ctgggcgcgc gtgctcggcg tgatctccgg ccgcgacgac gtggtcttcg gcacgctgct   62880
gctgggccgg ttcagcaccg gcgccgaccg ggtgcccggc ccgttcatca acacgcttcc   62940
ggtgcgggcc cggctcggcg gcacgggcgc cgcggcggcg gtggcggaga tgcgccggct   63000
gctggccgag ctgctcgagc acgagcacgc gccgctgacc acggcgcagc aggccagcgg   63060
actctccgga aacctcccgc tgttcacggc gctgttcaac tatcggcaca acacgtcgcc   63120
gggtgcggac ccgtcgcccg cggccggccc gaccgagggc atccgcccgg tctccatgcg   63180
ggagcgcacc aactatccga tctcggtggc ggtggacgac gacggcgagg gcctcggcgt   63240
ggcggtcaac gcgatcccgc cggtgcggcc ggaggcggtg tgcgagctcg tggcgaccgc   63300
gaccgagagc ctgacctcgg cgctggagct gttcctcgac ggcggtccgg acaccgcggt   63360
cggcgagctc gacgtgctgc cgccggggga gcggtcgcgg ctgctggtgg agtggaacga   63420
cacggctcgt ccggtggtgg agtcgtcggt gccggcgttg ttcgccgagc gggtggcggc   63480
cgcgccggat gcggtcgcgg tggtgggcga gggtgtgtcg tggtcctatc gcgagcttga   63540
ccgtcgctcg gatgtgctgg cgcggagtct ggtggcggcg ggtgtgggcc tggagtcgcc   63600
ggtggtggtg gccctcgaac ggtccgccga cgtgctgacc gcgtttctcg ccgtcgcgaa   63660
ggccggcggt gtcttcgttc cggtggactt gtcctggccg cagacgcgta tcgatgcggt   63720
gatcgcggac agccggccgg ttctggtgtt ggacagcgtg gatctgccgg ccgcggaggc   63780
cgacctgccg cgggtgccgg ccggtgcggg cgtgtatcgg atgtacacct cgggttccac   63840
gggccggccc aagggtgtgg tgaccaccca ccagaatctg gtggatctgg cgaccgacac   63900
gtgtttgggga tcgacgccgc gggtgttgtt ccacgccccg cacgccttcg acgcgtcgtc   63960
gtacgaaatc tgggtgccgt tgttgaatgg cggcacggtc gtggtggccc gcggcgcag    64020
catcgacgcc accgtcctga gggacctggt ccgcgggcat gagttgacgc acgtgcatgt   64080
gaccgcgggc ctgttgcggg tgctggaccc gtcgtgcttc gcggggctga ccgaggtttt   64140
gaccggcggg gatgccgtgt cggcggaggc ggtgcgccgg gtcaaggaag cgaacccggg   64200
tctgcgggtg cgccagttgt acggcccgac cgaggtgacc ttgtgcgcca cgcagcatct   64260
gctggatgac ggggtgccga tcgggcggcc gttggacaac acccgcgtct acgttctcga   64320
```

```
cgacctcctg cggccggtcc cgacgggtgt ggtgggggag ctgtatgtgg ccgggtcggg    64380
tctggcgcgt ggctatgcgg gcatgccggg tttgacggcc gagcgatttg tcgccgaccc    64440
gttctcggtg ggtggtcgcc tctaccgcac cggtgatctg gtccggtgga ccgacgacgg    64500
tgtgctgcac ttcgccgggc gggccgatga tcaggtgaag atccgcggct atcgggtgga    64560
gccgggcgag gttgaagcgg ttctggctca acaccccgac gtcagccagg tcgcggtcgt    64620
cgtccgagag gacgcgccag gggataagcg gctggtcgcc tatgtcgtcg gcggggatgt    64680
cgaggcgtat gcgcaggagc gccttcccgg ctacatggtt ccgtcggcct tcgtccatct    64740
ggaagcgctc ccgctgaccg cgaaccagaa ggtcgaccgg gccgccctgc ccgcgcccga    64800
gcgggagacg acgacaccgg gtaaggcacc cgcccccgga ccgctcggca acctcgagga    64860
gtcgatgtgc caggcgttcg ccgaggtgct cggcctcgac agcgtcggcc cggacgacga    64920
cttcttcgcc ctgggcggcc actcgctgct cgccgtcgcg ctcgtgcagc ggctcaaggc    64980
acgcggtgtc gccgtcacgg tgcaggacat catggccgcg cccacggtct cggagctgat    65040
gggctcgctg agcatgtcgt cgatccggga ctccctcggc acgctcctgc cgatccggcg    65100
caccggcgag ctgccgccgc tgttctgcgt ccatccggcc ggcgggctca gctggtgcta    65160
cctgccgctg gcccggcacg tgccggccga ccgcccgatc tacggtctgc aggcgcgcgg    65220
cgccgacggc cgggagccgc tcgcaccgtc gctgcgcgag atggccgccg actacgtgag    65280
ccggatgcgc gccgtgcagc ccgaggggcc gtaccacgtg ctcggcttct ccttcggcgt    65340
ggcgcccgcg cacgagatcg ccgtccagct gcgcgagcag ggcgccgagg tcgtgctggt    65400
gctcatggac tcctatccca tggaggatgc ggagtccggc gagcaggcgg ccgacgagga    65460
ggagctgccg tgggaggagc tcatcgagcg cgagttcggc cgggtgctcg gcggcttctc    65520
ccgcgacgaa ctggcggcct tcgccgccgt cttccgcaac aacaccaaga ttcgcgcacg    65580
ccaccggctg ggccgcttcg acggggacgc cctgctgatc gcctcgaccg acagcgcacc    65640
cgacggcgag tccaacacct ggcggtgggc gccgtacatc accggtgaga tcacccaggt    65700
ggtgctcccc tgcgagcaca ccgacctggt acgccccgac atgctcgcgc tgctctggcc    65760
ggccgtcgag gcgtggcagg ccgggcggca ccgaccttag tcaccacagc gtcgagagga    65820
ccgacatgca gaagatcccg ctcgtgtgtg tgccgttcgc cggtgccggc gcctcgttct    65880
tccacccgtg ggccgagctc gccgggccgg accggccgat cgtcgcgctc cagcttccgg    65940
gccgggagtg gcggctgctc gacgaaccgt acgcggacgt cgtcgcggcg gccgcggacc    66000
tggcgctcac cgtcgccgac gaggtggggcg cgggggggccg ggtggcgctc ttcgggcaca    66060
gcctcggcgc cgtcctcgcg tacgagatag cgcacgcgct ggtgcgcgac ggcgaggtgg    66120
gcgtggagcg gctcttcgtc agcggctcgc ccgatccctg gacccctcgc accaaccggg    66180
cgagcggcct ggacgacgag gagttcctgc tgcgggtgcg cgagttcgcc ggttacgacc    66240
acgaggcgct cgccgatccg gacatgcgcg agctgatcct gcccgcgctg cgcgccgacg    66300
tcgagatgca cgagagctac gtggcgggca gcgccgatcc gctgcccgca cccgtcaccg    66360
cgctgcacgc ccgcgacgac gcgctggtct ccgccgagca gacggccggg tggagcaagg    66420
ccaccagcgg cccgttccag ctggtcgagg tggacggcgg ccacatgtac ctcaccgagg    66480
acccggccgg cctgctgcgc ctgatcgccg ccgacctgga ccgtgactga cccgaggag    66540 aacccgtgcg cttgaccggc aagaccgcca tcgtcaccgg cgcggccgc ggcctcggcc    66600 gcgcctgcgc cgtggccttc gccgccgagg gagccgacct ggtgctcctg gaccgcgcgg    66660
ccgacctgcc gggggtgccc tatccgctgg gcaccgtggg ccagctggag cacaccgccg    66720
```

```
acctctgccg caagcagggc gccgcggtgc tcaccgtccg ggcggacgtg cgcgacctcg    66780
cggcgctcac cgcggcggcc gatcgggcga tcgaccgctt cggcggcatc gacgtgctcg    66840
tcaacaacgc gggcatcgcc gcgccgtccg gaaaggtcac ccacgagatc accgaggacg    66900
agtggcagct gatgatcgac gtcgacctct ccggcgcgtg gcgcatgacg gcggcggtcg    66960
gccggcacat gaccgagcgc cgctcgggca gcatcgtcaa catcgcctcg acggccggtc    67020
aggtcggcta ccggcacttc gccggctacg tcgccgccaa gcacggcatc gtcgggctca    67080
cccgggccgc cgcgctcgac tacgcgccag cgaaggtgcg ggtcaacgcc gtctgcccgg    67140
gttcggtgcg cgacgatccg cagttcgagg gccggatgct gtcggagatc gcccggtcgc    67200
tcgacgtgcc ggtcgccgag cacgagcaga ccttcctgca ggcgcagccc atgaacgccc    67260
tcatcgagcc ggacgacgtc gccaacgccg cgatctggct cgcctccgac gaatcgcgcc    67320
aggtcaccgg ctccgtcgtc acggtcgacg gcggattcac cacgcgctga acggggagaa    67380
gacgtgccca gtcccagcc cgccaccaga accgcggcgc ccggcgccgc cgagtgccac    67440
gcgcttgccg tgcgcctggc cggaccgatc gacccggcgc cgatcgagcg gcggctcgcc    67500
gcccgcatgc cgttctggca cgagcacgtg gcggcccggc cgggcgatga ggccgcgctg    67560
cgccgccgcg agcgcgaact cgcccgcccg gtgccgccgg agcccggtgc gcgggcggtg    67620
ctgctcgcct acgcggacgg ctcggccgac ctggtgctgg tggcccgccg cgaccgcctg    67680
gaccgcgacg cgctgatcgc cctggcccgc ccggagcggg cgccgcgcgg gcgcaaaccg    67740
gcggaaccgg acgcgccgcc gccctcggcc gcgcccgcct ggggcctggg cgacggcggc    67800
ccggacgacc ggtgggccga gctgcgcgtg ccggcgcgcg gccggccga cccggcgcgc    67860
tggcccgccg cgctcgccaa ggtcctcgcc cggtacgagc cgggcgcggc tgcgggctcg    67920
ggcgcggcgg cgggcttggg cgcggcggcg ggctcgggtg tggcggcggg ctccagcgcc    67980
gcctcgggct ccggcgccgc cgcggtcccc ggcccggtgg cgctggcctt cgacggcgac    68040
ctcgccccgc cggacgagta cgtgcccttc ctggcgccca cccacccgct caccgtgcag    68100
gtctcccgga cgcccggcgg cggcaccgag ctgcggtgcc gccaccggct cggcgcggtc    68160
tcgccggccg ccgccgaagc gttcgcccgg atgctggccg cggcacacgg cgagccgccg    68220
gccgatgacg gcgcgaccgc cgagcccacg ccgccggccg cacccgcacc cgcacccgca    68280
cctgcgcccg cgccgccggc tgcggctcgc acgctgaccg ggctcttcgc cgagcaggtc    68340
gccgctcgtc ccacgccgt cgccgtctcg gacgatcggg gtcggcacac ctaccgcgag    68400
ctcgacgagt ggtccggccg gctggcccgg gggctgcgga aggccggcgt gcgcgacggc    68460
gacgcggtcg gcgtctgcct cgaccgctcg gccgagctcg tcgccgtgct cctcgcggtc    68520
ctcaaggccg gcgccgccta tgtgccgctc gacgcggcgt accggccga ccgcatcgcc    68580
tacaccgtcg gcgacgccgg cctcgcggtc gtggtcacca cctcggcgga ctttcccgac    68640
gtggacggtg tgcggctgct cgcgccggag agcctcgccg aggccggcga cgacccgggc    68700
atcccgctcg ccaccccggc cggcccggag cggccggcct atgtcatcta cacgtccggt    68760
tccacgggcc ggcccaaggg cgtggtcgtc ccgcacgcca acgtgtccgc gctgctcgac    68820
gccacgcgcg aggagtacgc gctcggcccc ggcgacgtgt ggaccttctt ccactcggcc    68880
gccttcgact tctccgtctg ggagatctgg ggctgcctgc tcaccggcgg ccacctcgtc    68940
gtcgtcccgt actgggtgtc ccgctcgccg gagcagttcc acgacctgct cgccgagcgc    69000
ggcgtcaccg tgctcaacca gacgccgtcc agcttcacgc agctcgtggc cgccgaccgc    69060
ggggcggagc gcgacctcgc cgtacgcctg gtgattttcg gtggtgagcc gctcgacgcc    69120
```

-continued

```
cggacggtgc tgccctggct ggaccgccgt cccgaggcgc gctgccggct ggtcaacatg    69180
ttcggcatca ccgagaccac cgtgcacgtc acggcggtcg acgtcacgcg cgcggccgcg    69240
ctcgccggct cccggtcggt cggccgcccg ctgcccggct gggccgtgcg cgtgctcgac    69300
gagcagcgcc gcgaggtgcc gccgggcgtg ccgggcgaga tctacgtggg cggcgccggc    69360
gtggcgatcg gctacctcaa ccgcccggag ctgaccgccg agcggttcgt caccggcccg    69420
gacggccggc gctggtaccg ctccggcgac cgcgccggc tgctgcccga cggcaccctg    69480
gaacacctgg gccggctcga cgaccaggtc aagctgcgcg gcttccggat cgagctggac    69540
gagatccggg gcgtgctcac cgagtgcgcc ggggtggcgg cggccgcggt cgtcatccgg    69600
cgctccactc cggacgatcc ggcgaccgcg cggctcgacg cgtacgtggt cgccgaggcc    69660
ggcgccacgc cgccggtggc cgagcacgcg gcccggatgc tgccggccta catgtgcccg    69720
gcgaccttca cgttcctgga cgcgctgccg atgacgccga acggcaaggt ggacaaggcc    69780
gccctgcccg agcccgcgcg cccggccgcc gacgctgcgg cgacgccggc cggcccgggt    69840
gaggacgggc tcgcgggcga cctggccgac gtgtggcagc aggtcttcgg ctgcccggtg    69900
accgtctcgg acaacttctt cgacctcggc ggcaactcgc tgctcgccgt gcggatggcg    69960
gcgctgatgc gccgccgcgg cctgccccgg ctgcatccgc gcaccctcta cctgcacccc    70020
accgtgcgcg gcctcgcgga cgcgttcgcc tcggcctgac agtcccctcg ccccctcgag    70080
aagtacggga gaagcaccat gcgaaacctg cgtcggacca ccggcatcgg actgctcgcg    70140
ctgctgagcg tggcggcgtg cagctcgacc cccgcggcga gcgagccccc gccgtccgcg    70200
gcgccgccct cggccgtgac ggccaccggc ccggcggccg agaaggccgt caagtcgggc    70260
acccagacct atcaccaggc gctcgacgcc ttcgtcgcgg cgagcaacaa gggcacgacc    70320
gacaccaccg agatcggcaa gtacgcgtcc ggccgggcgc tgatgacctt ccagggcatc    70380
ctcgcctcct accagcagca gggcgtgcac accagcggcg agccgcgcat cgacgagccg    70440
gtcgtcaccg ggctcacccc gccggccgac cccaccggcg tccagctgcg cggctgcatc    70500
gacatcagcg cctggccgct gacgaaggcc gacgggaccc cggccgacaa ggtgggcggg    70560
cagcagggca gcgggcccag cgcgatcctg gcgaacgtcg cccgctcggg tgccacctgg    70620
caggtgaccg agctgccat ccagggaccc tgcgcggcgt gaccgtccgg cgatggctac    70680
cggccgggct cacggtcctg gcgttcgccg ccggcttctg gcagaagctg ccctgccagg    70740
ccgctggctg gccggacgac accgcgacgc tgttcggccg ctactgctac agcgacgtgc    70800
cgattctctt ccgggagcgc ggccttttcg acggcatttt cccgtacgag tccgggccgg    70860
gcgcccagcc gctggagtac ccggtcctca ccggctacct gatggacgcc acggccggc    70920 tcgttcgcgc gatcctgccc ggcgcggacg tggccgtcgc ctcccgggcg tacttcctca    70980
cgacggtcct ggtgctgctc gccctcgcgg tcctgaccgt gtgggcgacc ggtgcggtgc    71040
tgcgccgcac cggcgggcgg ccgggcgacg cgctgctggt cgccgccgca ccgtgctga    71100 tcctggccgg cacggtgaac tgggacctgc tcgcggtcgc ggcggcggtg ctcgcgatcc    71160
tcgcctggga acgggaccgc ccgctgctgg ccggcgtgct gatcgggctg gcacggcgg    71220 ccaagctgtt cccgctggtg ctgctcggcc cggtgctgct gctctgcctc cggcagcggc    71280
ggatgcggcg gttcgcccgc gtggccgccg gtgccgccgg gcctggctt ctggtcaacc    71340 tgccggtggt cgcgctgcaa ccggacggct ggatggagtt ctggcggttc aacgccgggc    71400
gcggggccga gttcggtcg ctctggttcg cgctggacgg gctcggcctg cacatgccgg    71460
cggtgaacgc cgtcgccctg gcgacgttcg gcgtgctgct ggccgggatc gcggtgctgg    71520
```

```
ctctgcggtc gcgccggccg ccggacctgg cgcaactcgc ctgcctggcc gtcggcgcgt   71580
tcctgctgac caacaaggtc tactcgccgc agtacgcgct ctggctcctg ccgctcgtgg   71640
tgatcgcccg tgggcgggtc ccgcggtggc cggtggtgcg cgactgggcc gtctggcagg   71700
ccgccgaggt gctctactgg ctcgcggtgt ggagctggct cgccggttcg ctgaccgacg   71760
agcggcagta cgcctgggca accgtcctgc gcgtgctcgc cacggcgtac gtctgtggtc   71820
aggtggtgtg ggacgtgctc gccgcccctc gcccgcaccg gccggcgccg ccccggcgg    71880
tcgccgagcc ggcccacccg ggctgacccg ggcaacgaga gatcccctcg ccgccggcgg   71940
cgagggatc tctgttcgtg tgctcagtcg gcggcgaccc acgtgaggcc gttgccggaa    72000
ggggtcagcc cgccctcgaa cagcggctgc tcctgcgtgc cctccgggcc caggatcgcg   72060
ccggcctgga tctgcgagcc ttcgaacatg gcctgcgcca cgacgctcga cccgcgcagg   72120
aagccggtgc cgccctcctc gaggccggcc accgcctggc ccagctccgc ggtctgccgg   72180
gagtgccgcc gcaccagctc ggtggagccg gtcagcgcgt cctcgccgga ggcgatgccg   72240
ccgaccaact cggtgaacga ctccatggcc ggtgcgctgc tctcggtcac cttgcgggcg   72300
gcccagaagt acgagctctc atcgacgtgc atgtcgtaga agctcaccag gaagtcgtgg   72360
aagacgccga actcgcgccg gtagcgctgc tcgaactcgg tgaaggcgcg gtcctcgtcc   72420
accgtgccgg ccagcacgct gttgatggag cgggccgcga gcaggccgct gtaggtcgcc   72480
aggtgcacgc cggaggagaa caccgggtcg atgaagcagg cggcgtcgcc gaccaggcac   72540
atgcccggcc gccagtacga ggtgctggag taggagtagt ccttgcggac ccggatctgg   72600
ccgtagtcgc cctcggtgac ccgggtggcg tcaccgagga agtcggcgat catcgggcac   72660
tcggcgatca gctcgaacag cgccttctcc tggtcgccct gcaccttgtg tgccatctcc   72720
cggcggacca ccgcgccgac gctggtcagc gtctcgctga gcgggatgta ccagaaccag   72780
ccggagccga aggcgacgca gaggatgttg ccggagttcg gcgcgggcag ccgccggccg   72840
ttctcgaagt agccgaagag cgcgaggttg cggaagaacg gcgagtattc gcgggtgccg   72900
ccgaccgtcg tgtgcagggt gctgcggttg cccgaggcgt cgacgacgaa gcgcgccagc   72960
gcggtgcggg tctgcccgtc ctgggtgaaa cggacgccgc ggacccgctc gtcgtcggcg   73020
atcgcctcgg tcaccgggtg gttctcccgg acgtcgacgc ccagccggcg cgcgttctcc   73080
agcaggatct ggtcgaaccg gcggcgctcc acctggaacg cgtgcgaggt cggcccggcc   73140
atccggggcg aggtggcgaa ggtgaacgtc cacggctcgg tactggtgcc ccacttgaac   73200
gtgccgccgt gcttgcgcat gaacccggcc ttggcgatct cgtcgccgac cccgagcagg   73260
ttgcagacac cgtgcacggt ggacggcagc agcgattcgc cgatctggta ccgcgggaac   73320
ttctcccgct ccagcagcag caccttggcg ccctgcttgg cggtcagcgc cgcggccgtg   73380
gaaccgcccg gcccgccgcc gaccacgatg acatcgaact cttccggttg agcagccacg   73440
aatcctcctc agcgaccatc tgagctgcat gatggttgcc gcgggccgct gtgcgccacg   73500
tgtccgccca cccgcggcgt tcgaccgcgg atgtcgccgg tcgcacgctc gcgcgggccg   73560
ggtcagctcc cctcgaccag ccggttctcc caggcccagg ccgccacgcc gacccggttg   73620
cgtacgccca atttggactg gatcgtggag gcgtgcccct tcaccgtgct cagcgagatg   73680
aagagatcgg ccgcgatctc ctggttcgtg cggccgcggg cgatcgcccg cgccacctcg   73740
agctcgcggt cggagagggg aatgggctcg gagccggccg gcgccgccga ggcgttcagg   73800
tggttcagca gccgcacggt gaccgacggc gagaccagcg cgtcgccctt gtgcgccgcc   73860
cggacggcct ccaccagcag tgtcgggccg gcgtccttga ggatgaagcc gaccgccccg   73920
```

-continued

```
ccgcgtagcg cgccgtagac gtattcgtcc gagtcgaacg tggtgaccac gatgacccgc    73980
agaggattga ccacgccggg gccggccagc gagcgggtca cctcgatgcc gtcgatgcgg    74040
ggcatgcgga tgtccaccag gcacacgtcc ggccgcagct tgcgcgcctg tgcgaccgcg    74100
tccacgccgt cgacggcctc ggccaccacc tcgatgtcgg gctcgtcctc gaggatcagg    74160
cgcaggccac tgcggatcat cgcctgatcg tcggcgatca ggacacggat cgtcatcgtc    74220
gctccctcgg tgggttgggc agggtggccg cgaccgacca gccgccgccg ggacggggc    74280 ccgtgctcag cgtgccgccg aggctctcca cccgctctcg catgccgacc agaccgtacc    74340
cgccgcggtg gtgcaaccgc ggtggggccg ccgccgcgtc gttggtgacc tcgaccctga    74400
tctcgtcggc ctgctccacg gtcacggtca cggtcacgtt gggtgcgtgc ggcgcgtgcc    74460
gggcgacgtt ggtgagcgcc tcgcggacga tccggtagac cgtggtggtc acctcgatcg    74520
gccactgctt catgccgtcg ggagtggtga ccgcaccgg gccgccctgc cgggagaagc    74580
gctcgacaag cgtgctcagc tcctcgggct ccggtgccga cggtgggccg tcgtcggcgt    74640
cgcgcagcag gcccacgacc cggcgcatgg ccgcgagggc ctcggtgccg ccgtttcga    74700 tgaccgccag ccgctcgggc acgcgccggg cgtcgcgccg cgcgagcacc tgggcggcct    74760
gggtctgcag gatcatgccg gtgatgtggt gcgcgaccac gtcgtgcagc tcccgggcca    74820
gttcgaggcg ttcctcctgg cggatgcgct cggcgttcgc gcgggcccgg ccgtccaccg    74880
tccgcagcga caacccggtg gccgtgccgc ccagccaggt gaggatgttc agccaggtca    74940
ccggcgccgg gccggcgtcc caggtcgcgg cggccacctg gctgagggcg accacgccga    75000
gggcggcgcc gcccacggcg aaggcgggga tcgtgggtgc ggcccgcacc gccgagccgg    75060
tgaggacggc cagggccagc gccatggccg ggccgggctc ggccggcatg tgcagcacgg    75120
ccgccgtgac gacggcgccc gccgcgatcg tgagcccggc cgcggcgcac ggcaccgggc    75180
cgcgccgccg gatcagggcg agcaggcaga cgagcgtcgc ggccgcgccg ccgatcaacc    75240
agtaggccag gccccagctc tgcgcgacgg cgacggcctc gacgacgacg gcggccacga    75300
agaggacggc cagccccgcg tcggccacca tggtggtcgt cctgtccgcc gtccgcacgg    75360
atccaagggt acggatgccg gcgccgtcgc cggcggcggg accggttgcg gccgcgatgt    75420
tcatgccgcc caaggatagg ggcgaatcgg gcgccgccaa ggggtcaaaa gtagggtgac    75480
gcccgaaatc aaccccttctt agggcggtac cggtccgcgg ggcgctcccc gacgatgaag    75540
gccatgtctc acgagcgctc cactcccgtt ctgcaggccg agggcctgac gaaacgctac    75600
ggccggcgga gggccctgac cgactgcacg ctctccgttc cctccggacg ggtgatcgcg    75660
ctggtcggac cgcgcggctc gggcaagtcc acactgctgc agctgtgctg cgggatggtc    75720
gcgccgagcc ggggccggat ccgggttctg ggggagcgcc cggacgcggg cgcggcgcac    75780
ctggcgcggg tgggatacgt accgcgggag ccggcggtgt acggctcgtt cacggtggaa    75840
gaccacctca cgatgggcgc gcggctcaat ccgcggtggg accggcggct ggccgaccgg    75900
cgcatcgcct cggccggcat tccgcgtacc cggcgcgcgg accggctctc cgccggccag    75960 cggggccgagc tggcgttgac cctggccggc ggcaagcgcc cggagctgct cgtgctcgac    76020
gagcccggcg cggtgctgga tgcgccggcc ccgcctcgt tcctgcgcgg cgtgctcgac    76080
ttcgtcgccg agatcgacgc gagcgtgctg atctccggtc accgtccgg agaggtggag    76140 cggctctgcg accacctgat cgtgctgtcc gactcccggg tgctcgtcgc cggcgacgtc    76200
cgggacctgc tcgcccggca ccaccgcatc atcgcgccgc gcggcgagct ggaccgcctg    76260
ccgccgggga tggagcccat ctgggtggag gacttcggct cgtacagcgg gggagtggtg    76320
```

```
cgggccgagg tggacctgcc ccggcggccg tggacggtgg agcgggtcga gctcgaggag    76380
ctggtgctca gctatctgag ccgggcctcg ggcgcgcccg cgctcgccgg ctgcctgatc    76440
gcgcccggtc agccggggag ctgacgggcg ctcaggtcca gcagccggct ggtgcgtacc    76500
cggtcggcgg ccatctcgaa gagctggtgc tccacgtgct cgcgctcggc cacgctcagc    76560
acggcctcgc cgccgagccg gccggccagc ccgtccagga cggccagcag cgccggccgg    76620
tggagccggc caccggcgcg ccacacaccg agggcgcagg ccgcggccag cagcacggtg    76680
taccggtcgg ccagcgcgaa ggcggccggg ttggcgtcga tcgtgatgtc ggccggcccc    76740
agctcccggc aggcgtcccg caggccggtc agctcccggt ggaaccgctc ggcgaaccgg    76800
ccgaccgggc cctcgtcgtg ccacgagtcg tgcaggacgc cggccagcgg gtcgccacgc    76860
atgccgctga ccagccggga gaagtccaac ggggacagct cgccgccgag ggtgaacacg    76920
ttgtccggcg gcggctcctc ggccgtccac gaccggcggg ccagccgggg caggtgcggc    76980
agcagcatca ccaggcaggc cgcgcgggac acgtgcgcga aggaggcggg cgcggcgtcg    77040
cggaccagct tctggaacat cgcgtacggg ccctgccgca gataaccctg cgcgcccagc    77100
accgagcgca gatcgtcgat cgcgtccagc acgatctgcg cggtcaggta cttcacggcg    77160
ggcgcgtaac cggccgtggc ctccggcagc aggtgcagcg cccgcaggcc cacgcccgag    77220
aagacgtcga cggtgagcag ggcagcatag gcgcgcgcga tggtggtgcg cacgtacggc    77280
aggtcggcga cggcggcccc gtacagccgg cgctccatcg ccatctcggt ggccagccgc    77340
accgcgctgt ccagcgggcc caccagcagg gccggcgaca ccatccgggt gacctgatag    77400
gcccgcagcg ccacctcgat gccgtgtccc tgttcgccca acagcgcgga ggacggcacc    77460
gggcagtcgt cgaagaccag cccgcccagg tcgatgccgc gcatcccgct gcccggatac    77520
cgcgggcggt ccaccgcccg cgcggccggc agctcgtcgc gcaccagcag gaactggctg    77580
tgcgaccggc tgccgcgcgc ctcgccggtg cgggcgaaca gcaccatcgc ctcggcccgg    77640
cgcaggttcg tcacgatctc cttgtgcccg gacagcaccc atccgccgcc ggccgggcgg    77700
gccgcgcact cggcggcgga gaagtcggtg ccgtgcgcga gctcgtggaa cgcggccgcg    77760
atgcgcttgt tggccagcag caggccggcc gccggcgcc gttgctcctc gttgccggcg    77820
caccacacgt tcaccgaggc gatgagcgag ctgaagccgt agcccagccc caggcacggg    77880
tcgcgccgcc agaccgcgcg cagcacctcg gccagccggt cggcgcgggc cagccggccg    77940
ccgtacgcca ccggcacgaa ctcggcgttg agctgatagc ggtcgagcag ccgctcgccc    78000
tcggccagca tctcctgccg ctcgtcgcg gcgagcacgc ccgcatagcc gaccgggttg    78060
ccggggtcgc gggcgtcgcc gagcagcttc tcgagcgccg cggcggtcac cggccgtcct    78120
ccgcccggac ggtgccggcg gcggccgcca gggccgtgcc gaacgggtc accggttcac    78180 cggtgcgtgc ggccgccgcg acccgcgcgg ccagcagccg gtcggcgccg tcgtcgtgcg    78240
ggccgggatc gggcgccggc gcccgcagca cccgggccag ctcccggcgc acggcacgca    78300
gcgcggccag cacccacagg ccgtccgccc agagcgggtc cgcggtgtgc cggccctccg    78360
ccgaggtcca cagcagcagg cacgccgcgc ccgcgtagca ccactcgtag gcggcggcca    78420
gctcgtggcc caccatggac ggcgggccg agggcccgag ctcggtcatc tgcccgcaga    78480
tccgccgcgc ctcgccggcc agcgcggccg cgtgccgggc cagccccgcc gggccacccc    78540
ggacggcggc cgacacggcg agcgccggca gcgcctgcac caccgagcac ccgtggcggg    78600
agagcagggt cagggcgccg cggtccagcg gcggtggcgg ctgaccggcc gcgctcgcct    78660
cggccagccc ctcggcggag acggcgccgg ccgcgaagcc ggccgcgagc cgcgggaact    78720
```

-continued

```
ggtgcgccag cgccgtgcgg acgaccgggg tgctgccgtc gaacaccgcg accacgtggt    78780
ggtcgcgcac cagcttgggg aacatgccgt gctcgtactc gtcacgcagg aaggaccgcg    78840
agccgagcag ttcggccagc tcacgcagca cgccggtccac caccgtgggc acgtacgcct   78900
tgacgatcgc cgacgtcacg ctcatctcgg ccgtgaggct gtgcaccgag cgcgtgccga    78960
cgacggcggt cgcctcggcc gcggcgagca gggcggcgca gcgcgccaga atcccggccg    79020
ggtggccccg gtcgagcagc ggccgccgca tgatcatccg ctgggccacg aagcgggcgg    79080
tcagccgcag cgcgcggtcg ccggcgccca gcgacagccc ggcgcacatg gtgcgggtca    79140
gctgcagcga gcgcagcacc gtctccagcc cgcttccggc ccgcccgagc agggccgtgc    79200
cgggcaggcc ggcgtcctcg aacgcgatgc cggagatgtc gatgccccgc accccgtgcg    79260
tggccacctt gggccggggc agccacgtgc cgggggcgag cgcctccttg tcgaccagga    79320
acaggctctg cccgcgggcg tcgccggccc ggccggtgcg ggccagcacg gtgaggtatc    79380
gggcccgggt cgcgttgttg atcgccact  tgagaccgcg cagccggtag ccggcgtcgt    79440
ggggcagggc cgtggtcgtg ccgtgcagca ggtcggcgcc gtggtcgggc tcggagagcg    79500
cccatgcgac cggggtgccg gcgagcaccg cggcggcaag cgtcgcgcgc tggccgtcgt    79560
caccggccag ccagaccggc gccgacccga ggtaggtctt gccgtgcgcg acggccgcgc    79620
tcaggtcgcg ccgggcgacc gcacgccaca ggtgcaggag ccgctcgtgg tcgccggggg    79680
caccgcccca ctccggcggt acgtaccagg attgcagacc gaaggagttc agccggtcgt    79740
gcagccgggc cgggaactcc tcggcgatgt cgcgggcggc cgtctcggcg tcccatgcgt    79800
cctcggggcc gagcaggtcg tccaggcgca cctccgcggg tggcgccagc gggcgtacgg    79860
tcatcggccc gcgcccgcct gcaccggccg cagcgccggc tcgagctcgg cgtgcagcgc    79920
cgtgatgccg ccggccagga accgctcgcg gaccgcggtc cggcggatct tgccgctcgt    79980
ggtccggcgc accgtgccgc gccgcaccag cagcacgttg cgtaccggca cgccaaggga   80040
gacggtgagc cggcggctga cggcgctcgc caccgcggc  agctcgtcga gcggcgtgcg    80100
cggatgcacc tcctgcacca gcacgatccg ctcgtcgggc gccggcaccc cgaacgccgc    80160
cccgatctgg tggtccaccg cgtcgtgcgc ggccgggcc  tcccgctcga ggtcgtgcgg    80220
ggccaggttg cggccgtgca cgatgagcag ctccttgagg cgtccggtga ggaacagctc    80280
gcctccggtc agcgcaccca ggtcacccgt tcgcacccag ccgccgtcct ggccgtcgcc    80340
cgcgggcctg gcgtcgaaga tgccggggtt gagctcggtc ctgccccagt agccggcgcc    80400
cgcgccgggc ccgcgcagcc agatctcgcc gacccggccc tcgggcagcg gccgtagccc    80460
gtccgggtcg acgatgagca cctcgaagtc gggcacccgg ccgacacccg gtatctcccg    80520
ggccgcggcg gggtcggccg ggcgcagggc cggcgacgcg cgtcctcca  gcgcgcgagg    80580
gtcggcggga agaaagaccg ccggcgcctc gaagaccttc gtcgacacgt acgcggtgaa    80640
ctcggccatg ccgtagcagg ggttcaccgc gtgggtgtgc aggccgaagg gggcgaagcg    80700
ctcggtgaac gcccggacgg tggccgggtt gaccggctcc gatccgttgt agagcgtgcg    80760
gatgcgggac aggtcgaggc cggcgatctg ctcgtcccgc acggcgcgca cgcacaggtc    80820
gtacgcgaag ttgggcgcgg cggagatggt gacccggtag cggtccatca tccgcagcca    80880
gtccgccggc cggcggacga aggccgtcgg cgacatcagc acgacgccgg cgccgttcag    80940
caggcccgcg gtgagcatgg cgaacaggcc catgtcgtgg tgcagcggca gccagctgcc    81000
gaacacgtcg tcgctgttgt gcccgctgct gcggtcgaac gcgcggaggt tggccagcac    81060
ggcccggtgg ctgagcatca cgcccttggg cgagccggtg gagcccgagc tgtactgcag    81120
```

-continued

```
gacggccagc gagtccggcc ggggcccgcg gggcggncgg atcgcttccg ccgcgagggg   81180
cggaagcgca ccgaccggca ggccggacag gccgcgctcg cgcaggacgg cggtgagcgg   81240
cgccgcgtcg tcggcgttga cgacggccag ggcgggggag cagtcggccg cgatgccgac   81300
ggtgcgctcg gaggcgccgg acgaccctcc gggcgggggc gccggcacgg cgaccaggcc   81360
ggcgtagagg cacgccaggt agagctcgac gaactcggcg ccggtgggca gggcgatgag   81420
gatgcgctcc ccgccggga accgggcggc gagccaggcc gccccgcgccg cggcgcgcg   81480 gtcgagctcg gcgtacgtga gggtgacggg ctcggcgtcc gggtcgccgg ggagcaccac   81540
gagggcgggc tcgccggggc gcgcgatcgc ctgcgcccgg aaggcgtcgg gaacggtggg   81600
ttgggtggcg gcgtcgatga ccatggcaac tgcctctccg gaagggtccg ccagggccgc   81660
gacgccgccg gcgggtcgcg ctcagctctg cggttgcttc tgcttctcca tcgccgcgat   81720
caggctcttg ggccgcatgt cggtccagga cttctcgatg tagtcgaggc agtcctgccg   81780
tccgccctcg ccgaacaccg tcgtccagcc gtcgggcacg tcggcgaaga ccggccagag   81840
tgagtgctgt ccctcgtcgt tgaccaggac caggtagttg gcgtcgggat cttcaaacgg   81900
attgggcaca gcgtcgcctc catcgaacgg atcggatgac ggtggtcagg agccgcacgg   81960
ccggcggttg gcgccaccgc cagcactatg gccgagactc ggaacggccg acaagcgtgc   82020
acgggctgtg cgactgcgcc gccggcgcgg ttggacagcg gtcagagcgg gccgcggccg   82080
gcccgcagga gcatgagcgc gatggtcgtg ccatcctcgc cgagcgcggc gcggaagcgc   82140
tggatgacct cctgctcccg ggagagcacc acccgggttc cgccggaggc cagccggatg   82200
gagccgatct tctgcgagat cgaggccctt tcctgccaca gccgcatgat ggcggcgtcg   82260
atctcgtcga tgcggttccg caggaccggg atgtccgcct ccggcacggc ctcgccgtgc   82320
tcggccggcg gtgcgcccgg cgccacgacc tgaatgacgt tctccaccat cgccgtctcc   82380
tgtgagcttg tcggtggtga ctcggggtgg gcagccggga cgttaacacc gccgcgcggc   82440
cgtccgggcg cgtgcgactg aggccgtccg tcagtcgaac gcacgctttc gtgcgcactg   82500
cccaaccagg ccgaacggct cctacagtcg ccgtcgatcg cagtcggtgt aacaccgtcg   82560
aaacgccgga ggatgccttg gccgccgtgg atgtcccgag ggtgcgcccg cccggtgccg   82620
cgcccgcgcc gcggcgtcgc cggtggcggt tctggcagtc gccggacggc cagccggcgt   82680
gggcccgccc ggcgctgctg ggcatcgcgg cgctggcggc cgtgctgtac acggcgaacc   82740
tcgcccgcag cggctacccc atgtactacg ccgtggcggt gaagagcatg tcggtgagct   82800
ggccggcgtt ctggaccggc gcgttcgacc cggccgcctc gatcacgatc gacaagctcg   82860
ccggcgcctt cgtcccgcag gcgctctccg cccgcgtctt cggcttccac cagtggtccc   82920
tggccctgcc gcaggccgtc gagggggtca tcgccgtgct ggtcctctac cggcggtgc   82980 ggcgctggca cgggcccggc gccgggctgg ccgcggccgg gctgttcgcc acgacgccga   83040
tcgtgtcctc gatgttcggc cactccatgg aggacggtgc gctgacgctc tgcctggtgc   83100
tcgcggccga cgcgttcggc gcggcggtga cccgcggcag cccggcccgg ctggcgctcg   83160
cgggcgcctg gatcgggctc ggcttccagg cgaagatgat gcaggcgtgg ctggtgctgc   83220
cggccctggt cgtcacctat ctcgccggcg caccggtgcg ggcgcgggcc cgggtcgtcc   83280
atgtcgcggc ggcggtggcg gcgacccctgg cggtctcgct gctctgggtg ctggcgctga   83340
ccctgctgcc cggctcgcac cggccgtggg cggacggcac cacctccggc aacgccttcg   83400
ccatggtgtt cggctacaac ggtttcgacc gggccggcat ccacgtgccg ggcgcgctga   83460
cgaccggctt caccgacggc ggggccgcgg ccggcggttc ctggacggcg cttgccgcgg   83520
```

```
atcgcctcgc cacccagatc gggtggtggt acccgctggc gctgaccggc ctgctgctcg   83580
gcctggcccg gtggcgcacc gcgcgcgccg gcctcctgtt ctggggactg tggttgctga   83640
cggccgcggt ggtgctcagc cggatcacca ttcagcacaa cgcctacctg gccgtgctgg   83700
ccccgccgct ggcggcgctc gcggcggccg gcgcggtgca gctctggcgc acgcaccgcg   83760
acggcacggc gccctggctg ctgcccgcgg tcgtggtcgt ccaggccggc tggaccctgt   83820
ggctggccac ccgctatccc tcgttcctgg ccgggctgac gtggacggcg ccgatcgccg   83880
ccgtcctggc cgtggtggtg ctggccgcgc ggccgacggc ccggcggccg gccgtcgtcg   83940
tggtggtcgc cggcctgctg gcggtgccgg tcgcgtgggg cgcctcggtg ctgaacccgc   84000
gatacgccgg cacgtcgttc gaggccggtg cggggccgag cgggccggtg ggcgtgcggc   84060
tcgacgacga caccaccgac cggctgacgc cgggcctgcg caggctcgac gactatctcg   84120
cggcccaccg cgacggccgc acctacctgg cggccacgtc ctcgtggcgc acggccggcc   84180
ggctcatcgt cccgaccggg cactcctacc tgccgctcgg cggcttcagc ggagcggcgc   84240
cgttcccgtc gctggccggc gtgcagcgcc tggtccgcga cggcgagctg cgctacttcg   84300
tcctcggcgg cccggagggc ctcggcgcg aggccaccga ggcgtaccgc atcaccggct   84360
gggtcctcga gacgtgcgcc accgtgccgc cggccgagca cggcgccgat ccggatctca   84420
cggtcctgcg atgcgacaag ccctgacaac cgacgtagca cgacgaaccc gggaggaaca   84480
gtggacaacg gcaccttcac cgatctgcgc atcgaccaca tcgaattcgc ggtcgcggac   84540
gtcgaatccg ccagcgcccc gtttacggag ggctacggct tctcggtgta cggcgggacc   84600
ggcgacgcgc acgcgccggt gcggcgggtg gcgctgggac gcgacgacat ccggctcgtg   84660
ctgaccgcgg cgcccggcgg ggaccatccg gccatggcct acgtcgagca gcacggcgac   84720
ggtgtgtcgg ccatcgcgct cagcacgaga gacgcccacg cggcgttcac cgaggcggtg   84780
cggcgaggcg ccgtcggggt atccgccccg gtcaccggca acggcgtgac cgtcgcgacc   84840
atccgcggct tcggtgacgt cctgcacacc ttcgtcgagc gggcgccggg cgcggacccc   84900
cggaccctgc ccggcctgga gctgcggcgg cccagcccca cccggttcga ctcgggcctg   84960
caggcgatcg accacatcgc cgtctgcctc gagccgggga ccctcgaccc gaccgtcgac   85020
ttctaccgcg acgtcctcga cttcgagatg atcttcgagg agcgcatcct ggtgggccgg   85080
caggcgatgg actccaaggt ggtgcagagc cgctcgggcg gtgtgacgct caccctcatc   85140
gagcccgaca cgtcgctcga gcagggccag atcgacacct tcctgaagaa ccacggcggg   85200
ccgggcgtgc agcacctcgc gttcatcacc gacgacgtgt tgcgctcggt cggccggatg   85260
tccgagcacg gcgtcgagtt cctgcacacc ccggactcgt actacggccg gctaccgggg   85320
cgcatcccgc aggccgggca cccgatccag gcgctgcgcg acctgaacgt gctcgtcgac   85380
caggaccacg acgggcagct gttccagatc ttcacgaagt cggtgcaccc ccgcgggacg   85440
atcttcatgg aggtgatcga gcgaatgggc gctcgcagct cggcagcgg caacatcaag   85500
gcgctgtacg aggcggtcga gctcgacatg tccaagcaga gcgcctgagc gccgatgga   85560
gtcgccggca acccacgcgg aactggtgat cgggaccgtc ctgctcgaca tcgcgctggt   85620
gctcgcggcc ggtgccctgc tcggccggtg ggtgcggcgg ctgcgccagc ccgcggtgat   85680
cggggagatc ctcgcgggca tcgcgctcgg cccgagcctg ctcggcctgc tgccgggcaa   85740
cccgacggcc tggctcttcc cggccgaggc ccggccgtac ctgtccgcgg tggcccagat   85800
cggcctggcc ctgttcacgt tcctgatcgg ctggagttc aacccggcga ctctggcccg   85860
gcaccgcggc accgccgccg cggtgtcgat cggctccatc gcggtctcgt tcggcctcgg   85920
```

```
catcgcgctg gccacggtgc tgcatccccg gcacgacacg accggggggcg ggaaggtcgg   85980
cttcaccgag ttcgcgctct tcctgggcgt ggccatgtcg atcaccgcgt tcccggtgct   86040
ggcccggatc ctcgcggagc ggcgcctcac cggcacgcgg gtgggcagca tcgcgctggt   86100
cagcgccgcg atcgacgacg tggtggcctg gtgcctgctg gccctggtga cggccatcgc   86160
cacggcgagc gggccggtcc agctcgtacg catcctcgcc ctgctggccg tcttcctggt   86220
ggtgctggtg acggtcgtac ggccgctgct ggtcttgctg gcgcggcggc cgtccgcgtc   86280
gtatcttctg gtggcggtgg tcgcggtcgt gctgctctcg gcatatgcga ccacctggat   86340
cggcctgcac gcgatcttcg gcgcgttctg cgccggcctg gtcatgcccc gggagccggc   86400
ggcggcgctg cgtgagcggg tgcggcagcc gctggaacac gtaagcgtgg tgctgctgcc   86460
ggtgttcttc atcgtcaccg gcctcggcgt cgacatcggc gcgctcaccg cggcgaacat   86520
cctcgaactc gccgcgatca tcgtgatcgc ctgcgccggc aagctggccg gcgcgatcgt   86580
gccggcggtg tcgctcggca tgtcgtggcg ggacgccaga accctcggcc tgctcgtcaa   86640
cacgcgcggc ctgaccgagc tcgtcgtgct caacgtcggt ctgcagctcg ccgtgctgga   86700
cggccagatg ttcacgatga tggtgctgat ggcgctggtg acgaccgccc ttgcgggccc   86760
gctgatcgga tcggcccgga caccggcggc cggcgcaccg gctcaggcgc tcccggccga   86820
accgcggacg cggcgggcgg cgtaggcccg gcgcatcttg atgtagttgc cgcatccggc   86880
catcgagcac cagcgccgcg cctggttgcg ggaggcgtcg tagtaggccc accggcaggt   86940
gtcccggtcg cagaccttca gccgggtcca cacctgcagc tcggcgcact gccggaccgc   87000
gtcgatcagc ccgccaggg cacggtcgaa cggcgtgccc ccggccggca gcaggcgcgg   87060
cgcgccgccg gccaggctca gccgcacggg aacggcggcc aggatctcct ccaggcggcg   87120
cagcgcggcc gggtcggcgg gatggccggc gtggcccagc agcacctggc gaaggccctc   87180
acgaagcgcg acggcccgtg ccaggtcggc cgggcgcacc ctcgcgccgg gggcgagcag   87240
gctttccccg gccagccacg cccgaagggc gtccgggtg ctcagcgact cgtcgtcgac   87300
ctgaggctca taggtgttga cgaaatcgcg caacagccgg gcaggggatg gcactgcggc   87360
ctcgtcactc accgttgacc tccttggtgg cgacagcgta gcgccttgac aggcgcgcga   87420
accgcctgga acgatccgct ttcacaccag caaaactact ttggtggtgt gaagaggcgc   87480
gaaggagcgg atcgtggcca ccacgctgag ggacgtggca cggctcgccc gggtgtcggt   87540
gaagacggtc tccaacgtcg tcaacgacca cccgcacgtc agcgacgacg tgcgccgccg   87600
ggtcgagacg gcgatccggc agctgggcta ccgtcccaac ctcgtcgccc gcgccctgcg   87660
cagcggccgc ggcagcggac tgctcgccct ggcgatgccg ggcgccggcg cgccgcagtc   87720
gcccgccctg atcgaggaga tcatccgcg ggcggccccg ctcggattcc gggtcctcat   87780
cgagccgctc gagtcgtcac ggccgaggcc gccggccccc ggcgtcgacg cccggctgct   87840
gaacgcggag cgcgccgggccc cgagctggt ggacgcccag gcggccacgg gcaccccgct   87900
ggtgctgctg accggcaccc ccgatccgcg atacgactgc gtcggccggg acgccgcccg   87960
cgcggccgag gacgcggtgg accacctgcg ccgtctcggc cggcgccgcg tcgccaccat   88020
cggcggctcg ctctccaccg gtccggccgg ctccggctcc gacttcggtt ccggctccgg   88080
ttccggctcc ggctccggtt ccggctccgg ctcgggctcc ggctcgggct cgggctccgg   88140
ctcgggctcc ggcttcggct cggcgctccgg cttcggctcg ggctccgcgg agggctaccg   88200
ggccgcacgg cagttgttag gccacgaaga tcgcccggac gcgatcgtct gcggcagcgt   88260
gcggctggcg gtcggcgtga tccgggccgc cgccgacgcc ggcctgcggg tgcccgagga   88320
```

```
cgtcgccgtg atcggcatcg gcgacggcga ggagggccgc tacacgcggc cggccctgac    88380
cacggtcgcc accgacccgg cgttcatcgc cggcaaggcg c                        88421
```

<210> SEQ ID NO 2
<211> LENGTH: 333
<212> TYPE: PRT
<213> ORGANISM: Actinoplanes sp.

<400> SEQUENCE: 2

```
Met Ser Trp Arg Gln Phe Arg Trp Gln Ala Leu Ala Gly Ala Val Ala
 1               5                  10                  15

Leu Val Pro Leu Val Ala Tyr Leu Ile Val Thr Ser Leu Asp Ile Arg
            20                  25                  30

Arg Ala His Asp Arg Tyr Gln Ala Gln Cys Ala Ser Ile Gly Asn Cys
        35                  40                  45

Ala Glu Ala Met Leu Gln Phe Gln Asn Asp Phe Arg Thr Arg Leu Leu
    50                  55                  60

Leu Leu Ala Ile Leu Leu Ala Ala Ile Pro Gly Ile Leu Gly Val Phe
65                  70                  75                  80

Trp Gly Ala Pro Leu Val Ala Arg Glu Leu Glu Thr Gly Thr His Arg
                85                  90                  95

Leu Val Trp Asn Gln Ser Val Thr Arg Arg Trp Leu Ala Val Lys
            100                 105                 110

Val Leu Phe Val Gly Val Ala Ala Met Ala Val Ala Thr Leu Val Ser
        115                 120                 125

Thr Leu Leu Thr Trp Ala Ser Ser Pro Val Asp Ala Val Ser Gln Asp
    130                 135                 140

Arg Phe Gly Ala Leu Val Phe Asp Ala Arg Asn Ile Val Pro Val Ala
145                 150                 155                 160

Tyr Ala Ala Phe Ala Leu Val Leu Gly Thr Val Ile Gly Leu Leu Val
                165                 170                 175

Arg Arg Thr Ile Pro Ala Met Ala Leu Thr Met Leu Val Phe Ala Val
            180                 185                 190

Val Gln Phe Thr Val Pro Ala Leu Ala Arg Pro His Leu Met Ala Pro
        195                 200                 205

Glu Thr Gln Thr Arg Gln Met Thr Leu Gln Glu Phe Gly Glu Val Arg
    210                 215                 220

Gly Phe Gly Asp Glu Pro Thr Val Asn Gly Leu Ser Ile Arg Gly Ala
225                 230                 235                 240

Trp Val Thr Ser Thr Ser Pro Leu Leu Thr Ala Asp Gly Thr Arg Leu
                245                 250                 255

Asp Lys Ala Thr Tyr Arg Lys Cys Val Thr Asp Pro Ala Val Ser
            260                 265                 270

Gly Gly Ala Pro Gly Val Gly Gly Thr Val Ala Cys Leu Ala Asp Leu
        275                 280                 285

Asp Leu His Val Glu Val Ala Tyr Gln Pro Asn Asp Arg Tyr Trp Thr
    290                 295                 300

Phe Gln Trp Ile Glu Ser Ala Leu Tyr Leu Ala Leu Gly Gly Leu Leu
305                 310                 315                 320

Leu Ala Val Gly Leu Trp Arg Ile Arg Arg His Val Ile
                325                 330
```

<210> SEQ ID NO 3
<211> LENGTH: 304
<212> TYPE: PRT
<213> ORGANISM: Actinoplanes sp.

<400> SEQUENCE: 3

Met Pro His Glu Asp Ser Ser Pro Val Leu Gln Ala Glu Gly Leu Thr
1               5                   10                  15

Lys Arg Tyr Gly Arg Arg Thr Ala Leu Gln Asp Cys Asn Leu Thr Ile
            20                  25                  30

Pro Arg Gly Arg Val Ile Gly Leu Val Gly Pro Asn Gly Ala Gly Lys
        35                  40                  45

Ser Thr Leu Leu Gln Leu Ala Cys Gly Leu Ile Thr Pro Ser Glu Gly
    50                  55                  60

Ser Leu Arg Val Leu Gly Glu Thr Pro Ala Ala Asn Ala Gly His Leu
65                  70                  75                  80

Ala Lys Val Gly Phe Val Ala Gln Asp Thr Pro Val Tyr Ser Asn Phe
                85                  90                  95

Thr Val Gly Asp His Leu Lys Met Gly Ala Lys Leu Asn Pro Thr Trp
            100                 105                 110

Asp Gln Ala Leu Ala Glu Arg Val Ala Gln Val Gly Leu Asn His
        115                 120                 125

Gly Gln Lys Ala Gly Arg Leu Ser Gly Gly Gln Arg Ala Gln Leu Ala
    130                 135                 140

Leu Thr Leu Ala Ala Ala Lys Arg Pro Glu Leu Leu Met Phe Asp Glu
145                 150                 155                 160

Pro Ala Ala Ala Leu Asp Pro Leu Ala Arg Asp Gly Phe Leu Gln Asn
                165                 170                 175

Leu Leu Glu Phe Val Thr Glu Leu Asp Ala Ser Ala Ile Leu Ser Ser
            180                 185                 190

His Leu Leu Gly Asp Val Glu Arg Val Cys Asn Tyr Leu Ile Val Leu
        195                 200                 205

Cys Ala Ser Arg Val Gln Val Ala Gly Asp Val Pro Asp Leu Leu Asn
    210                 215                 220

Thr His Tyr Arg Ile Val Ala Pro Arg Gly Glu Leu Asp His Pro Pro
225                 230                 235                 240

Ala Gly Leu Glu Val Ile Arg Ala Gln His Ala Asp Arg Tyr Thr Thr
                245                 250                 255

Ala Val Val Arg Gly Asp Gly Ser Arg Pro Ser Thr Trp Thr Ile Glu
            260                 265                 270

Pro Ile Gln Leu Glu Glu Leu Val Leu Ala Tyr Met Thr Arg Ala Met
        275                 280                 285

Gly Val Thr Gly Glu Pro Leu Met Ala Ala Ser Gly Glu Val Val Arg
    290                 295                 300

<210> SEQ ID NO 4
<211> LENGTH: 336
<212> TYPE: PRT
<213> ORGANISM: Actinoplanes sp.

<400> SEQUENCE: 4

Met Ser Trp Arg Gln Phe Arg Gly Gln Ala Val Val Gly Val Val Val
1               5                   10                  15

Leu Ala Leu Leu Ala Ala Tyr Leu Val Tyr Leu Gly Val Asp Ile Arg
            20                  25                  30

```
Gly Ala Tyr Asp Asp Tyr Arg Ala Gln Cys Pro Ala Gly Gly Asp Cys
            35                  40                  45

Ala Gly Pro Leu Gly Gln Phe Ser Leu Asp Tyr Glu Asn Thr Leu Leu
 50                  55                  60

Tyr Leu Ala Gly Val Leu Ala Leu Val Pro Gly Leu Leu Gly Met Phe
 65                  70                  75                  80

Trp Gly Ala Pro Leu Ile Thr Arg Glu Leu Glu Asn Gly Thr Gln Arg
                 85                  90                  95

Leu Val Trp Asn Gln Ser Val Thr Arg Arg Trp Leu Leu Ile Lys
             100                 105                 110

Leu Leu Val Val Gly Leu Ala Cys Met Val Val Ala Gly Val Pro Ser
            115                 120                 125

Leu Leu Leu Thr Trp Ala Ala Pro Val Asp Asn Val Ala Asp Asn
            130                 135                 140

Arg Phe Ser Thr Val Met Phe Gly Ala Arg Phe Leu Pro Pro Ile Ala
145                 150                 155                 160

Tyr Ala Ala Phe Ala Phe Val Leu Gly Thr Leu Ile Gly Leu Leu Val
                165                 170                 175

Arg Arg Thr Val Pro Ala Met Ala Leu Thr Leu Val Ala Phe Val Ile
            180                 185                 190

Phe Gln Phe Leu Val Pro Asn Leu Val Arg Pro His Leu Met Pro Ala
            195                 200                 205

Lys His Leu Val Lys Pro Met Thr Val Ser Ala Ile Asn Glu Ala Lys
            210                 215                 220

Ser Leu Gly Ser Ile Thr Gly Ala Pro Val Leu Asn Gly Leu Ser Ile
225                 230                 235                 240

Ser Gln Gly Trp Ile Thr Asp Val Ser Ala Leu Lys Thr Ala Asp Gly
                245                 250                 255

Arg Ser Leu Asp Ala Lys Thr Phe Asp Asn Cys Tyr Met Asn Ala Pro
            260                 265                 270

Lys Thr Gly Ala Thr Glu Gly Pro Tyr Gly Asp Val Ala Val Cys Leu
            275                 280                 285

Ala Lys Leu Asp Leu His Val Asp Ile Ala Tyr Gln Pro Trp Asn Arg
            290                 295                 300

Tyr Trp Ala Phe Gln Phe Leu Glu Ser Gly Phe Tyr Val Leu Leu Ser
305                 310                 315                 320

Gly Leu Leu Ile Gly Ala Ala Val Trp Arg Val Gln Arg Arg Pro Ser
                325                 330                 335
```

<210> SEQ ID NO 5
<211> LENGTH: 283
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will contain a
      methionineresidue at this position

<400> SEQUENCE: 5

```
Val Arg Ser Ala Val Val Gly Thr Gly Leu Ile Gly Thr Ser Val
 1               5                  10                  15

Gly Leu Ala Leu Thr Gln Arg Asp Ile Thr Val His Leu Leu Asp Ala
                 20                  25                  30

Asp Pro Ala Ala Ala Arg Ala Ala Ala Leu Gly Ala Gly Ile Ala
             35                  40                  45
```

```
Gly Glu Pro Arg Thr Arg Val Asp Val Ala Val Ile Ala Val Pro Pro
     50                  55                  60

Ala Ala Val Ala Pro Val Leu Ala Asp Leu Gln Arg Arg Gly Thr Ala
 65                  70                  75                  80

Arg Val His Thr Asp Ala Ala Ser Val Lys Val Leu Pro Ser Arg Gln
                 85                  90                  95

Ile Glu Val Leu Gly Cys Asp Ala Ser Ser His Val Gly Gly His Pro
            100                 105                 110

Leu Ala Gly Ser Glu Arg Ser Gly Pro His Ala Ala Arg Gly Ser Leu
        115                 120                 125

Phe Glu Gly Arg Pro Trp Val Leu Ser Pro Gly Arg Ser Ser Thr
    130                 135                 140

Ala Ala Val Asp Gly Ala Leu Ala Val Ser Ala Cys Gly Ala Thr
145                 150                 155                 160

Pro Val Leu Met Ser Ala Glu Glu His Asp Arg Ala Val Ala Leu Val
                165                 170                 175

Ser His Val Pro His Leu Val Ala Gly Leu Leu Ala Ala Arg Met Leu
            180                 185                 190

Asp Gly Thr Pro Ala Gln Leu Gly Leu Ala Gly Gln Gly Val Arg Asp
        195                 200                 205

Thr Thr Arg Ile Ala Gly Gly Arg Ala Ala Leu Trp Thr Glu Ile Leu
    210                 215                 220

Ala Ala Asn Ala Gly Ala Val Ala Asp Val Leu Asp Asp Leu Ser Ala
225                 230                 235                 240

Glu Leu Ala Ala Thr Ile Ser Ala Leu Arg Glu Leu Glu Ala His Pro
                245                 250                 255

Gly Arg Ala Glu Ala Leu Ala Ala Leu Thr Gly Met Leu Gln Arg Gly
            260                 265                 270

Val Asp Gly Arg Asp Arg Ile Ala Ala Ser Pro
        275                 280

<210> SEQ ID NO 6
<211> LENGTH: 336
<212> TYPE: PRT
<213> ORGANISM: Actinoplanes sp.

<400> SEQUENCE: 6

Met Glu Ser Leu His Ile Ala Ser Ala Arg His Glu Pro Asp Arg His
1               5                  10                  15

Asp Glu Thr Gln Met Asn Thr Pro Ser Met Met Arg Val Glu Trp Leu
             20                  25                  30

Pro Val Asp Ser Leu Glu Met Leu Asp Ser Pro Arg Leu Ala Gly Glu
         35                  40                  45

Asp Pro Arg His Thr Gln Met Leu Ala Ser Leu Asp Ala Glu Leu Pro
     50                  55                  60

Pro Ile Ile Val His Arg Ala Ser Met Arg Val Ile Asp Gly Ala His
 65                  70                  75                  80

Arg Leu Gly Ala Ala Arg Leu Arg Gly Asp Glu Leu Ile Lys Ala Ala
                 85                  90                  95

Met Phe Glu Gly Ser Glu Gln Glu Ala Phe Val Leu Gly Val Lys Ala
            100                 105                 110

Asn Ile Ala His Gly Leu Pro Leu Ser Thr Ala Asp Arg Thr Arg Ala
        115                 120                 125

Ala Glu Arg Ile Ile Glu Ser His Pro Ser Trp Ser Asp Arg Thr Ile
    130                 135                 140
```

```
Ala Ala Ser Ser Gly Leu Ser Ala Arg Thr Val Gly Asn Ile Arg Arg
145                 150                 155                 160

Arg Leu Glu Leu Ser Gly Asp Ile Gly Gln Gly Ser Arg Thr Arg Val
            165                 170                 175

Gly Arg Asp Gly Arg Val Arg Pro Leu Asp Asn Ser Glu Gly Arg Leu
        180                 185                 190

Lys Ala Val Ser Tyr Ile Gln Gln Pro Asp Ala Ser Leu Arg Glu
    195                 200                 205

Ile Ala Lys Asn Ala Gly Val Ser Pro Ser Thr Ala Arg Asp Val Arg
    210                 215                 220

Asn Arg Leu Gln Arg Gly Glu Asp Pro Leu Pro Gly Pro Arg Arg Thr
225                 230                 235                 240

Gly Gly His Arg Asp Asp Ile Ser Phe Asp Lys Glu Asn Thr Ile Arg
                245                 250                 255

Leu Leu Glu Pro Thr Val Arg Ser Ile Leu Gln Gly Leu Lys Asn Asp
            260                 265                 270

Pro Ser Leu Arg Phe Thr Glu Ser Gly Arg Asn Leu Leu Arg Trp Val
        275                 280                 285

Leu Ala Arg Thr Val Gln Asp Asp Glu Trp Lys Asp Met Leu Asp Ala
290                 295                 300

Val Pro Ser His Cys Thr Tyr Val Leu Ala Asn Val Ala Arg Arg Cys
305                 310                 315                 320

Ser Gln Glu Trp Leu Glu Phe Ala Glu Thr Leu Glu Lys Asn Ala Ala
                325                 330                 335

<210> SEQ ID NO 7
<211> LENGTH: 444
<212> TYPE: PRT
<213> ORGANISM: Actinoplanes sp.

<400> SEQUENCE: 7

Met Ser Ile Leu Arg Glu Ala Pro Gly Thr Gly Arg Val Leu Arg Arg
1               5                   10                  15

Glu Asp Leu His Gln Ser Leu Ser Asp Pro Leu Leu Asp Thr Met Asn
            20                  25                  30

Phe Leu Asn Glu Val Thr Ala Arg Tyr Pro Arg Ala Val Ser Phe Ala
        35                  40                  45

Pro Gly Arg Pro Phe Asp Gly Phe Asp Val Glu Gln Ile Phe Arg
    50                  55                  60

Gly Ile Arg Gly Tyr Leu Glu His Leu Ala Gly Gln Gly Arg Ser Pro
65                  70                  75                  80

Ala Glu Ile Arg Asp Ala Val Phe Gln Tyr Gly Pro Ala Ala Gly Arg
                85                  90                  95

Ile Arg Glu Val Ile Ala Gln Trp Leu Arg Arg Asp Glu Gly Ile Asp
            100                 105                 110

Val Ala Pro Glu Ser Ile Val Thr Val Gly Ala Gln Glu Ala Met
        115                 120                 125

Leu Leu Ala Leu Arg Ala Leu Ile Arg Asp Glu Arg Asp Ala Leu Phe
130                 135                 140

Val Ala Ser Pro Cys Tyr Val Gly Ile Thr Gly Ala Ala Arg Leu Leu
145                 150                 155                 160

Asp Ile Asp Pro Val Pro Val Ala Glu Arg Glu Asp Gly Phe His Pro
                165                 170                 175

Glu Asp Leu Ala Arg Ala Val His Ala Glu Leu Ser Arg Gly Arg Arg
            180                 185                 190
```

-continued

```
Pro Arg Ala Phe Tyr Val Val Pro Asp His Thr Asn Pro Ser Gly Ala
        195                 200                 205

Thr Met Pro Leu Glu Ala Arg His Ala Leu Leu Asp Leu Ala Gly Glu
    210                 215                 220

Leu Gly Leu Leu Val Ile Glu Asp Ser Pro Tyr Arg Leu Val Ser Pro
225                 230                 235                 240

Gly Gln Gln Leu Pro Ser Leu Lys Ala Leu Asp Pro Gly Arg His Val
                245                 250                 255

Val His Leu Gly Ser Phe Ser Lys Thr Leu Phe Pro Gly Ala Arg Val
            260                 265                 270

Gly Phe Ala Ile Ala Asp Gln Pro Val Ser Asp Ala Ala Gly Gly Ala
        275                 280                 285

Gly Leu Leu Ala Asp Glu Leu Ala Lys Val Lys Ser Met Val Thr Val
    290                 295                 300

Asn Thr Ser Pro Leu Ser Gln Ala Ala Val Ala Gly Met Leu Leu Ala
305                 310                 315                 320

Ala Gly Gly Thr Ala Ala Glu Ala Ser Ala Glu Ser Ser Ala His Tyr
                325                 330                 335

Gly Ala Ala Met Arg Arg Thr Leu Asp Arg Leu Glu Glu His Leu Pro
            340                 345                 350

Ala Ser Phe Arg Ala Arg Thr Gly Val Arg Trp Asn Arg Pro Ser Gly
        355                 360                 365

Gly Phe Phe Leu Ala Val Asn Val Pro Phe Thr Ala Asp Asn Ala Ala
    370                 375                 380

Leu Ser Arg Ser Ala Glu Asp His Gly Val Ile Trp Thr Pro Met Ser
385                 390                 395                 400

Tyr Phe Tyr Pro Ala Gly Gly Glu Gln Gly Ile Arg Leu Ser Ile
                405                 410                 415

Ser Tyr Leu Thr Pro Glu Glu Ile Asp Glu Gly Val Lys Arg Leu Ala
            420                 425                 430

Gly Phe Ile Thr Thr Glu Ile Ala Ala Leu Arg Pro
        435                 440

<210> SEQ ID NO 8
<211> LENGTH: 356
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 8

Val Thr Ala Thr Ala Leu Leu Pro Leu Thr Leu Ala Asp Tyr Glu Gln
1               5                  10                  15

Leu Ala Gln Ala Arg Met Glu Pro Pro Val Trp Asp Phe Ile Ala Gly
                20                  25                  30

Gly Ala Gly Glu Glu Leu Thr Leu Ala Ala Asn Thr Ala Ala Phe Ala
            35                  40                  45

Pro Pro Arg Leu Arg Pro Arg Val Leu Thr Gly Ala Gly Ala Pro Asp
        50                  55                  60

Thr Gly Thr Thr Ile Leu Gly Arg Arg Trp Ala Ala Pro Ile Gly Val
65                  70                  75                  80

Ala Pro Leu Gly Tyr His Thr Leu Val Asp Pro Ala Gly Glu Val Ala
                85                  90                  95
```

```
Thr Ala Ala Ala Ala Gly Ala Ala Gly Leu Pro Leu Val Val Ser Thr
            100                 105                 110

Phe Ser Gly Arg Thr Val Glu Asp Ile Ala Ala Thr Thr Ala Pro
        115                 120                 125

Arg Trp Leu Gln Val Tyr Cys Phe Arg Asp Arg Ala Val Thr Ala Ala
    130                 135                 140

Leu Val Thr Arg Ala Val Arg Ala Gly Phe Glu Ala Leu Val Leu Thr
145                 150                 155                 160

Val Asp Ala Pro Arg Leu Gly Arg Arg Leu Arg Asp Ile Arg Asn Asp
                165                 170                 175

Phe Arg Leu Pro Pro Gly Val Ala Pro Ala Asn Leu Thr Gly Asp Gly
            180                 185                 190

Phe Ala Ser Pro Ser Gly His Ala Leu Gly Ala Phe Asp Ala Ala Met
            195                 200                 205

Asp Trp Thr Val Val Ala Trp Leu Arg Glu Leu Ser Gly Leu Pro Val
        210                 215                 220

Leu Leu Lys Gly Val Leu Thr Ala Asp Gly Ala Arg Arg Ala Leu Asp
225                 230                 235                 240

Ala Gly Ala Asp Gly Ile Val Val Ser Asn His Gly Gly Arg Gln Leu
                245                 250                 255

Asp Gly Val Pro Ala Thr Leu Asp Val Leu Pro Glu Val Val Ala Ala
            260                 265                 270

Val Ala Gly Arg Cys Pro Val Leu Leu Asp Gly Gly Val Arg Arg Gly
            275                 280                 285

Arg Asp Val Leu Leu Ser Leu Ala Leu Gly Ala Asp Ala Val Leu Val
    290                 295                 300

Gly Arg Pro Val Leu Tyr Gly Leu Ala Val Gly Gly Thr Ala Gly Val
305                 310                 315                 320

Arg His Val Leu Asp Ile Leu Ala Gly Glu Leu Thr Asp Asp Met Ala
                325                 330                 335

Leu Ala Gly Val Ala Ser Pro Ala Asp Ala Gly Ala Asp Leu Ala Gly
            340                 345                 350

Pro Val Ala Pro
        355

<210> SEQ ID NO 9
<211> LENGTH: 640
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine at this position

<400> SEQUENCE: 9

Val Ala Thr Ile Asp Gly Pro Asp Leu Gly Val Ile Gly Leu Arg Val
1               5                   10                  15

Asp Gly Leu Ile Pro Met Gln Lys Val Arg Pro Gly Thr Val Arg Arg
            20                  25                  30

Ile Leu Pro Tyr Ala Lys Lys His Arg Trp Ser Leu Ala Val Ala Leu
        35                  40                  45

Leu Met Thr Val Val Asp Ala Ala Leu Thr Val Ala Asn Pro Leu Leu
    50                  55                  60

Leu Lys Gln Ile Ile Asp Arg Gly Ile Val Ala Gly Arg Leu Asp Val
65                  70                  75                  80
```

-continued

```
Val Val Gly Leu Ser Leu Val Val Ala Gly Leu Ala Leu Val Asn Val
                85                  90                  95

Ala Ala Ile His Val Gln Thr Leu Ala Ser Gly Arg Val Gly Gln Gly
            100                 105                 110

Leu Ile Tyr Asp Leu Arg Thr Lys Val Phe Ala His Val Met Arg Gln
        115                 120                 125

Pro Leu Ala Phe Phe Thr Arg Ala Gln Thr Gly Ser Leu Val Ser Arg
    130                 135                 140

Leu Asn Thr Asp Val Val Gly Ala Glu Gln Ala Met Thr Ser Met Ile
145                 150                 155                 160

Thr Gln Thr Val Ser Thr Val Leu Thr Val Leu Val Ile Gly Ala
                165                 170                 175

Met Phe Tyr Leu Ser Trp Ala Ile Ala Leu Val Ala Leu Val Leu Ile
                180                 185                 190

Pro Leu Phe Phe Leu Pro Gly Lys Leu Ile Ala Gly Arg Leu Glu Arg
            195                 200                 205

Leu Ala Arg Gly Gly Met Gln Val Asp Ala Glu Leu Gly Ser Met Met
    210                 215                 220

Asn Glu Arg Phe Asn Val Ser Gly Ala Met Leu Val Lys Leu Tyr Gly
225                 230                 235                 240

Arg Pro Glu Ser Glu Glu Thr Ala Phe Ala Gly Arg Ala Ala Arg Val
                245                 250                 255

Arg Asp Ile Ala Ile Ser Met Gly Val His Ala Arg Leu Leu Phe Ile
            260                 265                 270

Ile Ala Thr Leu Leu Thr Thr Val Thr Thr Ala Met Val Tyr Gly Phe
    275                 280                 285

Gly Gly Ala Leu Val Ile Asp Gly Thr Leu Gly Ile Gly Thr Leu Val
    290                 295                 300

Ala Met Val Ala Leu Leu Ala Gln Leu Tyr Gly Pro Val Asn Gln Leu
305                 310                 315                 320

Thr Asn Ile Gln Val Asp Val Thr Ala Leu Val Ser Phe Asp Arg
                325                 330                 335

Val Phe Glu Val Leu Asp Leu Asp Pro Leu Val Lys Glu Arg Pro Gly
                340                 345                 350

Ala Arg Ala Leu Pro Ala Ala Glu Pro Gly Arg Ser Ala Ala Pro Asp
            355                 360                 365

Ile Glu Phe Asp Asn Val Val Phe Arg Tyr Pro Gly Ala Asp Glu Val
        370                 375                 380

Ser Leu Ala Ser Leu Glu Thr Val Ala Gln Arg Ser Ser Asp Gly Thr
385                 390                 395                 400

Ala Glu Arg Pro Val Leu Asn Gly Ile Ser Phe Leu Ala Pro Ala Gly
                405                 410                 415

Lys Leu Thr Ala Leu Val Gly Pro Ser Gly Ala Gly Lys Thr Thr Ile
            420                 425                 430

Thr His Leu Val Pro Arg Leu Tyr Asp Thr Thr Ser Gly Thr Val Arg
        435                 440                 445

Ile Ala Gly His Asp Val Arg Asp Leu Thr Leu Arg Ser Leu Ser Glu
    450                 455                 460

Ser Ile Gly Val Val Thr Gln Asp Ala His Leu Phe His Asp Thr Ile
465                 470                 475                 480

Arg Ala Asn Leu Leu Tyr Gly Arg Pro Asp Ala Gly Glu Arg Asp Leu
                485                 490                 495
```

-continued

```
Val Ala Ala Cys Glu Ala Ala Arg Ile Trp Glu Met Val Ser Ser Leu
            500                 505                 510

Pro Asp Gly Leu Asp Thr Val Gly Asp Arg Gly Tyr Arg Leu Ser
            515                 520                 525

Gly Gly Glu Lys Gln Arg Leu Ala Leu Ala Arg Leu Leu Leu Lys Ser
            530                 535                 540

Pro Pro Val Val Leu Asp Glu Ala Thr Ala His Leu Asp Ser Glu
545                 550                 555                 560

Ser Glu Ala Ala Ile Gln Arg Ala Leu Asp Thr Ala Leu Ala Gly Arg
                565                 570                 575

Thr Ser Leu Val Ile Ala His Arg Leu Ala Thr Ile Leu Asp Ala Asp
            580                 585                 590

Gln Ile Leu Val Ile Asp Asp Gly Arg Val Val Glu Arg Gly Thr His
            595                 600                 605

Asp Glu Leu Ile Ala His Gly Gly Leu Tyr Ala Glu Leu Tyr Arg Thr
            610                 615                 620

Gln Phe Ala Gly Gln Arg Thr Glu Glu Arg Gln Pro Ala Val Pro Ser
625                 630                 635                 640
```

<210> SEQ ID NO 10
<211> LENGTH: 271
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 10

```
Val Ser Ala Ala Gly Ser Gly Phe Val Thr Thr Asn Gly Val Arg Leu
1               5                   10                  15

Ala Tyr Arg Arg Ser Gly Ala Gly Glu Pro Val Leu Met Ile Met Gly
                20                  25                  30

Ser Gly Ser Ala Gly Gln Thr Trp Thr Val His Gln Thr Pro Ala Leu
            35                  40                  45

His Glu Ala Gly Tyr Ser Thr Val Val Phe Asp Ser Arg Gly Ile Pro
        50                  55                  60

Pro Ser Asp Val Pro Ala Gly Lys Tyr Ser Leu Ala Asp Met Thr Ala
65                  70                  75                  80

Asp Thr Arg Gly Leu Ile Glu Ala Leu Asp Leu Ala Pro Cys Arg Ile
                85                  90                  95

Val Gly Thr Ser Leu Gly Ala Met Ile Ala Gln Glu Leu Ala Val Asp
            100                 105                 110

His Pro Glu Leu Val Arg Cys Ala Val Leu Ile Ala Thr Leu Ala Arg
        115                 120                 125

Pro Asp Ala Ala Arg Ala Ala Gln Asn Gln Ala Asp Ile Asp Leu Leu
    130                 135                 140

Glu Ser Gly Val Thr Leu Pro Ala Ala Tyr Glu Ala Ala Thr Ala Val
145                 150                 155                 160

Phe Lys Met Phe Ser Pro Ala Thr Leu Asn Asp Val Ala Val Arg
                165                 170                 175

Glu Trp Leu Asp Ile Phe Glu Leu Ser Gly Thr Gly Val Ser Ala Gly
            180                 185                 190

Gly Gln Ala Trp Ala Glu Leu Thr Gly Asp Arg Arg Ala Ala Leu Arg
        195                 200                 205
```

-continued

Ser Val Thr Ala Pro Cys Arg Val Ile Ser Phe Ala Asp Asp Leu Ile
    210                 215                 220

Thr Pro Pro His Leu Ala Ala Glu Val Ala Glu Ala Ile Pro Asp Cys
225                 230                 235                 240

Asp Leu Val Glu Ile Ser Arg Cys Gly His Leu Gly Tyr Leu Glu Arg
                245                 250                 255

Pro Asp Ala Val Asn Ala Ala Ile Leu Glu Phe Leu Asp Ser His
            260                 265                 270

<210> SEQ ID NO 11
<211> LENGTH: 529
<212> TYPE: PRT
<213> ORGANISM: Actinoplanes sp.

<400> SEQUENCE: 11

Met Gly Asn Ala Asp Gln Pro Arg Tyr Leu Arg Ser Asn Val Ile Ala
1               5                   10                  15

Glu Pro Leu Val Asp Arg Phe Tyr Ala Trp Leu His Thr Val Ala Pro
            20                  25                  30

Val Pro Ala Ser Met Asn Leu Ala Phe Leu Gln Val Pro Leu Leu Glu
        35                  40                  45

Ser Tyr Leu Gln Ser Pro Pro Val His Val Ala Ala Ser Thr Asn Pro
50                  55                  60

Lys Met Arg Gly Gly Tyr Phe Val Ala Val Glu Glu Ser Arg Ser Asp
65                  70                  75                  80

Glu Val Ala Glu Leu Leu Lys Thr Ile Lys Asn Glu Arg Ala Asp Met
                85                  90                  95

Leu Gly Phe Ala Ala Ala Val Ala Glu Ala Glu Asp Leu Ile Arg Glu
            100                 105                 110

Asn Ala Val Gly Tyr Asp Leu Thr Pro Leu Tyr Pro Arg Leu Pro Ala
        115                 120                 125

Ala Leu Asn Gly Leu Val Glu Ile Ala Tyr Asp Thr Ser Asn Gln Pro
130                 135                 140

Ser Leu His Phe Leu Glu Pro Leu Leu Tyr Arg Ser Pro Ala Tyr Asp
145                 150                 155                 160

Glu Arg Arg Gln Ser Val Gln Leu Ser Leu Asp Asp Gly Val Glu Arg
                165                 170                 175

Pro Phe Ile Leu Ser Thr Pro Arg Leu Pro Arg Ala Gly Val Leu Asp
            180                 185                 190

Leu Pro Leu Pro Leu Arg His Pro Gly Leu Thr Glu Leu Phe Asp Ala
        195                 200                 205

Arg Val Arg Pro Thr Ser Leu Asn Arg Leu Arg Glu Ala Leu Glu Leu
210                 215                 220

Asp Asp Ala Gly Ala Ala Leu Asp Ala Leu Thr Asp Glu Pro
225                 230                 235                 240

Ser Leu Ser Pro Asp Arg His Ile Glu Ser Gly Gly Arg Val Arg Tyr
                245                 250                 255

Tyr Gly His Ala Cys Val Val Met Gln Thr Glu Gln Ala Ala Val Val
            260                 265                 270

Thr Asp Pro Phe Ile Ser Thr Asp Asn Arg His Gly Asp Arg Tyr Thr
        275                 280                 285

Leu Asp Asp Leu Pro Asp His Ile Asp Leu Val Leu Ile Thr His Gly
290                 295                 300

His Gln Asp His Ile Val Leu Glu Thr Leu Leu Gln Leu Arg Gly Arg
305                 310                 315                 320

```
Ile Gly Thr Val Val Pro Arg Thr Ser Arg Gly Asn Leu Pro Asp
            325                 330                 335

Pro Ser Ile Ala Leu Tyr Leu Arg Arg Ile Gly Phe Thr Val Val Glu
        340                 345                 350

Val Glu Glu Phe Asp Glu Val Pro Phe Pro Gly Gly Thr Val Thr Ala
            355                 360                 365

Thr Pro Phe Leu Gly Glu His Ala Asp Leu Asp Ile Arg Gly Lys Ser
370                 375                 380

Thr Tyr Phe Val Arg Met Ala Gly Arg Thr Ile Phe Ile Gly Ala Asp
385                 390                 395                 400

Ser Ser Gly Ile Asp Pro Val Leu Tyr Arg Tyr Ile Arg Asp His Val
                405                 410                 415

Gly Gln Val Asp Met Ala Phe Leu Gly Met Glu Cys Asp Gly Ala Pro
            420                 425                 430

Leu Asn Trp Leu Tyr Lys Gly Leu Leu Thr Lys Pro Val Asn Lys Lys
        435                 440                 445

Met Ser Ala Ser Arg Arg Leu Ser Gly Ser Asn Ala Glu Gln Ala Gly
    450                 455                 460

Ala Ile Met Thr Glu Leu Gly Ala Thr Ala Gly Tyr Ile Tyr Ala Met
465                 470                 475                 480

Gly Glu Glu Ser Trp Gln Gly His Val Met Ala Thr Thr Tyr Asn Glu
                485                 490                 495

Asp Thr Tyr Gln Leu Lys Gln Ile Asp Glu Phe Leu Ala Trp Cys Ala
            500                 505                 510

Asp Arg Gly Phe Thr Ala Glu His Leu Phe Asn Lys Arg Glu Trp Arg
        515                 520                 525

Trp

<210> SEQ ID NO 12
<211> LENGTH: 90
<212> TYPE: PRT
<213> ORGANISM: Actinoplanes sp.

<400> SEQUENCE: 12

Met Ser Glu Thr Asp Leu Ser Ala Ala Arg His Thr Pro Glu Gln Ile
1               5                   10                  15

Arg Ser Trp Leu Ile Asp Arg Ile Ala Tyr Tyr Val Met Leu Pro Thr
            20                  25                  30

Gln Glu Ile Glu Pro Asp Val Ser Leu Ala Glu Tyr Gly Leu Asp Ser
        35                  40                  45

Val Tyr Ala Phe Ala Leu Cys Gly Glu Ile Glu Asp Thr Leu Gly Ile
    50                  55                  60

Pro Ile Glu Pro Thr Leu Leu Trp Asp Val Asp Thr Val Ala Thr Leu
65                  70                  75                  80

Thr Ala His Leu Ala Asp Arg Val Asn Arg
                85                  90

<210> SEQ ID NO 13
<211> LENGTH: 1051
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard codon.  It is
      expected that the biosynthesized protein will have a
      formylmethionine residue at this position
```

-continued

<400> SEQUENCE: 13

```
Val Pro Thr Pro Asp Leu Arg Pro Leu Thr Pro Ala Gln Leu Ala Val
1               5                   10                  15

Trp His Ala Gln Gln Leu Ala Pro His Ser Pro Val Tyr Gln Val Gly
            20                  25                  30

Glu Phe Val Glu Ile Asp Gly Glu Cys Asp Pro Asp Leu Leu Val Ala
        35                  40                  45

Ala Leu Arg Gln Val Met Gly Glu Ala Ser Ala Arg Leu Arg Phe
    50                  55                  60

Arg Val Ile Asp Gly Thr Pro Trp Gln Tyr Val Ala Glu Asp Gly Asp
65                  70                  75                  80

Asp Pro Ile Gln Val Val Asp Leu Gly Ala Ala Asp Pro Arg Ala
                85                  90                  95

Ala Ala Leu Gly Arg Met Ala Ala Asp Leu Asp Arg Pro Gly Asp Leu
            100                 105                 110

Arg Asp Gly Pro Leu Val Glu His His Val Tyr Leu Leu Gly Glu Gly
        115                 120                 125

Arg Val Ile Trp Tyr His Arg Ala His His Ile Val Cys Asp Gly Gly
130                 135                 140

Ser Leu Gly Ile Val Ala Ser Arg Val Ala Gly Val Tyr Ser Ala Leu
145                 150                 155                 160

Ala Ala Gly Gly Asp Val Arg Pro Gly Ala Leu Pro Pro Leu Ser Val
                165                 170                 175

Leu Leu Ser Ala Ala Asp Ala Tyr Glu Arg Ser Gly Ser Arg Asp Arg
            180                 185                 190

Asp Arg Glu His Trp Arg Ser Ala Leu Ala Gly Leu Pro Ala Glu Leu
        195                 200                 205

Leu Ala Gly Ala Gly Arg Pro Arg Pro Leu Pro Gly Pro Pro Val Arg
    210                 215                 220

His Glu His Asp Leu Ser Ala Ala Glu Ala Gly Arg Leu Arg Ala Gly
225                 230                 235                 240

Ala Arg Arg Leu Arg Thr Ser Val Ala Gln Ala Gly Ile Ala Ala Ala
                245                 250                 255

Ala Leu Tyr Gln His Arg Leu Thr Gly Ala Arg Asp Val Leu Val Ala
            260                 265                 270

Val Pro Val Ala Gly Arg Thr Thr Arg Pro Glu Phe Asp Val Pro Gly
        275                 280                 285

Met Thr Ser Asn Val Val Pro Val Arg Leu Ala Val Thr Pro Ala Thr
    290                 295                 300

Thr Val Gly Glu Leu Leu Arg Asp Val Ala Arg Gly Val Arg Asp Gly
305                 310                 315                 320

Leu Arg His Gln Arg Tyr Pro Tyr Pro Asn Ile Val Asp Asp Leu Gly
                325                 330                 335

Leu Ala Asp Arg Ala Ala Leu Arg Pro Val Thr Val Asn Ala Leu Ala
            340                 345                 350

Leu Gly Arg Pro Leu Arg Phe Gly Ser Ala Val Gly Val Arg Ser Gly
        355                 360                 365

Leu Ser Ala Gly Pro Val Asp Asp Val Thr Ile Gly Leu Tyr Glu Lys
    370                 375                 380

Val Ser Gly Gly Gly Met Gln Thr Ile Ala Glu Leu Asn Pro Gly Arg
385                 390                 395                 400

Thr Asp Arg Pro Asp Ala Ala Glu Val Ser Arg Trp Phe Arg Thr Leu
                405                 410                 415
```

-continued

```
Leu Arg Gly Leu Ala Glu Ser Asp Ala Gly Asp Pro Val Ala Arg Ile
            420                 425                 430

Asp Ile Val Asp Glu Pro Glu Arg Arg Leu Leu Asp Glu Trp Asn
        435                 440                 445

Ala Thr Ala Ala Pro Ser Ser Asp Thr Val Leu Ala Arg Phe Glu Glu
        450                 455                 460

Gln Ala Ala Arg Thr Pro Glu Ala Pro Ala Val Val Cys Gly Asp Val
465                 470                 475                 480

Thr Val Thr Tyr Ala Glu Leu Glu Ala Gly Ala Asn Arg Leu Ala Arg
                485                 490                 495

Val Leu Arg Ala Arg Gly Ala Gly Pro Glu Ser Val Val Ala Leu Cys
            500                 505                 510

Leu Pro Arg Gly Pro Glu Val Val Thr Gly Ile Leu Ala Ala Trp Lys
            515                 520                 525

Ala Gly Ala Ala Tyr Leu Pro Val Asp Thr Glu Leu Pro Ala Glu Arg
            530                 535                 540

Val Ala Tyr Leu Leu Gly Asp Ser Ala Ala Val Arg Leu Gly Thr
545                 550                 555                 560

Ala Glu Thr Leu Ala Ala Leu Pro Asp Gly Pro Ala Ala Asp Val Asp
                565                 570                 575

Val His Ala Pro Glu Ile Ala Arg Glu Ser Pro Ser Pro Leu Arg Leu
            580                 585                 590

Glu Pro Leu Pro Asp Gln Leu Ala Tyr Val Ile Tyr Thr Ser Gly Ser
            595                 600                 605

Thr Gly Leu Ser Lys Gly Val Gly Val Ser His Gly Gly Leu Ala Asn
            610                 615                 620

Tyr Val Gly Trp Ala Ser Val Leu Tyr Gly Gly Leu Ser Ala Pro Leu
625                 630                 635                 640

His Ser Ser Leu Ala Phe Asp Leu Thr Val Thr Ser Val Phe Val Pro
                645                 650                 655

Leu Val Cys Gly Gly Ser Val Val Ser Ala Ala Gly Gly Gly Arg
            660                 665                 670

Gly Leu Ala Ser Leu Leu Ala Ala Gly Asp Gly Phe Ser Leu Val Lys
            675                 680                 685

Val Val Pro Gly His Leu Arg Leu Leu Ala Glu Leu Val Pro Ala Gly
            690                 695                 700

Glu Met Ala Ala Val Gly Ser Leu Val Ala Gly Gly Glu Val Leu Ala
705                 710                 715                 720

Gly Gly Asp Val Arg Glu Trp Leu Ser Arg Val Pro Gly Ser Val Val
                725                 730                 735

Val Asn Glu Tyr Gly Pro Thr Glu Thr Val Val Gly Cys Ser Val Phe
            740                 745                 750

Ser Val Ala Ala Gly Asp Val Val Gly Asp Val Pro Val Gly Arg
            755                 760                 765

Pro Val Ala Asn Thr Arg Leu Phe Val Leu Asp Glu Gly Leu Arg Pro
            770                 775                 780

Val Pro Ala Gly Val Ala Gly Glu Leu Tyr Val Ala Gly Ser Gln Val
785                 790                 795                 800

Ala Arg Gly Tyr Val Gly Arg Ser Gly Leu Thr Ala Ser Arg Phe Val
                805                 810                 815

Ala Cys Pro Phe Gly Val Gly Glu Arg Met Tyr Arg Thr Gly Asp Val
            820                 825                 830
```

```
Val Arg Leu Ala Gly Gly Asp Leu Val Phe Val Gly Arg Val Asp Glu
        835                 840                 845

Gln Val Lys Ile Arg Gly Tyr Arg Val Glu Pro Asp Glu Val Arg Leu
    850                 855                 860

Val Val Ala Gly His Pro Arg Val Ala Gly Ala Val Val Ala Arg
865                 870                 875                 880

Pro Asp Ala Val Gly Glu Arg Gln Leu Val Ala Tyr Val Val Ala Ala
                885                 890                 895

Gly Glu Pro Ala Gly Leu Ala Glu Ser Val Arg Ala His Val Ala Glu
                900                 905                 910

Arg Leu Pro Glu Tyr Met Val Pro Ala Ala Val Thr Leu Asp Glu
            915                 920                 925

Ile Pro Leu Thr Val Asn Gly Lys Val Asp Arg Ala Ala Leu Pro Glu
    930                 935                 940

Pro Gly Pro Val Ala Thr Gly Asn Ala Asp Arg Glu Pro Thr Thr Glu
945                 950                 955                 960

Arg Glu Ser Leu Leu Cys Gly Ala Phe Ala Asp Val Leu Gly Ile Glu
                965                 970                 975

Arg Val Gly Val Asp Asp Asp Phe Phe Ser Leu Gly His Ser Leu
            980                 985                 990

Leu Ala Thr Ser Leu Val Ser Arg  Val Arg Leu Val Leu  Gly Glu Glu
            995                 1000                1005

Leu Pro  Ile Glu Glu Leu Phe  Ala Thr Pro Thr Pro  Ala Glu Leu
    1010                1015                1020

Ala Ala  Trp Leu Gln Arg Asn  Ala Asp Arg Pro Gln  Pro Ala Arg
    1025                1030                1035

Pro Ala  Leu Arg Pro Met His  Glu Arg Glu Thr Thr  Ala
    1040                1045                1050

<210> SEQ ID NO 14
<211> LENGTH: 6893
<212> TYPE: PRT
<213> ORGANISM: Actinoplanes sp.

<400> SEQUENCE: 14

Met Thr Pro Met Ser Tyr Ala Gln Arg Arg Leu Trp Phe Gln Leu Arg
1               5                   10                  15

Val Glu Gly Pro Asp Ala Thr Tyr Asn Ser Pro Ala Val Leu Arg Leu
            20                  25                  30

Thr Gly Glu Leu Asp Thr Ala Ala Leu Glu His Ala Leu Arg Asp Val
        35                  40                  45

Leu Glu Arg His Glu Val Leu Arg Thr Val Tyr Pro Asp Val Gly Gly
    50                  55                  60

Glu Pro Arg Gln Arg Val Val Arg Pro Asp Asp Met Val Trp Glu Leu
65                  70                  75                  80

Pro Thr Thr Arg Val Ser Gly Ala Gly Ala Gly Asp Asp Arg Leu Val
                85                  90                  95

Thr Leu Asp Glu Leu Pro Trp Asp Arg Pro Val Leu Asp Leu Pro Ser
            100                 105                 110

Pro Ala Pro Ala Gly Arg Glu Pro Asp Gly Glu Ile Thr Val Asp Glu
        115                 120                 125

Leu Pro Gly Ala Ile Ala Arg Val Ala Ala His Pro Phe Asp Leu Ser
    130                 135                 140

Ile Glu Ile Pro Val Arg Ala Arg Leu Phe Ala Leu Gly Pro Arg His
145                 150                 155                 160
```

-continued

```
His Val Leu Val Val Leu His His Ile Ala Thr Asp Gly Ser Ser
            165                 170                 175

Gly Gly Pro Phe Ala Arg Asp Leu Ala Ala Ala Tyr Arg Ala Arg Arg
            180                 185                 190

Thr Gly Thr Ala Pro Gln Trp Ala Pro Leu Pro Val Gln Tyr Ala Asp
            195                 200                 205

Tyr Ala Ala Trp Gln Gln Glu Leu Leu Gly Ala Glu Asp Asp Pro Asp
210                 215                 220

Ser Val Ile Ser Arg Gln Leu Ala His Trp Gln Glu Arg Leu Ala Gly
225                 230                 235                 240

Met Pro Val Glu Leu Asp Leu Pro Ala Asp Arg Pro Arg Pro Ala Glu
            245                 250                 255

Pro Gly His Gly Gly His Thr Lys Ala Leu Ser Leu Pro Pro Ala Val
            260                 265                 270

His Arg Gly Leu Ala Thr Leu Ala Arg Arg Arg Ala Thr Leu Gln
            275                 280                 285

Met Val Val Gln Thr Gly Val Ala Ile Leu Leu Ser Lys Leu Gly Ala
            290                 295                 300

Gly Arg Asp Val Pro Leu Gly Ile Pro Val Ala Gly Arg Thr Asp Ala
305                 310                 315                 320

Ala Leu Asp Asp Leu Ile Gly Phe Phe Val Asn Thr Leu Val Val Arg
            325                 330                 335

Ala Asp Leu Ser Gly Asp Pro Thr Val Ala Asp Ala Leu Gly Arg Val
            340                 345                 350

Arg Gly Gly Ala Val Ala Ala Leu Ala Asp Gln Asp Val Pro Phe Asp
            355                 360                 365

Lys Leu Val Glu Arg Leu Ala Pro Ala Arg Val Leu Gly Arg His Pro
            370                 375                 380

Leu Phe Gln Val Met Val Ala Pro Leu Asp Asp Gly Thr Pro Ile Asp
385                 390                 395                 400

Leu Asp Gly Val Arg Gly Glu Pro Leu Thr Ile Gly Arg Ser Gly Ala
            405                 410                 415

Lys Phe Asp Val Glu Val Met Thr Gly Glu Val Arg Ala Ala Asp Gly
            420                 425                 430

Ala Pro Ala Gly Ile Arg Gly Ile Leu Thr Leu Ser Ala Asp Leu Phe
            435                 440                 445

Asp Glu Ala Thr Ala Gly Arg Met Ala Ala Gly Leu Val Arg Val Leu
            450                 455                 460

Thr Ala Met Ala Glu Ala Pro Glu Arg Arg Leu Ser Gly Ile Glu Val
465                 470                 475                 480

Leu Ser Pro Gly Glu Arg Ser Arg Leu Leu Val Glu Trp Asn Asp Thr
            485                 490                 495

Ala Arg Pro Val Val Glu Ser Ser Val Pro Ala Leu Phe Ala Lys Arg
            500                 505                 510

Val Ala Ala Thr Pro Asp Ala Thr Ala Val Val Gly Glu Gly Val Ser
            515                 520                 525

Trp Ser Tyr Arg Glu Leu Asp Arg Arg Ser Asp Val Leu Ala Arg Arg
            530                 535                 540

Leu Val Ala Ala Gly Val Gly Val Glu Ser Pro Val Val Ala Leu
545                 550                 555                 560

Glu Arg Ser Pro Glu Val Leu Ser Ala Phe Leu Ala Val Ala Lys Ala
            565                 570                 575
```

-continued

```
Gly Gly Val Phe Val Pro Val Asp Leu Ser Trp Pro Gln Ala Arg Val
            580                 585                 590

Asp Ala Val Val Ala Asp Cys Ala Ala Arg Val Ala Val Ala Asp Arg
            595                 600                 605

Pro Met Ser Gly Leu Thr Val Val Ser Ala Gly Leu Gly Gly Asp Ser
610                 615                 620

Ala Val Val Ser Ala Asp Leu Thr Ala Asp Arg Ala Val Val Leu Pro
625                 630                 635                 640

Ser Arg Pro Val Pro Gly Ala Ala Val Tyr Arg Met Tyr Thr Ser Gly
            645                 650                 655

Ser Thr Gly Arg Pro Lys Gly Val Val Thr Thr His Gln Asn Leu Val
            660                 665                 670

Asp Leu Ala Thr Asp Thr Cys Trp Gly Pro Thr Pro Arg Val Leu Phe
            675                 680                 685

His Ala Pro His Ala Phe Asp Ala Ser Ser Tyr Glu Ile Trp Val Pro
            690                 695                 700

Leu Leu Asn Gly Gly Thr Val Val Ala Pro Gln Arg Ser Ile Asp
705                 710                 715                 720

Ala Thr Val Leu Lys Asp Leu Ile Arg Ala His Asp Leu Thr His Val
            725                 730                 735

His Val Thr Ala Gly Leu Leu Arg Val Leu Asp Pro Ser Cys Phe Ala
            740                 745                 750

Gly Leu Thr Glu Val Leu Thr Gly Gly Asp Ala Val Ser Ala Glu Ala
            755                 760                 765

Val Arg Arg Val Lys Asp Ala Asn Pro Gly Leu Arg Val Arg Gln Leu
            770                 775                 780

Tyr Gly Pro Thr Glu Val Thr Leu Cys Ala Thr Gln His Leu Leu Asp
785                 790                 795                 800

Asp Gly Val Pro Ile Gly Arg Pro Leu Asp Asn Thr Arg Val Tyr Val
            805                 810                 815

Leu Asp Asp Leu Leu Gln Pro Val Pro Val Gly Val Thr Gly Glu Leu
            820                 825                 830

Tyr Val Ala Gly Ala Gly Val Ala Arg Gly Tyr Ala Gly Met Pro Gly
            835                 840                 845

Leu Thr Ala Glu Arg Phe Val Ala Asp Pro Phe Asn Thr Gly Gly Arg
850                 855                 860

Leu Tyr Arg Thr Gly Asp Leu Val Arg Trp Thr Asp Asp Gly Val Leu
865                 870                 875                 880

His Phe Ala Gly Arg Ala Asp Asp Gln Val Lys Ile Arg Gly Tyr Arg
            885                 890                 895

Val Glu Pro Gly Glu Val Glu Ala Val Leu Ala Gln His Pro Asp Val
            900                 905                 910

Ser Gln Val Ala Val Val Arg Glu Asp Thr Pro Gly Asp Lys Arg
            915                 920                 925

Leu Val Ala Tyr Val Val Gly Gly Asp Ile Glu Ala Tyr Gly Gln Glu
            930                 935                 940

Arg Leu Pro Gly Tyr Met Val Pro Ser Ala Phe Val His Leu Asp Ala
945                 950                 955                 960

Leu Pro Leu Thr Ser Asn Gln Lys Val Asp Arg Ala Ala Leu Pro Ala
            965                 970                 975

Pro Ser Met Glu Ser Gly Ala Gly Arg Ala Pro Ala Asp Ala Arg Glu
            980                 985                 990
```

-continued

```
Glu Leu Val Cys Ala Ala Phe Ala Glu Val Leu Gly Leu Asp Arg Val
    995                 1000                1005

Gly Val Asp Asp Phe Phe Ala Leu Gly Gly His Ser Leu Leu
    1010                1015                1020

Ala Val Ser Leu Val Glu Asp Leu Arg Gln Arg Gly Leu His Val
    1025                1030                1035

Ser Val Arg Ala Leu Phe Ala Thr Pro Thr Pro Ala Ala Leu Ala
    1040                1045                1050

Val Ser Thr Val Ala Ala Pro Ile Glu Val Pro Pro Asn Leu Ile
    1055                1060                1065

Pro Gln Gly Gly Ala Arg Glu Leu Thr Pro Asp Met Leu Pro Leu
    1070                1075                1080

Val Asp Leu Thr Gly Glu Glu Leu Ala Thr Ile Val Ala Ala Val
    1085                1090                1095

Pro Gly Gly Ala Ala Asn Ile Ala Asp Ile Tyr Pro Leu Ala Pro
    1100                1105                1110

Leu Gln Glu Gly Ile Phe Phe His His Leu Met Thr Glu Gly Asp
    1115                1120                1125

Thr Ala Asp Val Tyr Ala Leu Pro Tyr Leu Leu Arg Val Gly Thr
    1130                1135                1140

Arg Glu Gln Leu Asp Ala Phe Leu Gly Ala Leu Gln Gln Val Val
    1145                1150                1155

Asp Arg His Asp Val Tyr Arg Thr Ala Ile Ala Trp Gln Asn Leu
    1160                1165                1170

Arg Glu Pro Val Gln Val Val His Arg His Ala Thr Leu Pro Val
    1175                1180                1185

Thr Glu Val Thr Pro Asp Gln Leu His Ala Ala Ala Thr Gly Gly
    1190                1195                1200

Arg Leu Pro Leu Asp His Ala Pro Leu Leu Ser Val His Ile Ala
    1205                1210                1215

Pro Glu Pro Asp Gly Gly Trp Leu Ala Leu Leu Arg Met His His
    1220                1225                1230

Leu Val Gln Asp His Thr Ala Leu Asp Ile Val Leu Asp Glu Ile
    1235                1240                1245

Arg Thr Ile Leu Ala Gly Ala Thr Asp His Leu Pro Pro Pro Val
    1250                1255                1260

Pro Phe Arg Asn Phe Val Ala Arg Ser Arg Arg Gly Ala Ala Glu
    1265                1270                1275

Ala Ala His Arg Asp Tyr Phe Thr Gly Leu Leu Gly Asp Val Thr
    1280                1285                1290

Glu Thr Thr Ala Pro Tyr Gly Leu Thr Asp Val His Gly Glu His
    1295                1300                1305

Ser Gly Val Arg Arg Gly Arg Leu Ala Val Ser Ala Gly Leu Ala
    1310                1315                1320

Gly Arg Val Arg Glu Thr Ala Arg Asp Arg Gly Val Ser Pro Ala
    1325                1330                1335

Thr Leu Phe His Leu Ala Trp Ala Arg Val Leu Ala Ala Val Ser
    1340                1345                1350

Gly Arg Asp Asp Val Val Phe Gly Thr Val Leu Leu Gly Arg Met
    1355                1360                1365

Asp Ala Gly Pro Gly Ala Asp Arg Val Pro Gly Leu Phe Met Asn
    1370                1375                1380
```

-continued

```
Thr Leu Pro Val Arg Val Arg Leu Gly Gly Arg Thr Val Asp Glu
    1385            1390                1395
Ala Leu His Gly Met Arg Ala Gln Leu Ala Asp Leu Leu Thr His
    1400            1405                1410
Glu His Ala Pro Leu Val Leu Ala Gln Gln Ser Ala Gly Leu Pro
    1415            1420                1425
Gly Gly Ser Pro Leu Phe Thr Ser Leu Phe Asn Tyr Arg His Asn
    1430            1435                1440
Ala Thr Asp Ile Glu Arg Ser Gly Thr Gly Ile Asp Gly Val Glu
    1445            1450                1455
Ala Leu Pro Thr Gly Asp Pro Ser Asn Tyr Pro Leu Asp Val Ser
    1460            1465                1470
Val Asn Gln Ser Pro Leu Gly Phe Glu Leu Val Val Glu Ala Thr
    1475            1480                1485
Glu Pro Ala Asp Pro Asp Gln Leu Cys Arg Leu Leu His Ala Cys
    1490            1495                1500
Leu Asp Asp Leu Ile Ala Ala Leu Asp Glu Gln Pro Gly Arg Ala
    1505            1510                1515
Leu Gly Thr Leu Asp Val Val Ala Gly Arg Glu Arg Asp Leu Leu
    1520            1525                1530
Leu Asp Gly Trp Asn Ala Thr Ala Val Pro Ala Gln Pro Ala Leu
    1535            1540                1545
Val Pro Glu Leu Phe Thr Ala Gln Ala Ala Arg Thr Pro Thr Trp
    1550            1555                1560
Pro Ala Leu Val Thr Ala Gly Ala Glu Met Ser Tyr Ala Glu Leu
    1565            1570                1575
Glu Glu Arg Ser Asn Arg Leu Ala Arg Trp Leu Ala Gly Arg Gly
    1580            1585                1590
Val Gly Ala Asp Asp Arg Val Ala Leu Met Met Arg Arg Gly Pro
    1595            1600                1605
Glu Leu Met Val Ala Ile Leu Ala Val Leu Lys Ala Gly Ala Ala
    1610            1615                1620
Tyr Leu Pro Val Asp Pro Asp Leu Pro Arg Asp Arg Val Asp Tyr
    1625            1630                1635
Leu Leu Ala Asp Ala Ala Pro Ala Phe Val Leu Ala Glu Arg Ala
    1640            1645                1650
Thr Ala Pro Trp Val Pro Val Ala Gly Gly Ile Pro Val Leu Val
    1655            1660                1665
Val Asp Ala Pro Ala Val Ala Ala Glu Val Ala Ala His Ser Gly
    1670            1675                1680
Glu Ala Val Thr Asp Arg Asp Arg Arg Ala Ala Leu Arg Gly Gly
    1685            1690                1695
His Leu Ala Tyr Val Ile Tyr Thr Ser Gly Ser Thr Gly Arg Pro
    1700            1705                1710
Lys Gly Val Leu Ile Thr His Asp Gly Leu Ala Asn Leu Thr Leu
    1715            1720                1725
Asp His Gly Arg Phe Gly Leu Gly Pro Gly Ala Arg Val Ala Gln
    1730            1735                1740
Phe Ala Ser Pro Gly Phe Asp Met Phe Val Asp Glu Trp Ser Met
    1745            1750                1755
Ala Leu Leu Ala Gly Ala Ala Leu Thr Phe Val Pro Pro Glu Arg
    1760            1765                1770
```

-continued

Arg Leu Gly Ala Asp Leu Ala Ala Phe Leu Ala Glu Tyr Gly Val
1775                1780                1785

Thr His Ala Thr Leu Pro Pro Ala Val Val Gly Thr Ile Pro Asp
1790                1795                1800

Gly Val Leu Pro Pro Ser Phe Val Leu Asp Val Gly Gly Asp Val
1805                1810                1815

Leu Pro Gly Asp Leu Ala Arg Arg Trp Leu Arg Asp Gly Arg Val
1820                1825                1830

Leu Phe Asn Ser Tyr Gly Pro Thr Glu Thr Thr Val Asn Ala Ala
1835                1840                1845

Thr Trp Arg Ala Glu Ala Gly Asp Trp Gly Ser Val Ala Pro Ile
1850                1855                1860

Gly Thr Pro Val Pro Asn Leu Arg Ala Tyr Val Leu Asp Gly Trp
1865                1870                1875

Leu Arg Pro Val Pro Val Gly Ala Asp Gly Glu Leu Tyr Val Ser
1880                1885                1890

Gly Ala Gly Leu Ala Arg Gly Tyr Leu Asn Arg Ala Gly Leu Thr
1895                1900                1905

Ala Glu Arg Phe Val Ala Cys Pro Phe Glu Pro Gly Glu Arg Met
1910                1915                1920

Tyr Arg Thr Gly Asp Val Val Arg Trp Thr Ala Glu Gly Arg Leu
1925                1930                1935

Val Phe Ala Gly Arg Ser Asp Asp Gln Val Lys Ile Arg Gly Phe
1940                1945                1950

Arg Ile Glu Pro Gly Glu Val Glu Ala Val Leu Ala Ala Gly Pro
1955                1960                1965

Gly Val Ser Gln Ala Ala Val Ile Val Arg Glu Asp Val Pro Gly
1970                1975                1980

Asp Lys Arg Leu Val Ala Tyr Val Val Gly Gly Asp Val Glu Ala
1985                1990                1995

Leu Arg Ser Tyr Ala Gln Gln Arg Leu Pro Gly Tyr Met Val Pro
2000                2005                2010

Ser Ala Phe Val Glu Leu Asp Arg Leu Pro Leu Thr Val Asn Gly
2015                2020                2025

Lys Leu Asp Arg Arg Ala Leu Pro Val Pro Asp Leu Ala Arg Gly
2030                2035                2040

Thr Gly Ser Gly Arg Pro Ala Gly Thr Pro Arg Glu Gln Leu Leu
2045                2050                2055

Cys Ala Gly Phe Ala Ala Val Leu Gly Val Asp Asp Val Gly Ala
2060                2065                2070

Asp Asp Asp Phe Phe Ala Leu Gly Gly His Ser Leu Leu Val Val
2075                2080                2085

Ser Leu Val Glu Trp Leu Arg Arg Arg Gly Val Ser Val Pro Val
2090                2095                2100

Arg Ala Leu Phe Thr Thr Pro Thr Pro Ala Gly Leu Ala Glu Ala
2105                2110                2115

Val Gly Asp Gly Ala Val Val Pro Pro Asn Leu Ile Pro Glu
2120                2125                2130

Gly Ala Ala Glu Leu Thr Pro Glu Met Val Pro Leu Ala Asp Leu
2135                2140                2145

Thr Ser Glu Glu Leu Ala Ile Val Val Ala Ser Val Pro Gly Gly
2150                2155                2160

-continued

```
Ala Ala Asn Val Ala Asp Val Tyr Pro Leu Ala Pro Leu Gln Glu
2165                2170                2175

Gly Ile Phe Phe Pro Val Ala Thr Gly Pro Gln Cys Tyr Ala Thr
    2180                2185                2190

Val Gly Ser Ser Leu Pro Asp Asp Gly Ser Ala Pro Cys Ser
    2195                2200                2205

Arg Phe Arg Arg Arg Cys Val Ser Thr Ser Val Val Trp Gln Gly
    2210                2215                2220

Leu Arg Glu Pro Val Gln Val Val Trp Arg His Ala Arg Leu Pro
    2225                2230                2235

Val Glu Glu Val Val Leu His Glu Gly Ala Asp Pro Val Glu Gln
    2240                2245                2250

Met Met Ala Leu Ala Gly Gly Trp Met Asp Leu Thr Arg Ala Pro
    2255                2260                2265

Leu Ile Asp Val His Ile Ala Ala Gly Pro Gly Gly Asp Arg Trp
    2270                2275                2280

Leu Ala Val Leu Arg Ile His His Leu Val Gln Asp His Thr Ala
    2285                2290                2295

Leu Glu Thr Leu Leu Asp Glu Leu Gln Ser Phe Leu Glu Gly Arg
    2300                2305                2310

Gly Gly Glu Leu Ala Glu Pro Val Pro Phe Arg Glu Phe Val Ala
    2315                2320                2325

Gln Ala Arg Leu Gly Val Pro Arg Glu Glu His Glu Arg Tyr Phe
    2330                2335                2340

Ala Glu Leu Leu Gly Asp Ile Thr Glu Thr Thr Ala Pro Tyr Asp
    2345                2350                2355

Leu Thr Asp Val His Gly Asp Gly Thr Gly Tyr Asp His Gly Ala
    2360                2365                2370

Leu Pro Leu Asp Ala Thr Val Ala Ala Arg Val Arg Glu Ala Ala
    2375                2380                2385

Arg Thr Leu Gly Val Ser Pro Ala Thr Leu Phe His Leu Ala Trp
    2390                2395                2400

Ala Arg Val Leu Gly Thr Leu Ala Gly Arg Asp Asp Val Val Phe
    2405                2410                2415

Gly Thr Val Leu Phe Gly Arg Met Asn Ser Gly Ala Gly Ala Asp
    2420                2425                2430

Arg Val Ser Gly Leu Phe Ile Asn Thr Leu Pro Val Arg Val Arg
    2435                2440                2445

Leu Gly Ala Pro Thr Gly Asp Ala Leu Gly Asp Leu Arg Asp Gln
    2450                2455                2460

Leu Ala Glu Leu Leu Val His Glu His Ala Ser Leu Ala Ser Ala
    2465                2470                2475

Gln Lys Ala Ser Gly Leu Pro Gly Gly Ser Pro Leu Phe Thr Ser
    2480                2485                2490

Ile Phe Asn Tyr Arg His Asn Gln Val Ser Ala Glu Arg Glu Thr
    2495                2500                2505

Ala Ala Leu Pro Gly Ile Arg Val Leu Ala Ala Arg Asp Ser Thr
    2510                2515                2520

Asn Tyr Pro Leu Thr Val Ala Val Asp Asp Gly His Gly Phe
    2525                2530                2535

Thr Leu Val Val Glu Val Ala Ser Thr Val Asp Ala Ala Gly Val
    2540                2545                2550
```

-continued

```
Cys Glu Leu Leu His Thr Ala Val Asp Asn Leu Ile Ala Ala Leu
2555                2560                2565

Thr Asp Arg Pro Gly Gly Pro Leu Ala Glu Val Asp Ile Leu Glu
2570                2575                2580

Arg Gly Leu Arg Asp Arg Leu Leu Thr Ala Trp Asn Glu Ala Arg
2585                2590                2595

Glu Pro Ala Pro Pro Val Thr Leu Pro Asp Leu Phe Asp Arg Gln
2600                2605                2610

Ala Arg Arg Thr Pro Glu Ala Val Ala Leu Thr Ala Asp Gly Val
2615                2620                2625

Ser Leu Thr Tyr Arg Glu Leu Ser Glu Arg Ala Asn Arg Ile Ala
2630                2635                2640

Arg Leu Leu Thr Ser Arg Gly Ile Gly Pro Glu Ser Leu Val Gly
2645                2650                2655

Val Val Leu Pro Arg Ser Ala Asp Leu Val Val Ala Leu Leu Gly
2660                2665                2670

Val Leu Gln Ala Gly Ala Ala Tyr Val Pro Val Asp Ala Asp Tyr
2675                2680                2685

Pro Ala Glu Arg Ile Gly Tyr Ile Leu Gly Asp Ala Gly Ala Val
2690                2695                2700

Cys Val Leu Thr Val Asp Ala Thr Ala Gly Ala Val Pro Pro Gly
2705                2710                2715

Val Pro Lys Leu Val Leu Asp His Pro Glu Thr Val Thr Ala Leu
2720                2725                2730

Ala Ala Cys Asp Thr Ala Pro Leu Gly Glu Ala Glu Arg Ala Gly
2735                2740                2745

Glu Leu Leu Pro Glu His Pro Ala Tyr Val Ile Tyr Thr Ser Gly
2750                2755                2760

Ser Thr Gly Thr Pro Lys Gly Val Leu Ile Pro His Arg Asn Val
2765                2770                2775

Val Glu Leu Phe Ala Ala Thr Arg Gly Ser Phe His Phe Gly Glu
2780                2785                2790

Gly Asp Val Trp Ser Trp Phe His Ser Val Ala Phe Asp Phe Ser
2795                2800                2805

Val Trp Glu Leu Trp Gly Ala Leu Leu His Gly Gly Arg Val Val
2810                2815                2820

Met Val Pro Phe Ala Val Ser Arg Ser Pro Arg Asp Phe Trp Glu
2825                2830                2835

Leu Leu Val Arg Glu Arg Val Thr Val Leu Ser Gln Thr Pro Ser
2840                2845                2850

Ala Phe Tyr Gln Leu Ala Ala Ala Ala Asp Asp Thr Pro Asp Ala
2855                2860                2865

Leu Arg Val Val Val Phe Gly Gly Glu Ala Leu Asp Pro Gly Arg
2870                2875                2880

Leu Ala Gly Trp Arg Glu Arg Arg Pro Asp Gly Pro Arg Leu Val
2885                2890                2895

Asn Met Tyr Gly Ile Thr Glu Thr Thr Val His Val Thr His Gln
2900                2905                2910

Asp Leu Ala Pro Ala Asp Thr Thr Gly Ser Pro Ile Gly Arg Gly
2915                2920                2925

Ile Pro Gly Leu Ser Val Tyr Val Leu Asp Glu Ala Leu Arg Pro
2930                2935                2940
```

-continued

```
Val Pro Pro Gly Val Ala Gly Glu Val Tyr Val Ala Gly Arg Gln
2945                2950                2955

Leu Ala Arg Ala Tyr Leu Gly Arg Ala Ala Leu Thr Gly Thr Arg
2960                2965                2970

Phe Val Ala Cys Pro Phe Leu Pro Ala Gly Glu Arg Met Tyr Arg
2975                2980                2985

Thr Gly Asp Arg Ala Arg Trp Ser Arg Gly Arg Leu Gln Phe Ala
2990                2995                3000

Gly Arg Thr Asp Asp Gln Val Gln Ile Arg Gly Phe Arg Ile Glu
3005                3010                3015

Pro Gly Glu Val Gln Ala Val Val Ala Ala His Pro Glu Ile Ala
3020                3025                3030

Ala Ala Ala Val Val Val Arg Glu Asp Val Pro Gly Asp Pro Arg
3035                3040                3045

Leu Thr Ala Tyr Val Val Pro Ala Gly Pro Arg Thr Ala Pro Ala
3050                3055                3060

Ala Val Ala Glu Thr Val Arg Arg Phe Ala Ala Asp Arg Leu Pro
3065                3070                3075

Ala Tyr Met Leu Pro Ser Ala Val Val Val Leu Asp Ala Leu Pro
3080                3085                3090

Leu Thr Asp His Gly Lys Leu Asp Arg Arg Ala Leu Pro Ala Pro
3095                3100                3105

Gln His Thr Gly Ala Ala Ser Gly Arg Ala Pro Ala Thr Val Ala
3110                3115                3120

Glu Glu Val Leu Cys Ala Ala Phe Ala Glu Val Leu Gly Val Glu
3125                3130                3135

Arg Val Gly Val Asp Asp Asp Phe Phe Ala Leu Gly Gly His Ser
3140                3145                3150

Leu Leu Ile Val Ser Leu Val Glu Arg Val Arg Arg Ala Gly Leu
3155                3160                3165

Ala Ile Pro Val Arg Ala Leu Phe Arg Ser Ala Thr Pro Ala Gly
3170                3175                3180

Leu Ala Ala Leu Ala Arg Pro Tyr Arg Val Asp Ile Pro Pro Asn
3185                3190                3195

Leu Val Pro Asp Gly Ala Arg Glu Ile Thr Pro Asp Met Leu Thr
3200                3205                3210

Leu Ala Ala Leu Thr Glu Ala Glu Ile Ala Thr Val Leu Ala Thr
3215                3220                3225

Val Pro Gly Gly Ala Val Asn Val Ala Asp Ile Tyr Pro Leu Ala
3230                3235                3240

Pro Leu Gln Glu Gly Ile Phe Phe His His Leu Met Ala Asp Ala
3245                3250                3255

Gly Arg Ala Asp Ala Tyr Ala Met Pro Tyr Val Leu His Leu Asp
3260                3265                3270

Thr Ala Glu Arg Leu Asp Val Leu Leu Gly Ala Leu Gln Arg Val
3275                3280                3285

Ile Asp Arg Asn Asp Ile Tyr Arg Thr Gly Val Val Ser Ala Gly
3290                3295                3300

Leu Arg Glu Pro Val Gln Val Trp Arg Ser Ala Val Leu Pro
3305                3310                3315

Val Glu Glu Val Ala Leu Asp Gly Gly His Asp Pro Val Glu Gln
3320                3325                3330
```

```
Leu Leu Ala Ala Ala Gly Glu Glu Phe Asp Leu Thr Arg Ala Pro
3335                3340                3345

Leu Ile Arg Ala His Val Ala Ala His Pro Asp Gly Gly Arg Leu
3350                3355                3360

Leu Leu Leu Arg Ile His His Leu Val Gln Asp His Thr Thr Phe
3365                3370                3375

Asp Val Val Leu Gly Glu Leu Arg Ala Phe Leu Glu Gly Arg Gly
3380                3385                3390

Gly Glu Leu Ala Glu Pro Val Pro Phe Arg Glu Phe Val Ala Gln
3395                3400                3405

Ala Arg Leu Gly Val Pro Arg Glu Glu His Glu Arg Tyr Phe Ala
3410                3415                3420

Glu Leu Leu Gly Asp Val Thr Glu Thr Thr Ala Pro Tyr Gly Leu
3425                3430                3435

Thr Asp Val His Gly Asp Gly Ser Arg Ala Val Gln Val Ser Leu
3440                3445                3450

Pro Val Ala Glu Ala Leu Ala Val Arg Val Arg Glu Val Ala Arg
3455                3460                3465

Thr Leu Gly Val Ser Pro Ala Thr Val Phe His Leu Ala Trp Ala
3470                3475                3480

Arg Val Leu Ser Val Ile Ala Gly Arg Asp Asp Val Val Phe Gly
3485                3490                3495

Thr Ile Leu Phe Gly Arg Met Asn Ser Gly Ala Ala Ala Glu Arg
3500                3505                3510

Val Pro Gly Leu Phe Ile Asn Thr Leu Pro Val Arg Val Arg Leu
3515                3520                3525

Asn Gly Thr Ser Val Gly Glu Ala Leu Thr Ala Leu Arg Asp Gln
3530                3535                3540

Met Ala Glu Leu Met Ala His Glu His Ala Pro Leu Ala Leu Ala
3545                3550                3555

Gln Arg Ala Gly Gly Val Pro Ala Gly Ser Pro Leu Phe Thr Ser
3560                3565                3570

Leu Phe Asn Tyr Arg His Asn Val Ala Gly Gly Gly Asp Gly Gly
3575                3580                3585

Ala Leu Glu Gly Val Thr Pro Val Leu His Arg Asp Thr Thr Asn
3590                3595                3600

Tyr Pro Val Val Val Ser Val Asp Asp Asp Gly Thr Ser Phe Asp
3605                3610                3615

Leu Val Val Glu Ala Val Ala Pro Ala Glu Ala Gly Arg Val Gly
3620                3625                3630

Arg Leu Met His Glu Cys Leu Ala Glu Leu Val Gly Ala Leu Ala
3635                3640                3645

Gly Ala Pro Glu Thr Pro Leu Ser Arg Val Arg Val Ile Asp Glu
3650                3655                3660

Ala Glu Ile Glu Arg Val Val His Ser Trp Asn Asp Thr Ala Arg
3665                3670                3675

Pro Val Val Glu Ser Ser Val Pro Ala Leu Phe Ala Glu Gln Val
3680                3685                3690

Ala Ala Ala Pro Asp Ala Thr Ala Val Val Gly Glu Gly Val Ser
3695                3700                3705

Trp Ser Tyr Arg Glu Leu Asp Ala Arg Ser Asp Ala Leu Ala Arg
3710                3715                3720
```

```
Ser Leu Val Ala Ala Gly Val Gly Val Glu Ser Pro Val Val Val
    3725            3730            3735

Ala Leu Glu Arg Ser Pro Glu Val Leu Ser Ala Phe Leu Ala Val
    3740            3745            3750

Ala Lys Ala Gly Gly Val Phe Val Pro Val Asp Leu Ser Trp Pro
    3755            3760            3765

Gln Ala Arg Ile Asp Ala Val Val Ala Asp Cys Ala Ala Arg Val
    3770            3775            3780

Ala Val Ala Asp Arg Pro Met Ser Gly Leu Thr Val Val Pro Ala
    3785            3790            3795

Asp Gln Val Gly Asp Ser Ala Val Val Leu Pro Ala Gly Pro Val
    3800            3805            3810

Pro Gly Ala Ala Val Tyr Arg Met Tyr Thr Ser Gly Ser Thr Gly
    3815            3820            3825

Arg Pro Lys Gly Val Val Thr Thr His Gln Asn Leu Val Asp Leu
    3830            3835            3840

Ala Thr Asp Thr Cys Trp Gly Pro Thr Pro Arg Val Leu Phe His
    3845            3850            3855

Ala Pro His Ala Phe Asp Ala Ser Ser Tyr Glu Ile Trp Val Pro
    3860            3865            3870

Leu Leu Asn Gly Gly Thr Val Val Val Ala Pro Gln Arg Ser Ile
    3875            3880            3885

Asp Ala Thr Val Leu Arg Asp Leu Ile Arg Gly His Glu Leu Thr
    3890            3895            3900

His Val His Val Thr Ala Gly Leu Leu Arg Val Leu Asp Pro Ser
    3905            3910            3915

Cys Phe Ala Gly Leu Thr Glu Val Leu Thr Gly Gly Asp Ala Val
    3920            3925            3930

Ser Ala Glu Ala Val Arg Arg Val Arg Glu Ala Asn Pro Gly Leu
    3935            3940            3945

Arg Val Arg Gln Leu Tyr Gly Pro Thr Glu Val Thr Leu Cys Ala
    3950            3955            3960

Thr Gln His Leu Leu Val Asp Gly Val Pro Ile Gly Arg Pro Leu
    3965            3970            3975

Asp Asn Thr Arg Val Tyr Val Leu Asp Asp Leu Leu Gln Pro Val
    3980            3985            3990

Pro Val Gly Val Thr Gly Glu Leu Tyr Val Ala Gly Ala Gly Leu
    3995            4000            4005

Ala Arg Gly Tyr Ala Gly Met Pro Gly Leu Thr Ala Glu Arg Phe
    4010            4015            4020

Val Ala Asp Pro Phe Ser Val Gly Gly Arg Leu Tyr Arg Thr Gly
    4025            4030            4035

Asp Leu Val Arg Trp Thr Asp Asp Gly Val Leu His Phe Ala Gly
    4040            4045            4050

Arg Ala Asp Asp Gln Val Lys Ile Arg Gly Tyr Arg Val Glu Pro
    4055            4060            4065

Gly Glu Val Glu Ala Val Leu Ala Gln His Pro Asp Val Ser Gln
    4070            4075            4080

Val Ala Val Val Val Arg Glu Asp Thr Pro Gly Asp Lys Arg Leu
    4085            4090            4095

Val Ala Tyr Val Val Gly Gly Asp Val Glu Ala Tyr Ala Gln Glu
    4100            4105            4110
```

```
Arg Leu Pro Gly Tyr Leu Val Pro Ser Ala Phe Val His Leu Asp
4115                4120                4125

Ala Leu Pro Leu Thr Ser Asn Gln Lys Val Asp Arg Ala Ala Leu
4130                4135                4140

Pro Ala Pro Ser Val Glu Ser Gly Val Gly Arg Ala Pro Ala Asp
4145                4150                4155

Ala Arg Glu Glu Leu Met Cys Ala Ala Phe Ala Glu Val Leu Asp
4160                4165                4170

Leu Asp Arg Val Gly Val Asp Asp Phe Phe Ala Leu Gly Gly
4175                4180                4185

His Ser Leu Leu Val Val Arg Leu Val Gly Arg Ile Arg Gln Val
4190                4195                4200

Phe Gly Val Glu Val Ser Ala Arg Leu Val Phe Asp Ala Arg Thr
4205                4210                4215

Pro Ala Gly Val Val Ala Arg Leu Ser Glu Gly Gly Thr Ala Arg
4220                4225                4230

Glu Ala Val Arg Ala Arg Val Arg Pro Ala Arg Val Pro Leu Ser
4235                4240                4245

Phe Ala Gln Arg Arg Leu Trp Phe Leu Ser Gln Leu Glu Gly Pro
4250                4255                4260

Ser Ala Thr Tyr Asn Ile Pro Val Ala Leu Arg Leu Asp Gly Pro
4265                4270                4275

Leu Asp Arg Asp Ala Leu Thr Ala Ala Leu His Asp Val Val Ala
4280                4285                4290

Arg His Glu Val Leu Arg Thr Val Phe Thr Val Ala Asp Gly Glu
4295                4300                4305

Pro Trp Gln Gln Ile Leu Asp Asp Pro Gln Val Ser Val Pro Val
4310                4315                4320

Val Glu Val Thr Pro Asp Arg Leu Pro Glu Ala Val Ala Val Ala
4325                4330                4335

Ala Gly His Arg Phe Asp Leu Gly Arg Glu Leu Pro Leu Arg Ala
4340                4345                4350

Val Leu Leu Ala Thr Gly Asp Asp Val His Val Leu Val Leu Val
4355                4360                4365

Val His His Ile Ala Ala Asp Gly Trp Ser Met Arg Pro Leu Ala
4370                4375                4380

Arg Asp Leu Ala Ala Ala Tyr Ala Ala Arg Ile Asp Ala Thr Ala
4385                4390                4395

Pro Ala Leu Gly Ala Leu Pro Val Gln Tyr Ala Asp Tyr Ala Leu
4400                4405                4410

Trp Gln Arg Asp Val Leu Gly Ser Glu His Asp Pro Asp Ser Val
4415                4420                4425

Ile Ser Gln Gln Val Ala Tyr Trp Arg Arg Gln Leu Ala Gly Val
4430                4435                4440

Pro Glu Glu Leu Asp Leu Pro Val Asp Arg Ala Arg Pro Ala Glu
4445                4450                4455

Ala Ser His Arg Gly His Thr Val Glu Phe Ala Val Pro Pro Ala
4460                4465                4470

Val His His Gln Leu Ala Glu Leu Ala Arg Arg Asn Gly Val Thr
4475                4480                4485

Val Phe Met Thr Val Gln Thr Ala Leu Ala Val Leu Leu Ser Lys
4490                4495                4500
```

-continued

```
Leu Gly Ala Gly Thr Asp Ile Pro Ile Gly Val Ala Val Ala Gly
    4505                4510                4515
Arg Thr Asp Pro Thr Leu Asp Asn Leu Ile Gly Phe Phe Val Asn
    4520                4525                4530
Thr Leu Val Leu Arg Thr Asp Leu Thr Gly Asn Pro Thr Ile Thr
    4535                4540                4545
Asp Leu Leu His Arg Thr Arg Asp Thr Thr Leu His Ala Phe Thr
    4550                4555                4560
His Gln Asp Val Pro Phe Glu Lys Leu Val Glu Asp Leu Ala Pro
    4565                4570                4575
Thr Arg Ser Leu Ala Arg His Pro Leu Phe Gln Val Met Met Thr
    4580                4585                4590
Leu Gln Ser Ala Ser Ala Asp Glu Glu Pro Leu Ala Leu Ala Gly
    4595                4600                4605
Leu Arg Val Thr Asp Leu Pro Ala Gly Glu Thr Pro Ala Lys Val
    4610                4615                4620
Asp Leu Asp Leu Thr Leu His Glu Val Ala Gly Arg Asp Gly Met
    4625                4630                4635
His Ala Thr Leu Leu Gly Ala Ala Asp Leu Phe Glu Gln Glu Thr
    4640                4645                4650
Val Arg Ala Leu Ala Asp Arg Leu Leu Arg Thr Leu Glu Ala Met
    4655                4660                4665
Ala Ala Ala Pro Asp Asp Arg Leu Asp Arg Ile Glu Val Leu Ser
    4670                4675                4680
Pro Gly Glu Arg Ser Arg Leu Leu Val Glu Trp Asn Asp Thr Ala
    4685                4690                4695
Arg Pro Val Val Glu Ser Ser Val Pro Ala Leu Phe Ala Glu Gln
    4700                4705                4710
Val Ala Ala Ala Pro Asp Ala Val Ala Val Val Gly Glu Gly Val
    4715                4720                4725
Ser Trp Thr Tyr Arg Glu Leu Asp Ala Arg Ser Asp Ala Leu Ala
    4730                4735                4740
Arg Ser Leu Val Ala Ala Gly Val Gly Val Glu Ser Pro Val Val
    4745                4750                4755
Val Ala Leu Glu Arg Ser Pro Glu Val Leu Ser Ala Phe Leu Ala
    4760                4765                4770
Val Ala Lys Ala Gly Gly Val Phe Val Pro Val Asp Leu Ser Trp
    4775                4780                4785
Pro Gln Ala Arg Val Asp Ala Val Val Ala Asp Cys Gly Ala Arg
    4790                4795                4800
Ile Ala Val Ala Asp Arg Pro Met Ser Gly Leu Thr Val Val Ser
    4805                4810                4815
Ala Gly Leu Gly Gly Asp Ser Ala Val Val Ser Gly Asp Leu Thr
    4820                4825                4830
Ala Asp Arg Ala Val Val Leu Pro Ala Gly Pro Val Pro Gly Ala
    4835                4840                4845
Ala Val Tyr Arg Met Tyr Thr Ser Gly Ser Thr Gly Arg Pro Lys
    4850                4855                4860
Gly Val Val Thr Thr His Gln Asn Leu Val Asp Leu Ala Thr Asp
    4865                4870                4875
Thr Cys Trp Gly Pro Thr Pro Arg Val Leu Phe His Ala Pro His
    4880                4885                4890
```

```
Ala Phe Asp Ala Ser Ser Tyr Glu Ile Trp Val Pro Leu Leu Asn
4895                    4900                4905

Gly Gly Thr Val Val Ala Pro Arg Arg Ser Ile Asp Ala Thr
4910                    4915                4920

Val Leu Arg Asp Leu Ile Gly Ala His Glu Leu Thr His Val His
4925                    4930                4935

Val Thr Ala Gly Leu Leu Arg Val Leu Asp Pro Ser Cys Phe Ala
4940                    4945                4950

Gly Leu Thr Glu Val Leu Thr Gly Gly Asp Ala Val Ser Ala Glu
4955                    4960                4965

Ala Val Arg Arg Val Lys Asp Ala Asn Pro Gly Leu Arg Val Arg
4970                    4975                4980

Gln Leu Tyr Gly Pro Thr Glu Val Thr Leu Cys Ala Thr Gln His
4985                    4990                4995

Leu Leu Asp Asp Gly Val Pro Ile Gly Arg Pro Leu Asp Asn Thr
5000                    5005                5010

Arg Val Tyr Val Leu Asp Asp Leu Leu Arg Pro Val Pro Thr Gly
5015                    5020                5025

Val Val Gly Glu Leu Tyr Val Ala Gly Ser Gly Leu Ala Arg Gly
5030                    5035                5040

Tyr Ala Gly Met Pro Gly Leu Thr Ala Glu Arg Phe Val Ala Asp
5045                    5050                5055

Pro Phe Asn Thr Gly Gly Arg Leu Tyr Arg Thr Gly Asp Leu Val
5060                    5065                5070

Arg Trp Ala Asp Asp Gly Val Leu His Phe Ala Gly Arg Ala Asp
5075                    5080                5085

Asp Gln Val Lys Ile Arg Gly Tyr Arg Val Glu Pro Gly Glu Val
5090                    5095                5100

Glu Ala Val Leu Ala Gln His Pro Asp Val Ser Gln Val Ala Val
5105                    5110                5115

Val Val Arg Glu Asp Thr Pro Gly Asp Lys Arg Leu Val Ala Tyr
5120                    5125                5130

Val Val Gly Gly Asp Val Glu Ala Tyr Ala Gln Glu Arg Leu Pro
5135                    5140                5145

Gly Tyr Met Val Pro Ser Ala Phe Val Gln Leu Asp Ala Leu Pro
5150                    5155                5160

Leu Thr Ser Asn Gln Lys Val Asp Arg Ala Ala Leu Pro Ala Pro
5165                    5170                5175

Ser Met Glu Ser Gly Ala Gly Arg Ala Pro Ala Asp Ala Arg Glu
5180                    5185                5190

Glu Leu Met Cys Ala Ala Phe Ala Glu Val Leu Asp Leu Asp Arg
5195                    5200                5205

Val Gly Val Asp Asp Asp Phe Phe Ala Leu Gly Gly His Ser Leu
5210                    5215                5220

Leu Ala Val Ser Leu Val Glu Asn Leu Arg Arg His Gly Val His
5225                    5230                5235

Ile Ser Val Arg Ala Leu Phe Ala Thr Pro Thr Pro Ala Ala Leu
5240                    5245                5250

Ala Ala Ser Ala Gly Thr Ala Val Pro Asp Val Pro Pro Asn Leu
5255                    5260                5265

Ile Pro Gln Gly Gly Ala Gln Glu Leu Thr Pro Asp Met Leu Pro
5270                    5275                5280
```

-continued

```
Leu Val Asp Leu Thr Gly Glu Glu Leu Ala Thr Ile Val Ala Ala
    5285                5290                5295

Val Pro Gly Gly Ala Pro Asn Ile Ala Asp Ile Tyr Pro Leu Ala
    5300                5305                5310

Pro Leu Gln Glu Gly Ile Phe Phe His His Leu Met Thr Glu Gly
    5315                5320                5325

Asp Ala Thr Asp Val Tyr Leu Leu Pro Arg Ile Leu Gly Phe Gly
    5330                5335                5340

Gly Arg Pro Glu Leu Asp Ala Phe Leu Gly Ala Leu Gln Gln Val
    5345                5350                5355

Val Asp Arg His Asp Val Tyr Arg Thr Ala Ile Ala Trp Gln Asn
    5360                5365                5370

Leu Arg Glu Pro Val Gln Val Val His Arg His Ala Thr Leu Pro
    5375                5380                5385

Val Thr Glu Val Thr Pro Asp Gln Leu His Ala Ala Ala Thr Gly
    5390                5395                5400

Gly Arg Leu Pro Leu Asp His Ala Pro Leu Leu Ser Val His Ile
    5405                5410                5415

Ala Pro Glu Pro Asp Gly Gly Trp Leu Ala Leu Leu Arg Met His
    5420                5425                5430

His Leu Val Gln Asp His Thr Ala Leu Asp Ile Val Leu Asp Glu
    5435                5440                5445

Ile Arg Thr Ile Leu Ala Gly Ala Thr Asp His Leu Pro Pro Pro
    5450                5455                5460

Val Pro Phe Arg Asp Phe Val Ala Gln Ala Arg Leu Gly Val Ser
    5465                5470                5475

Arg Ala Glu Gln Glu Arg Tyr Phe Ala Gly Leu Leu Gly Asp Val
    5480                5485                5490

Thr Glu Thr Thr Ala Pro Tyr Gly Leu Ala Asp Val Thr Asn Asp
    5495                5500                5505

Gly Thr Ala Ser Val Arg Ala Glu Val Glu Leu Asp Ala Ala Leu
    5510                5515                5520

Ala Ala Arg Leu Arg Asp Leu Ala Arg Asp Arg Gly Val Ser Pro
    5525                5530                5535

Ala Thr Val Phe His Leu Ala Trp Ala Arg Val Leu Ala Ala Val
    5540                5545                5550

Ala Asp Arg Glu Asp Val Val Phe Gly Thr Val Leu Phe Gly Arg
    5555                5560                5565

Met Ala Ser Gly Ala Arg Arg Val Pro Gly Leu Phe Met Asn Thr
    5570                5575                5580

Leu Pro Val Arg Val Arg Leu Ser Gly Thr Ala Ala Glu Ala Leu
    5585                5590                5595

Gly Gln Val Arg Asp Arg Leu Ala Glu Leu Met Ala His Glu His
    5600                5605                5610

Ala Pro Leu Ala Leu Ala Gln Gln Ala Ser Gly Leu Pro Ala Gly
    5615                5620                5625

Ser Pro Leu Phe Thr Ser Leu Phe Asn Tyr Arg Tyr Ala Arg Pro
    5630                5635                5640

Pro Ala Ala Thr Pro Asp Asp Pro Leu Ala Gly Val Arg Thr Leu
    5645                5650                5655

Phe Ala Trp Glu Arg Asn Asn Tyr Pro Val Thr Val Ser Ile Asp
    5660                5665                5670
```

-continued

Asp Asp Gly Thr Gly Phe Ala Val Thr Val Asp Val Val Ala Pro
5675              5680              5685

Ala Asp Ala Asp Glu Val Val Arg Leu Leu Arg Thr Thr Leu Thr
5690              5695              5700

Arg Leu Ala Ala Ala Leu Glu Arg Thr Pro Glu Met Pro Val Ala
5705              5710              5715

Asp Val Arg Pro Gly Arg Val Ser Arg Pro Ala Ala Gly Arg Ala
5720              5725              5730

Val Leu Val Pro Val Pro Ala Gly Glu Arg Ala Thr Gly Ala Gly
5735              5740              5745

Arg Ala Pro Ala Thr Ala Tyr Glu Glu Leu Ile Cys Gln Ala Tyr
5750              5755              5760

Ala Gln Val Leu Glu Val Asp Arg Val Ala Ala Asp Asp Asp Phe
5765              5770              5775

Phe Ala Leu Gly Gly Asn Ser Leu Leu Ala Thr Arg Leu Val Ser
5780              5785              5790

Arg Ile Arg Ser Ala Leu Gly Val Glu Val Thr Ile Arg Ala Leu
5795              5800              5805

Phe Glu Thr Leu Thr Pro Gln Arg Leu Ala Ala Arg Leu Thr Arg
5810              5815              5820

Ala Ser Ala Pro Gly Arg Val Ala Pro Ala Pro Arg Thr Arg Pro
5825              5830              5835

Glu Arg Ile Pro Leu Ser Phe Ala Gln Arg Arg Leu Trp Phe Leu
5840              5845              5850

Gly Glu Leu Glu Gly Ser Ser Ala Thr Tyr Ser Asn Thr Thr Ala
5855              5860              5865

Leu Arg Leu Ser Gly Glu Leu Asp Pro Ala Ala Leu Thr Ala Ala
5870              5875              5880

Leu His Asp Val Ile Gly Arg His Glu Val Leu Arg Thr Val Ile
5885              5890              5895

Pro Ala Glu Asp Gly Arg Pro Tyr Gln Leu Val Leu Pro Pro Glu
5900              5905              5910

Glu Ala Arg Pro Ala Val Glu Ile Val Glu Val Ala Pro Gly Glu
5915              5920              5925

Leu Gly Ala Ala Val Asp Glu Val Ala Gly Tyr Ala Phe Asp Leu
5930              5935              5940

Ala Ala Glu Ile Pro Val Arg Ala Arg Leu Ile Arg Leu Gly Ala
5945              5950              5955

Thr Asp His Val Leu Val Leu Val Ile His His Ile Ala Thr Asp
5960              5965              5970

Gly Trp Ser Met Ala Pro Leu Ala Arg Asp Leu Ala Ala Ala Tyr
5975              5980              5985

Glu Ala Arg Leu Ala Gly Arg Ala Pro Arg Trp Glu Pro Leu Pro
5990              5995              6000

Leu Gln Tyr Ala Asp Tyr Ala Leu Trp Gln Glu Glu Leu Leu Gly
6005              6010              6015

Ala Ala Gly Asp Pro Glu Ser Leu Arg Glu Arg Gln Leu Ala Tyr
6020              6025              6030

Trp Arg Asp Thr Leu Ala Gly Met Pro Pro Glu Ile Pro Leu Pro
6035              6040              6045

Ala Asp Arg Ser Arg Pro Pro Val Ala Ser His Arg Gly Gly Glu
6050              6055              6060

```
Val Pro Ile Ala Ile Pro Ala Asp Leu His Arg Arg Leu Ala Glu
    6065            6070            6075

Leu Ala Val Ala Glu Arg Ala Thr Leu Phe Met Val Leu Gln Ala
    6080            6085            6090

Gly Phe Ala Ala Leu Leu Ser Arg Leu Gly Ala Gly Thr Asp Val
    6095            6100            6105

Pro Ile Gly Thr Ala Leu Ala Gly Arg Thr Asp Asp Ala Leu Asp
    6110            6115            6120

Glu Leu Val Gly Phe Phe Val Asn Met Leu Val Leu Arg Thr Asp
    6125            6130            6135

Val Ser Gly Asp Pro Gly Phe Gly Thr Leu Leu Arg Arg Val Arg
    6140            6145            6150

Glu Thr Gly Leu Ala Ala Tyr Ala His Gln Asp Val Pro Phe Asp
    6155            6160            6165

Gln Val Val Glu Glu Leu Val Thr Glu Arg Ser Leu Ala Arg His
    6170            6175            6180

Pro Leu Phe Gln Val Ala Leu Thr Val Gln Asn Ala Pro Gly Ala
    6185            6190            6195

Arg Pro Arg Leu Ala Gly Leu Glu Val Gly Thr Glu Pro Ile Glu
    6200            6205            6210

His Gly Ile Ala Arg Tyr Asp Leu Thr Leu Thr Val Thr Glu Arg
    6215            6220            6225

Arg Asp Glu His Gly Ala Pro Asp Gly Leu Glu Gly His Leu Glu
    6230            6235            6240

Phe Ser Arg Asp Leu Phe Asp Ala Pro Thr Val Ala Thr Leu Gly
    6245            6250            6255

Asp Arg Leu Ile Arg Leu Leu Thr Ala Ala Val Ala Asp Pro Glu
    6260            6265            6270

Leu Pro Leu Ser Arg Ile Asp Leu Met Ala Pro Ala Glu Arg Arg
    6275            6280            6285

Asn Val Leu Glu Gly Trp Ser Thr Ala Arg Arg Asp Val Pro Ala
    6290            6295            6300

Ala Thr Val Pro Glu Leu Val Ala Ala Gln Val Ala Arg Arg Pro
    6305            6310            6315

Gly Ala Val Ala Leu Arg Ser Glu Asp Gly Glu Ile Thr Tyr Ala
    6320            6325            6330

Glu Leu Asp Ala Arg Ala Gly Arg Leu Ala Ala Val Leu Arg Arg
    6335            6340            6345

Arg Gly Ile Gly Pro Glu Ser Arg Val Ala Val Leu Leu Pro Arg
    6350            6355            6360

Gly Val Glu Gln Val Val Ala Phe Leu Ala Val Val Arg Ala Gly
    6365            6370            6375

Gly Thr Tyr Leu Pro Ile Asp Pro Ala Tyr Pro Arg Asp Arg Val
    6380            6385            6390

Asp Tyr Leu Val Arg Asp Ala Glu Pro Ala Cys Leu Leu Thr Val
    6395            6400            6405

Ala Gly His Arg Ala Ala Ala Pro Ala Ala Pro Ala Val Val Glu
    6410            6415            6420

Leu Asp Asp Pro Ala Thr Ala Ala Glu Ile Ala Asp Ala Glu Pro
    6425            6430            6435

Glu Pro Pro Val Ala Val Arg Pro Thr His Ser Ala Tyr Leu Ile
    6440            6445            6450
```

-continued

```
Tyr Thr Ser Gly Ser Thr Gly Arg Pro Lys Gly Val Val Val Thr
6455                6460                6465

His Arg Gly Val Ala Ala Leu Val Ala Thr Gln Ala Glu Arg Leu
6470                6475                6480

Ala Val Thr Gly Glu Ser Arg Val Leu Gln Phe Ala Ser Val Gly
6485                6490                6495

Phe Asp Ala Ser Ile Trp Glu Met Val Met Ala Leu Cys Ala Gly
6500                6505                6510

Ala Thr Leu Val Val Ala Pro Ala Asp Asp Leu Leu Pro Gly Pro
6515                6520                6525

Ala Leu Ala Ala Thr Leu Ser Gly His Ala Val Thr His Ala Thr
6530                6535                6540

Leu Pro Pro Ala Val Leu Ala Ala Ser Ala Pro Gly Asp Leu Ala
6545                6550                6555

Pro Leu Ala Val Leu Val Ser Ala Gly Glu Ala Leu Gly Pro Asp
6560                6565                6570

Leu Val Arg Gln Phe Ala Pro Gly Arg Ala Leu Val Asn Ala Tyr
6575                6580                6585

Gly Pro Thr Glu Thr Thr Val Cys Ala Thr Ala Ser Ala Pro Leu
6590                6595                6600

Gly Pro Glu Asp Pro Pro His Ile Gly Ala Pro Val Ala Asp Ser
6605                6610                6615

Arg Val Tyr Val Leu Asp Asp Ala Leu Thr Pro Val Pro Pro Gly
6620                6625                6630

Val Thr Gly Glu Leu Tyr Val Ser Gly Ala Ser Leu Ala Arg Gly
6635                6640                6645

Tyr Ala Gly Arg Ala Ala Leu Thr Ala Glu Arg Phe Val Ala Cys
6650                6655                6660

Pro Phe Ala Pro Gly Glu Arg Met Tyr Arg Thr Gly Asp Arg Ala
6665                6670                6675

Arg Trp Asp Ala Ala Gly Arg Leu Thr Phe Ala Gly Arg Ala Asp
6680                6685                6690

Asp Gln Val Lys Ile Arg Gly Phe Arg Val Glu Pro Gly Glu Val
6695                6700                6705

Ala Ala Val Leu Gly Glu His Pro Ala Val Ala Arg Ala Ala Val
6710                6715                6720

Val Ala Arg Thr Asp Gly Pro Gln Gly Ala Arg Leu Val Ala Tyr
6725                6730                6735

Leu Val Ala Ala Asp Pro Ala Gly Pro Asp Leu Ala Ala Ala Val
6740                6745                6750

Arg Ala Tyr Ala Ala Ala Thr Leu Pro Ala His Leu Leu Pro Ala
6755                6760                6765

Ala Phe Val Pro Leu Asp Arg Leu Pro Leu Thr Thr Asn Gly Lys
6770                6775                6780

Leu Asp Arg Ala Ala Leu Pro Glu Pro Glu Thr Gly Ala Gly Arg
6785                6790                6795

Glu Pro Ser Gly Pro Val Glu Arg Leu Leu Cys Glu Ala Phe Ala
6800                6805                6810

Asp Val Leu Gly Leu Asp Arg Val Gly Ala Asp Gly His Phe Phe
6815                6820                6825

Asp Leu Gly Gly His Ser Leu Leu Ala Thr Arg Leu Leu Ser Arg
6830                6835                6840
```

-continued

```
Leu Arg Ser Ala Ala Gly Ile Asp Val Pro Val Arg Val Leu Phe
    6845                6850                6855

Glu Asn Pro Thr Pro Ala Gly Leu Ala Ala Trp Val Glu Thr His
    6860                6865                6870

Ala Gly Ser Arg Arg Lys Ser Arg Pro Ala Leu Arg Pro Met Arg
    6875                6880                6885

His Gln Lys Glu Ser
    6890

<210> SEQ ID NO 15
<211> LENGTH: 8695
<212> TYPE: PRT
<213> ORGANISM: Actinoplanes sp.

<400> SEQUENCE: 15

Met Ile Pro Leu Ser Phe Ala Gln Arg Arg Leu Trp Phe Leu Gly Arg
1               5                   10                  15

Leu Glu Gly Pro Ser Ala Thr Tyr Asn Ile Pro Leu Val Leu Gly Leu
            20                  25                  30

Thr Gly Thr Val Asp Ala Ala Leu Glu Thr Ala Leu Arg Asp Val
        35                  40                  45

Leu Glu Arg His Glu Val Leu Arg Thr Val Tyr Pro Asp Ala Gly Gly
    50                  55                  60

Glu Pro His Gln Arg Ile Leu Pro Leu Gly Glu Thr Gly Phe Gly Leu
65                  70                  75                  80

Arg Val Ala Glu Val Thr Asp Gly Glu Leu Asp Ala Ala Val Ala Asp
                85                  90                  95

Ala Thr Gly His Ala Phe Asp Leu Ala Thr Glu Ile Pro Val Arg Ala
            100                 105                 110

Ser Leu Leu Thr Val Glu Pro Gly Arg His Val Leu Ala Leu Val Leu
        115                 120                 125

His His Ile Ala Ala Asp Gly Trp Ser Met Gly Pro Leu Leu Arg Asp
    130                 135                 140

Leu Ser Thr Ala Tyr Thr Ala Arg Leu Ala Gly Gly Glu Pro Ala Trp
145                 150                 155                 160

Ser Pro Leu Pro Val Gln Tyr Ala Asp Tyr Ala Leu Trp Gln Gln Glu
                165                 170                 175

Val Leu Gly Ala Gly Asp Asp Pro Glu Ser Leu Leu Arg Glu Gln Val
            180                 185                 190

Gly Tyr Trp Arg Ser Ala Leu Ala Gly Ala Pro Glu Glu Leu Arg Leu
        195                 200                 205

Pro Ala Asp His Arg Arg Pro Pro Val Ser Ser Ser Arg Ala His Met
    210                 215                 220

Ala Glu Phe Ala Val Pro Ala Ala His Gly Asp Leu Thr Ala Leu
225                 230                 235                 240

Thr Arg Glu Leu Gly Ala Thr Leu Phe Met Ala Val His Ala Ala Thr
                245                 250                 255

Ala Met Val Leu Ser Gly Leu Gly Ala Gly Asp Asp Leu Pro Ile Gly
            260                 265                 270

Thr Val Val Ala Gly Arg Thr Asp Ala Gly Leu Asp Asp Leu Val Gly
        275                 280                 285

Cys Phe Val Asn Asn Leu Val Ile Arg Ala Asp Leu Thr Gly Asp Pro
    290                 295                 300

Thr Phe Ala Asp Leu Leu Arg Gln Val Arg Glu Arg Ala Leu Asp Ala
305                 310                 315                 320
```

-continued

```
Tyr Gly His Gln Asp Val Pro Phe Glu Lys Leu Val Glu Glu Leu Ala
                325                 330                 335

Pro Ser Arg Ser Leu Ser Arg His Pro Leu Phe Gln Val Ala Val Ala
            340                 345                 350

Val Glu Thr Asp Asp Leu Ile Gly Gly Arg Gly Gly Gly Pro Ala Leu
        355                 360                 365

Arg Leu Pro Gly Leu Gly Ile Glu Val Leu Pro Gly Glu Pro Ser Ala
    370                 375                 380

Arg Asp Leu Asp Leu Asp Leu Val Val Arg Glu Thr Phe Asp Ala Glu
385                 390                 395                 400

Gly Arg Pro Ala Gly Leu Thr Gly Ala Leu Ile Gly Ala Ala Gly Leu
                405                 410                 415

Phe Asp Ala Ala Ser Val Glu Arg Leu Ala Ala Leu Leu Ala Arg Ala
            420                 425                 430

Leu Glu Ala Leu Ala Ala Asp Pro Arg Thr Arg Ala Gly Asp Leu Asp
        435                 440                 445

Leu Leu Ser Pro Ala Asp Arg Arg Leu Ile Leu Arg Gly Trp Asn Asp
    450                 455                 460

Thr Ala Ala Pro Ala Pro Ala Gly Leu Val Pro Asp Leu Phe Ala Ala
465                 470                 475                 480

Gln Ala Ala Arg Thr Pro Asp Ala Val Ala Val Ala Gly Pro Asp Arg
                485                 490                 495

Glu Leu Thr Tyr Ala Glu Leu Asp Glu Arg Ser Gly Arg Leu Ala Arg
            500                 505                 510

Trp Leu Ile Arg Arg Gly Val Ala Ala Asp Thr Arg Val Ala Leu Val
        515                 520                 525

Leu Glu Arg Ser Ala Glu Leu Pro Val Ala Ile Leu Ala Val Leu Lys
    530                 535                 540

Ala Gly Gly Ala Tyr Leu Pro Ile Asp Pro Ala Gln Pro Pro Arg Arg
545                 550                 555                 560

Ile Ala Asp Ile Val Ala Asp Ala Ala Pro Ala Leu Val Leu Ala Gln
                565                 570                 575

Ala Ser Thr Ala Asp Val Val Ala Asp Ala Ser Pro Ala Leu Val Leu
            580                 585                 590

Ala Pro Ala Ser Asp Gly Val Pro Thr Gly Ala Val Pro Val His Leu
        595                 600                 605

Leu Asp Ser Pro Ala Val Arg Asp Glu Val Ala Gln Cys Pro Ala Gly
    610                 615                 620

Ala Val Thr Asp Ala Asp Arg Arg Gly Val Leu Leu Gly Gly His Ala
625                 630                 635                 640

Ala Tyr Val Ile Tyr Thr Ser Gly Ser Thr Gly Arg Pro Lys Gly Val
                645                 650                 655

Val Val Ser His Asp Ala Phe Ala Asn Leu Val Leu Asp Gln Arg Arg
            660                 665                 670

Leu Gly Ile Gly Pro Gly Ser Arg Val Ala Gln Phe Ala Ser Pro Gly
        675                 680                 685

Phe Asp Met Phe Val Asp Glu Trp Ser Met Ala Leu Leu Ala Gly Ala
    690                 695                 700

Ala Leu Val Ile Val Pro Pro Glu Arg Arg Leu Gly Ala Asp Leu Ala
705                 710                 715                 720

Ala Phe Leu Thr Glu Arg Gly Val Thr His Ala Thr Leu Pro Pro Ala
                725                 730                 735
```

-continued

```
Val Val Ala Thr Leu Pro Glu Ser Leu Pro Arg Ser Phe Val Leu
            740                 745                 750

Asp Ile Gly Gly Asp Ala Leu Pro Asp Leu Ala Arg Arg Trp Leu
            755                 760                 765

Arg Asp Gly Arg Trp Leu Gly Asn Ser Tyr Gly Pro Thr Glu Thr Thr
770                 775                 780

Val Asn Ala Ala Thr Trp Arg Cys Glu Pro Gly Thr Trp Glu Gly Ala
785                 790                 795                 800

Thr Pro Ile Gly Arg Pro Val Ala Asn Leu Arg Ala Tyr Val Leu Asp
                805                 810                 815

Gly Arg Leu Arg Pro Val Pro Val Gly Val Glu Gly Glu Leu Tyr Val
            820                 825                 830

Ser Gly Ala Gly Leu Ala Arg Gly Tyr Leu Asn Arg Ala Gly Leu Thr
            835                 840                 845

Ala Gly Ser Phe Val Ala Cys Pro Phe Glu Pro Gly Glu Arg Met Tyr
850                 855                 860

Arg Thr Gly Asp Ile Val Arg Trp Asp Ala Arg Gly Arg Leu Val Tyr
865                 870                 875                 880

Ala Gly Arg Ala Asp Asp Gln Ala Lys Ile Arg Gly Phe Arg Val Glu
                885                 890                 895

Pro Gly Glu Val Glu Ala Val Leu Ala Ala Gly Pro Gly Val Asn Gln
            900                 905                 910

Val Ala Val Ile Val Arg Glu Asp Val Pro Gly Asp Lys Arg Leu Val
            915                 920                 925

Ala Tyr Val Val Gly Gly Asp Val Glu Thr Leu Arg Ser Tyr Ala Gln
            930                 935                 940

Gln Arg Leu Pro Gly Tyr Leu Val Pro Ser Ala Ile Val Ala Leu Ala
945                 950                 955                 960

Glu Leu Pro Leu Thr Pro Ser Ala Lys Val Asp Arg Arg Ala Leu Pro
                965                 970                 975

Val Pro Asp Tyr Gly Arg Asp Ala Gly Gly Arg Ala Pro Ala Asn
            980                 985                 990

Ala Arg Glu Glu Val Leu Cys Arg Ala Phe Ala Glu Val Leu Gly Val
            995                 1000                1005

Glu Arg Val Gly Val Glu Asp Asp Phe Phe Ala Leu Gly Gly His
            1010                1015                1020

Ser Leu Leu Val Val Ser Leu Val Glu Arg Leu Arg Arg Gln Gly
            1025                1030                1035

Ile Ser Val Pro Val Arg Ala Leu Phe Thr Thr Pro Thr Pro Ala
            1040                1045                1050

Gly Leu Ala Glu Ala Val Gly Asp Gly Ala Val Val Val Pro Pro
            1055                1060                1065

Asn Leu Ile Pro Glu Gly Ala Ala Glu Leu Thr Pro Glu Met Leu
            1070                1075                1080

Pro Leu Ala Asp Leu Thr Ala Asp Glu Leu Ala Val Val Val Asp
            1085                1090                1095

Ser Val Pro Gly Gly Ala Ala Asn Ile Ala Asp Val Tyr Pro Leu
            1100                1105                1110

Ala Pro Leu Gln Glu Gly Ile Phe Phe His His Met Met Ala Asp
            1115                1120                1125

Arg Asp Ser Ala Asp Val Tyr Val Thr Pro Thr Val Val Glu Phe
            1130                1135                1140
```

-continued

```
Asp Ser Arg Asp Arg Leu Asp Gly Phe Leu Ala Ala Leu Gln Gln
1145                1150                1155

Val Val Asp Arg Thr Asp Val Tyr Arg Thr Ser Val Val Trp Gln
1160                1165                1170

Gly Leu Arg Glu Pro Val Gln Val Val Trp Arg His Ala Arg Leu
1175                1180                1185

Pro Val Asp Glu Val Val Leu Arg Asp Asp Leu Asp Pro Val Glu
1190                1195                1200

Gln Leu Asn Ala Leu Gly Thr Ala Trp Met Asp Leu Ser Glu Ala
1205                1210                1215

Pro Leu Val Gln Ala Val Val Ala Ala Arg Pro Gly Asp Pro Gln
1220                1225                1230

Arg Trp Leu Ala Val Leu Arg Ile His His Leu Val Gln Asp His
1235                1240                1245

Thr Ala Leu Asp Ile Leu Leu Glu Glu Leu Ala Ala Tyr Leu Ala
1250                1255                1260

Gly Arg Gly Gly Asp Leu Pro Glu Pro Val Pro Phe Arg Glu Phe
1265                1270                1275

Val Ala His Thr Arg Leu Gly Val Pro Arg Glu Glu His Glu Arg
1280                1285                1290

Tyr Phe Ala Gly Leu Leu Gly Asp Val Thr Glu Thr Thr Ala Pro
1295                1300                1305

Tyr Gly Leu Leu Asp Val His Ser Gly Gly Leu Ala Ser Ala Gln
1310                1315                1320

Ala His Leu Arg Leu Asp Gly Pro Leu Gly Arg Arg Val Ala Ala
1325                1330                1335

Phe Ala Arg Glu His Gly Val Ser Pro Ala Thr Leu Phe His Leu
1340                1345                1350

Ala Trp Ala Arg Val Leu Gly Thr Leu Ala Gly Arg Asp Asp Val
1355                1360                1365

Val Phe Gly Thr Val Leu Phe Gly Arg Met Asn Ser Gly Ala Gly
1370                1375                1380

Ala Asp Arg Val Pro Gly Leu Phe Ile Asn Thr Leu Pro Val Arg
1385                1390                1395

Val Arg Leu Gly Ala Pro Val Gly Asp Ala Leu Asp Gly Leu Arg
1400                1405                1410

Asp Gln Leu Ile Glu Leu Ile Ala His Glu His Ala Pro Leu Ala
1415                1420                1425

Val Ala Gln Gln Ala Ala Asn Leu Phe Gly Arg Pro Leu Phe Thr
1430                1435                1440

Ser Ile Phe Asn Tyr Arg Tyr Ala Arg Gly Ala Glu Pro Ala Gly
1445                1450                1455

Ala Ala Leu Asp Gly Ile Arg Leu Leu Ser Ala Arg Asp Leu Thr
1460                1465                1470

Asn Tyr Pro Leu Ala Val Ala Val Asp Ala Glu Gly Asp Thr Phe
1475                1480                1485

Ser Leu Thr Val Asp Ala Val Ala Pro Ala Asp Pro Val Gln Val
1490                1495                1500

Gly Glu Leu Leu Val Thr Ala Leu Arg Asn Leu Thr Arg Thr Ala
1505                1510                1515

Glu Asn Ala Pro Gly Thr Pro Leu Ala Ala Val Gly Val Leu Gly
1520                1525                1530
```

-continued

```
Glu Asp Glu Leu Ser Arg Val Val Ser Gly Trp Asn Asp Thr Ala
1535                1540                1545

Arg Arg Val Arg Gln Ala Ser Val Pro Glu Leu Phe Ala Glu Arg
    1550                1555                1560

Val Ala Ala Ala Pro Gly Ala Pro Ala Val Ala Ala Gly Asp Leu
1565                1570                1575

Arg Trp Thr Tyr Ala Asp Leu Asp Ala Arg Ser Asp Ala Leu Ala
    1580                1585                1590

Arg Ser Leu Val Ala Ala Gly Val Thr Ala Glu Ser Pro Val Val
1595                1600                1605

Val Ala Leu Glu Arg Ser Ala Asp Val Leu Thr Ala Phe Leu Ala
1610                1615                1620

Val Ala Lys Ala Gly Gly Val Phe Val Pro Val Asp Leu Ser Trp
1625                1630                1635

Pro Arg Ala Arg Val Asp Ala Val Ile Ala Asp Cys Ala Ala Trp
1640                1645                1650

Ile Ala Val Ala Asp Arg Pro Met Thr Gly Leu Thr Val Val Pro
1655                1660                1665

Ala Asn Arg Ala Gly Asp Pro Ala Val Ala Leu Pro Pro Arg Pro
1670                1675                1680

Leu Pro Gly Ala Ala Ala Tyr Arg Met Tyr Thr Ser Gly Ser Thr
1685                1690                1695

Gly Arg Pro Lys Gly Val Val Thr Thr His Gln Asn Val Val Asp
1700                1705                1710

Leu Val Thr Asp Arg Cys Trp Gly Pro Thr Pro Arg Val Leu Phe
1715                1720                1725

His Ala Pro His Ala Phe Asp Ala Ser Ser Phe Glu Leu Trp Val
1730                1735                1740

Pro Leu Leu Thr Gly Gly Thr Val Val Val Ala Pro Gly Glu Ser
1745                1750                1755

Ile Asp Thr Gly Val Leu Arg Gln Leu Ile Arg Ala His Glu Leu
1760                1765                1770

Thr His Val His Val Thr Ala Gly Leu Leu Arg Val Leu Ala Glu
1775                1780                1785

Asp Pro Ser Cys Phe Ala Gly Leu Thr Glu Val Leu Thr Gly Gly
1790                1795                1800

Asp Val Val Pro Ala Glu Ala Val Arg Arg Val Leu Asp Ala Asn
1805                1810                1815

Pro Gly Val Arg Val Arg Gln Leu Tyr Gly Pro Thr Glu Val Thr
1820                1825                1830

Leu Cys Ala Thr Gln His Val Val Arg Glu Pro Ser Pro Val Leu
1835                1840                1845

Pro Ile Gly Arg Pro Leu Asp Asn Thr Arg Val Tyr Val Leu Asp
1850                1855                1860

Gly Leu Leu Gln Pro Val Pro Val Gly Val Thr Gly Glu Leu Tyr
1865                1870                1875

Ile Ala Gly Ala Gly Val Ala Arg Gly Tyr Ala Asp Met Pro Gly
1880                1885                1890

Thr Thr Ala Glu Arg Phe Val Ala Asp Pro Phe Thr Ala Gly Gly
1895                1900                1905

Arg Leu Tyr Arg Thr Gly Asp Leu Val Arg Trp Thr Gly Glu Gly
1910                1915                1920
```

```
Glu Leu Val Phe Ala Gly Arg Ala Asp Gln Val Lys Ile Arg
    1925                1930            1935

Gly Tyr Arg Val Glu Pro Gly Glu Val Glu Ala Val Leu Ala Ala
    1940                1945            1950

Leu Pro Gly Val Ser Gln Ala Ala Val Ile Val Arg Glu Asp Val
    1955                1960            1965

Pro Gly Asp Lys Arg Leu Val Ala Tyr Leu Val Ala Ala Pro Glu
    1970                1975            1980

Thr Val Glu Ala Ala Arg Ala His Ala Glu Gln Arg Leu Pro Ser
    1985                1990            1995

Tyr Leu Val Pro Ser Ala Phe Val Gln Leu Asp Ala Leu Pro Leu
    2000                2005            2010

Thr Gly Asn Gln Lys Val Asp Arg Ala Ala Leu Pro Ala Pro Leu
    2015                2020            2025

Gly Phe Glu Ala Gly Ala Gly Arg Ala Pro Ala Asp Ala Arg Glu
    2030                2035            2040

Glu Leu Val Gly Ala Ala Phe Ala Glu Val Leu Asp Leu Gly Arg
    2045                2050            2055

Val Gly Pro Asp Asp Asp Phe Phe Ala Leu Gly Gly His Ser Leu
    2060                2065            2070

Leu Ala Leu Ala Leu Val Glu Arg Leu Arg Arg Gln Gly Leu Gly
    2075                2080            2085

Val Ser Val Arg Ala Val Phe Asp Ala Arg Thr Pro Ala Ala Leu
    2090                2095            2100

Thr Arg Arg Gly Asp Gly Gly Ala Asp Asp Arg Pro Ala Leu Arg
    2105                2110            2115

Ala Gly Ala Arg Pro Ala Arg Leu Pro Leu Ser Tyr Ala Gln Arg
    2120                2125            2130

Arg Leu Trp Phe Leu Ala Gln Leu Glu Gly Pro Ser Ala Thr Tyr
    2135                2140            2145

Asn Ile Pro Val Ala Leu Arg Leu Glu Gly Asp Leu Asp Arg Asp
    2150                2155            2160

Ala Leu Thr Ala Ala Leu Arg Asp Val Val Ala Arg His Glu Val
    2165                2170            2175

Leu Arg Thr Val Phe Thr Val Ala Asp Gly Glu Pro Trp Gln His
    2180                2185            2190

Ile Leu Asp Pro Ala Arg Ala Glu Pro Ala Leu Pro Val Val Asp
    2195                2200            2205

Val Pro Ala Gly Arg Val Glu Glu Ala Val Ala Glu Ala Ala Ala
    2210                2215            2220

Tyr Ala Phe Asp Leu Ala Arg Glu Ile Pro Leu Arg Ala Val Leu
    2225                2230            2235

Leu Ala Pro Gly Asp Gly Thr His Val Leu Val Leu Val Leu His
    2240                2245            2250

His Ile Ala Ala Asp Gly Trp Ser Met Arg Pro Leu Ala Arg Asp
    2255                2260            2265

Leu Ala Thr Ala Tyr Ala Ala Arg Arg Arg Gly Gln Ala Pro Glu
    2270                2275            2280

Ser Glu Thr Leu Pro Val Gln Tyr Ala Asp Tyr Ala Leu Trp Gln
    2285                2290            2295

Arg Asp Leu Leu Gly Ser Asp Ser Asp Pro Ala Ser Leu Ile Ser
    2300                2305            2310
```

-continued

```
Arg Gln Ile Ala His Trp Arg Glu Arg Leu Asp Gly Val Pro Glu
    2315            2320            2325

Glu Leu Asp Leu Pro Ala Asp Arg Pro Arg Pro Ala Ala Ala Ser
    2330            2335            2340

His Arg Gly His Leu His Ser Ala Glu Ile Pro Ala Asp Val His
    2345            2350            2355

Arg Ser Leu Arg Arg Val Ala Ala Asp His Gly Ala Thr Val Phe
    2360            2365            2370

Met Thr Leu Gln Ala Ala Val Ala Val Leu Leu Ser Arg Leu Gly
    2375            2380            2385

Ala Gly Thr Asp Val Pro Ile Gly Thr Val Val Ala Gly Arg Ala
    2390            2395            2400

Asp Arg Ala Leu Glu Asn Leu Val Gly Phe Phe Val Asn Thr Leu
    2405            2410            2415

Val Leu Arg Thr Asp Leu Thr Gly Asp Pro Arg Leu Thr Asp Val
    2420            2425            2430

Leu Gly Gln Val Arg Glu Leu Thr Leu Arg Ala Leu Ala His Gln
    2435            2440            2445

Asp Val Pro Phe Glu Lys Leu Val Glu Glu Leu Thr Pro Ala Arg
    2450            2455            2460

Ser Leu Ala Arg His Pro Leu Phe Gln Val Met Val Thr Leu Asp
    2465            2470            2475

Gly Gly Gly Pro Asp Gly Ala Glu Leu Pro Gly Leu Ala Met Ser
    2480            2485            2490

Val Val Pro Thr Gly Ala Val Pro Ala Lys Phe Asp Leu Asp Leu
    2495            2500            2505

Thr Phe Thr Glu Thr Phe Asp Ala Ala Gly Glu Pro Ala Gly Leu
    2510            2515            2520

Arg Val Asp Leu Ile Ala Ala Asp Leu Phe Asp Ala Gly Thr
    2525            2530            2535

Ala Ala Arg Leu Ala Gly Tyr Leu Ser Arg Val Leu Gly Val Leu
    2540            2545            2550

Ala Ala Asp Pro Arg Arg Leu Ala Glu Val Asp Pro Leu Glu
    2555            2560            2565

Ala Glu Glu Ser Arg Leu Met Leu Ala Ala Gly Glu Glu Pro Ala
    2570            2575            2580

Pro Ala Leu Pro Glu Ile Thr Val Ala Ala Leu Val Ala Glu Gln
    2585            2590            2595

Cys Ala Arg Thr Pro Gly Ala Val Ala Val Thr Gly Pro Asp Ala
    2600            2605            2610

Ser Leu Thr Tyr Ala Glu Leu Asp Glu Arg Ala Ala Arg Ile Ala
    2615            2620            2625

Arg Trp Leu Arg Arg His Gly Ala Gly Pro Gly Ala Ala Val Cys
    2630            2635            2640

Val Leu Met Glu Arg Ser Ala Glu Leu Val Ala Val Leu Leu Gly
    2645            2650            2655

Val Met Arg Ala Gly Ala Ala Tyr Val Pro Val Asp Pro Ala Tyr
    2660            2665            2670

Pro Ala Glu Arg Ile Arg Phe Val Val Thr Asp Ala Arg Ala Ala
    2675            2680            2685

Cys Val Val Ser Glu Ser Ala Ser Ala Gly Leu Val Pro Asp Gly
    2690            2695            2700
```

-continued

```
Val Pro Cys Leu Ala Ile Asp Asp Pro Ala Ala Ala Glu Pro
2705                2710                2715

Ala Glu Pro Gly Asp Asp Pro Gly Asp Ala Ala Gly Pro Arg Pro
2720                2725                2730

Asp Asp Pro Ala Tyr Ile Ile Tyr Thr Ser Gly Ser Thr Gly Thr
2735                2740                2745

Pro Lys Gly Val Val Val Ser His Arg Asn Val Ala Leu Leu
2750                2755                2760

Thr Ala Thr Arg Pro Leu Phe Gly Phe Ala Gly Asp Glu Val Trp
2765                2770                2775

Ser Trp Phe His Ser Val Ala Phe Asp Phe Ser Val Trp Glu Leu
2780                2785                2790

Trp Gly Ala Leu Thr His Gly Gly Arg Val Val Val Pro Tyr
2795                2800                2805

Ala Val Ser Arg Ser Pro Arg Asp Phe Trp Glu Leu Val Val Arg
2810                2815                2820

Glu Gly Val Thr Val Leu Ser Gln Thr Pro Ser Ala Phe Ala Gln
2825                2830                2835

Leu Met Ala Ala Ala Gly Asp Asp Asp Arg Asp Ala Leu Arg Phe
2840                2845                2850

Val Val Phe Gly Gly Glu Ala Leu Asp Pro Gly Arg Leu Ala Gly
2855                2860                2865

Trp Leu Ala Arg Arg Pro Asp Lys Pro Arg Leu Val Asn Met Tyr
2870                2875                2880

Gly Ile Thr Glu Thr Thr Val His Thr Thr Tyr Gln His Ile Ala
2885                2890                2895

Pro Gly Thr Thr Gly Ser Val Ile Gly Arg Gly Leu Pro Gly Phe
2900                2905                2910

Gly Leu Tyr Val Leu Asp Glu Ala Leu Arg Pro Val Pro Ala Gly
2915                2920                2925

Val Pro Gly Glu Val Tyr Ala Arg Gly Pro Gln Val Ala Arg Gly
2930                2935                2940

Tyr Ile Gly Arg Pro Gly Leu Thr Ala Glu Arg Phe Val Ala Ser
2945                2950                2955

Pro Phe Ala Pro Gly Glu Arg Met Tyr Arg Thr Gly Asp Val Ala
2960                2965                2970

Arg Trp Thr Ala Asp Gly Arg Leu Val Phe Ala Gly Arg Ser Asp
2975                2980                2985

Asp Gln Ile Lys Ile Arg Gly Phe Arg Ile Glu Pro Gly Glu Val
2990                2995                3000

Glu Ala Val Leu Ala Ala Gly Pro Gly Val Ser Gln Ala Ala Val
3005                3010                3015

Ile Val Arg Glu Asp Val Pro Gly Asp Lys Arg Leu Val Ala Tyr
3020                3025                3030

Val Val Gly Gly Asp Ala Glu Thr Leu Arg Ser His Ala Gln Gln
3035                3040                3045

Arg Leu Pro Gly Tyr Leu Val Pro Ser Ala Phe Val Glu Leu Asp
3050                3055                3060

Arg Leu Pro Leu Thr Val Asn Gly Lys Leu Asp Arg Arg Ala Leu
3065                3070                3075

Pro Val Pro Asp Tyr Gly Arg Asp Ala Gly Gly Arg Ala Pro
3080                3085                3090
```

-continued

```
Ala Asn Ala Arg Glu Glu Val Leu Cys Arg Ala Phe Ala Glu Val
    3095                3100                3105

Leu Gly Val Glu Arg Val Gly Val Glu Asp Phe Phe Ala Leu
    3110                3115                3120

Gly Gly His Ser Leu Leu Val Val Ser Leu Val Glu Arg Leu Arg
    3125                3130                3135

Arg Gln Gly Ile Ser Val Pro Val Arg Ala Leu Phe Thr Thr Pro
    3140                3145                3150

Thr Pro Ala Gly Leu Ala Glu Ala Val Gly Asp Gly Ala Val Val
    3155                3160                3165

Val Pro Pro Asn Leu Ile Pro Glu Asp Ala Ala Glu Leu Thr Pro
    3170                3175                3180

Glu Met Leu Pro Leu Ala Asp Leu Thr Ala Asp Glu Leu Ala Val
    3185                3190                3195

Val Val Ala Ser Val Pro Gly Gly Ala Ala Asn Ile Ala Asp Val
    3200                3205                3210

Tyr Pro Leu Ala Pro Leu Gln Glu Gly Ile Phe Phe His His Met
    3215                3220                3225

Met Ala Asp Arg Asp Ser Ala Asp Val Tyr Val Thr Pro Thr Val
    3230                3235                3240

Val Glu Phe Asp Ser Arg Asp Arg Leu Asp Gly Phe Leu Ala Ala
    3245                3250                3255

Leu Gln Gln Val Val Asp Arg Thr Asp Val Tyr Arg Thr Ser Val
    3260                3265                3270

Val Trp Gln Gly Leu Arg Glu Pro Val Gln Val Trp Arg His
    3275                3280                3285

Ala Arg Leu Pro Ile Asp Glu Val Glu Leu His Glu Gly Thr Asp
    3290                3295                3300

Pro Ala Glu Gln Leu Ile Ala Leu Ala Thr Glu Arg Val Asp Leu
    3305                3310                3315

Asp Arg Ala Pro Leu Ile Arg Thr Thr Thr Ala Ala Val Pro Gly
    3320                3325                3330

Ser Gly Arg Trp Leu Ala Leu Leu Arg Ile His His Leu Val Gln
    3335                3340                3345

Asp His Thr Thr Leu Asp Val Leu Leu Gly Glu Leu Arg Ala Phe
    3350                3355                3360

Leu Glu Gly Arg Gly Asp Glu Leu Pro Glu Pro Val Pro Phe Arg
    3365                3370                3375

Glu Phe Val Ala Gln Ala Arg Leu Gly Val Pro Arg Glu Glu His
    3380                3385                3390

Glu Arg Tyr Phe Ala Glu Leu Leu Gly Asp Val Thr Glu Thr Thr
    3395                3400                3405

Ala Pro Tyr Gly Leu Thr Glu Val His Gly Asp Gly Ser Ala Ala
    3410                3415                3420

Val His Ser Arg Arg Glu Val Asp Asp Asp Leu Ala Ala Arg Leu
    3425                3430                3435

His Arg Leu Ala Arg Ser Leu Gly Val Ser Pro Ala Ala Leu Phe
    3440                3445                3450

His Leu Ala Trp Ala Arg Val Leu Gly Ala Val Ser Gly Arg Asp
    3455                3460                3465

Asp Val Val Phe Gly Thr Val Leu Phe Gly Arg Met Asn Ser Gly
    3470                3475                3480
```

-continued

| | | | | | | | | | | | | |
|---|---|---|---|---|---|---|---|---|---|---|---|---|
|Ala|Ala|Ala|Asp|Arg|Val|Gln|Gly|Leu|Phe|Ile|Asn|Thr|Leu|Pro|
|   |3485|   |   |   |3490|   |   |   |3495|   |   |   |

Ala Ala Ala Asp Arg Val Gln Gly Leu Phe Ile Asn Thr Leu Pro
      3485                 3490              3495

Val Arg Val Arg Leu Ala Ala Gly Ser Thr Arg Asp Ala Leu Thr
      3500                 3505              3510

Gly Leu Arg Asp Gln Leu Ala Gly Leu Leu Val His Glu His Ala
      3515                 3520              3525

Pro Leu Ala Leu Ala Gln Arg Ala Ala Gly Ile Thr Asp Gly Ser
      3530                 3535              3540

Pro Leu Phe Ala Ser Ile Phe Asn Tyr Arg His Asn Gln Asp Asp
      3545                 3550              3555

Pro Ala Ala Ser Ala Gly Leu Glu Gly Ile Arg Thr Val Tyr Ser
      3560                 3565              3570

Ala Glu His Thr Asn Tyr Pro Leu Asp Ala Ser Ile Asp Val Thr
      3575                 3580              3585

Gly Asp Arg Phe Ala Ile Thr Val Asn Ala Val Ala Pro Ala Asp
      3590                 3595              3600

Ala Ala Arg Ile Ala Glu Leu Met His Thr Cys Leu Gly His Leu
      3605                 3610              3615

Ala Asp Val Leu Glu Asp Ala Pro Glu Thr Pro Leu Ser Trp Val
      3620                 3625              3630

Ser Pro Leu Ser Ala Glu Asp Leu Gly Arg Ile Val Gly Asp Trp
      3635                 3640              3645

Asn Glu Thr Arg Arg Ala Val Thr Arg Ala Ser Val Pro Glu Leu
      3650                 3655              3660

Phe Ala Lys Gln Val Ala Ala Thr Pro Asp Ala Ile Ala Val Ala
      3665                 3670              3675

Gly Glu Gly Val Ser Trp Ser Tyr Arg Glu Leu Asp Val Arg Ser
      3680                 3685              3690

Asp Ala Leu Ala Arg Ser Leu Val Ala Ala Gly Val Gly Ile Glu
      3695                 3700              3705

Ser Pro Val Val Val Ala Leu Asp Arg Ser Pro Glu Val Pro Thr
      3710                 3715              3720

Ala Phe Leu Ala Val Ala Lys Ala Gly Gly Val Phe Val Pro Val
      3725                 3730              3735

Asp Leu Ser Trp Pro Gln Ala Arg Val Asp Ala Val Ile Ala Asp
      3740                 3745              3750

Cys Ala Ala Arg Val Ala Val Ala Asp Arg Pro Met Thr Gly Leu
      3755                 3760              3765

Thr Val Val Pro Ala Asp Ala Ala Gly Asp Pro Ala Ala Glu Leu
      3770                 3775              3780

Pro Pro Arg Pro Leu Pro Gly Ala Glu Val Tyr Arg Met Tyr Thr
      3785                 3790              3795

Ser Gly Ser Thr Gly Arg Pro Lys Gly Val Val Thr Thr His Gln
      3800                 3805              3810

Asn Leu Val Asp Leu Ala Thr Asp Thr Cys Trp Gly Pro Thr Pro
      3815                 3820              3825

Arg Val Leu Phe His Ala Pro His Ala Phe Asp Ala Ser Ser Tyr
      3830                 3835              3840

Glu Ile Trp Val Pro Leu Leu Asn Gly Gly Thr Val Val Val Ala
      3845                 3850              3855

Pro Gly Arg Ser Ile Asp Ala Ala Val Leu Gly Glu Leu Ile Arg
      3860                 3865              3870

-continued

```
Ala His Glu Leu Thr His Val His Val Thr Ala Gly Leu Leu Arg
3875             3880             3885

Val Leu Asp Pro Ser Cys Phe Ala Gly Leu Thr Glu Val Leu Thr
3890             3895             3900

Gly Gly Asp Ala Val Ser Ala Glu Ala Val Arg Arg Val Met Glu
3905             3910             3915

Ala Asn Pro Gly Leu Arg Val Arg Gln Leu Tyr Gly Pro Thr Glu
3920             3925             3930

Val Thr Leu Cys Ala Thr Gln Gln Val Leu Asp Gly Thr Gly Val
3935             3940             3945

Pro Ile Gly Arg Pro Leu Asp Asn Thr Arg Val Tyr Val Leu Asp
3950             3955             3960

Asp Leu Leu Gln Pro Val Pro Val Gly Val Thr Gly Glu Leu Tyr
3965             3970             3975

Val Ala Gly Ala Gly Leu Ala Arg Gly Tyr Ala Gly Met Pro Gly
3980             3985             3990

Leu Thr Ala Glu Arg Phe Val Ala Asp Pro Phe Ser Ser Gly Gly
3995             4000             4005

Arg Leu Tyr Arg Thr Gly Asp Leu Val Arg Trp Thr Asp Asp Gly
4010             4015             4020

Val Leu Val Phe Ala Gly Arg Ala Asp Asp Gln Val Lys Ile Arg
4025             4030             4035

Gly Tyr Arg Val Glu Pro Gly Glu Val Glu Ala Val Leu Ala Ala
4040             4045             4050

His Pro Asp Val Ala Gln Val Ala Val Val Val Arg Glu Asp Thr
4055             4060             4065

Pro Gly Asp Lys Arg Leu Val Ala Tyr Val Val Gly Gly Asp Val
4070             4075             4080

Glu Ala Tyr Ala Gln Glu Arg Leu Pro Gly Tyr Leu Val Pro Ser
4085             4090             4095

Ala Phe Val His Leu Asp Ala Leu Pro Leu Thr Ser Asn Gln Lys
4100             4105             4110

Val Asp Arg Ala Ala Leu Pro Ala Pro Ser Val Glu Ser Gly Ala
4115             4120             4125

Gly Arg Ala Pro Ala Asp Ala Arg Glu Glu Leu Met Cys Ala Ala
4130             4135             4140

Phe Ala Glu Val Leu Asp Leu Asp Arg Val Gly Val Asp Asp Asp
4145             4150             4155

Phe Phe Ala Leu Gly Gly His Ser Leu Leu Val Val Arg Leu Val
4160             4165             4170

Gly Arg Ile Arg Gln Val Phe Gly Val Glu Val Ser Ala Arg Leu
4175             4180             4185

Val Phe Asp Ala Arg Thr Pro Ala Gly Val Val Ala Arg Leu Ser
4190             4195             4200

Glu Gly Gly Thr Ala Arg Glu Ala Val Arg Ala Arg Val Arg Pro
4205             4210             4215

Ala Arg Val Pro Leu Ser Phe Ala Gln Arg Arg Leu Trp Phe Leu
4220             4225             4230

Ser Gln Leu Asp Gly Thr Ser Thr Thr Tyr Asn Ile Pro Val Ala
4235             4240             4245

Leu Gln Leu Asp Gly Pro Leu Asp Arg Asp Ala Phe Thr Ala Ala
4250             4255             4260
```

-continued

```
Leu His Asp Val Val Ala Arg His Glu Val Leu Arg Thr Val Phe
    4265                4270                4275

Thr Val Ala Asp Gly Glu Pro Trp Gln His Ile Leu Asp Thr Pro
    4280                4285                4290

Ser Val Ser Val Pro Val Ile Glu Val Pro Ala Asp Gly Leu Pro
    4295                4300                4305

Glu Ala Val Ala Ala Ala Ala His Thr Phe Asp Leu Ser Arg
    4310                4315                4320

Glu Ile Pro Leu Arg Ala Val Leu Leu Ala Thr Gly Ala Asp Arg
    4325                4330                4335

His Val Leu Val Leu Val Val His His Ile Ala Ala Asp Gly Trp
    4340                4345                4350

Ser Met Gln Pro Leu Ala Arg Asp Leu Ala Val Ala Tyr Ala Ala
    4355                4360                4365

Arg Ile Arg Gly Glu Ala Pro Ala Trp Thr Ala Leu Pro Val Gln
    4370                4375                4380

Tyr Ala Asp Tyr Ala Leu Trp Gln Arg Asp Val Leu Gly Ser Glu
    4385                4390                4395

His Asp Pro Asp Ser Ala Ile Ser Gln Gln Val Ala His Trp Arg
    4400                4405                4410

Arg Gln Leu Ala Gly Ala Pro Asp Glu Leu Pro Leu Pro Ala Asp
    4415                4420                4425

His Pro Arg Pro Ala Glu Ala Thr Tyr Arg Gly His Thr Val Glu
    4430                4435                4440

Phe Thr Val Pro Pro Ala Val His His Gln Leu Ala Glu Leu Ala
    4445                4450                4455

Arg Arg Asn Gly Val Thr Val Phe Met Thr Val Gln Thr Ala Leu
    4460                4465                4470

Ala Val Leu Leu Ser Lys Leu Gly Ala Gly Thr Asp Ile Pro Ile
    4475                4480                4485

Gly Val Ala Val Ala Gly Arg Thr Asp Pro Thr Leu Asp Asn Leu
    4490                4495                4500

Ile Gly Phe Phe Val Asn Thr Leu Val Leu Arg Thr Asp Leu Thr
    4505                4510                4515

Gly Asn Pro Thr Ile Thr Asp Leu Leu His Arg Thr Arg Asp Thr
    4520                4525                4530

Thr Leu His Ala Phe Thr His Gln Asp Val Pro Phe Glu Lys Leu
    4535                4540                4545

Val Glu Asp Leu Ala Pro Thr Arg Ser Leu Ala Arg His Pro Leu
    4550                4555                4560

Phe Gln Val Met Met Thr Leu Gln Ser Thr Gly Arg Ala Gly Glu
    4565                4570                4575

Ala Ala Glu Leu Pro Gly Leu Glu Thr Ala Val Leu Ser Pro Gly
    4580                4585                4590

Gly Val Ala Ala Lys Val Asp Leu Asp Leu Ser Leu Ser Glu Ala
    4595                4600                4605

Tyr Asp Asp Asp Gly Arg Pro Ala Gly Leu Ala Gly Thr Leu Val
    4610                4615                4620

Ala Ala Ala Asp Leu Phe Glu His Gly Thr Ala Glu Arg Ile Ala
    4625                4630                4635

Gly Tyr Leu Ala Arg Leu Leu Ala Val Leu Pro Ala Asp Pro Gly
    4640                4645                4650
```

```
Ala Arg Leu Gly Asp Val Asp Leu Leu Asp Gly Glu Glu Arg Arg
4655                 4660                 4665

Leu Val Leu Thr Gly Trp Asn Asp Thr Thr Ala Ala Val Pro Ala
4670                 4675                 4680

Val Ala Val Pro Glu Leu Ile Glu Arg Arg Ala Ala Ala Glu Pro
4685                 4690                 4695

Glu Ala Gly Ala Val Trp Cys Gly Asp Thr His Leu Arg Tyr Gly
4700                 4705                 4710

Glu Leu Asn Ala Arg Ala Asn Arg Leu Ala Arg Leu Leu Val Glu
4715                 4720                 4725

Arg Gly Ala Gly Pro Glu Ser Ile Val Ala Val Cys Leu Glu Arg
4730                 4735                 4740

Ser Ala Asp Leu Val Val Thr Leu Leu Ala Val Leu Lys Thr Gly
4745                 4750                 4755

Ala Ala Tyr Leu Pro Ile Asp Pro Gly Tyr Pro Ala Gly Arg Ile
4760                 4765                 4770

Ala Tyr Met Leu Ala Asp Ala Arg Pro Ala Leu Leu Val Thr Ser
4775                 4780                 4785

Pro Ala Val Ala Ser Gly Asp Ser Leu Pro Asp Gly Gly Ala Gln
4790                 4795                 4800

Arg Ile Val Leu Gly Asp Pro Asp Thr Ala Ala Ala Leu Asp Gly
4805                 4810                 4815

Leu Ala Gly Thr Asp Leu Leu Val Ser Glu Arg Arg Gly Val Thr
4820                 4825                 4830

His Pro Ala His Pro Ala Tyr Val Ile Tyr Thr Ser Gly Ser Thr
4835                 4840                 4845

Gly Arg Pro Lys Gly Val Val Val Pro His Gly Ala Leu Thr Asn
4850                 4855                 4860

Phe Val Ala Ala Met Ser Asp Arg Leu Ala Leu Gly Ala Gly Asp
4865                 4870                 4875

Arg Leu Leu Ala Val Thr Thr Val Ala Phe Asp Ile His Val Leu
4880                 4885                 4890

Glu Leu Tyr Val Pro Leu Val Gly Gly Ala Gly Val Val Val Ala
4895                 4900                 4905

Glu Asp Ala Val Val Arg Asp Pro Ala Ala Val Ala Ala Leu Leu
4910                 4915                 4920

Asp Arg His Ala Val Thr Ile Val Gln Ala Thr Pro Ala Leu Trp
4925                 4930                 4935

Gln Ala Leu Leu Ala Gly His Ala Asp Ala Val Arg Asp Val Arg
4940                 4945                 4950

Leu Leu Val Gly Gly Glu Ala Leu Pro Pro Ala Leu Ala Gly Arg
4955                 4960                 4965

Met Ala Ala Ala Gly Arg Gly Val Thr Asn Leu Tyr Gly Pro Thr
4970                 4975                 4980

Glu Val Thr Val Trp Ala Thr Val Ala Asp Leu Gly Ala Ser Pro
4985                 4990                 4995

Ala Gly Pro Val Pro Ile Gly Thr Pro Leu Arg Asn Thr Arg Ala
5000                 5005                 5010

Phe Val Leu Asp Asp Ala Leu Arg Pro Val Pro Pro Gly Val Pro
5015                 5020                 5025

Gly Glu Leu Tyr Leu Ala Gly Asp Gln Leu Ala Arg Gly Tyr His
5030                 5035                 5040
```

-continued

```
Gly Arg Ala Gly Leu Thr Ala Glu Arg Phe Val Ala Asp Pro Phe
5045                5050                5055

Gly Arg Gly Glu Arg Met Tyr Arg Thr Gly Asp Arg Val Arg Trp
5060                5065                5070

Thr Arg Gly Gly Ser Leu Glu Phe Leu Gly Arg Val Asp Asp Gln
5075                5080                5085

Val Lys Ile Arg Gly Phe Arg Ile Glu Leu Gly Glu Val Glu Ala
5090                5095                5100

Ala Leu Ala Ala Phe Gly Pro Val Ala Arg Ala Ala Ala Val
5105                5110                5115

Arg Glu Asp Val Pro Gly Asp Arg Arg Leu Val Gly Tyr Val Val
5120                5125                5130

Pro Ala Ala Gly Glu Pro Glu Pro Asp Pro Ala Ala Val Arg Ala
5135                5140                5145

His Val Ala Ala Gln Leu Pro Ala Tyr Met Val Pro Ser Ala Val
5150                5155                5160

Val Val Leu Pro Asp Leu Pro Leu Thr Ala Asn Gly Lys Leu Asp
5165                5170                5175

Arg Lys Ala Leu Pro Ala Pro Asp Tyr Gly Ala Ala Ser Ala Gly
5180                5185                5190

Arg Ala Pro Ala Asp Glu Arg Glu Ala Leu Ile Cys Ala Val Phe
5195                5200                5205

Ala Glu Thr Leu Gly Val Thr Asp Val Ala Ala Asp Ala Asp Phe
5210                5215                5220

Phe Ala Leu Gly Gly His Ser Leu Leu Ala Val Ser Leu Val Glu
5225                5230                5235

Arg Leu Arg Glu His Gly Ile Ala Val Pro Val Arg Ala Leu Phe
5240                5245                5250

Gln Ser Gly Thr Pro Glu Gly Leu Ala Ala Ala Arg Ala Glu
5255                5260                5265

Gly Pro Asp Glu Pro Ala Val Pro Ala Asn Gly Ile Pro Asp Gly
5270                5275                5280

Ala Thr Ala Leu Thr Pro Ala Met Leu Thr Leu Val Asp Leu Asp
5285                5290                5295

Ala Glu Glu Ile Ala Arg Val Val Ala Ala Val Pro Gly Gly Ala
5300                5305                5310

Ala Asn Val Ala Asp Val Tyr Pro Leu Ala Pro Leu Gln Glu Gly
5315                5320                5325

Leu Leu Phe His Ser Leu Met Asp Gly Gly Asp Val Tyr Val
5330                5335                5340

Leu Pro Ala Val Leu Gly Phe Asp Ser Arg Ser Arg Leu Asp Ala
5345                5350                5355

Phe Leu Ala Ala Leu Gln His Val Ile Asp Arg His Asp Thr Tyr
5360                5365                5370

Arg Thr Ala Val Val His Asp Gly Leu Arg Glu Pro Val Gln Val
5375                5380                5385

Val Trp Arg Arg Ala Thr Leu Pro Val Glu Glu Val Thr Leu Thr
5390                5395                5400

Ala Gly Ala Asp Pro Val Gln Glu Leu Leu Ala Thr Ala Pro Val
5405                5410                5415

Glu Phe Ala Leu Asp Arg Ala Pro Leu Leu Arg Val Arg Cys Ala
5420                5425                5430
```

```
Ala Arg Pro Asp Gly Gly Gly Trp Leu Ala Leu Leu Gln Ile His
    5435            5440                    5445

His Leu Val Gln Asp His Ala Thr Leu Asp Ala Met Leu Ala Glu
    5450            5455                    5460

Ile Gln Ala Phe Leu Ala Gly Arg Gly Gly Glu Leu Ala Ala Pro
    5465            5470                    5475

Glu Pro Phe Arg Gly Tyr Val Ala Arg Ala Arg Leu Ala Gly Ala
    5480            5485                    5490

Pro Ala Glu His Arg Ala Tyr Phe Ser Arg Leu Leu Gly Asp Val
    5495            5500                    5505

Thr Glu Ser Thr Ala Pro Tyr Gly Leu Thr Asp Ala Arg Asp Ala
    5510            5515                    5520

Arg Pro Thr Gly Lys Ala His Arg Glu Val Asp Arg Arg Leu Ala
    5525            5530                    5535

Ala Arg Val Arg Ala Thr Ala Ser Glu Leu Gly Val Ser Pro Ala
    5540            5545                    5550

Thr Val Phe His Leu Ala Trp Ala Arg Val Leu Gly Thr Leu Ala
    5555            5560                    5565

Gly Arg Asp Asp Val Val Phe Gly Thr Val Leu Leu Gly Arg Leu
    5570            5575                    5580

Gly Ala Gly Ala Arg Ser Gly Arg Ala Leu Gly Pro Phe Ile Asn
    5585            5590                    5595

Thr Leu Pro Val Arg Val Arg Leu Ala Ala Ala Gly Ser Arg Glu
    5600            5605                    5610

Thr Leu Ala Gly Leu Arg Ala Gln Leu Ala Glu Leu Ile Gly His
    5615            5620                    5625

Glu His Ala Pro Leu Thr Leu Ala Gln Ala Ala Ser Gly Val Pro
    5630            5635                    5640

Gly Gly Thr Pro Leu Phe Thr Ser Ile Leu Asn Tyr Arg Gln Gly
    5645            5650                    5655

Pro Pro Ala Gly Asp Asp Thr Gly Asp Glu Glu Ile Glu Gly Ile
    5660            5665                    5670

Glu Leu Leu Ser Thr Glu Glu Arg Ser Asn Tyr Pro Val Ala Val
    5675            5680                    5685

Ser Val Asp Asp Asp Gly Ser Gly Phe Arg Leu Thr Val Asp Ala
    5690            5695                    5700

Ala Gln Pro Ala Ala Pro Asp Arg Val Ala Glu Leu Leu His Thr
    5705            5710                    5715

Cys Leu His Arg Leu Thr Asp Ala Leu Ala Gly Thr Pro Asp Val
    5720            5725                    5730

Glu Pro Ala Arg Ile Asp Val Leu Gly Glu Ala Glu Arg Arg Glu
    5735            5740                    5745

Val Leu Arg Thr Pro Asn Ala Thr Ala Arg Asp Val Ala Ala Ala
    5750            5755                    5760

Thr Leu Pro Ala Ile Val Gly Glu Trp Ala Arg Thr Thr Pro Gly
    5765            5770                    5775

Ala Thr Ala Val Thr Ala Glu Asn Asp Arg Leu Thr Tyr Ala Glu
    5780            5785                    5790

Leu Asp Ala Arg Ala Asn Arg Leu Ala Arg Ser Leu Ile Ala Arg
    5795            5800                    5805

Gly Val Gly Pro Gly Ala Val Val Gly Met Leu Leu Pro Arg Ser
    5810            5815                    5820
```

```
Pro Gly Leu Val Val Ala Met Leu Ala Ile Val Lys Ala Gly Gly
    5825                5830                5835

Ala Tyr Leu Pro Leu Asp Pro Gly Tyr Pro Ala Pro Arg Leu Ala
    5840                5845                5850

Arg Met Val Glu Asp Ala Ala Pro Ala Leu Leu Leu Ala Thr Ala
    5855                5860                5865

Gly Thr Ala Asp Ala Val Pro Ala Gly Pro Gln Arg Leu Leu Leu
    5870                5875                5880

Asp Asp Pro Gly Thr Ala Ala Glu Leu Ala Arg Leu Asp Gly Asp
    5885                5890                5895

Pro Ile Arg Asp Glu Glu Arg Thr His Pro Leu Arg Pro Gly His
    5900                5905                5910

Pro Ala Tyr Leu Met Phe Thr Ser Gly Ser Thr Gly Arg Pro Lys
    5915                5920                5925

Gly Val Leu Val Pro His Ala Gly Ile Asp Arg Met Val Arg Arg
    5930                5935                5940

Ser Thr Cys Leu Gln Leu Ala Pro Asp Asp Val Leu Pro His Leu
    5945                5950                5955

Ser Ser Val Ser Phe Asp Ala Ala Thr Phe Glu Ile Trp Gly Ala
    5960                5965                5970

Leu Leu Asn Gly Ala Thr Leu Ala Val Ala Pro Ala Glu Thr Leu
    5975                5980                5985

Ser Val Ala Glu Leu Arg Ala Phe Leu Ala Asp Arg Gly Ala Thr
    5990                5995                6000

Lys Leu Phe Leu Thr Thr Gly Leu Leu His Glu Val Ile Asp Ala
    6005                6010                6015

Asp Val Thr Ala Leu Ala Gly Leu Lys Ala Val Tyr Thr Gly Gly
    6020                6025                6030

Asp Val Leu Ser Pro Ala His Cys Arg Ser Leu Leu Asp Arg Val
    6035                6040                6045

Pro Gly Leu Glu Leu Tyr Asn Ala Tyr Gly Pro Thr Glu Asn Thr
    6050                6055                6060

Thr Ile Thr Thr Leu His Arg Val Arg Pro Glu Asp Leu Asp Ala
    6065                6070                6075

Gly Thr Gly Val Pro Ile Gly Val Pro Ile Ser Asp Thr Arg Val
    6080                6085                6090

Tyr Val Leu Asp Asp Ala Leu Arg Pro Val Pro Val Gly Val Ala
    6095                6100                6105

Gly Glu Leu Tyr Thr Ser Gly Ile Gly Leu Ala His Gly Tyr Ala
    6110                6115                6120

Gly Arg Pro Ala Pro Thr Ala Glu Arg Phe Val Ala Cys Pro Phe
    6125                6130                6135

Ala Pro Gly Glu Arg Met Tyr Arg Thr Gly Asp Leu Val Arg Trp
    6140                6145                6150

Thr Ala Asp Gly Arg Leu Leu Phe Ala Gly Arg Ala Asp Asn Gln
    6155                6160                6165

Val Lys Ile Arg Gly Phe Arg Val Glu Pro Gly Glu Leu Glu Thr
    6170                6175                6180

Val Leu Ser Gly His Pro Ala Val Ala Arg Ala Ala Val Leu Ala
    6185                6190                6195

Arg Glu Asp Thr Pro Gly Ala Lys Arg Leu Val Ala Tyr Val Val
    6200                6205                6210
```

-continued

```
Pro Ala Arg Pro Asp Glu Asp Gly Asp Ala Leu Ala Glu Ser Val
6215                 6220                 6225

Arg Ala Tyr Ala Ala Arg Gln Val Pro Asp Tyr Leu Met Pro Ala
6230                 6235                 6240

Ala Thr Val Val Leu Pro Asp Leu Pro Leu Thr Ser Ser Gly Lys
6245                 6250                 6255

Val Asp Arg Ala Ala Leu Pro Ala Pro Asp Val Pro Gly Gly Pro
6260                 6265                 6270

Gly Arg Ala Ala Gly Thr Leu Thr Glu Glu Ile Leu Cys Gly Val
6275                 6280                 6285

Phe Ala Gln Val Leu Gly Leu Pro Thr Val Gly Val Asp Asp Asp
6290                 6295                 6300

Phe Phe Ala Ser Gly Gly His Ser Leu Leu Ala Thr Arg Leu Val
6305                 6310                 6315

Ser Arg Leu Arg Ala Val Phe Gly Ala Glu Leu Pro Ile Arg Ala
6320                 6325                 6330

Val Phe Glu Ala Pro Thr Pro Ala Thr Leu Ala Thr Arg Leu Gly
6335                 6340                 6345

Ala Ser Ala Pro Arg Arg Leu Ala Leu Gly Glu Arg Ala Arg Pro
6350                 6355                 6360

Glu Asn Val Pro Leu Ser Tyr Ala Gln Arg Arg Leu Trp Phe Leu
6365                 6370                 6375

Asp Arg Leu Glu Gly Gln Asp Gly Thr Tyr Thr Ile Pro Leu Thr
6380                 6385                 6390

Val Arg Leu Asp Gly Pro Val Asp Arg Ala Ala Leu Ala Ala Ala
6395                 6400                 6405

Leu Arg Asp Val Leu Glu Arg His Glu Val Leu Arg Thr Val Phe
6410                 6415                 6420

Pro Leu Val Asp Gly Glu Pro Val Gln Arg Val Leu Pro Val His
6425                 6430                 6435

Asp Thr Gly Phe Thr Leu Gly Gly Gly Asp Val Ala Ala Ala Asp
6440                 6445                 6450

Leu Gly Ala Ala Val Ala Glu Ala Thr Ala Gly Thr Phe Asp Leu
6455                 6460                 6465

Ala Ala Glu Ile Pro Val Arg Ala Trp Leu Phe Arg Ala Gly Pro
6470                 6475                 6480

Glu Asp His Thr Leu Val Leu Leu Val His His Val Ala Gly Asp
6485                 6490                 6495

Gly Trp Ser Met Thr Pro Leu Ala Arg Asp Ile Ala Thr Ala Tyr
6500                 6505                 6510

Asp Ser Arg Arg Glu Ser Arg Ala Pro Gln Trp Glu Pro Leu Pro
6515                 6520                 6525

Val Gln Tyr Ala Asp Tyr Ala Leu Trp Gln Arg Glu Leu Leu Gly
6530                 6535                 6540

Ala Glu Asp Asp Pro Glu Ser Leu Leu Ser Arg Gln Leu Ala Tyr
6545                 6550                 6555

Trp Arg Asp Ala Leu Asp Gly Val Pro Glu Glu Leu Asp Leu Pro
6560                 6565                 6570

Ala Asp Arg Pro Arg Pro Ala Glu Ala Thr His Arg Gly His Glu
6575                 6580                 6585

Val Pro Val Arg Val Pro Ala Glu Val His Arg Arg Leu Ala Glu
6590                 6595                 6600
```

-continued

```
Leu Ala Arg Ser Glu Gly Val Thr Val Phe Met Val Leu Gln Ala
    6605                6610                6615

Ala Phe Gly Thr Leu Leu Ser Arg Leu Gly Ala Gly Ala Asp Ile
    6620                6625                6630

Pro Ile Gly Thr Ala Val Ala Gly Arg Thr Asp Gln Ala Leu Asp
    6635                6640                6645

Glu Leu Val Gly Phe Phe Val Asn Thr Leu Val Ile Arg Ala Asp
    6650                6655                6660

Leu Ser Gly Asp Pro Thr Phe Arg Glu Leu Leu Gly Arg Val Arg
    6665                6670                6675

Ala Thr Gly Leu Ser Ala Tyr Glu His Gln Asp Val Pro Phe Glu
    6680                6685                6690

Arg Leu Val Glu Val Leu Ala Pro Ala Arg Ser Leu Ala Arg His
    6695                6700                6705

Pro Leu Phe Gln Val Met Leu Thr Leu Gln Asn Thr Gly Arg Ala
    6710                6715                6720

Asp Ala Gly Asp Gln Ala Val Pro Pro Ala Ala Gly Ser Ala Ala
    6725                6730                6735

Ala Lys Phe Asp Leu Glu Ile Ser Ile Ala Glu Thr Phe Ala Ala
    6740                6745                6750

Asp Gly Glu Pro Ala Gly Leu Ser Gly Val Leu Ile Ala Ala Ala
    6755                6760                6765

Asp Leu Phe Glu Pro Ala Thr Ala Ala Ala Phe Ala Glu Arg Leu
    6770                6775                6780

Ala Arg Val Leu Ala Ala Ala Gly Ala Asp Pro Arg Leu Arg Val
    6785                6790                6795

Ser Gln Val Asp Ile Leu Ser Ala Glu Glu Arg Glu Ala Val Leu
    6800                6805                6810

Ser Gly Gly Asn Gly Gly Thr Ala Pro Val Pro Val Thr Thr Val
    6815                6820                6825

Pro Ala Leu Phe Ala Glu Gln Ala Arg Arg Thr Pro Gly Ala Val
    6830                6835                6840

Ala Ala Leu Ser Glu Gly Met Ser Leu Thr Tyr Ala Asp Leu Ala
    6845                6850                6855

Ala Arg Val Asn Arg Leu Ala Arg His Leu Val Ser Leu Gly Ala
    6860                6865                6870

Gly Pro Glu Thr Val Val Gly Ile Ala Met Ser Arg Gly Leu Asp
    6875                6880                6885

Met Leu Val Ala Val Leu Ala Val Gly Gln Ala Gly Ala Ala Tyr
    6890                6895                6900

Leu Pro Val Asp Pro Ser Tyr Pro Asp Glu Arg Lys Glu Phe Met
    6905                6910                6915

Leu Thr Asp Ala Gly Ala Ala Tyr Val Leu Thr Leu Ala Ser Asp
    6920                6925                6930

Ala Asp Arg Val Pro Pro Gly Thr Pro Ala Ala Ala Val Val Leu
    6935                6940                6945

Asp Glu Pro Val Thr Ala Ala Arg Ile Ala Gly Leu Asp Pro Ala
    6950                6955                6960

Asp Leu Thr Asp Ala Asp Arg Val Ala Pro Leu Leu Pro Ala His
    6965                6970                6975

Arg Ala Tyr Val Ile Tyr Thr Ser Gly Ser Thr Gly Arg Pro Lys
    6980                6985                6990
```

```
Gly Val Ala Val Glu His Arg Thr Val Val Asn Leu Leu Ser Trp
6995                     7000                    7005

Ala Ala Gly Arg Phe Gly Gly Ala Asp Phe Ala Arg Thr Leu Ala
7010                     7015                    7020

Ala Thr Ser Leu Asn Phe Asp Val Ser Val Phe Glu Ile Phe Gly
7025                     7030                    7035

Pro Leu Val Ser Gly Gly Ser Ile Glu Ile Val Thr Asp Leu Leu
7040                     7045                    7050

Ala Leu Ala Asp Pro Ala Ser Pro Ala Trp Glu Ala Ser Leu Val
7055                     7060                    7065

Ser Gly Val Pro Ser Ala Phe Ser Arg Val Leu Asp Arg Gly Asp
7070                     7075                    7080

Ile Ala Ala Arg Thr Arg Ser Val Val Leu Ala Gly Glu Ala Leu
7085                     7090                    7095

Thr Ala Asp Val Val Asn Ala Thr Arg Ala Ala Leu Pro Gly Val
7100                     7105                    7110

Arg Val Ala Asn Ile Tyr Gly Pro Thr Glu Ala Thr Val Tyr Ser
7115                     7120                    7125

Thr Ala Trp His Thr Asp Arg Asp Val Thr Gly Gly Ala Ala Pro
7130                     7135                    7140

Ile Gly Arg Pro Val Thr Asn Thr Arg Ala Tyr Val Leu Asp Asp
7145                     7150                    7155

Arg Leu Thr Pro Val Pro Pro Gly Val Val Gly Glu Leu Tyr Leu
7160                     7165                    7170

Ala Gly Ala Gln Leu Ala Arg Gly Tyr Leu Gly Arg Pro Gly Leu
7175                     7180                    7185

Thr Gly Glu Arg Phe Val Ala Cys Pro Phe Gly Pro Gly Gly Glu
7190                     7195                    7200

Arg Met Tyr Arg Thr Gly Asp Arg Val Arg Trp Asn Ala Asp Gly
7205                     7210                    7215

Asp Leu Val Phe Ala Gly Arg Ala Asp Asp Gln Val Lys Ile Arg
7220                     7225                    7230

Gly Phe Arg Ile Glu Pro Gly Glu Val Gln Ala Val Val Ala Arg
7235                     7240                    7245

Gln Ala Gly Val Ala Arg Ala Val Val Leu Ala Arg Ser Asp Ser
7250                     7255                    7260

Pro Gly Asp Ala Arg Leu Val Ala Tyr Val Val Pro Ala Asp Arg
7265                     7270                    7275

Asp Ala Asp Arg Arg Ala Leu Ala Ala Thr Val Arg Ser Asp Thr
7280                     7285                    7290

Ala Arg Glu Leu Pro Ala Tyr Leu Val Pro Ala Ala Val Val Val
7295                     7300                    7305

Leu Asp Glu Leu Pro Val Thr Ala Asn Gly Lys Leu Asp Arg Arg
7310                     7315                    7320

Ala Leu Pro Ala Pro Gly Leu Ala Glu Ala Gly Ser Gly Arg Gly
7325                     7330                    7335

Pro Val Thr His Arg Glu Glu Val Leu Cys Glu Val Phe Ala Gln
7340                     7345                    7350

Val Leu Gly Leu Pro Ser Val Gly Val Asp Asp Phe Phe Ala
7355                     7360                    7365

Leu Gly Gly His Ser Leu Leu Ala Val Ser Leu Val Glu Gln Leu
7370                     7375                    7380
```

```
Arg Arg Arg Gly Val Thr Val Gly Val Arg Ala Leu Phe Gln Thr
7385            7390                7395
Pro Thr Val Ala Gly Leu Ala Glu Ala Ala Ala Pro Thr Thr Val
7400            7405                7410
Ala Val Pro Pro Asn Leu Ile Pro Glu Asp Ala Arg His Ile Thr
7415            7420                7425
Pro Gly Leu Leu Pro Leu Val Glu Leu Glu Gln Ala Glu Ile Asp
7430            7435                7440
Gln Val Val Ala Thr Val Asp Gly Gly Ala Ala Asn Val Ala Asp
7445            7450                7455
Ile Tyr Pro Leu Ala Pro Leu Gln Gln Gly Met Leu Phe His His
7460            7465                7470
Leu Met Ala Gly Asp Asp Gly Glu Asp Val Tyr Ile Met Pro Ala
7475            7480                7485
Val Val Glu Phe Asp Ser Ala Asp Arg Phe Gly Ala Phe Val Asp
7490            7495                7500
Ala Leu Gln His Val Ile Asp Arg Asn Asp Val Tyr Arg Thr Gly
7505            7510                7515
Val Val Trp Asp Gly Leu Arg Glu Pro Val Gln Val Val Trp Arg
7520            7525                7530
Arg Ala Pro Leu Pro Val Thr Glu Val Thr Leu Asp Pro Ala Gly
7535            7540                7545
Gly Asp Pro Ala Ala Gln Leu His Ala Ala Ala Gly Ala Arg Met
7550            7555                7560
Asp Leu Asn Arg Ala Pro Leu Leu Asp Leu His Val Ala Ala Arg
7565            7570                7575
Pro Glu Asp Gly Gln Arg Leu Ala Leu Leu Arg Val His His Met
7580            7585                7590
Val Gln Asp His Met Gly Leu Glu Val Leu Leu Gly Glu Val Gln
7595            7600                7605
Ala Phe Leu Ala Gly Arg Gly Asp Glu Leu Pro Asp Pro Leu Pro
7610            7615                7620
Phe Arg Asp Phe Val Ala Gln Thr Arg Gly Gly Val Pro Glu Ala
7625            7630                7635
Glu His Arg Arg Phe Phe Ala Gly Leu Leu Gly Asp Val Thr Glu
7640            7645                7650
Pro Thr Ala Pro Tyr Gly Leu Leu Asp Val His Arg Asp Gly Val
7655            7660                7665
Gly Leu Val Arg Gln Glu Arg Pro Leu Asp Gly Glu Val Val Ala
7670            7675                7680
Arg Leu Arg Ala Val Ala Arg Arg Leu Gly Val Ser Pro Ala Thr
7685            7690                7695
Val Met His Val Ala Trp Ala Arg Val Leu Gly Val Ile Ser Gly
7700            7705                7710
Arg Asp Asp Val Val Phe Gly Thr Leu Leu Gly Arg Phe Ser
7715            7720                7725
Thr Gly Ala Asp Arg Val Pro Gly Pro Phe Ile Asn Thr Leu Pro
7730            7735                7740
Val Arg Ala Arg Leu Gly Gly Thr Gly Ala Ala Ala Val Ala
7745            7750                7755
Glu Met Arg Arg Leu Leu Ala Glu Leu Leu Glu His Glu His Ala
7760            7765                7770
```

-continued

```
Pro Leu Thr Thr Ala Gln Gln Ala Ser Gly Leu Ser Gly Asn Leu
    7775            7780            7785

Pro Leu Phe Thr Ala Leu Phe Asn Tyr Arg His Asn Thr Ser Pro
    7790            7795            7800

Gly Ala Asp Pro Ser Pro Ala Gly Pro Thr Glu Gly Ile Arg
    7805            7810            7815

Pro Val Ser Met Arg Glu Arg Thr Asn Tyr Pro Ile Ser Val Ala
    7820            7825            7830

Val Asp Asp Asp Gly Glu Gly Leu Gly Val Ala Val Asn Ala Ile
    7835            7840            7845

Pro Pro Val Arg Pro Glu Ala Val Cys Glu Leu Val Ala Thr Ala
    7850            7855            7860

Thr Glu Ser Leu Thr Ser Ala Leu Glu Leu Phe Leu Asp Gly Gly
    7865            7870            7875

Pro Asp Thr Ala Val Gly Glu Leu Asp Val Leu Pro Pro Gly Glu
    7880            7885            7890

Arg Ser Arg Leu Leu Val Glu Trp Asn Asp Thr Ala Arg Pro Val
    7895            7900            7905

Val Glu Ser Ser Val Pro Ala Leu Phe Ala Glu Arg Val Ala Ala
    7910            7915            7920

Ala Pro Asp Ala Val Ala Val Gly Glu Gly Val Ser Trp Ser
    7925            7930            7935

Tyr Arg Glu Leu Asp Arg Arg Ser Asp Val Leu Ala Arg Ser Leu
    7940            7945            7950

Val Ala Ala Gly Val Gly Leu Glu Ser Pro Val Val Val Ala Leu
    7955            7960            7965

Glu Arg Ser Ala Asp Val Leu Thr Ala Phe Leu Ala Val Ala Lys
    7970            7975            7980

Ala Gly Gly Val Phe Val Pro Val Asp Leu Ser Trp Pro Gln Thr
    7985            7990            7995

Arg Ile Asp Ala Val Ile Ala Asp Ser Arg Pro Val Leu Val Leu
    8000            8005            8010

Asp Ser Val Asp Leu Pro Ala Ala Glu Ala Asp Leu Pro Arg Val
    8015            8020            8025

Pro Ala Gly Ala Gly Val Tyr Arg Met Tyr Thr Ser Gly Ser Thr
    8030            8035            8040

Gly Arg Pro Lys Gly Val Val Thr Thr His Gln Asn Leu Val Asp
    8045            8050            8055

Leu Ala Thr Asp Thr Cys Trp Gly Ser Thr Pro Arg Val Leu Phe
    8060            8065            8070

His Ala Pro His Ala Phe Asp Ala Ser Ser Tyr Glu Ile Trp Val
    8075            8080            8085

Pro Leu Leu Asn Gly Gly Thr Val Val Val Ala Pro Arg Arg Ser
    8090            8095            8100

Ile Asp Ala Thr Val Leu Arg Asp Leu Val Arg Gly His Glu Leu
    8105            8110            8115

Thr His Val His Val Thr Ala Gly Leu Leu Arg Val Leu Asp Pro
    8120            8125            8130

Ser Cys Phe Ala Gly Leu Thr Glu Val Leu Thr Gly Gly Asp Ala
    8135            8140            8145

Val Ser Ala Glu Ala Val Arg Arg Val Lys Glu Ala Asn Pro Gly
    8150            8155            8160
```

```
Leu Arg Val Arg Gln Leu Tyr Gly Pro Thr Glu Val Thr Leu Cys
8165                8170                8175

Ala Thr Gln His Leu Leu Asp Asp Gly Val Pro Ile Gly Arg Pro
8180                8185                8190

Leu Asp Asn Thr Arg Val Tyr Val Leu Asp Asp Leu Leu Arg Pro
8195                8200                8205

Val Pro Thr Gly Val Val Gly Glu Leu Tyr Val Ala Gly Ser Gly
8210                8215                8220

Leu Ala Arg Gly Tyr Ala Gly Met Pro Gly Leu Thr Ala Glu Arg
8225                8230                8235

Phe Val Ala Asp Pro Phe Ser Val Gly Gly Arg Leu Tyr Arg Thr
8240                8245                8250

Gly Asp Leu Val Arg Trp Thr Asp Asp Gly Val Leu His Phe Ala
8255                8260                8265

Gly Arg Ala Asp Asp Gln Val Lys Ile Arg Gly Tyr Arg Val Glu
8270                8275                8280

Pro Gly Glu Val Glu Ala Val Leu Ala Gln His Pro Asp Val Ser
8285                8290                8295

Gln Val Ala Val Val Val Arg Glu Asp Ala Pro Gly Asp Lys Arg
8300                8305                8310

Leu Val Ala Tyr Val Val Gly Gly Asp Val Glu Ala Tyr Ala Gln
8315                8320                8325

Glu Arg Leu Pro Gly Tyr Met Val Pro Ser Ala Phe Val His Leu
8330                8335                8340

Glu Ala Leu Pro Leu Thr Ala Asn Gln Lys Val Asp Arg Ala Ala
8345                8350                8355

Leu Pro Ala Pro Glu Arg Glu Thr Thr Thr Pro Gly Lys Ala Pro
8360                8365                8370

Ala Pro Gly Pro Leu Gly Asn Leu Glu Glu Ser Met Cys Gln Ala
8375                8380                8385

Phe Ala Glu Val Leu Gly Leu Asp Ser Val Gly Pro Asp Asp Asp
8390                8395                8400

Phe Phe Ala Leu Gly Gly His Ser Leu Leu Ala Val Ala Leu Val
8405                8410                8415

Gln Arg Leu Lys Ala Arg Gly Val Ala Val Thr Val Gln Asp Ile
8420                8425                8430

Met Ala Ala Pro Thr Val Ser Glu Leu Met Gly Ser Leu Ser Met
8435                8440                8445

Ser Ser Ile Arg Asp Ser Leu Gly Thr Leu Leu Pro Ile Arg Arg
8450                8455                8460

Thr Gly Glu Leu Pro Pro Leu Phe Cys Val His Pro Ala Gly Gly
8465                8470                8475

Leu Ser Trp Cys Tyr Leu Pro Leu Ala Arg His Val Pro Ala Asp
8480                8485                8490

Arg Pro Ile Tyr Gly Leu Gln Ala Arg Gly Ala Asp Gly Arg Glu
8495                8500                8505

Pro Leu Ala Pro Ser Leu Arg Glu Met Ala Ala Asp Tyr Val Ser
8510                8515                8520

Arg Met Arg Ala Val Gln Pro Glu Gly Pro Tyr His Val Leu Gly
8525                8530                8535

Phe Ser Phe Gly Val Ala Pro Ala His Glu Ile Ala Val Gln Leu
8540                8545                8550
```

-continued

```
Arg Glu Gln Gly Ala Glu Val Val Leu Val Leu Met Asp Ser Tyr
    8555                8560                8565

Pro Met Glu Asp Ala Glu Ser Gly Glu Gln Ala Ala Asp Glu Glu
    8570                8575                8580

Glu Leu Pro Trp Glu Leu Ile Glu Ala Glu Phe Gly Arg Val
    8585                8590                8595

Leu Gly Gly Phe Ser Arg Asp Glu Leu Ala Ala Phe Ala Ala Val
    8600                8605                8610

Phe Arg Asn Asn Thr Lys Ile Arg Ala Arg His Arg Leu Gly Arg
    8615                8620                8625

Phe Asp Gly Asp Ala Leu Leu Ile Ala Ser Thr Asp Ser Ala Pro
    8630                8635                8640

Asp Gly Glu Ser Asn Thr Trp Arg Trp Ala Pro Tyr Ile Thr Gly
    8645                8650                8655

Glu Ile Thr Gln Val Val Leu Pro Cys Glu His Thr Asp Leu Val
    8660                8665                8670

Arg Pro Asp Met Leu Ala Leu Leu Trp Pro Ala Val Glu Ala Trp
    8675                8680                8685

Gln Ala Gly Arg His Arg Pro
    8690                8695

<210> SEQ ID NO 16
<211> LENGTH: 234
<212> TYPE: PRT
<213> ORGANISM: Actinoplanes sp.

<400> SEQUENCE: 16

Met Gln Lys Ile Pro Leu Val Cys Val Pro Phe Ala Gly Ala Gly Ala
1               5                   10                  15

Ser Phe Phe His Pro Trp Ala Glu Leu Ala Gly Pro Asp Arg Pro Ile
                20                  25                  30

Val Ala Leu Gln Leu Pro Gly Arg Glu Trp Arg Leu Leu Asp Glu Pro
            35                  40                  45

Tyr Ala Asp Val Val Ala Ala Ala Asp Leu Ala Leu Thr Val Ala
    50                  55                  60

Asp Glu Val Gly Ala Gly Gly Arg Val Ala Leu Phe Gly His Ser Leu
65                  70                  75                  80

Gly Ala Val Leu Ala Tyr Glu Ile Ala His Ala Leu Val Arg Asp Gly
                85                  90                  95

Glu Val Gly Val Glu Arg Leu Phe Val Ser Gly Ser Pro Asp Pro Trp
            100                 105                 110

Thr Pro Arg Thr Asn Arg Ala Ser Gly Leu Asp Asp Glu Glu Phe Leu
        115                 120                 125

Leu Arg Val Arg Glu Phe Ala Gly Tyr Asp His Glu Ala Leu Ala Asp
    130                 135                 140

Pro Asp Met Arg Glu Leu Ile Leu Pro Ala Leu Arg Ala Asp Val Glu
145                 150                 155                 160

Met His Glu Ser Tyr Val Ala Gly Ser Ala Asp Pro Leu Pro Ala Pro
                165                 170                 175

Val Thr Ala Leu His Ala Arg Asp Asp Ala Leu Val Ser Ala Glu Gln
            180                 185                 190

Thr Ala Gly Trp Ser Lys Ala Thr Ser Gly Pro Phe Gln Leu Val Glu
        195                 200                 205
```

-continued

Val Asp Gly Gly His Met Tyr Leu Thr Glu Asp Pro Ala Gly Leu Leu
        210                 215                 220

Arg Leu Ile Ala Ala Asp Leu Asp Arg Asp
225                 230

<210> SEQ ID NO 17
<211> LENGTH: 274
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine reidue at this position

<400> SEQUENCE: 17

Val Arg Leu Thr Gly Lys Thr Ala Ile Val Thr Gly Ala Ala Arg Gly
1               5                   10                  15

Leu Gly Arg Ala Cys Ala Val Ala Phe Ala Ala Glu Gly Ala Asp Leu
            20                  25                  30

Val Leu Leu Asp Arg Ala Ala Asp Leu Pro Gly Val Pro Tyr Pro Leu
        35                  40                  45

Gly Thr Val Gly Gln Leu Glu His Thr Ala Asp Leu Cys Arg Lys Gln
    50                  55                  60

Gly Ala Ala Val Leu Thr Val Arg Ala Asp Val Arg Asp Leu Ala Ala
65                  70                  75                  80

Leu Thr Ala Ala Ala Asp Arg Ala Ile Asp Arg Phe Gly Gly Ile Asp
                85                  90                  95

Val Leu Val Asn Asn Ala Gly Ile Ala Ala Pro Ser Gly Lys Val Thr
            100                 105                 110

His Glu Ile Thr Glu Asp Glu Trp Gln Leu Met Ile Asp Val Asp Leu
        115                 120                 125

Ser Gly Ala Trp Arg Met Thr Ala Ala Val Gly Arg His Met Thr Glu
    130                 135                 140

Arg Arg Ser Gly Ser Ile Val Asn Ile Ala Ser Thr Ala Gly Gln Val
145                 150                 155                 160

Gly Tyr Arg His Phe Ala Gly Tyr Val Ala Ala Lys His Gly Ile Val
                165                 170                 175

Gly Leu Thr Arg Ala Ala Ala Leu Asp Tyr Ala Pro Ala Lys Val Arg
            180                 185                 190

Val Asn Ala Val Cys Pro Gly Ser Val Arg Asp Pro Gln Phe Glu
        195                 200                 205

Gly Arg Met Leu Ser Glu Ile Ala Arg Ser Leu Asp Val Pro Val Ala
    210                 215                 220

Glu His Glu Gln Thr Phe Leu Gln Ala Gln Pro Met Asn Ala Leu Ile
225                 230                 235                 240

Glu Pro Asp Asp Val Ala Asn Ala Ala Ile Trp Leu Ala Ser Asp Glu
                245                 250                 255

Ser Arg Gln Val Thr Gly Ser Val Val Thr Val Asp Gly Gly Phe Thr
            260                 265                 270

Thr Arg

<210> SEQ ID NO 18
<211> LENGTH: 891
<212> TYPE: PRT
<213> ORGANISM: Actinoplanes sp.

```
<220> FEATURE:
<221> NAME/KEY: misc_feature
<222> LOCATION: (1)..(1)
<223> OTHER INFORMATION: V is a non-standard initiator codon.  It is
      expected that the biosynthesized protein will have a
      formylmethionine residue at this position

<400> SEQUENCE: 18

Val Pro Lys Ser Gln Pro Ala Thr Arg Thr Ala Ala Pro Gly Ala Ala
1               5                   10                  15

Glu Cys His Ala Leu Ala Val Arg Leu Ala Gly Pro Ile Asp Pro Ala
            20                  25                  30

Pro Ile Glu Arg Arg Leu Ala Ala Arg Met Pro Phe Trp His Glu His
        35                  40                  45

Val Ala Ala Arg Pro Gly Asp Glu Ala Ala Leu Arg Arg Arg Glu Arg
50                  55                  60

Glu Leu Ala Arg Pro Val Pro Pro Glu Pro Gly Ala Arg Ala Val Leu
65                  70                  75                  80

Leu Ala Tyr Ala Asp Gly Ser Ala Asp Leu Val Leu Val Ala Arg Arg
                85                  90                  95

Asp Arg Leu Asp Arg Asp Ala Leu Ile Ala Leu Ala Arg Pro Glu Arg
            100                 105                 110

Ala Pro Arg Gly Arg Lys Pro Ala Glu Pro Asp Ala Pro Pro Ser
        115                 120                 125

Ala Ala Pro Ala Trp Gly Leu Gly Asp Gly Pro Asp Asp Arg Trp
130                 135                 140

Ala Glu Leu Arg Val Pro Ala Arg Gly Pro Ala Asp Pro Ala Arg Trp
145                 150                 155                 160

Pro Ala Ala Leu Ala Lys Val Leu Ala Arg Tyr Glu Pro Gly Ala Ala
                165                 170                 175

Ala Gly Ser Gly Ala Ala Ala Gly Leu Gly Ala Ala Gly Ser Gly
            180                 185                 190

Val Ala Ala Gly Ser Ser Ala Ala Ser Gly Ser Gly Ala Ala Ala Val
            195                 200                 205

Pro Gly Pro Val Ala Leu Ala Phe Asp Gly Asp Leu Ala Pro Pro Asp
210                 215                 220

Glu Tyr Val Pro Phe Leu Ala Pro Thr His Pro Leu Thr Val Gln Val
225                 230                 235                 240

Ser Arg Thr Pro Gly Gly Gly Thr Glu Leu Arg Cys Arg His Arg Leu
                245                 250                 255

Gly Ala Val Ser Pro Ala Ala Ala Glu Ala Phe Ala Arg Met Leu Ala
            260                 265                 270

Ala Ala His Gly Glu Pro Pro Ala Asp Asp Gly Ala Thr Ala Glu Pro
            275                 280                 285

Thr Pro Pro Ala Ala Pro Ala Pro Ala Pro Ala Pro Ala Pro Ala Pro
            290                 295                 300

Pro Ala Ala Ala Arg Thr Leu Thr Gly Leu Phe Ala Glu Gln Val Ala
305                 310                 315                 320

Ala Arg Pro Thr Ala Val Ala Val Ser Asp Asp Arg Gly Arg His Thr
                325                 330                 335

Tyr Arg Glu Leu Asp Glu Trp Ser Gly Arg Leu Ala Arg Gly Leu Arg
            340                 345                 350

Lys Ala Gly Val Arg Asp Gly Asp Ala Val Gly Val Cys Leu Asp Arg
            355                 360                 365
```

-continued

```
Ser Ala Glu Leu Val Ala Val Leu Ala Val Leu Lys Ala Gly Ala
370                 375                 380

Ala Tyr Val Pro Leu Asp Ala Ala Tyr Pro Ala Asp Arg Ile Ala Tyr
385                 390                 395                 400

Thr Val Gly Asp Ala Gly Leu Ala Val Val Thr Thr Ser Ala Asp
                405                 410                 415

Phe Pro Asp Val Asp Gly Val Arg Leu Leu Ala Pro Glu Ser Leu Ala
            420                 425                 430

Glu Ala Gly Asp Asp Pro Gly Ile Pro Leu Ala Thr Pro Ala Gly Pro
            435                 440                 445

Glu Arg Pro Ala Tyr Val Ile Tyr Thr Ser Gly Ser Thr Gly Arg Pro
450                 455                 460

Lys Gly Val Val Val Pro His Ala Asn Val Ser Ala Leu Leu Asp Ala
465                 470                 475                 480

Thr Arg Glu Glu Tyr Ala Leu Gly Pro Gly Asp Val Trp Thr Phe Phe
                485                 490                 495

His Ser Ala Ala Phe Asp Phe Ser Val Trp Glu Ile Trp Gly Cys Leu
            500                 505                 510

Leu Thr Gly Gly His Leu Val Val Val Pro Tyr Trp Val Ser Arg Ser
        515                 520                 525

Pro Glu Gln Phe His Asp Leu Leu Ala Glu Arg Gly Val Thr Val Leu
530                 535                 540

Asn Gln Thr Pro Ser Ser Phe Thr Gln Leu Val Ala Ala Asp Arg Gly
545                 550                 555                 560

Ala Glu Arg Asp Leu Ala Val Arg Leu Val Ile Phe Gly Gly Glu Pro
                565                 570                 575

Leu Asp Ala Arg Thr Val Leu Pro Trp Leu Asp Arg Arg Pro Glu Ala
            580                 585                 590

Arg Cys Arg Leu Val Asn Met Phe Gly Ile Thr Glu Thr Thr Val His
            595                 600                 605

Val Thr Ala Val Asp Val Thr Arg Ala Ala Ala Leu Ala Gly Ser Arg
610                 615                 620

Ser Val Gly Arg Pro Leu Pro Gly Trp Ala Val Arg Val Leu Asp Glu
625                 630                 635                 640

Gln Arg Arg Glu Val Pro Pro Gly Val Pro Gly Glu Ile Tyr Val Gly
                645                 650                 655

Gly Ala Gly Val Ala Ile Gly Tyr Leu Asn Arg Pro Glu Leu Thr Ala
            660                 665                 670

Glu Arg Phe Val Thr Gly Pro Asp Gly Arg Arg Trp Tyr Arg Ser Gly
            675                 680                 685

Asp Arg Gly Arg Leu Leu Pro Asp Gly Thr Leu Glu His Leu Gly Arg
            690                 695                 700

Leu Asp Asp Gln Val Lys Leu Arg Gly Phe Arg Ile Glu Leu Asp Glu
705                 710                 715                 720

Ile Arg Gly Val Leu Thr Glu Cys Ala Gly Val Ala Ala Ala Val
                725                 730                 735

Val Ile Arg Arg Ser Thr Pro Asp Pro Ala Thr Ala Arg Leu Asp
            740                 745                 750

Ala Tyr Val Val Ala Glu Ala Gly Ala Thr Pro Val Ala Glu His
        755                 760                 765

Ala Ala Arg Met Leu Pro Ala Tyr Met Cys Pro Ala Thr Phe Thr Phe
770                 775                 780
```

-continued

```
Leu Asp Ala Leu Pro Met Thr Pro Asn Gly Lys Val Asp Lys Ala Ala
785                 790                 795                 800

Leu Pro Glu Pro Ala Arg Pro Ala Ala Asp Ala Ala Thr Pro Ala
            805                 810                 815

Gly Pro Gly Glu Asp Gly Leu Ala Gly Asp Leu Ala Asp Val Trp Gln
            820                 825                 830

Gln Val Phe Gly Cys Pro Val Thr Val Ser Asp Asn Phe Phe Asp Leu
            835                 840                 845

Gly Gly Asn Ser Leu Leu Ala Val Arg Met Ala Ala Leu Met Arg Arg
            850                 855                 860

Arg Gly Leu Pro Arg Leu His Pro Arg Thr Leu Tyr Leu His Pro Thr
865                 870                 875                 880

Val Arg Gly Leu Ala Asp Ala Leu Arg Ser Ala
            885                 890

<210> SEQ ID NO 19
<211> LENGTH: 187
<212> TYPE: PRT
<213> ORGANISM: Actinoplanes sp.

<400> SEQUENCE: 19

Met Arg Asn Leu Arg Arg Thr Thr Gly Ile Gly Leu Leu Ala Leu Leu
1               5                   10                  15

Ser Val Ala Ala Cys Ser Ser Thr Pro Ala Ala Ser Glu Pro Pro
            20                  25                  30

Ser Ala Ala Pro Pro Ser Ala Val Thr Ala Thr Gly Pro Ala Ala Glu
            35                  40                  45

Lys Ala Val Lys Ser Gly Thr Gln Thr Tyr His Gln Ala Leu Asp Ala
    50                  55                  60

Phe Val Ala Ala Ser Asn Lys Gly Thr Thr Asp Thr Thr Glu Ile Gly
65                  70                  75                  80

Lys Tyr Ala Ser Gly Arg Ala Leu Met Thr Phe Gln Gly Ile Leu Ala
                85                  90                  95

Ser Tyr Gln Gln Gln Gly Val His Thr Ser Gly Glu Pro Arg Ile Asp
            100                 105                 110

Glu Pro Val Val Thr Gly Leu Thr Pro Pro Ala Asp Pro Thr Gly Val
            115                 120                 125

Gln Leu Arg Gly Cys Ile Asp Ile Ser Ala Trp Pro Leu Thr Lys Ala
    130                 135                 140

Asp Gly Thr Pro Ala Asp Lys Val Gly Gly Gln Gln Gly Ser Gly Pro
145                 150                 155                 160

Ser Ala Ile Leu Ala Asn Val Ala Arg Ser Gly Ala Thr Trp Gln Val
                165                 170                 175

Thr Glu Leu Ala Ile Gln Gly Pro Cys Ala Ala
            180                 185

<210> SEQ ID NO 20
<211> LENGTH: 415
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position
```

```
<400> SEQUENCE: 20

Val Thr Val Arg Arg Trp Leu Pro Ala Gly Leu Thr Val Leu Ala Phe
1               5                   10                  15

Ala Ala Gly Phe Trp Gln Lys Leu Pro Cys Gln Ala Ala Gly Trp Pro
            20                  25                  30

Asp Asp Thr Ala Thr Leu Phe Gly Arg Tyr Cys Tyr Ser Asp Val Pro
            35                  40                  45

Ile Leu Phe Arg Glu Arg Gly Leu Phe Asp Gly Ile Phe Pro Tyr Glu
        50                  55                  60

Ser Gly Pro Gly Ala Gln Pro Leu Glu Tyr Pro Val Leu Thr Gly Tyr
65                  70                  75                  80

Leu Met Asp Ala Thr Ala Arg Leu Val Arg Ala Ile Leu Pro Gly Ala
                85                  90                  95

Asp Val Ala Val Ala Ser Arg Ala Tyr Phe Leu Thr Thr Val Leu Val
                100                 105                 110

Leu Leu Ala Leu Ala Val Leu Thr Val Trp Ala Thr Gly Ala Val Leu
            115                 120                 125

Arg Arg Thr Gly Gly Arg Pro Gly Asp Ala Leu Leu Val Ala Ala Ala
        130                 135                 140

Pro Val Leu Ile Leu Ala Gly Thr Val Asn Trp Asp Leu Leu Ala Val
145                 150                 155                 160

Ala Ala Ala Val Leu Ala Ile Leu Ala Trp Glu Arg Asp Arg Pro Leu
                165                 170                 175

Leu Ala Gly Val Leu Ile Gly Leu Gly Thr Ala Ala Lys Leu Phe Pro
            180                 185                 190

Leu Val Leu Leu Gly Pro Val Leu Leu Cys Leu Arg Gln Arg Arg
        195                 200                 205

Met Arg Arg Phe Ala Arg Val Ala Ala Gly Ala Ala Gly Ala Trp Leu
    210                 215                 220

Leu Val Asn Leu Pro Val Val Ala Leu Gln Pro Asp Gly Trp Met Glu
225                 230                 235                 240

Phe Trp Arg Phe Asn Ala Gly Arg Gly Ala Glu Phe Gly Ser Leu Trp
                245                 250                 255

Phe Ala Leu Asp Gly Leu Gly Leu His Met Pro Ala Val Asn Ala Val
            260                 265                 270

Ala Leu Ala Thr Phe Gly Val Leu Leu Ala Gly Ile Ala Val Leu Ala
        275                 280                 285

Leu Arg Ser Arg Arg Pro Pro Asp Leu Ala Gln Leu Ala Cys Leu Ala
    290                 295                 300

Val Gly Ala Phe Leu Leu Thr Asn Lys Val Tyr Ser Pro Gln Tyr Ala
305                 310                 315                 320

Leu Trp Leu Leu Pro Leu Val Val Ile Ala Arg Gly Arg Val Pro Arg
                325                 330                 335

Trp Pro Val Val Arg Asp Trp Ala Val Trp Gln Ala Ala Glu Val Leu
            340                 345                 350

Tyr Trp Leu Ala Val Trp Ser Trp Leu Ala Gly Ser Leu Thr Asp Glu
        355                 360                 365

Arg Gln Tyr Ala Trp Ala Thr Val Leu Arg Val Leu Ala Thr Ala Tyr
    370                 375                 380

Val Cys Gly Gln Val Val Trp Asp Val Leu Ala Ala Pro Arg Pro His
385                 390                 395                 400

Arg Pro Ala Pro Pro Ala Val Ala Glu Pro Ala His Pro Gly
                405                 410                 415
```

```
<210> SEQ ID NO 21
<211> LENGTH: 491
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 21

Val Ala Ala Gln Pro Glu Glu Phe Asp Val Ile Val Val Gly Gly Gly
1               5                   10                  15

Pro Gly Gly Ser Thr Ala Ala Leu Thr Ala Lys Gln Gly Ala Lys
            20                  25                  30

Val Leu Leu Leu Glu Arg Glu Lys Phe Pro Arg Tyr Gln Ile Gly Glu
        35                  40                  45

Ser Leu Leu Pro Ser Thr Val His Gly Val Cys Asn Leu Leu Gly Val
    50                  55                  60

Gly Asp Glu Ile Ala Lys Ala Gly Phe Met Arg Lys His Gly Gly Thr
65                  70                  75                  80

Phe Lys Trp Gly Thr Ser Thr Glu Pro Trp Thr Phe Thr Phe Ala Thr
                85                  90                  95

Ser Pro Arg Met Ala Gly Pro Thr Ser His Ala Phe Gln Val Glu Arg
            100                 105                 110

Arg Arg Phe Asp Gln Ile Leu Leu Glu Asn Ala Arg Arg Leu Gly Val
        115                 120                 125

Asp Val Arg Glu Asn His Pro Val Thr Glu Ala Ile Ala Asp Asp Glu
    130                 135                 140

Arg Val Arg Gly Val Arg Phe Thr Gln Asp Gly Gln Thr Arg Thr Ala
145                 150                 155                 160

Leu Ala Arg Phe Val Val Asp Ala Ser Gly Asn Arg Ser Thr Leu His
                165                 170                 175

Thr Thr Val Gly Gly Thr Arg Glu Tyr Ser Pro Phe Phe Arg Asn Leu
            180                 185                 190

Ala Leu Phe Gly Tyr Phe Glu Asn Gly Arg Arg Leu Pro Ala Pro Asn
        195                 200                 205

Ser Gly Asn Ile Leu Cys Val Ala Phe Gly Ser Gly Trp Phe Trp Tyr
    210                 215                 220

Ile Pro Leu Ser Glu Thr Leu Thr Ser Val Gly Ala Val Val Arg Arg
225                 230                 235                 240

Glu Met Ala His Lys Val Gln Gly Asp Gln Glu Lys Ala Leu Phe Glu
                245                 250                 255

Leu Ile Ala Glu Cys Pro Met Ile Ala Asp Phe Leu Gly Asp Ala Thr
            260                 265                 270

Arg Val Thr Glu Gly Asp Tyr Gly Gln Ile Arg Val Arg Lys Asp Tyr
        275                 280                 285

Ser Tyr Ser Ser Thr Ser Tyr Trp Arg Pro Gly Met Cys Leu Val Gly
    290                 295                 300

Asp Ala Ala Cys Phe Ile Asp Pro Val Phe Ser Ser Gly Val His Leu
305                 310                 315                 320

Ala Thr Tyr Ser Gly Leu Leu Ala Ala Arg Ser Ile Asn Ser Val Leu
                325                 330                 335

Ala Gly Thr Val Asp Glu Asp Arg Ala Phe Thr Glu Phe Glu Gln Arg
            340                 345                 350
```

-continued

```
Tyr Arg Arg Glu Phe Gly Val Phe His Asp Phe Leu Val Ser Phe Tyr
        355                 360                 365

Asp Met His Val Asp Glu Ser Ser Tyr Phe Trp Ala Ala Arg Lys Val
    370                 375                 380

Thr Glu Ser Ser Ala Pro Ala Met Glu Ser Phe Thr Glu Leu Val Gly
385                 390                 395                 400

Gly Ile Ala Ser Gly Glu Asp Ala Leu Thr Gly Ser Thr Glu Leu Val
                405                 410                 415

Arg Arg His Ser Arg Gln Thr Ala Glu Leu Gly Gln Ala Val Ala Gly
            420                 425                 430

Leu Glu Glu Gly Gly Thr Gly Phe Leu Arg Gly Ser Ser Val Val Ala
        435                 440                 445

Gln Ala Met Phe Glu Gly Ser Gln Ile Gln Ala Gly Ala Ile Leu Gly
    450                 455                 460

Pro Glu Gly Thr Gln Glu Gln Pro Leu Phe Glu Gly Leu Thr Pro
465                 470                 475                 480

Ser Gly Asn Gly Leu Thr Trp Val Ala Ala Asp
                485                 490
```

<210> SEQ ID NO 22
<211> LENGTH: 217
<212> TYPE: PRT
<213> ORGANISM: Actinoplanes sp.

<400> SEQUENCE: 22

```
Met Thr Ile Arg Val Leu Ile Ala Asp Asp Gln Ala Met Ile Arg Ser
1               5                   10                  15

Gly Leu Arg Leu Ile Leu Glu Asp Glu Pro Asp Ile Glu Val Val Ala
            20                  25                  30

Glu Ala Val Asp Gly Val Asp Ala Val Gln Ala Arg Lys Leu Arg
        35                  40                  45

Pro Asp Val Cys Leu Val Asp Ile Arg Met Pro Arg Ile Asp Gly Ile
    50                  55                  60

Glu Val Thr Arg Ser Leu Ala Gly Pro Gly Val Val Asn Pro Leu Arg
65                  70                  75                  80

Val Ile Val Val Thr Thr Phe Asp Ser Asp Glu Tyr Val Tyr Gly Ala
                85                  90                  95

Leu Arg Gly Gly Ala Val Gly Phe Ile Leu Lys Asp Ala Gly Pro Thr
            100                 105                 110

Leu Leu Val Glu Ala Val Arg Ala Ala His Lys Gly Asp Ala Leu Val
        115                 120                 125

Ser Pro Ser Val Thr Val Arg Leu Leu Asn His Leu Asn Ala Ser Ala
    130                 135                 140

Ala Pro Ala Gly Ser Glu Pro Ile Pro Leu Ser Asp Arg Glu Leu Glu
145                 150                 155                 160

Val Ala Arg Ala Ile Ala Arg Gly Arg Thr Asn Gln Glu Ile Ala Ala
                165                 170                 175

Asp Leu Phe Ile Ser Leu Ser Thr Val Lys Gly His Ala Ser Thr Ile
            180                 185                 190

Gln Ser Lys Leu Gly Val Arg Asn Arg Val Gly Val Ala Ala Trp Ala
        195                 200                 205

Trp Glu Asn Arg Leu Val Glu Gly Ser
    210                 215
```

-continued

<210> SEQ ID NO 23
<211> LENGTH: 403
<212> TYPE: PRT
<213> ORGANISM: Actinoplanes sp.

<400> SEQUENCE: 23

Met Asn Ile Ala Ala Ala Thr Gly Pro Ala Ala Gly Asp Gly Ala Gly
1               5                   10                  15

Ile Arg Thr Leu Gly Ser Val Arg Thr Ala Asp Arg Thr Thr Thr Met
            20                  25                  30

Val Ala Asp Ala Gly Leu Ala Val Leu Phe Val Ala Ala Val Val Val
        35                  40                  45

Glu Ala Val Ala Val Ala Gln Ser Trp Gly Leu Ala Tyr Trp Leu Ile
50                  55                  60

Gly Gly Ala Ala Ala Thr Leu Val Cys Leu Leu Ala Leu Ile Arg Arg
65                  70                  75                  80

Arg Gly Pro Val Pro Cys Ala Ala Gly Leu Thr Ile Ala Ala Gly
                85                  90                  95

Ala Val Val Thr Ala Ala Val Leu His Met Pro Ala Glu Pro Gly Pro
            100                 105                 110

Ala Met Ala Leu Ala Leu Ala Val Leu Thr Gly Ser Ala Val Arg Ala
        115                 120                 125

Ala Pro Thr Ile Pro Ala Phe Ala Val Gly Gly Ala Ala Leu Gly Val
    130                 135                 140

Val Ala Leu Ser Gln Val Ala Ala Ala Thr Trp Asp Ala Gly Pro Ala
145                 150                 155                 160

Pro Val Thr Trp Leu Asn Ile Leu Thr Trp Leu Gly Gly Thr Ala Thr
                165                 170                 175

Gly Leu Ser Leu Arg Thr Val Asp Gly Arg Ala Arg Ala Asn Ala Glu
            180                 185                 190

Arg Ile Arg Gln Glu Glu Arg Leu Glu Leu Ala Arg Glu Leu His Asp
        195                 200                 205

Val Val Ala His His Ile Thr Gly Met Ile Leu Gln Thr Gln Ala Ala
    210                 215                 220

Gln Val Leu Ala Arg Arg Asp Ala Gly Arg Val Pro Glu Arg Leu Ala
225                 230                 235                 240

Val Ile Glu Thr Ala Gly Thr Glu Ala Leu Ala Ala Met Arg Arg Val
                245                 250                 255

Val Gly Leu Leu Arg Asp Ala Asp Asp Gly Pro Pro Ser Ala Pro Glu
            260                 265                 270

Pro Glu Glu Leu Ser Thr Leu Val Glu Arg Phe Ser Arg Gln Gly Gly
        275                 280                 285

Pro Val Arg Leu Thr Thr Pro Asp Gly Met Lys Gln Trp Pro Ile Glu
    290                 295                 300

Val Thr Thr Thr Val Tyr Arg Ile Val Arg Glu Ala Leu Thr Asn Val
305                 310                 315                 320

Ala Arg His Ala Pro His Ala Pro Asn Val Thr Val Thr Val Thr Val
                325                 330                 335

Glu Gln Ala Asp Glu Ile Arg Val Glu Val Thr Asn Asp Ala Ala Ala
            340                 345                 350

Ala Pro Pro Arg Leu His His Arg Gly Gly Tyr Gly Leu Val Gly Met
        355                 360                 365

Arg Glu Arg Val Glu Ser Leu Gly Gly Thr Leu Ser Thr Gly Pro Arg
    370                 375                 380

```
Pro Gly Gly Gly Trp Ser Val Ala Ala Thr Leu Pro Asn Pro Pro Arg
385                 390                 395                 400

Glu Arg Arg

<210> SEQ ID NO 24
<211> LENGTH: 309
<212> TYPE: PRT
<213> ORGANISM: Actinoplanes sp.

<400> SEQUENCE: 24

Met Lys Ala Met Ser His Glu Arg Ser Thr Pro Val Leu Gln Ala Glu
1               5                   10                  15

Gly Leu Thr Lys Arg Tyr Gly Arg Arg Ala Leu Thr Asp Cys Thr
            20                  25                  30

Leu Ser Val Pro Ser Gly Arg Val Ile Ala Leu Val Gly Pro Arg Gly
        35                  40                  45

Ser Gly Lys Ser Thr Leu Leu Gln Leu Cys Cys Gly Met Val Ala Pro
    50                  55                  60

Ser Arg Gly Arg Ile Arg Val Leu Gly Glu Arg Pro Asp Ala Gly Ala
65                  70                  75                  80

Ala His Leu Ala Arg Val Gly Tyr Val Pro Arg Glu Pro Ala Val Tyr
                85                  90                  95

Gly Ser Phe Thr Val Glu Asp His Leu Thr Met Gly Ala Arg Leu Asn
            100                 105                 110

Pro Arg Trp Asp Arg Arg Leu Ala Asp Arg Ile Ala Ser Ala Gly
        115                 120                 125

Ile Pro Arg Thr Arg Arg Ala Asp Arg Leu Ser Ala Gly Gln Arg Ala
    130                 135                 140

Glu Leu Ala Leu Thr Leu Ala Gly Gly Lys Arg Pro Glu Leu Leu Val
145                 150                 155                 160

Leu Asp Glu Pro Gly Ala Val Leu Asp Ala Pro Ala Arg Ala Ser Phe
                165                 170                 175

Leu Arg Gly Val Leu Asp Phe Val Ala Glu Ile Asp Ala Ser Val Leu
            180                 185                 190

Ile Ser Gly His Pro Ser Gly Glu Val Glu Arg Leu Cys Asp His Leu
        195                 200                 205

Ile Val Leu Ser Asp Ser Arg Val Leu Val Ala Gly Asp Val Arg Asp
    210                 215                 220

Leu Leu Ala Arg His His Arg Ile Ile Ala Pro Arg Gly Glu Leu Asp
225                 230                 235                 240

Arg Leu Pro Pro Gly Met Glu Pro Ile Trp Val Glu Asp Phe Gly Ser
                245                 250                 255

Tyr Ser Gly Gly Val Val Arg Ala Glu Val Asp Leu Pro Arg Arg Pro
            260                 265                 270

Trp Thr Val Glu Arg Val Glu Leu Glu Glu Leu Val Leu Ser Tyr Leu
        275                 280                 285

Ser Arg Ala Ser Gly Ala Pro Ala Leu Ala Gly Cys Leu Ile Ala Pro
    290                 295                 300

Gly Gln Pro Gly Ser
305

<210> SEQ ID NO 25
<211> LENGTH: 553
<212> TYPE: PRT
<213> ORGANISM: Actinoplanes sp.
```

```
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 25
```

| | | | | | | | | | | | | | | | |
|---|---|---|---|---|---|---|---|---|---|---|---|---|---|---|---|
|Val|Thr|Ala|Ala|Ala|Leu|Glu|Lys|Leu|Leu|Gly|Asp|Ala|Arg|Asp|Pro|
|1| | | |5| | | | |10| | | | |15| |

| | | | | | | | | | | | |
|---|---|---|---|---|---|---|---|---|---|---|---|
|Gly|Asn|Pro|Val|Gly|Tyr|Ala|Ala|Val|Leu|Ala|Ala|Asp|Glu|Arg|Gln|
| | | |20| | | | |25| | | | |30| | |

|Glu|Met|Leu|Ala|Glu|Gly|Glu|Arg|Leu|Leu|Asp|Arg|Tyr|Gln|Leu|Asn|
| | | |35| | | | |40| | | | |45| | |

|Ala|Glu|Phe|Val|Pro|Val|Ala|Tyr|Gly|Gly|Arg|Leu|Ala|Arg|Ala|Asp|
| |50| | | | |55| | | | |60| | | | |

|Arg|Leu|Ala|Glu|Val|Leu|Arg|Ala|Val|Trp|Arg|Arg|Asp|Pro|Cys|Leu|
|65| | | | |70| | | | |75| | | | |80|

|Gly|Leu|Gly|Tyr|Gly|Phe|Ser|Ser|Leu|Ile|Ala|Ser|Val|Asn|Val|Trp|
| | | | |85| | | | |90| | | | |95| |

|Cys|Ala|Gly|Asn|Glu|Glu|Gln|Arg|Arg|Arg|Ala|Ala|Gly|Leu|Leu|Leu|
| | | |100| | | | |105| | | | |110| | |

|Ala|Asn|Lys|Arg|Ile|Ala|Ala|Ala|Phe|His|Glu|Leu|Ala|His|Gly|Thr|
| | |115| | | | |120| | | | |125| | | |

|Asp|Phe|Ser|Ala|Ala|Glu|Cys|Ala|Ala|Arg|Pro|Ala|Gly|Gly|Gly|Trp|
| |130| | | | |135| | | | |140| | | | |

|Val|Leu|Ser|Gly|His|Lys|Glu|Ile|Val|Thr|Asn|Leu|Arg|Arg|Ala|Glu|
|145| | | | |150| | | | |155| | | | |160|

|Ala|Met|Val|Leu|Phe|Ala|Arg|Thr|Gly|Glu|Ala|Arg|Gly|Ser|Arg|Ser|
| | | | |165| | | | |170| | | | |175| |

|His|Ser|Gln|Phe|Leu|Leu|Val|Arg|Asp|Glu|Leu|Pro|Ala|Ala|Arg|Ala|
| | | |180| | | | |185| | | | |190| | |

|Val|Asp|Arg|Pro|Arg|Tyr|Pro|Gly|Ser|Gly|Met|Arg|Gly|Ile|Asp|Leu|
| | |195| | | | |200| | | | |205| | | |

|Gly|Gly|Leu|Val|Phe|Asp|Asp|Cys|Pro|Val|Pro|Ser|Ser|Ala|Leu|Leu|
| |210| | | | |215| | | | |220| | | | |

|Gly|Glu|Gln|Gly|His|Gly|Ile|Glu|Val|Ala|Leu|Arg|Ala|Tyr|Gln|Val|
|225| | | | |230| | | | |235| | | | |240|

|Thr|Arg|Met|Val|Ser|Pro|Ala|Leu|Leu|Val|Gly|Pro|Leu|Asp|Ser|Ala|
| | | | |245| | | | |250| | | | |255| |

|Val|Arg|Leu|Ala|Thr|Glu|Met|Ala|Met|Glu|Arg|Arg|Leu|Tyr|Gly|Ala|
| | | |260| | | | |265| | | | |270| | |

|Ala|Val|Ala|Asp|Leu|Pro|Tyr|Val|Arg|Thr|Thr|Ile|Ala|Arg|Ala|Tyr|
| | |275| | | | |280| | | | |285| | | |

|Ala|Ala|Leu|Leu|Thr|Val|Asp|Val|Phe|Ser|Gly|Val|Gly|Leu|Arg|Ala|
| |290| | | | |295| | | | |300| | | | |

|Leu|His|Leu|Leu|Pro|Glu|Ala|Thr|Ala|Gly|Tyr|Ala|Pro|Ala|Val|Lys|
|305| | | | |310| | | | |315| | | | |320|

|Tyr|Leu|Thr|Ala|Gln|Ile|Val|Leu|Asp|Ala|Ile|Asp|Asp|Leu|Arg|Ser|
| | | | |325| | | | |330| | | | |335| |

|Val|Leu|Gly|Ala|Gln|Gly|Tyr|Leu|Arg|Gln|Gly|Pro|Tyr|Ala|Met|Phe|
| | | |340| | | | |345| | | | |350| | |

|Gln|Lys|Leu|Val|Arg|Asp|Ala|Ala|Pro|Ala|Ser|Phe|Ala|His|Val|Ser|
| | |355| | | | |360| | | | |365| | | |

```
Arg Ala Ala Cys Leu Val Met Leu Leu Pro His Leu Pro Arg Leu Ala
    370                 375                 380

Arg Arg Ser Trp Thr Ala Glu Glu Pro Pro Asp Asn Val Phe Thr
385                 390                 395                 400

Leu Gly Gly Glu Leu Ser Pro Leu Asp Phe Ser Arg Leu Val Ser Gly
                405                 410                 415

Met Arg Gly Asp Pro Leu Ala Gly Val Leu His Asp Ser Trp His Asp
            420                 425                 430

Glu Gly Pro Val Gly Arg Phe Ala Glu Arg Phe His Arg Glu Leu Thr
        435                 440                 445

Gly Leu Arg Asp Ala Cys Arg Glu Leu Gly Pro Ala Asp Ile Thr Ile
    450                 455                 460

Asp Ala Asn Pro Ala Ala Phe Ala Leu Ala Asp Arg Tyr Thr Val Leu
465                 470                 475                 480

Leu Ala Ala Ala Cys Ala Leu Gly Val Trp Arg Ala Gly Gly Arg Leu
                485                 490                 495

His Arg Pro Ala Leu Leu Ala Val Leu Asp Gly Leu Ala Gly Arg Leu
            500                 505                 510

Gly Gly Glu Ala Val Leu Ser Val Ala Glu Arg Glu His Val Glu His
        515                 520                 525

Gln Leu Phe Glu Met Ala Ala Asp Arg Val Arg Thr Ser Arg Leu Leu
    530                 535                 540

Asp Leu Ser Ala Arg Gln Leu Pro Gly
545                 550

<210> SEQ ID NO 26
<211> LENGTH: 585
<212> TYPE: PRT
<213> ORGANISM: Actinoplanes sp.

<400> SEQUENCE: 26

Met Thr Val Arg Pro Leu Ala Pro Pro Ala Glu Val Arg Leu Asp Asp
1               5                   10                  15

Leu Leu Gly Pro Glu Asp Ala Trp Asp Ala Glu Thr Ala Ala Arg Asp
                20                  25                  30

Ile Ala Glu Glu Phe Pro Ala Arg Leu His Asp Arg Leu Asn Ser Phe
            35                  40                  45

Gly Leu Gln Ser Trp Tyr Val Pro Glu Trp Gly Gly Ala Pro Gly
        50                  55                  60

Asp His Glu Arg Leu Leu His Leu Trp Arg Ala Val Ala Arg Arg Asp
65                  70                  75                  80

Leu Ser Ala Ala Val Ala His Gly Lys Thr Tyr Leu Gly Ser Ala Pro
                85                  90                  95

Val Trp Leu Ala Gly Asp Asp Gly Gln Arg Ala Thr Leu Ala Ala Ala
            100                 105                 110

Val Leu Ala Gly Thr Pro Val Ala Trp Ala Leu Ser Glu Pro Asp His
        115                 120                 125

Gly Ala Asp Leu Leu His Gly Thr Thr Thr Ala Leu Pro His Asp Ala
    130                 135                 140

Gly Tyr Arg Leu Arg Gly Leu Lys Trp Pro Ile Asn Asn Ala Thr Arg
145                 150                 155                 160

Ala Arg Tyr Leu Thr Val Leu Ala Arg Thr Gly Arg Ala Gly Asp Ala
                165                 170                 175

Arg Gly Gln Ser Leu Phe Leu Val Asp Lys Glu Ala Leu Ala Pro Gly
            180                 185                 190
```

```
Thr Trp Leu Pro Arg Pro Lys Val Ala Thr His Gly Val Arg Gly Ile
        195                 200                 205

Asp Ile Ser Gly Ile Ala Phe Glu Asp Ala Gly Leu Pro Gly Thr Ala
    210                 215                 220

Leu Leu Gly Arg Ala Gly Ser Gly Leu Glu Thr Val Leu Arg Ser Leu
225                 230                 235                 240

Gln Leu Thr Arg Thr Met Cys Ala Gly Leu Ser Leu Gly Ala Gly Asp
                245                 250                 255

Arg Ala Leu Arg Leu Thr Ala Arg Phe Val Ala Gln Arg Met Ile Met
            260                 265                 270

Arg Arg Pro Leu Leu Asp Arg Gly His Pro Ala Gly Ile Leu Ala Arg
        275                 280                 285

Cys Ala Ala Leu Leu Ala Ala Ala Glu Ala Thr Ala Val Val Gly Thr
    290                 295                 300

Arg Ser Val His Ser Leu Thr Ala Glu Met Ser Val Thr Ser Ala Ile
305                 310                 315                 320

Val Lys Ala Tyr Val Pro Thr Val Val Asp Arg Val Leu Arg Glu Leu
                325                 330                 335

Ala Glu Leu Leu Gly Ser Arg Ser Phe Leu Arg Asp Glu Tyr Glu His
            340                 345                 350

Gly Met Phe Pro Lys Leu Val Arg Asp His His Val Ala Val Ala Phe
        355                 360                 365

Asp Gly Ser Thr Pro Val Val Arg Thr Ala Leu Ala His Gln Phe Pro
    370                 375                 380

Arg Leu Ala Ala Gly Phe Ala Ala Gly Ala Val Ser Ala Glu Gly Leu
385                 390                 395                 400

Ala Glu Ala Ser Ala Ala Gly Gln Pro Pro Pro Leu Asp Arg Gly
                405                 410                 415

Ala Leu Thr Leu Leu Ser Arg His Gly Cys Ser Val Val Gln Ala Leu
            420                 425                 430

Pro Ala Leu Ala Val Ser Ala Ala Val Arg Gly Gly Pro Ala Gly Leu
        435                 440                 445

Ala Arg His Ala Ala Ala Leu Ala Gly Glu Ala Arg Arg Ile Cys Gly
    450                 455                 460

Gln Met Thr Glu Leu Gly Pro Ser Ala Arg Pro Ser Met Val Gly His
465                 470                 475                 480

Glu Leu Ala Ala Ala Tyr Glu Trp Cys Tyr Ala Gly Ala Ala Cys Leu
                485                 490                 495

Leu Leu Trp Thr Ser Ala Glu Gly Arg His Thr Ala Asp Pro Leu Trp
            500                 505                 510

Ala Asp Gly Leu Trp Val Leu Ala Leu Arg Ala Val Arg Arg Glu
        515                 520                 525

Leu Ala Arg Val Leu Arg Ala Pro Ala Pro Asp Pro Gly Pro His Asp
530                 535                 540

Asp Gly Ala Asp Arg Leu Leu Ala Ala Arg Val Ala Ala Ala Ala Arg
545                 550                 555                 560

Thr Gly Glu Pro Val Thr Pro Phe Gly Thr Ala Leu Arg Pro Pro Ala
                565                 570                 575

Gly Thr Val Arg Ala Glu Asp Gly Arg
            580                 585
```

<210> SEQ ID NO 27
<211> LENGTH: 587
<212> TYPE: PRT
<213> ORGANISM: Actinoplanes sp.

<400> SEQUENCE: 27

```
Met Val Ile Asp Ala Ala Thr Gln Pro Thr Val Pro Asp Ala Phe Arg
1               5                   10                  15

Ala Gln Ala Ile Ala Arg Pro Gly Glu Pro Ala Leu Val Val Leu Pro
            20                  25                  30

Gly Asp Pro Asp Ala Glu Pro Val Thr Leu Thr Tyr Ala Glu Leu Asp
        35                  40                  45

Arg Arg Ala Ala Ala Arg Ala Ala Trp Leu Ala Ala Arg Phe Pro Ala
    50                  55                  60

Gly Glu Arg Ile Leu Ile Ala Leu Pro Thr Gly Ala Glu Phe Val Glu
65                  70                  75                  80

Leu Tyr Leu Ala Cys Leu Tyr Ala Gly Leu Val Ala Val Pro Ala Pro
                85                  90                  95

Pro Pro Gly Gly Ser Ser Gly Ala Ser Glu Arg Thr Val Gly Ile Ala
            100                 105                 110

Ala Asp Cys Ser Pro Ala Leu Ala Val Val Asn Ala Asp Asp Ala Ala
        115                 120                 125

Pro Leu Thr Ala Val Leu Arg Glu Arg Gly Leu Ser Gly Leu Pro Val
    130                 135                 140

Gly Ala Leu Pro Pro Leu Ala Ala Glu Ala Ile Arg Pro Pro Arg Gly
145                 150                 155                 160

Pro Arg Pro Asp Ser Leu Ala Val Leu Gln Tyr Ser Ser Gly Ser Thr
                165                 170                 175

Gly Ser Pro Lys Gly Val Met Leu Ser His Arg Ala Val Leu Ala Asn
            180                 185                 190

Leu Arg Ala Phe Asp Arg Ser Ser Gly His Asn Ser Asp Asp Val Phe
        195                 200                 205

Gly Ser Trp Leu Pro Leu His His Asp Met Gly Leu Phe Ala Met Leu
    210                 215                 220

Thr Ala Gly Leu Leu Asn Gly Ala Gly Val Val Leu Met Ser Pro Thr
225                 230                 235                 240

Ala Phe Val Arg Arg Pro Ala Asp Trp Leu Arg Met Met Asp Arg Tyr
                245                 250                 255

Arg Val Thr Ile Ser Ala Ala Pro Asn Phe Ala Tyr Asp Leu Cys Val
            260                 265                 270

Arg Ala Val Arg Asp Glu Gln Ile Ala Gly Leu Asp Leu Ser Arg Ile
        275                 280                 285

Arg Thr Leu Tyr Asn Gly Ser Glu Pro Val Asn Pro Ala Thr Val Arg
    290                 295                 300

Ala Phe Thr Glu Arg Phe Ala Pro Phe Gly Leu His Thr His Ala Val
305                 310                 315                 320

Asn Pro Cys Tyr Gly Met Ala Glu Phe Thr Ala Tyr Val Ser Thr Lys
                325                 330                 335

Val Phe Glu Ala Pro Ala Val Phe Leu Pro Ala Asp Pro Arg Ala Leu
            340                 345                 350

Glu Asp Ala Ala Ser Pro Ala Leu Arg Pro Ala Asp Pro Ala Ala Ala
        355                 360                 365

Arg Glu Ile Pro Gly Val Gly Arg Val Pro Asp Phe Glu Val Leu Ile
    370                 375                 380
```

```
Val Asp Pro Asp Gly Leu Arg Pro Leu Pro Glu Gly Arg Val Gly Glu
385                 390                 395                 400

Ile Trp Leu Arg Gly Pro Gly Ala Gly Ala Gly Tyr Trp Gly Arg Thr
                405                 410                 415

Glu Leu Asn Pro Gly Ile Phe Asp Ala Arg Pro Ala Gly Asp Gly Gln
            420                 425                 430

Asp Gly Gly Trp Val Arg Thr Gly Asp Leu Gly Ala Leu Thr Gly Gly
        435                 440                 445

Glu Leu Phe Leu Thr Gly Arg Leu Lys Glu Leu Leu Ile Val His Gly
    450                 455                 460

Arg Asn Leu Ala Pro His Asp Leu Glu Arg Glu Ala Arg Ala Ala His
465                 470                 475                 480

Asp Ala Val Asp His Gln Ile Gly Ala Ala Phe Gly Val Pro Ala Pro
                485                 490                 495

Asp Glu Arg Ile Val Leu Val Gln Glu Val His Pro Arg Thr Pro Leu
            500                 505                 510

Asp Glu Leu Pro Arg Val Ala Ser Ala Val Ser Arg Leu Thr Val
        515                 520                 525

Ser Phe Gly Val Pro Val Arg Asn Val Leu Leu Val Arg Arg Gly Thr
530                 535                 540

Val Arg Arg Thr Thr Ser Gly Lys Ile Arg Arg Thr Ala Val Arg Glu
545                 550                 555                 560

Arg Phe Leu Ala Gly Gly Ile Thr Ala Leu His Ala Glu Leu Glu Pro
                565                 570                 575

Ala Leu Arg Pro Val Gln Ala Gly Ala Gly Arg
            580                 585

<210> SEQ ID NO 28
<211> LENGTH: 75
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      Ti is expected that the biosynthesized protein will have a
      formylmethionine residue at this position

<400> SEQUENCE: 28

Val Pro Asn Pro Phe Glu Asp Pro Asp Ala Asn Tyr Leu Val Leu Val
1               5                   10                  15

Asn Asp Glu Gly Gln His Ser Leu Trp Pro Val Phe Ala Asp Val Pro
            20                  25                  30

Asp Gly Trp Thr Thr Val Phe Gly Glu Ala Gly Arg Gln Asp Cys Leu
        35                  40                  45

Asp Tyr Ile Glu Lys Ser Trp Thr Asp Met Arg Pro Lys Ser Leu Ile
    50                  55                  60

Ala Ala Met Glu Lys Gln Lys Gln Pro Gln Ser
65                  70                  75

<210> SEQ ID NO 29
<211> LENGTH: 94
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V is a non-standard initiator codon.  It is
      expected that the biosynthesized protein will have a
      formylmethionine residue at this position
```

```
<400> SEQUENCE: 29

Val Ala Pro Gly Ala Pro Pro Ala Glu His Gly Glu Ala Val Pro Glu
1               5                   10                  15

Ala Asp Ile Pro Val Leu Arg Asn Arg Ile Asp Glu Ile Asp Ala Ala
            20                  25                  30

Ile Met Arg Leu Trp Gln Glu Arg Ala Ser Ile Ser Gln Lys Ile Gly
        35                  40                  45

Ser Ile Arg Leu Ala Ser Gly Gly Thr Arg Val Val Leu Ser Arg Glu
    50                  55                  60

Gln Glu Val Ile Gln Arg Phe Arg Ala Ala Leu Gly Glu Asp Gly Thr
65                  70                  75                  80

Thr Ile Ala Leu Met Leu Leu Arg Ala Gly Arg Gly Pro Leu
                85                  90
```

<210> SEQ ID NO 30
<211> LENGTH: 619
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

```
<400> SEQUENCE: 30

Val Asp Val Pro Arg Val Arg Pro Pro Gly Ala Ala Pro Ala Pro Arg
1               5                   10                  15

Arg Arg Arg Trp Arg Phe Trp Gln Ser Pro Asp Gly Gln Pro Ala Trp
            20                  25                  30

Ala Arg Pro Ala Leu Leu Gly Ile Ala Ala Leu Ala Ala Val Leu Tyr
        35                  40                  45

Thr Ala Asn Leu Ala Arg Ser Gly Tyr Pro Met Tyr Tyr Ala Val Ala
    50                  55                  60

Val Lys Ser Met Ser Val Ser Trp Pro Ala Phe Trp Thr Gly Ala Phe
65                  70                  75                  80

Asp Pro Ala Ala Ser Ile Thr Ile Asp Lys Leu Ala Gly Ala Phe Val
                85                  90                  95

Pro Gln Ala Leu Ser Ala Arg Val Phe Gly Phe His Gln Trp Ser Leu
            100                 105                 110

Ala Leu Pro Gln Ala Val Glu Gly Val Ile Ala Val Leu Val Leu Tyr
        115                 120                 125

Arg Ala Val Arg Arg Trp His Gly Pro Gly Ala Gly Leu Ala Ala Ala
    130                 135                 140

Gly Leu Phe Ala Thr Thr Pro Ile Val Ser Ser Met Phe Gly His Ser
145                 150                 155                 160

Met Glu Asp Gly Ala Leu Thr Leu Cys Leu Val Leu Ala Ala Asp Ala
                165                 170                 175

Phe Gly Ala Ala Val Thr Arg Gly Ser Pro Ala Arg Leu Ala Leu Ala
            180                 185                 190

Gly Ala Trp Ile Gly Leu Gly Phe Gln Ala Lys Met Met Gln Ala Trp
        195                 200                 205

Leu Val Leu Pro Ala Leu Val Val Thr Tyr Leu Ala Gly Ala Pro Val
    210                 215                 220

Arg Ala Arg Ala Arg Val Val His Val Ala Ala Ala Val Ala Ala Thr
225                 230                 235                 240
```

```
Leu Ala Val Ser Leu Leu Trp Val Leu Ala Leu Thr Leu Leu Pro Gly
                245                 250                 255

Ser His Arg Pro Trp Ala Asp Gly Thr Thr Ser Gly Asn Ala Phe Ala
            260                 265                 270

Met Val Phe Gly Tyr Asn Gly Phe Asp Arg Ala Gly Ile His Val Pro
        275                 280                 285

Gly Ala Leu Thr Thr Gly Phe Thr Asp Gly Ala Ala Ala Gly Gly
        290                 295                 300

Ser Trp Thr Ala Leu Ala Ala Asp Arg Leu Ala Thr Gln Ile Gly Trp
305                 310                 315                 320

Trp Tyr Pro Leu Ala Leu Thr Gly Leu Leu Gly Leu Ala Arg Trp
                325                 330                 335

Arg Thr Ala Arg Ala Gly Leu Leu Phe Trp Gly Leu Trp Leu Leu Thr
            340                 345                 350

Ala Ala Val Val Leu Ser Arg Ile Thr Ile Gln His Asn Ala Tyr Leu
                355                 360                 365

Ala Val Leu Ala Pro Pro Leu Ala Leu Ala Ala Gly Ala Val
            370                 375                 380

Gln Leu Trp Arg Thr His Arg Asp Gly Thr Ala Pro Trp Leu Leu Pro
385                 390                 395                 400

Ala Val Val Val Val Gln Ala Gly Trp Thr Leu Trp Leu Ala Thr Arg
                405                 410                 415

Tyr Pro Ser Phe Leu Ala Gly Leu Thr Trp Thr Ala Pro Ile Ala Ala
                420                 425                 430

Val Leu Ala Val Val Leu Ala Ala Arg Pro Thr Ala Arg Arg Pro
            435                 440                 445

Ala Val Val Val Val Ala Gly Leu Leu Ala Val Pro Val Ala Trp
            450                 455                 460

Gly Ala Ser Val Leu Asn Pro Arg Tyr Ala Gly Thr Ser Phe Glu Ala
465                 470                 475                 480

Gly Ala Gly Pro Ser Gly Pro Val Gly Val Arg Leu Asp Asp Asp Thr
                485                 490                 495

Thr Asp Arg Leu Thr Pro Gly Leu Arg Arg Leu Asp Asp Tyr Leu Ala
            500                 505                 510

Ala His Arg Asp Gly Arg Thr Tyr Leu Ala Ala Thr Ser Ser Trp Arg
            515                 520                 525

Thr Ala Gly Arg Leu Ile Val Pro Thr Gly His Ser Tyr Leu Pro Leu
            530                 535                 540

Gly Gly Phe Ser Gly Ala Ala Pro Phe Pro Ser Leu Ala Gly Val Gln
545                 550                 555                 560

Arg Leu Val Arg Asp Gly Glu Leu Arg Tyr Phe Val Leu Gly Pro
                565                 570                 575

Glu Gly Leu Gly Gly Glu Ala Thr Glu Ala Tyr Arg Ile Thr Gly Trp
            580                 585                 590

Val Leu Glu Thr Cys Ala Thr Val Pro Pro Ala Glu His Gly Ala Asp
                595                 600                 605

Pro Asp Leu Thr Val Leu Arg Cys Asp Lys Pro
        610                 615

<210> SEQ ID NO 31
<211> LENGTH: 355
<212> TYPE: PRT
<213> ORGANISM: Actinoplanes sp.
```

<220> FEATURE:
<221> NAME/KEY: misc_feature
<222> LOCATION: (1)..(1)
<223> OTHER INFORMATION: V represents a non-standard initiator codon.
    It is expected that the biosynthesized protein will have a
    formylmethionine residue at this position

<400> SEQUENCE: 31

```
Val Asp Asn Gly Thr Phe Thr Asp Leu Arg Ile Asp His Ile Glu Phe
1               5                   10                  15

Ala Val Ala Asp Val Glu Ser Ala Ser Ala Pro Phe Thr Glu Gly Tyr
            20                  25                  30

Gly Phe Ser Val Tyr Gly Gly Thr Gly Asp Ala His Ala Pro Val Arg
        35                  40                  45

Arg Val Ala Leu Gly Arg Asp Asp Ile Arg Leu Val Leu Thr Ala Ala
    50                  55                  60

Pro Gly Gly Asp His Pro Ala Met Ala Tyr Val Glu Gln His Gly Asp
65                  70                  75                  80

Gly Val Ser Ala Ile Ala Leu Ser Thr Arg Asp Ala His Ala Ala Phe
                85                  90                  95

Thr Glu Ala Val Arg Arg Gly Ala Val Gly Val Ser Ala Pro Val Thr
            100                 105                 110

Gly Asn Gly Val Thr Val Ala Thr Ile Arg Gly Phe Gly Asp Val Leu
        115                 120                 125

His Thr Phe Val Glu Arg Ala Pro Gly Ala Asp Pro Arg Thr Leu Pro
    130                 135                 140

Gly Leu Glu Leu Arg Arg Pro Ser Pro Thr Arg Phe Asp Ser Gly Leu
145                 150                 155                 160

Gln Ala Ile Asp His Ile Ala Val Cys Leu Glu Pro Gly Thr Leu Asp
                165                 170                 175

Pro Thr Val Asp Phe Tyr Arg Asp Val Leu Asp Phe Glu Met Ile Phe
            180                 185                 190

Glu Glu Arg Ile Leu Val Gly Arg Gln Ala Met Asp Ser Lys Val Val
        195                 200                 205

Gln Ser Arg Ser Gly Gly Val Thr Leu Thr Leu Ile Glu Pro Asp Thr
    210                 215                 220

Ser Leu Glu Gln Gly Gln Ile Asp Thr Phe Leu Lys Asn His Gly Gly
225                 230                 235                 240

Pro Gly Val Gln His Leu Ala Phe Ile Thr Asp Asp Val Leu Arg Ser
                245                 250                 255

Val Gly Arg Met Ser Glu His Gly Val Glu Phe Leu His Thr Pro Asp
            260                 265                 270

Ser Tyr Tyr Gly Arg Leu Pro Gly Arg Ile Pro Gln Ala Gly His Pro
        275                 280                 285

Ile Gln Ala Leu Arg Asp Leu Asn Val Leu Val Asp Gln Asp His Asp
    290                 295                 300

Gly Gln Leu Phe Gln Ile Phe Thr Lys Ser Val His Pro Arg Gly Thr
305                 310                 315                 320

Ile Phe Met Glu Val Ile Glu Arg Met Gly Ala Arg Ser Phe Gly Ser
                325                 330                 335

Gly Asn Ile Lys Ala Leu Tyr Glu Ala Val Glu Leu Asp Met Ser Lys
            340                 345                 350

Gln Ser Ala
        355
```

-continued

<210> SEQ ID NO 32
<211> LENGTH: 429
<212> TYPE: PRT
<213> ORGANISM: Actinoplanes sp.

<400> SEQUENCE: 32

Met Glu Ser Pro Ala Thr His Ala Glu Leu Val Ile Gly Thr Val Leu
1               5                   10                  15

Leu Asp Ile Ala Leu Val Leu Ala Gly Ala Leu Leu Gly Arg Trp
            20                  25                  30

Val Arg Arg Leu Arg Gln Pro Ala Val Ile Gly Glu Ile Leu Ala Gly
        35                  40                  45

Ile Ala Leu Gly Pro Ser Leu Gly Leu Leu Pro Gly Asn Pro Thr
    50                  55                  60

Ala Trp Leu Phe Pro Ala Glu Ala Arg Pro Tyr Leu Ser Ala Val Ala
65                  70                  75                  80

Gln Ile Gly Leu Ala Leu Phe Thr Phe Leu Ile Gly Trp Glu Phe Asn
                85                  90                  95

Pro Ala Thr Leu Ala Arg His Arg Gly Thr Ala Ala Val Ser Ile
            100                 105                 110

Gly Ser Ile Ala Val Ser Phe Gly Leu Gly Ile Ala Leu Ala Thr Val
        115                 120                 125

Leu His Pro Arg His Asp Thr Thr Gly Gly Gly Lys Val Gly Phe Thr
130                 135                 140

Glu Phe Ala Leu Phe Leu Gly Val Ala Met Ser Ile Thr Ala Phe Pro
145                 150                 155                 160

Val Leu Ala Arg Ile Leu Ala Glu Arg Arg Leu Thr Gly Thr Arg Val
                165                 170                 175

Gly Ser Ile Ala Leu Val Ser Ala Ala Ile Asp Asp Val Val Ala Trp
            180                 185                 190

Cys Leu Leu Ala Leu Val Thr Ala Ile Ala Thr Ala Ser Gly Pro Val
        195                 200                 205

Gln Leu Val Arg Ile Leu Ala Leu Leu Ala Val Phe Leu Val Val Leu
    210                 215                 220

Val Thr Val Val Arg Pro Leu Leu Val Leu Leu Ala Arg Arg Pro Ser
225                 230                 235                 240

Ala Ser Tyr Leu Leu Val Ala Val Val Ala Val Leu Leu Ser Ala
                245                 250                 255

Tyr Ala Thr Thr Trp Ile Gly Leu His Ala Ile Phe Gly Ala Phe Cys
            260                 265                 270

Ala Gly Leu Val Met Pro Arg Glu Pro Ala Ala Ala Leu Arg Glu Arg
        275                 280                 285

Val Arg Gln Pro Leu Glu His Val Ser Val Val Leu Leu Pro Val Phe
    290                 295                 300

Phe Ile Val Thr Gly Leu Gly Val Asp Ile Gly Ala Leu Thr Ala Ala
305                 310                 315                 320

Asn Ile Leu Glu Leu Ala Ala Ile Ile Val Ile Ala Cys Ala Gly Lys
                325                 330                 335

Leu Ala Gly Ala Ile Val Pro Ala Val Ser Leu Gly Met Ser Trp Arg
            340                 345                 350

Asp Ala Arg Thr Leu Gly Leu Leu Val Asn Thr Arg Gly Leu Thr Glu
        355                 360                 365

Leu Val Val Leu Asn Val Gly Leu Gln Leu Ala Val Leu Asp Gly Gln
    370                 375                 380

```
Met Phe Thr Met Met Val Leu Met Ala Leu Val Thr Ala Leu Ala
385                 390                 395                 400

Gly Pro Leu Ile Gly Ser Ala Arg Thr Pro Ala Ala Gly Ala Pro Ala
                405                 410                 415

Gln Ala Leu Pro Ala Glu Pro Thr Arg Arg Ala Ala
            420                 425
```

<210> SEQ ID NO 33
<211> LENGTH: 189
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 33

```
Val Ser Asp Glu Ala Ala Val Pro Ser Pro Ala Arg Leu Leu Arg Asp
1               5                   10                  15

Phe Val Asn Thr Tyr Glu Pro Gln Val Asp Asp Glu Ser Leu Ser Thr
                20                  25                  30

Pro Asp Ala Leu Arg Ala Trp Leu Ala Gly Glu Ser Leu Leu Ala Pro
            35                  40                  45

Gly Ala Arg Val Arg Pro Ala Asp Leu Ala Arg Ala Val Ala Leu Arg
        50                  55                  60

Glu Gly Leu Arg Gln Val Leu Leu Gly His Ala Gly His Pro Ala Asp
65                  70                  75                  80

Pro Ala Ala Leu Arg Arg Leu Glu Glu Ile Leu Ala Ala Val Pro Val
                85                  90                  95

Arg Leu Ser Leu Ala Gly Gly Ala Pro Arg Leu Leu Pro Ala Gly Gly
                100                 105                 110

Thr Pro Phe Asp Arg Ala Leu Ala Gly Leu Ile Asp Ala Val Arg Gln
            115                 120                 125

Cys Ala Glu Leu Gln Val Trp Thr Arg Leu Lys Val Cys Asp Arg Asp
130                 135                 140

Thr Cys Arg Trp Ala Tyr Tyr Asp Ala Ser Arg Asn Gln Ala Arg Arg
145                 150                 155                 160

Trp Cys Ser Met Ala Gly Cys Gly Asn Tyr Ile Lys Met Arg Arg Ala
                165                 170                 175

Tyr Ala Ala Arg Arg Val Arg Gly Ser Ala Gly Ser Ala
            180                 185
```

<210> SEQ ID NO 34
<211> LENGTH: 309
<212> TYPE: PRT
<213> ORGANISM: Actinoplanes sp.
<220> FEATURE:
<221> NAME/KEY: misc_feature
<222> LOCATION: (1)..(1)
<223> OTHER INFORMATION: V represents a non-standard initiator codon.
      It is expected that the biosynthesized protein will have a
      formylmethionine residue at this position

<400> SEQUENCE: 34

```
Val Ala Thr Thr Leu Arg Asp Val Ala Arg Leu Ala Arg Val Ser Val
1               5                   10                  15

Lys Thr Val Ser Asn Val Val Asn Asp His Pro His Val Ser Asp Asp
                20                  25                  30
```

-continued

```
Val Arg Arg Arg Val Glu Thr Ala Ile Arg Gln Leu Gly Tyr Arg Pro
            35                  40                  45

Asn Leu Val Ala Arg Ala Leu Arg Ser Gly Arg Gly Ser Gly Leu Leu
 50                  55                  60

Ala Leu Ala Met Pro Gly Ala Gly Ala Pro Gln Ser Pro Ala Leu Ile
 65                  70                  75                  80

Glu Glu Ile Ile Arg Arg Ala Ala Pro Leu Gly Phe Arg Val Leu Ile
                85                  90                  95

Glu Pro Leu Glu Ser Ser Arg Pro Arg Pro Ala Pro Gly Val Asp
            100                 105                 110

Ala Arg Leu Leu Asn Ala Glu Ala Pro Ala Glu Leu Val Asp Ala
            115                 120                 125

Gln Ala Ala Thr Gly Thr Pro Leu Val Leu Thr Gly Thr Pro Asp
130                 135                 140

Pro Arg Tyr Asp Cys Val Gly Pro Asp Ala Ala Arg Ala Ala Glu Asp
145                 150                 155                 160

Ala Val Asp His Leu Arg Arg Leu Gly Arg Arg Val Ala Thr Ile
                165                 170                 175

Gly Gly Ser Leu Ser Thr Gly Pro Ala Gly Ser Gly Ser Asp Phe Gly
                180                 185                 190

Ser Gly Ser Gly Ser Gly Ser Gly Ser Gly Ser Gly Ser Gly
                195                 200                 205

Ser Gly Ser Gly Ser Gly Ser Gly Ser Gly Phe Gly Ser Gly
                210                 215                 220

Ser Gly Phe Gly Ser Gly Ser Ala Glu Gly Tyr Arg Ala Ala Arg Gln
225                 230                 235                 240

Leu Leu Gly His Glu Asp Arg Pro Asp Ala Ile Val Cys Gly Ser Val
                245                 250                 255

Arg Leu Ala Val Gly Val Ile Arg Ala Ala Asp Ala Gly Leu Arg
                260                 265                 270

Val Pro Glu Asp Val Ala Val Ile Gly Ile Gly Asp Gly Glu Glu Gly
                275                 280                 285

Arg Tyr Thr Arg Pro Ala Leu Thr Thr Val Ala Thr Asp Pro Ala Phe
                290                 295                 300

Ile Ala Gly Lys Ala
305
```

<210> SEQ ID NO 35
<211> LENGTH: 542
<212> TYPE: PRT
<213> ORGANISM: Bacillus brevis

<400> SEQUENCE: 35

```
Met Leu Asn Ser Ser Lys Ser Ile Leu Ile His Ala Gln Asn Lys Asn
 1               5                  10                  15

Gly Thr His Glu Glu Gln Tyr Leu Phe Ala Val Asn Asn Thr Lys
                20                  25                  30

Ala Glu Tyr Pro Arg Asp Lys Thr Ile His Gln Leu Phe Glu Glu Gln
                35                  40                  45

Val Ser Lys Arg Pro Asn Asn Val Ala Ile Val Cys Glu Asn Glu Gln
 50                  55                  60

Leu Thr Tyr His Glu Leu Asn Val Lys Ala Asn Gln Leu Ala Arg Ile
 65                  70                  75                  80

Phe Ile Glu Lys Gly Ile Gly Lys Asp Thr Leu Val Gly Ile Met Met
                85                  90                  95
```

-continued

Glu Lys Ser Ile Asp Leu Phe Ile Gly Ile Leu Ala Val Leu Lys Ala
                100                 105                 110

Gly Gly Ala Tyr Val Pro Ile Asp Ile Glu Tyr Pro Lys Glu Arg Ile
            115                 120                 125

Gln Tyr Ile Leu Asp Asp Ser Gln Ala Arg Met Leu Leu Thr Gln Lys
        130                 135                 140

His Leu Val His Leu Ile His Asn Ile Gln Phe Asn Gly Gln Val Glu
145                 150                 155                 160

Ile Phe Glu Glu Asp Thr Ile Lys Ile Arg Glu Gly Thr Asn Leu His
                165                 170                 175

Val Pro Ser Lys Ser Thr Asp Leu Ala Tyr Val Ile Tyr Thr Ser Gly
            180                 185                 190

Thr Thr Gly Asn Pro Lys Gly Thr Met Leu Glu His Lys Gly Ile Ser
        195                 200                 205

Asn Leu Lys Val Phe Phe Glu Asn Ser Leu Asn Val Thr Glu Lys Asp
    210                 215                 220

Arg Ile Gly Gln Phe Ala Ser Ile Ser Phe Asp Ala Ser Val Trp Glu
225                 230                 235                 240

Met Phe Met Ala Leu Leu Thr Gly Ala Ser Leu Tyr Ile Ile Leu Lys
                245                 250                 255

Asp Thr Ile Asn Asp Phe Val Lys Phe Glu Gln Tyr Ile Asn Gln Lys
            260                 265                 270

Glu Ile Thr Val Ile Thr Leu Pro Pro Thr Tyr Val Val His Leu Asp
        275                 280                 285

Pro Glu Arg Ile Leu Ser Ile Gln Thr Leu Ile Thr Ala Gly Ser Ala
    290                 295                 300

Thr Ser Pro Ser Leu Val Asn Lys Trp Lys Glu Lys Val Thr Tyr Ile
305                 310                 315                 320

Asn Ala Tyr Gly Pro Thr Glu Thr Thr Ile Cys Ala Thr Thr Trp Val
                325                 330                 335

Ala Thr Lys Glu Thr Ile Gly His Ser Val Pro Ile Gly Ala Pro Ile
            340                 345                 350

Gln Asn Thr Gln Ile Tyr Ile Val Asp Glu Asn Leu Gln Leu Lys Ser
        355                 360                 365

Val Gly Glu Ala Gly Glu Leu Cys Ile Gly Gly Glu Gly Leu Ala Arg
    370                 375                 380

Gly Tyr Trp Lys Arg Pro Glu Leu Thr Ser Gln Lys Phe Val Asp Asn
385                 390                 395                 400

Pro Phe Val Pro Gly Glu Lys Leu Tyr Lys Thr Gly Asp Gln Ala Arg
                405                 410                 415

Trp Leu Ser Asp Gly Asn Ile Glu Tyr Leu Gly Arg Ile Asp Asn Gln
            420                 425                 430

Val Lys Ile Arg Gly His Arg Val Glu Leu Glu Glu Val Glu Ser Ile
        435                 440                 445

Leu Leu Lys His Met Tyr Ile Ser Glu Thr Ala Val Ser Val His Lys
    450                 455                 460

Asp His Gln Glu Gln Pro Tyr Leu Cys Ala Tyr Phe Val Ser Glu Lys
465                 470                 475                 480

His Ile Pro Leu Glu Gln Leu Arg Gln Phe Ser Ser Glu Glu Leu Pro
                485                 490                 495

Thr Tyr Met Ile Pro Ser Tyr Phe Ile Gln Leu Asp Lys Met Pro Leu
            500                 505                 510

Thr Ser Asn Gly Lys Ile Asp Arg Lys Gln Leu Pro Glu Pro Asp Leu
            515                 520                 525

Thr Phe Gly Met Arg Val Asp Tyr Glu Ala Pro Arg Asn Glu
        530                 535                 540

<210> SEQ ID NO 36
<211> LENGTH: 582
<212> TYPE: PRT
<213> ORGANISM: Mycobacterium bovis

<400> SEQUENCE: 36

Met Ala Met Ser Val Arg Ser Leu Pro Ala Ala Leu Arg Ala Cys Ala
1               5                   10                  15

Cys Leu Gln Pro His Asp Pro Ala Phe Thr Phe Met Asp Tyr Glu Gln
            20                  25                  30

Asp Trp Asp Gly Val Ala Ile Thr Leu Thr Trp Ser Gln Leu Tyr Arg
        35                  40                  45

Arg Thr Leu Asn Val Ala Arg Glu Leu Ser Arg Cys Gly Ser Thr Gly
    50                  55                  60

Asp Arg Val Val Ile Ser Ala Pro Gln Gly Leu Glu Tyr Val Val Ala
65                  70                  75                  80

Phe Leu Gly Ala Leu Gln Ala Gly Arg Ile Ala Val Pro Leu Ser Val
                85                  90                  95

Pro Gln Gly Gly Val Thr Asp Glu Arg Ser Asp Ser Val Leu Ser Asp
            100                 105                 110

Ser Ser Pro Val Ala Ile Leu Thr Thr Ser Ser Ala Val Asp Asp Val
            115                 120                 125

Val Gln His Val Ala Arg Arg Pro Gly Glu Ser Pro Pro Ser Ile Ile
        130                 135                 140

Glu Val Asp Leu Leu Asp Leu Asp Ala Pro Asn Gly Tyr Thr Phe Lys
145                 150                 155                 160

Glu Asp Glu Tyr Pro Ser Thr Ala Tyr Leu Gln Tyr Thr Ser Gly Ser
                165                 170                 175

Thr Arg Thr Pro Ala Gly Val Val Met Ser His Gln Asn Val Arg Val
            180                 185                 190

Asn Phe Glu Gln Leu Met Ser Gly Tyr Phe Ala Asp Thr Asp Gly Ile
        195                 200                 205

Pro Pro Pro Asn Ser Ala Leu Val Ser Trp Leu Pro Phe Tyr His Asp
    210                 215                 220

Met Gly Leu Val Ile Gly Ile Cys Ala Pro Ile Leu Gly Gly Tyr Pro
225                 230                 235                 240

Ala Val Leu Thr Ser Pro Val Ser Phe Leu Gln Arg Pro Ala Arg Trp
                245                 250                 255

Met His Leu Met Ala Ser Asp Phe His Ala Phe Ser Ala Ala Pro Asn
            260                 265                 270

Phe Ala Phe Glu Leu Ala Ala Arg Thr Thr Asp Asp Met Ala
        275                 280                 285

Gly Arg Asp Leu Gly Asn Ile Leu Thr Ile Leu Ser Gly Ser Glu Arg
    290                 295                 300

Val Gln Ala Ala Thr Ile Lys Arg Phe Ala Asp Arg Phe Ala Arg Phe
305                 310                 315                 320

Asn Leu Gln Glu Arg Val Ile Arg Pro Ser Tyr Gly Leu Ala Glu Ala
                325                 330                 335

Thr Val Tyr Val Ala Thr Ser Lys Pro Gly Gln Pro Pro Glu Thr Val
            340                 345                 350

```
Asp Phe Asp Thr Glu Ser Leu Ser Ala Gly His Ala Lys Pro Cys Ala
        355                 360                 365

Gly Gly Gly Ala Thr Ser Leu Ile Ser Tyr Met Leu Pro Arg Ser Pro
    370                 375                 380

Ile Val Arg Ile Val Asp Ser Asp Thr Cys Ile Glu Cys Pro Asp Gly
385                 390                 395                 400

Thr Val Gly Glu Ile Trp Val His Gly Asp Asn Val Gly Asn Gly Tyr
                405                 410                 415

Trp Gln Lys Pro Asp Glu Ser Glu Arg Thr Phe Gly Gly Lys Ile Val
            420                 425                 430

Thr Pro Ser Pro Gly Thr Pro Glu Gly Pro Trp Leu Arg Thr Gly Asp
        435                 440                 445

Ser Gly Phe Val Thr Asp Gly Lys Met Phe Ile Ile Gly Arg Ile Lys
    450                 455                 460

Asp Leu Leu Ile Val Tyr Gly Arg Asn His Ser Pro Asp Asp Ile Glu
465                 470                 475                 480

Glu Thr Ile Gln Glu Ile Thr Arg Gly Arg Cys Ala Ala Ile Ser Val
                485                 490                 495

Pro Gly Asp Arg Arg Thr Glu Lys Leu Val Ala Ile Ile Glu Leu Lys
            500                 505                 510

Lys Arg Gly Asp Ser Asp Gln Asp Ala Met Ala Arg Leu Gly Ala Ile
        515                 520                 525

Lys Arg Glu Val Thr Ser Ala Leu Ser Ser Ser His Gly Leu Ser Val
    530                 535                 540

Ala Asp Leu Val Leu Val Ala Pro Gly Ser Ile Pro Ile Thr Thr Ser
545                 550                 555                 560

Gly Lys Val Arg Arg Gly Ala Cys Val Glu Gln Tyr Arg Gln Asp Gln
                565                 570                 575

Phe Ala Arg Leu Asp Ala
            580

<210> SEQ ID NO 37
<211> LENGTH: 619
<212> TYPE: PRT
<213> ORGANISM: Mycobacterium tuberculosis

<400> SEQUENCE: 37

Met Lys Thr Asn Ser Ser Phe His Ala Ala Gly Glu Val Ala Thr Gln
1               5                   10                  15

Pro Ala Trp Gly Thr Gly Glu Gln Ala Ala Gln Pro Leu Asn Gly Ser
            20                  25                  30

Thr Ser Arg Phe Ala Met Ser Glu Ser Ser Leu Ala Asp Leu Leu Gln
        35                  40                  45

Lys Ala Ala Ser Gln Tyr Pro Asn Arg Ala Ala Tyr Lys Phe Ile Asp
    50                  55                  60

Tyr Asp Thr Asp Pro Ala Gly Phe Thr Glu Thr Val Thr Trp Trp Gln
65                  70                  75                  80

Val His Arg Arg Ala Met Ile Val Ala Glu Glu Leu Trp Ile Tyr Ala
                85                  90                  95

Ser Ser Gly Asp Arg Val Ala Ile Leu Ala Pro Gln Gly Leu Glu Tyr
            100                 105                 110

Ile Ile Ala Phe Met Gly Val Leu Gln Ala Gly Leu Ile Ala Val Pro
        115                 120                 125

Leu Pro Val Pro Gln Phe Gly Ile His Asp Glu Arg Ile Ser Ser Ala
    130                 135                 140
```

-continued

```
Leu Arg Asp Ser Ala Pro Ser Ile Ile Leu Thr Thr Ser Ser Val Ile
145                 150                 155                 160

Asp Glu Val Thr Thr Tyr Ala Pro His Ala Cys Ala Ala Gln Gly Gln
                165                 170                 175

Ser Ala Pro Ile Val Val Ala Val Asp Ala Leu Asp Leu Ser Ser Ser
            180                 185                 190

Arg Ala Leu Asp Pro Thr Arg Phe Glu Arg Pro Ser Thr Ala Tyr Leu
        195                 200                 205

Gln Tyr Thr Ser Gly Ser Thr Arg Ala Pro Ala Gly Val Val Leu Ser
    210                 215                 220

His Lys Asn Val Ile Thr Asn Cys Val Gln Leu Met Ser Asp Tyr Ile
225                 230                 235                 240

Gly Asp Ser Glu Lys Val Pro Ser Thr Pro Val Ser Trp Leu Pro Phe
                245                 250                 255

Tyr His Asp Met Gly Leu Met Leu Gly Ile Ile Leu Pro Met Ile Asn
                260                 265                 270

Gln Asp Thr Ala Val Leu Met Ser Pro Met Ala Phe Leu Gln Arg Pro
        275                 280                 285

Ala Arg Trp Met Gln Leu Leu Ala Lys His Arg Ala Gln Ile Ser Ser
    290                 295                 300

Ala Pro Asn Phe Gly Phe Glu Leu Ala Val Arg Arg Thr Ser Asp Asp
305                 310                 315                 320

Asp Met Ala Gly Leu Asp Leu Gly His Val Arg Thr Ile Val Thr Gly
                325                 330                 335

Ala Glu Arg Val Asn Val Ala Thr Leu Arg Arg Phe Thr Glu Arg Phe
                340                 345                 350

Ala Pro Phe Asn Leu Ser Glu Thr Ala Ile Arg Pro Ser Tyr Gly Leu
        355                 360                 365

Ala Glu Ala Thr Val Tyr Val Ala Thr Ala Gly Pro Gly Arg Ala Pro
    370                 375                 380

Lys Ser Val Cys Phe Asp Tyr Gln Gln Leu Ser Val Gly Gln Ala Lys
385                 390                 395                 400

Arg Ala Glu Asn Gly Ser Glu Gly Ala Asn Leu Val Ser Tyr Gly Ala
                405                 410                 415

Pro Arg Ala Ser Thr Val Arg Ile Val Asp Pro Glu Thr Arg Met Glu
                420                 425                 430

Asn Pro Ala Gly Thr Val Gly Glu Ile Trp Val Gln Gly Asp Asn Val
        435                 440                 445

Gly Leu Gly Tyr Trp Arg Asn Pro Gln Gln Thr Glu Ala Thr Phe Arg
    450                 455                 460

Ala Arg Leu Val Thr Pro Ser Pro Gly Thr Ser Glu Gly Pro Trp Leu
465                 470                 475                 480

Arg Thr Gly Asp Leu Gly Val Ile Phe Glu Gly Glu Leu Phe Ile Thr
                485                 490                 495

Gly Arg Ile Lys Glu Leu Leu Val Val Asp Gly Ala Asn His Tyr Pro
                500                 505                 510

Glu Asp Ile Glu Ala Thr Ile Gln Glu Ile Thr Gly Gly Arg Val Val
        515                 520                 525

Ala Ile Ala Val Pro Asp Asp Arg Thr Glu Lys Leu Val Thr Ile Ile
    530                 535                 540

Glu Leu Met Lys Arg Gly Arg Thr Asp Glu Glu Glu Lys Asn Arg Leu
545                 550                 555                 560
```

```
Arg Thr Val Lys Arg Glu Val Ala Ser Ala Ile Ser Arg Ser His Arg
            565                 570                 575

Leu Arg Val Ala Asp Val Val Met Val Ala Pro Gly Ser Ile Pro Val
            580                 585                 590

Thr Thr Ser Gly Lys Val Arg Arg Ser Ala Ser Val Glu Arg Tyr Leu
            595                 600                 605

His His Glu Phe Ser Arg Leu Asp Ala Met Ala
            610                 615

<210> SEQ ID NO 38
<211> LENGTH: 560
<212> TYPE: PRT
<213> ORGANISM: Streptomyces verticillus

<400> SEQUENCE: 38

Met Ser Arg Pro Ala Gly Ile Val Asp Ile Ala Arg Arg His Ala Glu
1               5                   10                  15

Arg Thr Pro Ala Arg Pro Ala Tyr Ala Phe Leu Pro Asp Gly Glu Thr
            20                  25                  30

Glu Ser Val Arg Phe Ser Phe Ala Asp Ile Asp Arg Arg Ala Arg Ala
        35                  40                  45

Val Ala Ala Val Leu Gln Asp Arg Gly Leu Ala Gly Glu Arg Val Leu
    50                  55                  60

Val Ala Tyr Pro Ser Gly Pro Glu Tyr Val Gln Ala Phe Leu Gly Cys
65                  70                  75                  80

Leu Tyr Ala Gly Val Val Ala Val Pro Cys Asp Glu Pro Arg Ser Gly
                85                  90                  95

Pro Ser Ala Glu Arg Leu Ala Gly Ile Arg Ala Asp Ala Arg Pro Ala
            100                 105                 110

Leu Ala Leu Thr Ala Gly Ala Pro Glu Ala Gly Leu Ala Gly Leu Ala
        115                 120                 125

Thr Leu Asp Val Ala Gly Val Pro Asp Ser Ala Ala Gly Ala Trp Thr
    130                 135                 140

Asp Pro Val Ala Gly Pro Asp Ala Leu Ala Phe Leu Gln Tyr Thr Ser
145                 150                 155                 160

Gly Ser Thr Arg Arg Pro Arg Gly Val Met Val Gly His Gly Asn Leu
                165                 170                 175

Leu Ala Asn Glu Arg Cys Ile Ala Ala Ala Cys Gly His Asp Arg Asp
            180                 185                 190

Ser Thr Phe Val Gly Trp Ala Pro Phe Phe His Asp Met Gly Leu Val
        195                 200                 205

Ala Asn Leu Leu Gln Pro Leu Tyr Leu Gly Ser Leu Ser Val Leu Met
    210                 215                 220

Pro Pro Met Ala Phe Leu Gln Arg Pro Ala Arg Trp Leu Arg Ala Val
225                 230                 235                 240

Ser Arg Tyr Arg Ala His Thr Ser Gly Gly Pro Asn Phe Ala Tyr Asp
                245                 250                 255

Leu Cys Val Asp Arg Val Gly Glu Asp Glu Arg Ala Gly Leu Asp Leu
            260                 265                 270

Ser Gly Trp Lys Val Ala Tyr Asn Gly Ala Glu Pro Val Arg Ala Asp
        275                 280                 285

Thr Leu Arg Arg Phe Thr Asp Arg Phe Ala Pro His Gly Phe Thr Pro
    290                 295                 300

Gly Ala His Phe Pro Thr Tyr Gly Leu Ala Glu Ala Thr Leu Leu Val
305                 310                 315                 320
```

-continued

```
Ala Thr Gly Pro Lys Gly Val Pro Pro Arg Thr Leu Thr Ala Asp Arg
            325                 330                 335

Ala Ala Leu Arg Ala Gly Arg Leu Arg Pro Ala Gly Pro Gly Glu Ala
            340                 345                 350

Gly Leu Glu Leu Val Gly Asn Gly Thr Ala Gly Leu Asp Thr Thr Leu
            355                 360                 365

Arg Ile Val Asp Pro Ala Thr Ala Arg Glu Cys Pro Pro Gly Glu Val
        370                 375                 380

Gly Glu Val Trp Val Arg Gly Pro Gly Val Ala Arg Gly Tyr Phe Gly
385                 390                 395                 400

Arg Pro Arg Glu Ser Ala Pro Leu Leu Ala Arg Leu Pro Gly Gly
                405                 410                 415

Glu Gly Pro Tyr Leu Arg Thr Gly Asp Leu Gly Ala Leu His Asp Gly
            420                 425                 430

Glu Leu Phe Leu Thr Gly Arg His Lys Asp Leu Ile Val Ile Arg Gly
            435                 440                 445

Gln Asn His His Pro His Asp Leu Glu Arg Thr Ala Glu Gln Ala His
    450                 455                 460

Pro Ala Leu Arg Pro Thr Cys Ala Ala Ala Phe Ala Val Pro Gly Asp
465                 470                 475                 480

Gly Ala Glu Arg Leu Val Leu Val Cys Glu Leu Thr Ser Tyr Arg Ala
                485                 490                 495

Val Asp Pro Ala Ala Val Ala Glu Ala Val Arg Ala Ala Leu Ala Ala
                500                 505                 510

Arg His Gly Val Ala Pro His Thr Leu Val Val Leu Arg Arg Gly Gly
        515                 520                 525

Ile Pro Lys Thr Thr Ser Gly Lys Val Arg Arg Gly His Cys Arg Thr
    530                 535                 540

Ala Tyr Leu Asp Gly Thr Leu Pro Val His Thr Ala Val Arg Leu Pro
545                 550                 555                 560

<210> SEQ ID NO 39
<211> LENGTH: 600
<212> TYPE: PRT
<213> ORGANISM: Myxococcus xanthus

<400> SEQUENCE: 39

Met Ala Cys Arg Pro Asp Ser Leu His Ala Ser Ala Val Thr Ser Arg
1               5                   10                  15

Arg Arg Met Arg His Thr Leu Val Glu Leu Leu Gln Glu Arg Ala Leu
            20                  25                  30

Ser Glu Pro Arg His Glu Ala Phe Thr Phe Leu Gly Glu Ala Gly Val
        35                  40                  45

Pro Ala Val Arg Val Asp Tyr Ser Ser Met Asp Val Leu Ala Arg Ala
    50                  55                  60

Ile Ala Ala Arg Leu Gln Ala Asp Gly Arg Val Gly Glu Arg Ala Leu
65                  70                  75                  80

Leu Leu Tyr Ala Pro Gly Pro Glu Tyr Val Ala Ala Phe Phe Gly Cys
                85                  90                  95

Leu Tyr Ala Gly Val Val Ala Val Pro Val Tyr Pro Pro Asp Thr Ala
            100                 105                 110

Arg Leu Glu Arg Ser Leu Leu Arg Leu Arg Thr Val Ala Arg Asp Ser
        115                 120                 125

Arg Ala Ser Val Val Leu Thr Thr Ser Phe Leu Gln Gly Leu Ala Gly
    130                 135                 140
```

```
Ala Met Phe Glu Leu Ala Pro Glu Leu Gly Glu Leu Ser Trp Val Ala
145                 150                 155                 160

Thr Asp Gly Ile Ala Leu Glu Glu Ala Gly Ala Trp Lys Pro Pro Gly
                165                 170                 175

Leu Ser Gly Asp Ser Val Ala Phe Leu Gln Tyr Thr Ser Gly Ser Thr
            180                 185                 190

Ala Asp Pro Lys Gly Val Val Leu Thr His Arg Asn Leu Met His Asn
        195                 200                 205

Leu Ser Val Ile His Glu Arg Phe Gln Leu Asn Arg Gly Ser Arg Gly
    210                 215                 220

Val Ile Trp Leu Pro Tyr His Asp Met Gly Leu Ile Gly Gly Val
225                 230                 235                 240

Leu Thr Pro Ile Phe Gly Gly Leu Pro Val Asp Leu Met Ser Pro Leu
                245                 250                 255

Ser Phe Leu Gln Glu Pro Leu Arg Trp Leu Lys Thr Leu Ser Glu Arg
            260                 265                 270

Arg Gly Thr Cys Ser Gly Pro Asn Phe Ala Tyr Glu Leu Cys Val
        275                 280                 285

Arg Lys Ile Ser Asp Glu Gln Lys Ala Gly Leu Asp Leu Ser Ser Trp
    290                 295                 300

Glu Leu Ala Phe Cys Gly Ala Glu Pro Ile Arg Pro Asp Thr Leu Glu
305                 310                 315                 320

Ala Phe Ser Lys Ala Phe Glu Pro Cys Gly Phe Arg Arg Glu Ala Phe
                325                 330                 335

Tyr Pro Cys Tyr Gly Leu Ala Glu Gly Thr Leu Ile Val Thr Gly Val
            340                 345                 350

Ser Lys Gly Arg Ala Ala Arg Val Glu His Phe Gln Arg Glu Ala Leu
        355                 360                 365

Glu Ala His Arg Ala Val Ala Ala Ser Ser Pro Gly Glu Ala Ala Arg
    370                 375                 380

Asp Thr Val Arg His Val Ser Cys Gly Thr Val Val Pro Asp Glu Gln
385                 390                 395                 400

Ile Leu Val Val Asp Pro Glu Thr Arg Thr Ala Leu Pro Pro Gly His
                405                 410                 415

Ile Gly Glu Ile Trp Val Arg Gly Pro Ser Val Ala Gln Gly Tyr Trp
            420                 425                 430

Leu Arg Pro Glu Glu Thr Ala Arg Thr Phe Gln Ala Arg Leu Ala Gly
        435                 440                 445

Gly Thr Glu Ala Pro Trp Leu Arg Thr Gly Asp Leu Gly Phe Leu His
    450                 455                 460

Asp Gly Glu Leu Phe Val Ser Gly Arg Arg Lys Asp Leu Leu Val Ile
465                 470                 475                 480

Arg Gly Arg Asn Tyr Tyr Pro Gln Asp Leu Glu Leu Thr Val Glu Arg
                485                 490                 495

Ser His Pro Ala Leu Arg Pro Gly Cys Ala Ala Val Phe Ser Val Ser
            500                 505                 510

Val Gly Ala Ser Glu Val Val Val Gln Glu Val Asp Arg Arg
        515                 520                 525

Tyr Pro Gly Gly Asp Trp Pro Asp Val Ile Ala Ala Ile Arg Arg Asp
    530                 535                 540

Ile Ser Glu Gln His Ala Leu Arg Val His Ala Val Val Leu Ile Lys
545                 550                 555                 560
```

```
Ser Gly Ser Leu Leu Lys Thr Ser Ser Gly Lys Val Gln Arg Gly Ala
                565                 570                 575

Thr Arg Glu Ala Tyr Leu Glu Gly Gln Leu Asp Thr Val Ser Ala Asp
            580                 585                 590

Ala Ala Gln Glu Pro Val Gly Glu
            595                 600

<210> SEQ ID NO 40
<211> LENGTH: 569
<212> TYPE: PRT
<213> ORGANISM: Bacillus subtilis

<400> SEQUENCE: 40

Met Tyr Thr Ser Gln Phe Gln Thr Leu Val Asp Val Ile Arg Asn Arg
1               5                   10                  15

Ser Asn Ile Ser Asp Arg Gly Ile Arg Phe Ile Glu Ser Asp Lys Ile
                20                  25                  30

Glu Thr Phe Val Ser Tyr Arg Gln Leu Phe Asp Glu Ala Gln Gly Phe
            35                  40                  45

Leu Gly Tyr Leu Gln His Ile Gly Ile Gln Pro Lys Gln Glu Ile Val
    50                  55                  60

Phe Gln Ile Gln Glu Asn Lys Ser Phe Val Val Ala Phe Trp Ala Cys
65                  70                  75                  80

Leu Leu Gly Gly Met Ile Pro Val Pro Val Ser Ile Gly Glu Asp Asn
                85                  90                  95

Asp His Lys Leu Lys Val Trp Arg Ile Trp Asn Ile Leu Asn Asn Pro
                100                 105                 110

Phe Leu Leu Ala Ser Glu Thr Val Leu Asp Lys Met Lys Lys Phe Ala
            115                 120                 125

Ala Asp His Asp Leu Gln Asp Phe His His Gln Leu Ile Glu Lys Ser
    130                 135                 140

Asp Ile Ile Gln Asp Arg Ile Tyr Asp His Pro Ala Ser Gln Tyr Glu
145                 150                 155                 160

Pro Glu Ala Asp Glu Leu Ala Phe Ile Gln Phe Ser Ser Gly Ser Thr
                165                 170                 175

Gly Asp Pro Lys Gly Val Met Leu Thr His His Asn Leu Ile His Asn
                180                 185                 190

Thr Cys Ala Ile Arg Asn Ala Leu Ala Ile Asp Leu Lys Asp Thr Leu
            195                 200                 205

Leu Ser Trp Met Pro Leu Thr His Asp Met Gly Leu Ile Ala Cys His
    210                 215                 220

Leu Val Pro Ala Leu Ala Gly Ile Asn Gln Asn Leu Met Pro Thr Glu
225                 230                 235                 240

Leu Phe Ile Arg Arg Pro Ile Leu Trp Met Lys Lys Ala His Glu His
                245                 250                 255

Lys Ala Ser Ile Leu Ser Ser Pro Asn Phe Gly Tyr Asn Tyr Phe Leu
                260                 265                 270

Lys Phe Leu Lys Asp Asn Lys Ser Tyr Asp Trp Asp Leu Ser His Ile
            275                 280                 285

Arg Val Ile Ala Asn Gly Ala Glu Pro Ile Leu Pro Glu Leu Cys Asp
    290                 295                 300

Glu Phe Leu Thr Arg Cys Ala Ala Phe Asn Met Lys Arg Ser Ala Ile
305                 310                 315                 320

Leu Asn Val Tyr Gly Leu Ala Glu Ala Ser Val Gly Ala Thr Phe Ser
                325                 330                 335
```

-continued

```
Asn Ile Gly Glu Arg Phe Val Pro Val Tyr Leu His Arg Asp His Leu
                340                 345                 350

Asn Leu Gly Glu Arg Ala Val Glu Val Ser Lys Glu Asp Gln Asn Cys
            355                 360                 365

Ala Ser Phe Val Glu Val Gly Lys Pro Ile Asp Tyr Cys Gln Ile Arg
        370                 375                 380

Ile Cys Asn Glu Ala Asn Glu Gly Leu Glu Asp Gly Phe Ile Gly His
385                 390                 395                 400

Ile Gln Ile Lys Gly Glu Asn Val Thr Gln Gly Tyr Tyr Asn Asn Pro
                405                 410                 415

Glu Ser Thr Asn Arg Ala Leu Thr Pro Asp Gly Trp Val Lys Thr Gly
            420                 425                 430

Asp Leu Gly Phe Ile Arg Lys Gly Asn Leu Val Val Thr Gly Arg Glu
        435                 440                 445

Lys Asp Ile Ile Phe Val Asn Gly Lys Asn Val Tyr Pro His Asp Ile
    450                 455                 460

Glu Arg Val Ala Ile Glu Leu Glu Ile Asp Leu Gly Arg Val Ala Ala
465                 470                 475                 480

Cys Gly Val Tyr Asp Gln Glu Thr Arg Ser Arg Glu Ile Val Leu Phe
                485                 490                 495

Ala Val Tyr Lys Lys Ser Ala Asp Arg Phe Ala Pro Leu Val Lys Asp
            500                 505                 510

Ile Lys Lys His Leu Tyr Gln Arg Gly Gly Trp Ser Ile Lys Glu Ile
        515                 520                 525

Leu Pro Ile Arg Lys Leu Pro Lys Thr Thr Ser Gly Lys Val Lys Arg
    530                 535                 540

Tyr Glu Leu Ala Glu Gln Tyr Glu Ser Gly Lys Phe Ala Leu Glu Ser
545                 550                 555                 560

Thr Lys Ile Lys Glu Phe Leu Glu Gly
                565

<210> SEQ ID NO 41
<211> LENGTH: 56
<212> TYPE: PRT
<213> ORGANISM: bacteria

<400> SEQUENCE: 41

Leu Val Glu Asp Asp Gly Ala Ala Leu Ile Asp Thr Gly Phe Thr
1               5                   10                  15

Ala Pro Ala Ala Lys Ala Leu Leu Arg Leu Leu Lys Asp Gly Gly Lys
            20                  25                  30

Lys Ile Asp Ala Ile Ile Leu Thr His Ala His Ala Asp His Ile Gly
        35                  40                  45

Gly Val Pro Glu Leu Leu Glu Arg
    50                  55

<210> SEQ ID NO 42
<211> LENGTH: 58
<212> TYPE: PRT
<213> ORGANISM: Stenophomonas maltophilia

<400> SEQUENCE: 42

Leu Val Gln Thr Pro Asp Gly Ala Val Leu Leu Asp Gly Gly Met Pro
1               5                   10                  15

Gln Met Ala Ser His Leu Leu Asp Asn Met Lys Ala Arg Gly Val Thr
            20                  25                  30
```

-continued

Pro Arg Asp Leu Arg Leu Ile Leu Leu Ser His Ala His Ala Asp His
        35                  40                  45

Ala Gly Pro Val Ala Glu Leu Lys Arg Arg
    50                  55

<210> SEQ ID NO 43
<211> LENGTH: 52
<212> TYPE: PRT
<213> ORGANISM: bacteria

<400> SEQUENCE: 43

Asp Pro Glu Arg Phe Leu Asp Glu Asn Gly Lys Phe Lys Lys Ser Tyr
1               5                   10                  15

Ala Phe Leu Pro Phe Gly Ala Gly Pro Arg Asn Cys Leu Gly Glu Arg
            20                  25                  30

Leu Ala Arg Met Glu Leu Phe Leu Phe Leu Ala Thr Leu Leu Gln Arg
        35                  40                  45

Phe Glu Leu Glu
    50

<210> SEQ ID NO 44
<211> LENGTH: 7
<212> TYPE: PRT
<213> ORGANISM: artificial sequence
<220> FEATURE:
<221> NAME/KEY: BINDING
<222> LOCATION: (1)..(7)
<223> OTHER INFORMATION: His binding motif of the active site of NRPS
      condensation domains

<400> SEQUENCE: 44

His His Xaa Xaa Xaa Asp Gly
1               5

<210> SEQ ID NO 45
<211> LENGTH: 31
<212> TYPE: DNA
<213> ORGANISM: artificial sequence
<220> FEATURE:
<221> NAME/KEY: primer_bind
<222> LOCATION: (1)..(31)
<223> OTHER INFORMATION: N-oligo PCR primer

<400> SEQUENCE: 45
cacacagaat tcaccagcgc cactcgcgct t                                      31

<210> SEQ ID NO 46
<211> LENGTH: 30
<212> TYPE: DNA
<213> ORGANISM: artificial sequence
<220> FEATURE:
<221> NAME/KEY: primer_bind
<222> LOCATION: (1)..(30)
<223> OTHER INFORMATION: C-oligo PCR primer

<400> SEQUENCE: 46
cacacatcga tgggcaacgc cgatcagccg                                        30

GENE ENCODING A NONRIBOSOMAL PEPTIDE SYNTHETASE FOR THE PRODUCTION OF RAMOPLANIN

CROSS-REFERENCE TO RELATED APPLICATIONS

This application claims benefit under 35 USC §120 as a divisional application of U.S. Ser. No. 09/976,059 filed on Oct. 15, 2001, now issued as U.S. Pat. No. 7,078,185, which in turn claims benefit under 35 USC §119 of provisional application U.S. Ser. No. 60/239,924 filed on Oct. 13, 2000 and of provisional application U.S. Ser. No. 60/283,296 filed Apr. 12, 2001. This application also claims benefit under 35 USC §120 as a continuation-in-part of U.S. Ser. No. 09/910,813, filed Jul. 24, 2001, now abandoned. Each of the priority applications is hereby incorporated by reference in its entirety for all purposes.

SEQUENCE LISTING ON COMPACT DISK

The contents of the following submissions on compact discs are incorporated herein by reference in its entirety: A compact disc copy of the Sequence Listing (COPY 1) (file name: 3002-28US Seq List ST25. txt, date recorded Aug. 12, 2005, size: 383 KB) and a duplicate compact disc copy of the Sequence Listing (COPY 2) (file name 3002-28US Seq List ST25. txt, date recorded Aug. 12, 2005, size: 383 KB).

FIELD OF INVENTION

The present invention relates to the field of antibiotics, and more specifically to genes involved in the biosynthesis of ramoplanin. The invention provides recombinant methods and materials for producing ramoplanins by recombinant DNA technology.

BACKGROUND

Ramoplanin is a naturally-occurring glycosylated lipodepsipeptide antibiotic active against Gram-positive aerobic and anaerobic bacteria. Ramoplanin kills Gram-positive bacteria by inhibiting one of the enzymes needed to construct the bacterial cell wall. Ramoplanin was first described as antibiotic A/16686 produced by fermentation of *Actinoplanes* sp. ATCC 33076, as described in U.S. Pat. No. 4,303,646. It was subsequently found that three closely related components could be isolated from antibiotic A/16686, which components were named antibiotic A/16686 factors A1, A2, and A3 (Ciabatti et al., 1989, J. Antibiot (Tokyo), Vol. 42, No. 2, pp. 254-267). These substances as well as their preparation and uses are described in U.S. Pat. No. 4,427,656. Three additional factors designated A'1, A'2, and A'3 were later shown to be present in the fermentation medium and were shown to differ from the respective parent components of the original complex by lacking one mannose unit from the glycosidic group (Gastaldo et al., 1992, J. Ind. Microbiol. Vol. 11, No.1, pp.13-18).

Ramoplanin consists of a mixture of three related polypeptides having a common cyclic depsipeptide core structure on which is carried a dimannosyl glycosidic group. The three forms of ramoplanin are differentiated by the presence of various acylamide moieties derived from 8-, 9-, or 10-carbon fatty acids that decorate the glycosylated depsipeptide core structure.

Depsipeptides are cyclic or branched peptides containing an ester linkage between a carboxylate group of the peptide and a terminal or side-chain hydroxyl group of the peptide. The ramoplanin depsipeptide core structure contains 17 amino acids. The order of amino acids, from N-terminal to C-terminal, is as follows: amino acid 1: asparagine (Asn); amino acid 2: beta-hydroxyasparagine (HAsn); amino acid 3: 4-hydroxyphenylglycine (HPG); amino acid 4: ornithine (Orn); amino acid 5: threonine (Thr); amino acid 6: HPG; amino acid 7: HPG; amino acid 8: Thr; amino acid 9: phenylalanine (Phe); amino acid 10: Orn; amino acid 11: HPG; amino acid 12: Thr; amino acid 13: HPG; amino acid 14: glycine (Gly); amino acid 15: leucine (Leu); amino acid 16: alanine (Ala); amino acid 17: 3-chloro-4-hydroxyphenylglycine (CHPG). The peptide is cyclized by ester bond formation between the carboxylate group of the C-terminal CHPG and the hydroxyl group of HAsn. The N-terminus of Asn in position 1 is acylated by three different fatty acids, resulting in the three different components A1-A3. Two D-mannose sugars are attached to the HPG in position 11 by a hemiacetal bond.

Many low molecular weight peptides produced by bacteria are synthesized nonribosomally on large multifunctional proteins termed peptide synthetases. (Konz & Marahiel, 1999, Chem. Biol., Vol. 6, pp. R39-R48). Peptide synthetases contain repeated units that each recognize specific amino acids and catalyze their stepwise joining into a peptide chain. The identity of the amino acid recognized by a particular unit can be determined by comparison with other units of known specificity. In many peptide synthetases, there is a strict correlation between the order of repeated units in a peptide synthetase and the order in which the respective amino acids appear in the peptide product, making it possible to correlate peptides of known structure with putative genes encoding their synthesis, as demonstrated by the identification of the mycobactin biosynthetic gene cluster from the genome of *Mycobacterium tuberculosis* (Quadri et al., 1998, Chem. Biol. Vol. 5, pp. 631-645).

The repeating units of a peptide synthetase are composed of smaller units or "domains" that each carry out a specific role in the recognition, activation, modification and joining of amino acid precursors to form the peptide product. One type of domain, the adenylation (A) domain, is responsible for selectively recognizing and activating the amino acid that is to be incorporated by a particular unit of the peptide synthetase. The activated amino acid is joined to the peptide synthetase through another type of domain, the thiolation (T) domain, that is generally located adjacent to the A domain. Amino acids joined to successive units of the peptide synthetase are subsequently linked together by the formation of amide bonds catalyzed by another type of domain, the condensation (C) domain.

Although the structure of ramoplanin has been identified, there remains the need to obtain novel structures with new activities or enhanced properties. There is also a need to improve production of ramoplanin. Accordingly, there is a need for genetic information regarding the biosynthesis of ramoplanin.

SUMMARY OF THE INVENTION

The present invention provides purified and isolated polynucleotide molecules that encode polypeptides of the ramoplanin biosynthetic pathway in microorganisms. In one form of the invention, polynucleotide molecules are selected from the contiguous DNA sequence (SEQ ID NO: 1) representing the full-length locus of the ramoplanin biosynthetic pathway and containing the 33 ORFs encoding the proteins forming the ramoplanin gene cluster. The amino acid sequence of the proteins is provided in SEQ ID NOS: 2 to 34. Structural and functional characterization is provided for the 33 ORFs.

Thus, in one aspect, the invention provides an isolated nucleic acid comprising a nucleic acid sequence selected from the group consisting of (a) nucleic acid encoding any of ramoplanin ORFs 1 to 33 (SEQ ID NOS: 2 to 34); (b) a nucleic acid encoding a polypeptide encoded by any of ramoplanin ORFs 1 to 33 (SEQ ID NOS: 2 to 34); and (c) a nucleic acid encoding a polypeptide that is at least 75%, preferably 80%, more preferably 85%, still more preferably 90% and most preferably 95% or more identical in amino acid sequence to a polypeptide of ramoplanin ORFs 4, 5, 9 to 19, 22 to 26, 29, 30 and 31 (SEQ ID NOS: 5, 6, 10 to 20, 23 to 27, 30, 31 and 32).

Certain embodiments of the invention specifically exclude one or more of ORFs 1 to 33, most notably ORFs 1, 2, 3, 6, 7, 8, 20, 21, 27, 28, 31 and 32 (SEQ ID NOS: 2, 3, 4, 7, 8, 9, 21, 22, 28, 29, 32 and 33) although other ORFs can be excluded without departing from the scope of the invention. Thus, another embodiment of the invention provides an isolated nucleic acid comprising a nucleic acid sequence selected from the group consisting of: (a) a nucleic acid encoding any of ramoplanin ORFs 4, 5, 9 to 19, 22 to 26, 29, 30 and 31 (SEQ ID NOS: 5, 6, 10 to 20, 23 to 27, 30, 31 and 32); (b) a nucleic acid encoding a polypeptide encoded by any of ramoplanin ORFs 4, 5, 9 to 19, 22 to 26, 29, 30 and 31 (SEQ ID NOS: 5, 6, 10 to 20, 23 to 27, 30, 31 and 32); and (c) a nucleic acid encoding a polypeptide that is at least 75%, preferably 80%, more preferably 85%, still more preferably 90% and most preferably 95% or more identical in amino acid sequence to a polypeptide of ramoplanin ORFs 4, 5, 9 to 19, 22 to 26, 29, 30 and 31 (SEQ ID NOS: 5, 6, 10 to 20, 23 to 27, 30, 31 and 32).

In one embodiment preferred nucleic acids encode at least two, more preferably three, still more preferably four, or most preferably five or more ORFs selected from ORFS 1 to 33 (SEQ ID NOS: 2 to 34) of the ramoplanin locus. In one embodiment, combinations of ORFs selected from ORFs 1 through 33 (SEQ ID NOS 2 to 34) are provided which encode polypeptides that form at least the depsipeptide core structure of ramoplanin. In another embodiment combinations of ORFs selected from ORFs 1 through 33 (SEQ ID NOS: 2 to 34) are provided which encode polypeptides that form at least the fatty-aid side chain of the depsipeptide core structure of ramoplanin. In another embodiment, combinations of ORFs selected from ORFs 1 through 33 (SEQ ID NOS: 2 to 34) are provided which encode polypeptides responsible for the synthesis of 4-hydroxyphenylglycine (HPG) of ramoplanin. In another embodiment, combinations of ORFs selected from ORFs 1 through 33 (SEQ ID NOS: 2 to 34) are provided that encode polypeptides that form at least the beta-hydroxyasparagine residue. In another embodiment, combinations of ORFs selected from ORFs 1 through 33 (SEQ ID NOS: 2 to 34) are provided which are involved in the regulation of ramoplanin biosynthesis. In another embodiment, combinations of ORFs selected from ORFs 1 through 33 (SEQ ID NOS: 2 to 34) are provided which encode polypeptides that are involved in resistance and subcellular localization of the ramoplanin biosynthetic machinery. A single ORF or a combination of ORFs selected from ORFs 1 through 33 (SEQ ID NOS: 2 to 34) are provided to enhance production of ramoplanin by altering the expression level of an ORF selected from ORFs 1 through 33 (SEQ ID NOS: 2 to 34). In another embodiment, the expression level of an ORF selected from ORFs 1 through 33 (SEQ ID NOS: 2 to 34) may be altered to increase the yield of a particular form of ramoplanin.

Those skilled in the art will readily understand that the invention, having provided the polynucleotide sequences encoding polypeptides of the ramoplanin biosynthetic pathway, also provides polynucleotides encoding fragments derived from such peptides. Moreover, the invention is understood to provide naturally occurring variants or derivatives of such polypeptides and fragments derived therefrom, such variants or derivatives resulting from the addition, deletion, or substitution of non-essential amino acids or conservative substitutions of essential amino acids as described herein. Those skilled in the art would also readily understand that the invention, having provided the polynucleotide sequences of the entire genetic locus from *Actinoplanes*, further provides naturally-occurring variants or homologs of the genes of the ramoplanin biosynthetic locus from other microorganisms, in particular, those of the family Actinomycetes.

It is also understood that the invention, having provided the polynucleotide sequences of the entire genetic locus as well as the coding sequences, further provides polynucleotides which regulate the expression of the polypeptides of the biosynthetic pathway. Such regulating polynucleotides include but are not limited to promoter and enhancer sequences, as well as sequences antisense to any of the aforementioned sequences. The antisense molecules are regulators of gene expression in that they are used to suppress expression of the gene from which they are derived. Expression cassettes and vectors comprising a polynucleotide as described herein, as well as cells transformed or transfected with such cassettes and vectors, are also within the scope of the invention.

In one aspect, the invention provides polynucleotides encoding a polypeptide selected from ORFs 9, 11 to 15, 17, 26 and 27 (SEQ ID NOS: 10, 12 to 16, 18, 27 and 28) or naturally occurring variants or derivatives of such polypeptides and fragments derived therefrom, such variants or derivatives resulting from the addition, deletion, or substitution of non-essential amino acids or conservative substitutions of essential amino acids of any one of ORFs 9, 11 to 15, 17, 26 and 27, for use in the synthesis of ramoplanin in vivo or in vitro. Such polynucleotides and polypeptides may also be used to generate derivatives of ramoplanin. In one embodiment, the order in which the modules occur within a single ORF may be changed so that the ramoplanin core structure is altered. In another embodiment, one or more module from one or more ORFs may be deleted or inserted so that the size of the ramoplanin core is altered. The polynucleotides and polypeptides related to ORFs 9, 11 to 15, 17, 26 and 27 may also be used to improve production or to produce variants of other antibiotics of the peptide class. In one embodiment, a module contained in any one or more of ORFs 9, 11 to 15, 17, 26 and 27 may be used to replace an existing module in a peptide synthetase involved in the synthesis of another peptide antibiotic to produce a peptide antibiotic derivative. In another embodiment, a module contained in any one or more of ORFs 9, 11 to 15, 17, 26 and 27 may be inserted into the sequence encoding the peptide synthetase involved in the synthesis of another peptide antibiotic to produce a peptide antibiotic derivative with a longer peptide length. In another embodiment, a module contained in any one or more of ORFs 9, 11 to 15, 17, 26 and 27 may be used in combination with the sequences of the present invention or in combination with other sequences which encode other peptide synthetases, to custom design a peptide antibiotic.

In another aspect, the invention provides polynucleotides encoding ORF17 (SEQ ID NOS: 18), or naturally occurring variants or derivatives of ORF17 and fragments derived therefrom, such variants or derivatives resulting from the addition, deletion, or substitution of non-essential amino acids or conservative substitutions of essential amino acids of ORF17, for use as an adenylation domain in conjunction with other peptide synthetase modules and allowing the incorporation of Thr into a peptide antibiotic precursor.

In another aspect, the invention provides polynucleotides encoding ORF 11, 12 or 26 (SEQ ID NOS: 12, 13 and 27), or naturally occurring variants or derivatives of ORF11, 12 or 26 and fragments derived therefrom, such variants or derivatives resulting from the addition, deletion, or substitution of non-essential amino acids or conservative substitutions of essential amino acids of ORF11, 12 or 26, for incorporating fatty acids into the core structure of a peptide antibiotic precursor. In one embodiment, ORF16, 24 or 25 or their variant or derivative is used in conjunction with ORF11, 12 or 26, for modifying fatty acid structure and/or enhancing fatty acid incorporation into the peptide antibiotic structure. In another embodiment, ORF1, 3, 19 or 29 or their variant or derivative is used in conjunction with ORF11, 12 or 26, for further enhancing fatty acid incorporation into the peptide antibiotic structure.

In another aspect, the invention provides polynucleotides encoding the adenylation and/or condensation domain of a module selected from module 1, 2, 3 and 5 of ORF 13 (SEQ ID NO: 14) and modules 1, 3 and 7 of ORF 14 (SEQ ID NO: 15), or naturally occurring variants or derivatives of such polypeptides and fragments derived therefrom, such variants or derivatives resulting from the addition, deletion, or substitution of non-essential amino acids or conservative substitutions of essential amino acids of an adenylation domain of a module selected from modules 1, 2, 3 and 5 of ORF 13 (SEQ ID NO: 14) and modules 1, 3 and 7 of ORF 14, for incorporating a D-amino acid into the core structure of a peptide antibiotic precursor.

In another aspect, the invention provides polynucleotides encoding any one of ORFs 4, 6, 7, 28 and 30 (SEQ ID NOS: 5, 7, 8, 29 and 31), or naturally occurring variants or derivatives of ORFs 4, 6, 7, 28 or 30 and fragments derived therefrom, such variants or derivatives resulting from the addition, deletion, or substitution of non-essential amino acids or conservative substitutions of essential amino acids of ORF 4, 6, 7, 28 or 30, for synthesis of hydroxyphenylglycine (HPG). In one embodiment, any one of ORFs 4, 6, 7, 28 and 30 or their variant or derivative is used to enhance production of an HPG-containing peptide antibiotic, including but not limited to nocardicin A, vancomycin, aridicin, chloroeremomycin, teicoplanin and related glycopeptide antibiotics, as well as the calcium-dependent antibiotic (CDA) of *Streptomyces coelicolor*.

In another aspect, the invention provides polynucleotides encoding any one of ORFs 2, 3, 8, 19, 23, 29 and 31 (SEQ ID NOS: 3, 4, 9, 20, 24, 30 and 32), or naturally occurring variants or derivatives of ORF 2, 3, 8, 19, 23, 29 or 31 and fragments derived therefrom, such variants or derivatives resulting from the addition, deletion, or substitution of non-essential amino acids or conservative substitutions of essential amino acids of ORF 2, 3, 8, 19, 23, 29 or 31, for enhancing secretion of ramoplanin or its variants and derivatives, or for enhancing uptake of precursors for ramoplanin biosynthesis. In one embodiment, any one of ORFs 2, 8, 23 and 31 may be used to confer resistance to ramoplanin or its variants and derivatives or improve production levels.

In another aspect, the invention provides polynucleotides encoding any one of ORFs 5, 21 and 22 (SEQ ID NOS: 6, 22 and 23), or naturally occurring variants or derivatives of ORF 5, 21 or 22 and fragments derived therefrom, such variants or derivatives resulting from the addition, deletion, or substitution of non-essential amino acids or conservative substitutions of essential amino acids of ORF 5, 21 or 22, for regulating biosynthesis of ramoplanin or its variants and derivatives. In one embodiment, any one of ORFs 5, 21 and 22 may be used to enhance production of ramoplanin or its variants and derivatives. In another embodiment, any one of ORFs 5, 21 and 22 may be used to link expression of ramoplanin or its variants and derivatives to an environmental or cellular signal.

In another aspect, the invention provides polynucleotides encoding ORF20 (SEQ ID NO: 21), or naturally occurring variants or derivatives of ORF20 and fragments derived therefrom, such variants or derivatives resulting from the addition, deletion, or substitution of non-essential amino acids or conservative substitutions of essential amino acids of ORF20, for halogenation of aromatic groups of a peptide antibiotic precursor. In one embodiment, ORF20 or its variants or derivatives are used to chlorinate HPG of a peptide antibiotic precursor.

BRIEF DESCRIPTION OF THE DRAWINGS

Various embodiments of the invention will now be described with reference to the attached Figures:

FIG. 3A is a clustal analysis of adenylation domains of ramoplanin biosynthetic enzymes (amino acids 471-959 of SEQ ID NO:13 (ORF 12), amino acids 518-990 of SEQ ID NO:14 (ORF 13 M1), amino acids 1561-2052 of SEQ ID NO:14 (ORF 13 M2), amino acids 2619-3122 of SEQ ID NO:14 (ORF 13 M3), amino acids 3698-4160 of SEQ ID NO:14 (ORF 13 M4), amino acids 4719-5192 of SEQ ID NO:14 (ORF 13 M5), amino acids 6318-6804 of SEQ ID NO:14 (ORF 13 M7), amino acids 487-993 of SEQ ID NO:15

Figure 1:
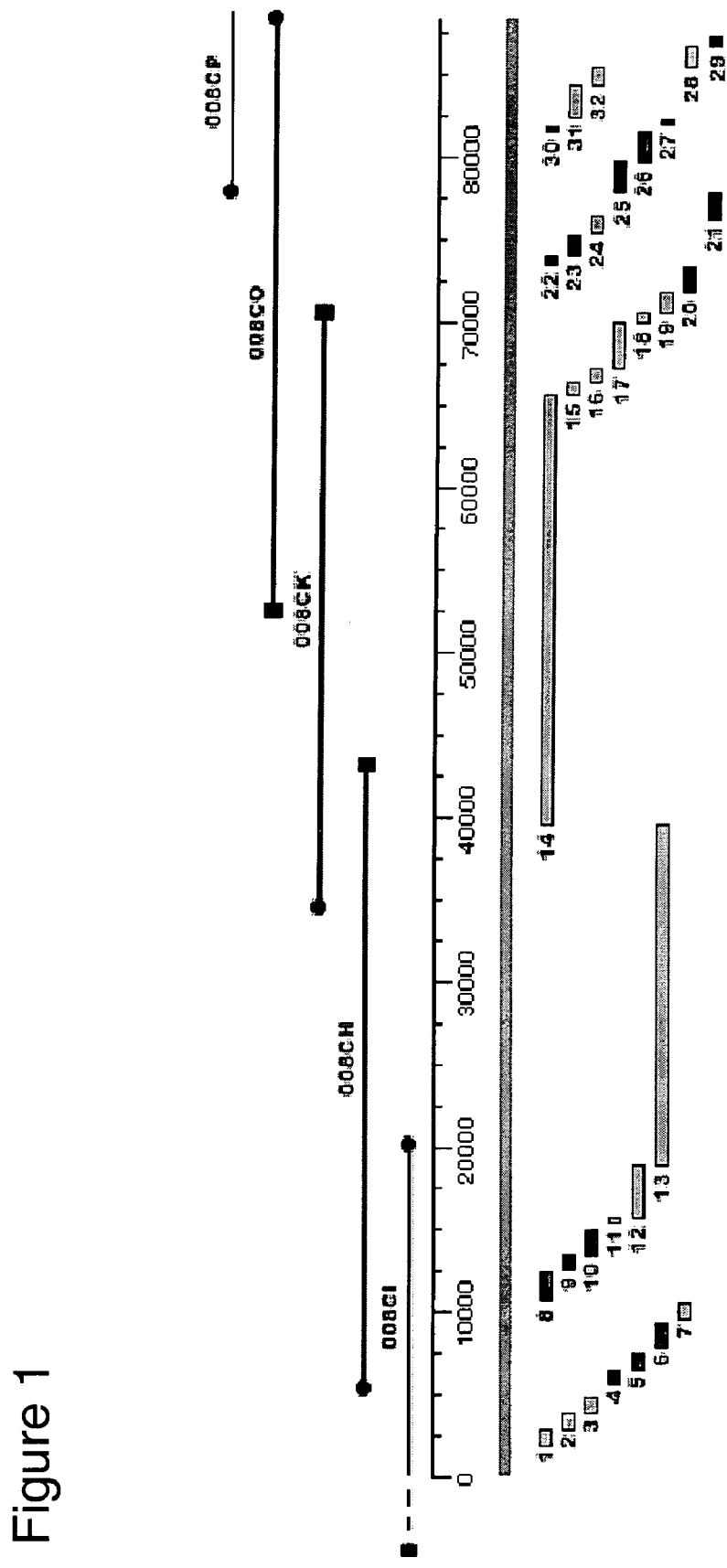
FIG. 1 is a graphical depiction of the ramoplanin biosynthetic locus showing a scale in kb, the relative position and orientation of the 32 ORFs, and the coverage of the deposited cosmids.

(ORF 14 M1), amino acids 1568-2041 of SEQ ID NO:15 (ORF 14 M2), amino acids 2603-3095 of SEQ ID NO:15 (ORF 14 M3), amino acids 3672-4135 of SEQ ID NO:15 (ORF 14 M4), amino acids 4699-5199 of SEQ ID NO:15 (ORF 14 M5), amino acids 5777-6280 of SEQ ID NO:15 (ORF 14 M6), amino acids 6840-7343 of SEQ ID NO:15 (ORF 14 M7), amino acids 7926-8380 of SEQ ID NO:15 (ORF 14 M8), and amino acids 309-804 of SEQ ID NO:18 (ORF 17), as defined in table 3. Shown is the alignment of the amino acid sequence (single letter code) of all adenylation domains found in the ramoplanin locus relative to the adenylation domain of gramicidin S synthetase GrsA (SEQ ID NO:35). Adenylation domains of multimodular non-ribosomal peptide synthetases ORF13 and ORF14 are labeled according to their corresponding module M1-M7 and M1-M8, respectively. Note that ORF13 does not contain an adenylation domain in module 6. Highly conserved core motifs A1-A10 of adenylation domains (Konz et al., 1999, Chem. Biol. Vol. 6, pp. R39-48) are highlighted by boxes. Key residues used to predict the substrate specificity of each adenylation domain are highlighted in black (see FIG. 3B).

FIG. 3B shows the predicted specificities of adenylation domains. The model of Challis et al. (Chem. Biol. 2000, Vol. 7, pp. 211-224) was used to extract key residues predicted to dictate the amino acid specificity of each adenylation domain (highlighted in black in FIG. 3A). The corresponding eight residues that align with GrsA amino acids 235, 236, 239, 278, 299, 301, 322, and 330 are grouped with signatures of adenylation domains of known specificities (data kindly provided by Jacques Ravel). The accession number, protein name, and module number as well as the known amino acid specificity is shown for the latter. Abbreviations: Cda, CDA peptide synthetase of *Streptomyces coelicolor*; Cep, chloroeremomycin peptide synthetase of *Amycolatopsis orientalis*; Acm, actinomycin synthetase of *Streptomyces chrysomallus*; Fen, fengycin peptide synthetase of *Bacillus subtilis*; Bac, bacitracin peptide synthetase of *Bacillus licheniformis*; Fxb, exochelin peptide synthetase of *Mycobacterium smegmatis*; Tyc, tyrocidine peptide synthetase of *Brevibacillus brevis*; GrsA, gramicidin peptide synthetase of *Bacillus brevis*; DhbF, siderophore 2,3-dihydroxybenzoate synthetase of *Bacillus subtilis*; Nos, nostopeptolide peptide synthetase of *Nostoc* sp.; Css, cyclosporine peptide synthetase of *Tolypocladium inflatum*; HPG, 4-hydroxy-phenylglycine; 5hOrn, 5-hydroxyornithine; Pch, pyochelin of *Pseudomonas aeruginosa*.

FIG. 3C shows the similarity between ORF26 (SEQ ID NO:27) and acyl-CoA ligases. Shown is the clustal analysis of ORF 26 versus several acyl-Coenzyme A ligases from diverse species: Mb, *Mycobacterium bovis* (SEQ ID NO:36); Mt, *Mycobacterium tuberculosis* (SEQ ID NO:37); Sv, *Streptomyces verticillus* (SEQ ID NO:38); Mx, *Myxococcus xanthus* (SEQ ID NO:39); Bs, *Bacillus subtilis* (SEQ ID NO:40). Highlighted by boxes are the highly conserved core motifs AL1-AL8 of acyl-CoA ligases.

Figure 4:
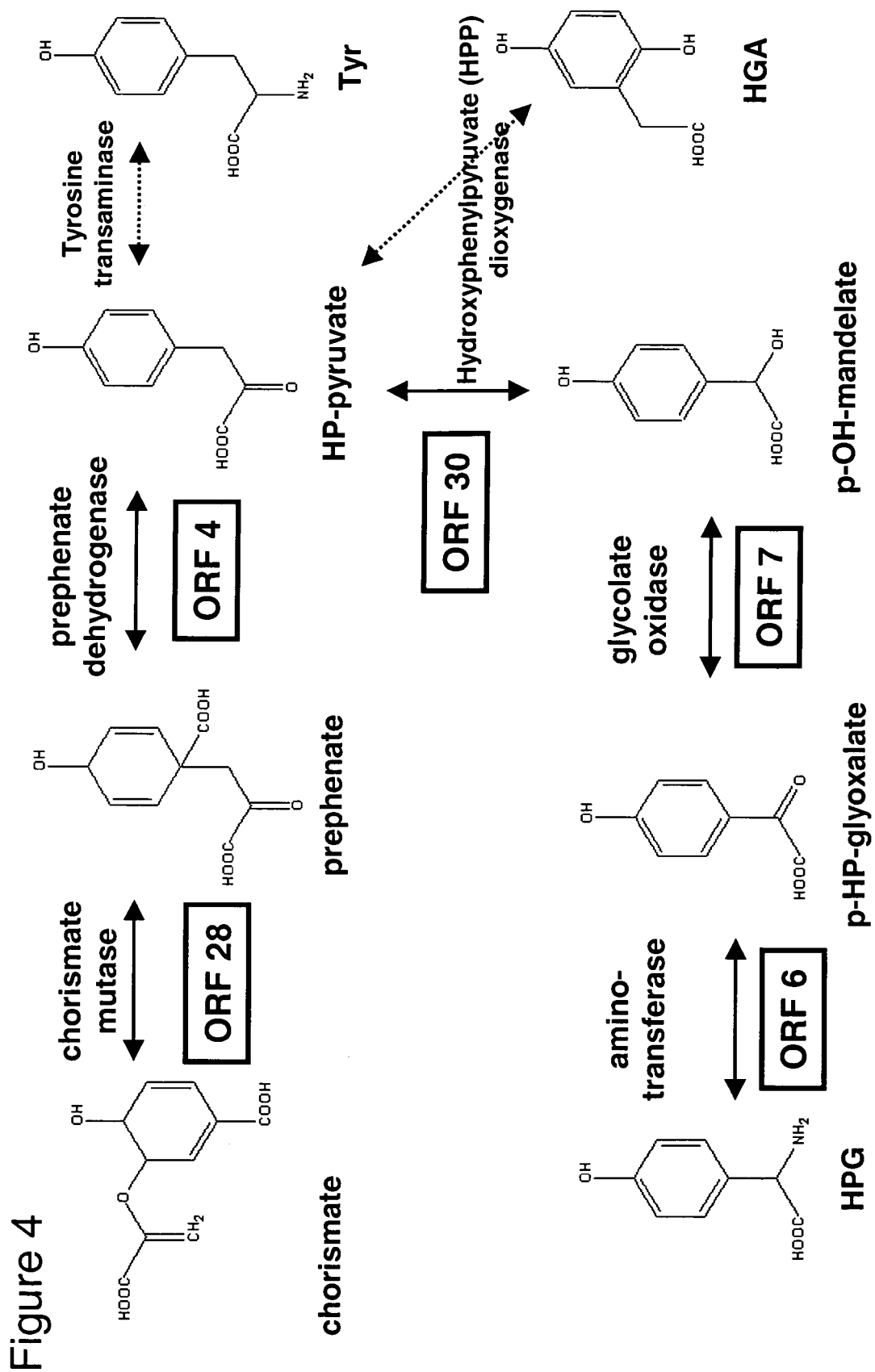

FIG. 4 illustrates the proposed biosynthetic pathway of the unusual amino acid 4-hydroxyphenylglycine (HPG). Chorismate (1), prephenate (2) and 4-hydroxyphenylpyruvate (3) are intermediates in the biosynthesis of the amino acid tyrosine (4). ORF 28 shows similarity to chorismate mutases of primary metabolism and therefore may catalyze the conversion of (1) to (2). ORF 4 shows amino acid similarity to prephenate dehydrogenases of primary metabolism and therefore may catalyze the conversion of (2) to (3). ORF 30 shows amino acid similarity to 4-hydroxyphenylpyruvate dioxygenases, which convert (3) to homogentisate (5), an important intermediate in the metabolism of tyrosine. ORF30 may therefore catalyze a similar oxidative decarboxylation reaction to generate 4-hydroxymandelate (6). ORF 7 shows amino acid similarity to glycolate oxidases, which catalyze the conversion of glycolate to glyoxalate. ORF 7 may therefore convert the glycolate structure found in (6) to the corresponding glyoxalate structure to produce 4-hydroxyphenylglyoxalate (7). ORF 6 shows amino acid similarity to many aminotransferases, and may catalyze the conversion of (7) to HPG (8). Biochemical studies with radiolabeled amino acids have established that the HPG residues of the antibiotic vancomycin are derived from tyrosine, and structures 6, 7, and 8 were proposed as possible intermediates in HPG biosynthesis (Nicas et al., in Biotechnology of Antibiotics, Marcel Dekker, Inc., 1997, pp. 363-392 and references therein).

FIG. 5 illustrates two clustal alignments. FIG. 5A shows the local amino acid sequence homology between ORF 10 (amino acids 263 to 318 of SEQ ID NO: 11) and a key motif found in pfam 00753 (SEQ ID NO:41) involved in coordinating two zinc molecules in the beta-lactamase superfamily. (For information regarding the Pfam Families Datebase, see Bateman et al. Nucleic Acids Research, 2000, Vol. 28, No. 1, 263-266). 1SML (SEQ ID NO:42) represents one member of this superfamily for which a crystal structure showing the intimate interaction between the zinc molecule and the highlighted residues is available (Ullah et al., J. Mol Biol., 1998 Nov. 20; 284(1):125-36). FIG. 5B shows the local amino acid sequence homology between ORF 10 (amino acids 405 to 452 of SEQ ID NO: 11) and a key motif found in pfam 00067 (SEQ ID NO:43) involved in coordinating an iron molecule in cytochrome P450 monooxygenases.

Figure 6:
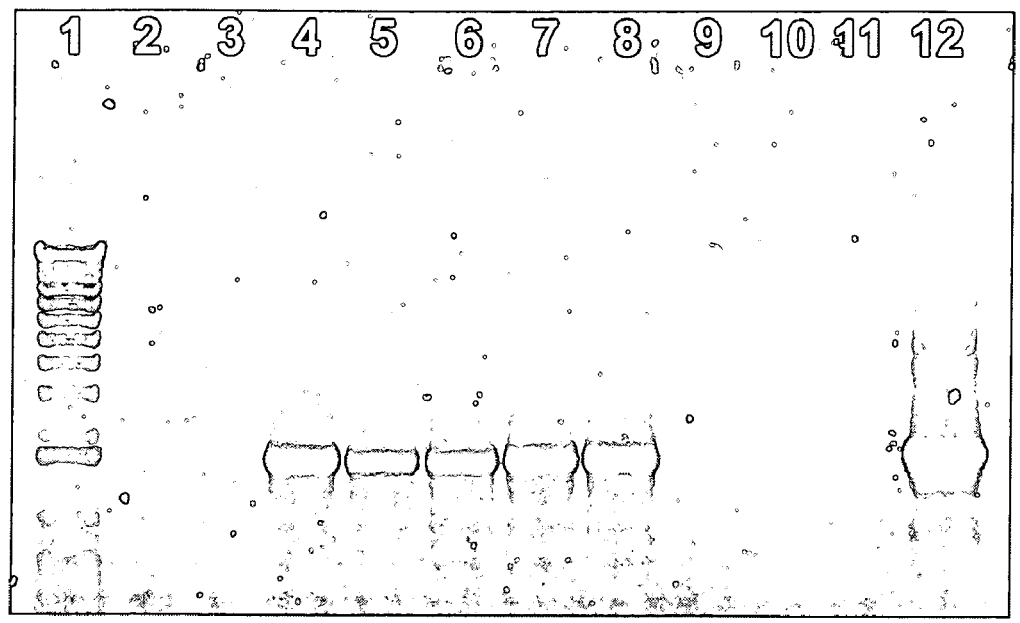

FIG. 6 illustrates a RT-PCR analysis of recombinant *S. lividans* clones expressing ramoplanin ORF 10 (SEQ ID NO: 11).

Figure 7:
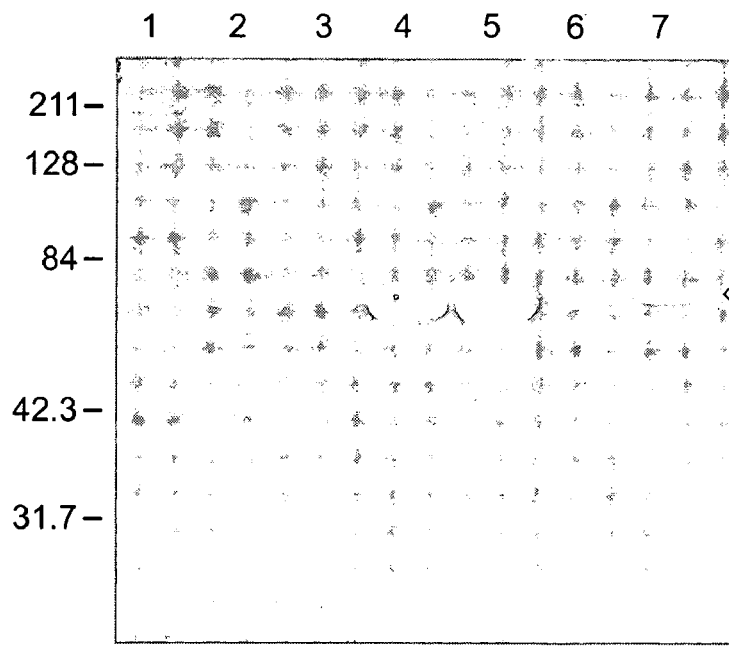

FIG. 7 illustrates a SDS-PAGE analysis of recombinant *S. lividans* clones expressing ramoplanin ORF 10 (SEQ ID NO: 11).

DETAILED DESCRIPTION OF THE INVENTION

Ramoplanins are naturally produced by the microorganism *Actinoplanes* sp. ATCC 33076. The genetic locus encoding the biosynthetic pathway for ramoplanin production was isolated and cloned by the procedure described in U.S. Ser. No. 09/910,813, from genomic DNA isolated from a ramoplanin producing strain of *Actinoplanes* sp. ATCC 33076 (obtained from the American Type Culture Collection, Manassas, Va., USA). This newly discovered locus encodes 33 individual proteins involved in the biosynthesis of ramoplanin by this organism. The 33 proteins are encoded by ORFs contained within the contiguous sequence of 88421 base pairs of DNA (SEQ ID NO: 1).

Three deposits, namely *E. coli* DH10B (008CH) strain, *E. coli* DH10B (008CK) strain and *E. coli* DH10B (008CO) strain each harbouring a cosmid clone of a partial biosynthetic locus for ramoplanin have been deposited with the International Depositary Authority of Canada, Bureau of Microbiology, Health Canada, 1015 Arlington Street, Winnipeg, Manitoba, Canada, R3E 3R2 on Sep. 19, 2001. Clone 008CH, which spans from base pair 5006 to base pair 42974 of SEQ ID NO: 1, was assigned accession number IDAC 190901-3. Clone 008CK, which spans from base pair 34296 to base pair 70934 of SEQ ID NO: 1, was assigned accession number IDAC 190901-1. Clone 008CO, which spans from base pair 52163 to base pair 88333 of SEQ ID NO: 1, was assigned accession number IDAC 190901-2. The cosmids deposited as *E. coli* strains harbouring them are referred to herein as "the deposited cosmids".

As shown in FIG. 1, the deposited cosmids comprise the biosynthetic locus for ramoplanin. The sequence of the polynucleotides comprised in the deposited cosmids, as well as the amino acid sequence of any polypeptide encoded thereby are controlling in the event of any conflict with any description of sequences herein.

The deposit of the cosmids has been made under the terms of the Budapest Treaty on the International Recognition of the Deposit of Micro-organisms for Purposes of Patent Procedure. The deposited cosmids will be irrevocably and without restriction or condition released to the public upon the issuance of a patent. The deposited cosmids are provided merely as convenience to those skilled in the art and are not an admission that a deposit is required for enablement, such as that required under 35 U.S.C. §112. A license may be required to make, use or sell the deposited cosmids, and compounds derived therefrom, and no such license is hereby granted.

Various reagents of the inventions can be isolated from the deposited strains. DNA sequence analysis was performed on various subclones of the inventions and facilitated the identification of the location of various ramoplanin ORFs, including the ORFs encoding the 32 individual proteins of the ramoplanin biosynthetic locus.

The ramoplanin biosynthetic locus spans approximately 88,500 base pairs and contains 32 ORFs. The contiguous nucleotide sequence of SEQ ID NO: 1 (88421 base pairs) contains the 33 deduced proteins listed in SEQ ID NOS: 2 to 34. ORF 1 (SEQ ID NO: 2) represents 333 amino acids deduced from residues 2077 to 3078 (sense strand) of SEQ ID NO: 1. ORF 2 (SEQ ID NO: 3) represents 304 amino acids deduced from residues 3118 to 4032 (sense strand) of SEQ ID NO: 1. ORF 3 (SEQ ID NO: 4) represents 336 amino acids deduced from residues 4038 to 5048 (sense strand) of SEQ ID NO: 1. ORF 4 (SEQ ID NO: 5) represents 283 amino acids deduced from residues 6665 to 5814 (antisense strand) of SEQ ID NO: 1. ORF 5 (SEQ ID NO: 6) represents 336 amino acids deduced from residues 7703 to 6693 (antisense strand) of SEQ ID NO: 1. ORF 6 (SEQ ID NO: 7) represents 444 amino acids deduced from residues 9464 to 8130 (antisense strand) of SEQ ID NO: 1. ORF 7 (SEQ ID NO: 8) represents 356 amino acids deduced from residues 9691 to 10761 (sense strand) of SEQ ID NO: 1. ORF 8 (SEQ ID NO: 9) represents 640 amino acids deduced from residues 12751 to 10829 (antisense strand) of SEQ ID NO: 1. ORF 9 (SEQ ID NO: 10) represents 271 amino acids deduced from residues 13617 to 12802 (antisense strand) of SEQ ID NO: 1. ORF 10 (SEQ ID NO: 11) represents 529 amino acids deduced from residues 15203 to 13614 (antisense strand) of SEQ ID NO: 1. ORF 11 (SEQ ID NO: 12) represents 90 amino acids deduced from residues 15591 to 15863 (sense strand) of SEQ ID NO: 1. ORF 12 (SEQ ID NO: 13) represents 1051 amino acids deduced from residues 15880 to 19035 (sense strand) of SEQ ID NO: 1. ORF 13 (SEQ ID NO: 14) represents 6893 amino acids deduced from residues 19032 to 39713 (sense strand) of SEQ ID NO: 1. ORF 14 (SEQ ID NO: 15) represents 8695 amino acids deduced from residues 39713 to 65800 (sense strand) of SEQ ID NO: 1. ORF 15 (SEQ ID NO: 16) represents 234 amino acids deduced from residues 65826 to 66530 (sense strand) of SEQ ID NO: 1. ORF 16 (SEQ ID NO: 17) represents 274 amino acids deduced from residues 66546 and 67370 (sense strand) of SEQ ID NO: 1. ORF 17 (SEQ ID NO: 18) represents 891 amino acids deduced from residues 67384 to 70059 (sense strand) of SEQ ID NO: 1. ORF 18 (SEQ ID NO: 19) represents 187 amino acids deduced from residues 70099 to 70662 (sense strand) of SEQ ID NO: 1. ORF 19 (SEQ ID NO: 20) represents 415 amino acids deduced from residues 70659 to 71906 (sense strand) of SEQ ID NO: 1. ORF 20 (SEQ ID NO: 21) represents 491 amino acids deduced from residues 73439 to 71964 (antisense strand) of SEQ ID NO: 1. ORF 21 (SEQ ID NO: 22) represents 217 amino acids deduced from residues 74216 to 73563 (antisense strand) of SEQ ID NO: 1. ORF 22 (SEQ ID NO: 23) represents 403 amino acids deduced from residues 75424 to 74213 (antisense strand) of SEQ ID NO: 1. ORF 23 (SEQ ID NO: 24) represents 309 amino acids deduced from residues 75535 to 76464 (sense strand) of SEQ ID NO: 1. ORF 24 (SEQ ID NO: 25) represents 553 amino acids deduced from residues 78110 to 76449 (antisense strand) of SEQ ID NO: 1. ORF 25 (SEQ ID NO: 26) represents 585 amino acids deduced from residues 79864 to 78107 (antisense strand) of SEQ ID NO: 1. ORF 26 (SEQ ID NO: 27) represents 587 amino acids deduced from residues 81624 to 79861 (antisense strand) of SEQ ID NO: 1. ORF 27 (SEQ ID NO: 28) represents 75 amino acids deduced from residues 81909 to 81682 (antisense strand) of SEQ ID NO: 1. ORF 28 (SEQ ID NO: 29) represents 94 amino acids deduced from residues 82346 to 82062 (antisense strand) of SEQ ID NO: 1. ORF 29 (SEQ ID NO: 30) represents 619 amino acids deduced from residues 82587 to 84446 (sense strand) of SEQ ID NO: 1. ORF 30 (SEQ ID NO: 31) represents 355 amino acids deduced from residues 84481 to 85548 (sense strand) of SEQ ID NO: 1. ORF 31 (SEQ ID NO: 32) represents 429 amino acids deduced from residues 85556 to 86845 (sense strand) of SEQ ID NO: 1. ORF 32 (SEQ ID NO: 33) represents 189 amino acids deduced from residues 87372 to 86803 (antisense strand) of SEQ ID NO: 1. ORF 33 (SEQ ID NO: 34) is incomplete and represents 309 amino acids (N-terminus only) deduced from residues 87494 to 88420 (sense strand) of SEQ ID NO: 1.

Some ORFs, namely ORFs 4, 7, 8, 9, 12, 16, 17, 19, 20, 27, 28, 29, 30, 32, and 33 (SEQ ID NOS: 5, 8, 9, 10, 13, 17, 18, 20, 21, 25, 28, 29, 30, 31, 33 and 34) are initiated with the non-standard initiation codon GTG (Valine) rather than the standard initiation codon ATG (Methionine). All ORFs are listed with Methionine or Valine amino acids at the amino-terminal position to indicate the specificity of the first codon in the ORF. It is expected, however, that in all cases the biosynthesized protein will contain a methionine residue, and more specifically a formylmethionine residue, at the amino terminal position in keeping with widely accepted principle that protein synthesis in bacteria initiates with methionine (formylmethionine) even when the encoding gene specifies a non-standard initiation codon (see e.g. Stryer, Biochemistry $3^{rd}$ edition, 1998, W. H. Freeman and Co., New York, pp. 752-754).

Section 1: Definitions

The term domain refers to a portion of a molecule, e.g. proteins or nucleic acids, that is structurally and/or functionally distinct from another portion of the molecule.

The term derivative or analog of a molecule refers to a portion derived from or a modified version of the molecule.

The term isolated nucleic acid molecule referred to in the present invention can be a deoxyribonucleic acid molecule (DNA), such as genomic DNA and complementary DNA (cDNA), which can be single (coding or noncoding strand) or double stranded, as well as synthetic DNA, such as synthesized, single stranded polynucleotide. The isolated nucleic acid molecule of the present invention can also be a ribonucleic acid molecule (RNA). In particular embodiments, the nucleic acid can include entire sequence of the gene cluster, the sequence of any one of the ORFs, a sequence encoding an ORF and an associated promoter, or smaller sequences useful for expressing peptides, polypeptides or full length proteins encoded in the fragment of the *Actinoplanes* sp. genome disclosed herein. In particular embodiments the nucleic acid can have natural, non-natural or modified nucleotides or internucleotide linkages or mixtures of these.

The term polynucleotide refers to full length or partial length sequences of ORFs disclosed herein. Polynucelotides of this invention can be either RNA or DNA (cDNA, genomic DNA or synthetic DNA), or modifications, variants, homologs or fragments thereof. If single stranded, the polynucleotides can be a coding or "sense" or positive strand or a complementary or "antisense" or negative strand. Antisense strands can be useful as modulators of the protein or proteins by interacting with RNA encoding the protein(s). Antisense strands are preferably less than full length strands having sequences unique or highly specific for RNA encoding the protein(s). Any one of the polynucleotide sequences of the invention as shown in the sequence listing is (a) a coding sequence, (b) a ribonucleotide sequence derived from transcription of (a), (c) a coding sequence which uses the redundancy or degeneracy of the genetic code to encode the same polypeptides, or (d) a regulatory sequence.

The term polypeptide or protein refers to any chain of amino acids, regardless of length or post-translational modification (e.g. proteolytic processing or phosphorylation). Both terms are used interchangeably in the present application. Those skilled in the art would readily understand that the polypeptides of the invention may be purified from a natural source, i.e., an *Actinoplanes* sp., or produced by recombinant means.

The terms ORF, ramoplanin open reading frame, and ramoplanin ORF refer to an open reading frame in the ramoplanin biosynthetic gene cluster as isolated from *Actinoplanes* sp. The term also embraces the same ORFs as present in other ramoplanin-synthesizing organisms (e.g. other strains and/or species of *Actinoplanes, Streptomyces, Actinomycetes*, and the like). The term encompasses allelic variants and single nucleotide polymorphisms (SNPs). In certain instances the term ramoplanin ORF is used synonymously with the polypeptide encoded by the ramoplanin ORF and may include conservative substitutions in that polypeptide. The particular usage will be clear from context.

The term "homologous amino acid sequence" is any polypeptide which is encoded, in whole or in part, by a nucleic acid sequence which hybridizes at 25-35° C. below critical melting temperature (Tm), to any portion of the coding region nucleic acid sequences of the sequence listing. A homologous amino acid sequence is one that differs from an amino acid sequence shown in the sequence listing by one or more conservative amino acid substitutions. Such a sequence also encompasses allelic variants (defined below) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any amino acid sequence shown in the sequence listing.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequence listing.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain optimal alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, more preferably 75% and most preferably 85% identical to any one of the coding sequences of the sequence listing.

The term "conservative substitution" is used in reference to proteins or peptides to reflect amino acid substitutions that do not substantially alter the activity (specificity or binding affinity) of the molecule. Typically conservative amino acid substitutions involve substitutions of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic Acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "isolated", "purified", or "biologically pure" refer to material which is substantially or essentially free from components which normally accompany it as found in its native state. With respect to nucleic acids and/or polypeptides, the term can refer to nucleic acids or polypeptides that are no longer flanked by the sequences typically flanking them in nature. Such isolated nucleic acids and/or polynucelotides may be part of a vector or composition and still be defined as isolated in that such a vector or composition is not part of the natural environment of such polynucleotide.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g. synthetic sequences having codons different than the native gene). Similarly, a host cell transformed with a construct which is not normally present in the host cell would be considered heterologous for purposes of this invention.

The term allelic variant refers to an alternate form of a polypeptide that is characterized as having a substitution, deletion, or addition of one or more amino acids that does not alter the biological function of the polypeptide.

The term "biological function" refers to the function of the polypeptide in the cells in which it naturally occurs. A polypeptide can have more than one biological function.

Section 2: Isolation, Preparation and Expression of Ramoplanin Nucleic Acids

Nucleic acids derived from the ramoplanin gene cluster can be isolated, optionally modified and inserted into a host cell to create and/or modify a metabolic (biosynthetic) pathway and thereby enable that host cell to synthesize and/or modify various metabolites. Alternatively, the ramoplanin gene cluster nucleic acids can be expressed in the host cell and the encoded ramoplanin polypeptide(s) recovered for use as chemical reagents, e.g. in the ex vivo synthesis and/or chemical modification of various metabolites. Either application typically entails insertion of one or more nucleic acids encoding one or more isolated and/or modified ramoplanin ORFs in a suitable host cell. The nucleic acid(s) are typically in an expression vector, a construct containing control elements suitable to direct expression of the ramoplanin polypeptides. The expressed ramoplanin polypeptides in the host cell then act as components of a metabolic/biosynthetic pathway (in which case the synthetic product of the pathway is typically recovered) or the ramoplanin polypeptides themselves are recovered. Using the sequence information provided herein, cloning and expression of ramoplanin nucleic acids can be accomplished using routine and well known methods.

A. Ramoplanin Nucleic Acids

The nucleic acids comprising the ramoplanin gene cluster are identified in Table 2 and are listed in the sequence listing provided herein. In particular, Table 2 identifies genes and functions of ORFs in the ramoplanin biosynthetic gene cluster. Using the sequence information provided therein, primers suitable for amplification/isolation of one or more ORFs can be determined according to standard methods well known to those of skill in the art (e.g. using methods described in Innis (1990) *PCR Protocols: A Guide to Methods and Applications* Academic Press Inc. San Diego, Calif., etc; using computer applications such as Vector NTI Suite™, InforMax, Gaithersberg, Md., USA).

Primers suitable for amplification/isolation of any one or more of the ORFs are designed according to the nucleotide sequence information provided in the sequence listing. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. Typically such amplifications will utilize the DNA or RNA of an organism containing the requisite genes (e.g. *Actinoplanes* sp.) as a template. A standard PCR reaction contains typically 0.5 to 5 Units of Taq DNA polymerase per 100 µL, 20 to 200 µM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. Adding DMSO to a final concentration of 5-10% is beneficial for PCR amplification of high G+C templates such as those from *Actinoplanes* sp. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+ 0.5×(% G+C)+1.6 log (positive ion concentration)−0.6×(% formamide). Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6× SSC containing 50% formamide, or (ii) within 4-16 hours at 65° C. in an aqueous 6× SSC solution (1 M NaCl, 0.1M sodium citrate (pH 7.0)).

In one embodiment, this invention provides nucleic acids for the recombinant expression of a ramoplanin (e.g. a ramoplanin or an analogue thereof). Such nucleic acids include isolated gene cluster(s) comprising ORFs encoding polypeptides sufficient to direct the synthesis of the ramoplanin. In other embodiments of this invention, the ORFs may be unchanged, but the control elements (e.g. promoters, ribosome binding sites, terminators, enhancers etc) may be modified. In still other embodiments, the nucleic acids may encode selected components (e.g. one or more ORFs or modified ORFs) and/or may optionally contain other heterologous biosynthetic elements including, but not limited to non-ribosomal polypeptide synthetases (NRPS) modules or enzymatic domains.

Such variations may be introduced by design, for example to modify a known molecule in a specific way, e.g. by replacing a single substitutent of the ramoplanin with another, thereby creating a derivative ramoplanin molecule of predicted structure. Alternatively, variations can be made randomly, for example by making a library of molecular variants of a known ramoplanin by systematically or haphazardly replacing one or more ORFs in the biosynthetic pathway.

Useful homologs and fragments thereof that do not occur naturally are designed using known methods for identifying regions of a polypeptide that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using the BLAST homology searching algorithm of Altschul et al., Nucleic Acids Res. 25:3389-3402 (1997).

Alternatively, identification of homologous polypeptides or polypeptide derivatives encoded by polynucleotides of the invention which have activity in the ramoplanin biosynthetic pathway may be achieved by screening for cross-reactivity with an antibody raised against the polypeptide of reference having an amino acid sequence of SEQ ID NOS 2 to 34. The procedure is as follows: an antibody is raised against a purified reference polypeptide, a fusion polypeptide (for example, an expression product of MBP, GST, or His-tag systems), or a synthetic peptide derived from the reference polypeptide. Where an antibody is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the antibody diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 μl of a preparation at about 10 μg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 μl PBS containing 1% bovine serum albumin (BSA) to prevent non-specific antibody binding. After 1 hour incubation at 37° C., the plate is washed with PBS/Tween buffer. The antibody is serially diluted in PBS/Tween buffer containing 0.5% BSA. 100 μl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 μg/ml is serially two-fold diluted in 50 mM Tris-HCl (pH 7.5). 100 μl of each dilution are applied to a nitrocellulose membrane 0.45 μm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antibody dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Using the information provided herein other approaches to cloning the desired sequences will be apparent to those of skill in the art, for example, the ramoplanin genes and/or optionally NRPS modules or enzymatic domains of interest can be obtained from an organism that expresses such, using recombinant methods, such as by screening cDNA or genomic libraries, derived from cells expressing the gene, or by deriving the gene from a vector known to include the same. The gene can then be isolated and combined with other desired biosynthetic elements using standard techniques. If the gene in question is already present in a suitable expression vector, it can be combined in situ with, e.g. other domains or subunits, as desired. The gene of interest can be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence (see e.g., Edge (1981) *Nature* 292:756; Nambair et al. (1984) *Science* 233:1299; Jay et al. (1984) *J. Biol. Chem.* 259:6311). In addition, it is noted that custom gene synthesis is commercially available (see e.g. Operon Technologies, Alameda, Calif.).

Examples of such techniques and instructions sufficient to direct persons of skill through many cloning exercises are found in Berger and Kimmel (1989) *Guide to Molecular Cloning Technique, Methods in Enzymology* 152 Academic Press, Inc., San Diego, Calif. (Berger); Sambrook et al. (1989) *Molecular Cloning—A Laboratory Manual* ($2^{nd}$ ed.) Vol. 1-3, Cold Spring Harbor Laboratory, Cold Spring Harbor Press, N.Y.; Ausubel (1994) *Current Protocols in Molecular Biology*, Current Protocols, a joint venture between Greene Publishing Associates, Inc. and John Wiley & Sons, Inc. U.S. Pat. No. 5,017,478; and European Patent No 0 246 864.

B. Expression of Ramoplanin ORFs

Preferably, a recombinant expression system is selected from prokaryotic hosts. Bacterial cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form. Any transducible cloning vector can be used as a cloning vector for the nucleic acid constructs of this invention. However, where large clusters are to be expressed, it is preferable that phagemids, cosmids, P1s, YACs, BACs, PACs, HACc or similar cloning vectors be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In preferred embodiments of this invention, vectors are used to introduce ramoplanin biosynthesis genes or gene clusters into host (e.g. *Streptomyces*) cells. With the guidelines described below, however, a selection of vectors, expression control sequences and hosts may be made without undue experimentation and without departing from the scope of this invention. Numerous vectors for use in particular host cells are well known to those of skill in the art. For example Malpartida and Hopwood, (1984) *Nature,* 309:462-464; Kao et al., (1994), *Science,* 265: 509-512; and Hopwood et al., (1987) *Methods Enzymol.*, 153:116-166 all describe vectors for use in various *Streptomyces* hosts. In selecting a vector, the appropriate host must be chosen such that it is compatible with the vector which is to exist and possibly replicate in it. Considerations are made with respect to the vector copy number, the ability to control the copy number and expression of other proteins such as antibiotic resistance. In one preferred embodiment, *Streptomyces* vectors are used that include sequences that allow their introduction and maintenance in *E. coli*. Such *Streptomyces/E. coli* shuttle vectors have been described (see, for example, Vara et al., (1989) *J. Bacteriol*, 171:5872-5881; Guilfoile & Hutchinson (1991) *Proc. Natl. Acad. Sci. USA*, 88; 8553-8557.)

The wildtype and/or modified ORFs of this invention can be inserted into one or more expression vectors, using methods known to those of skill in the art. Expression vectors (e.g., plasmids) are widely known and are readily available to those skilled in the art. For bacterial vectors, the polynucleotide of the invention is inserted into the bacterial genome or remains in a free state as part of a plasmid. Methods for transforming host cells with expression vectors are well-known in the art. Expression vectors will include control sequences operably linked to the desired ORF. In selecting an expression control sequence, a number of variables are considered. Among the important variables are the relative strength of the sequence (e.g. the ability to drive expression under various conditions), the ability to control the sequence's function and compatibility between the polynucleotide to be expressed and the control sequence (e.g. secondary structures are considered in order to avoid hairpin structures which may prevent efficient transcription).

Suitable expression systems for use with the present invention include systems that function in eucaryotic and/or prokaryotic host cells. However, as explained above, prokaryotic systems are preferred, and in particular, systems compatible with *Streptomyces* sp. are of particular interest.

The choice of the expression cassette depends on the host system selected as well as the features desired for the expressed polypeptide or natural product. Typically, an expression cassette includes a promoter that is functional in the selected host system and can be constitutive or inducible; a ribosome binding site; a start codon (ATG) if necessary; optionally a region encoding a leader peptide; a DNA molecule of the invention; a stop codon; and optionally a 3' terminal region (translation and/or transcription terminator). Where applicable, i.e. secreted or membrane proteins, the leader peptide encoding region is adjacent to the polynucleotide of the invention and placed in proper reading frame. The leader peptide-encoding region, if present, is homologous or heterologous to the DNA molecule encoding the mature polypeptide and is compatible with the secretion apparatus of the host used for expression. The ORF constituted by the DNA molecule of the invention, solely or together with the leader peptide, is placed under the control of the promoter so that transcription and translation occur in the host system. Promoters and leader peptide encoding regions are widely known and available to those skilled in the art. Particularly useful promoters include control sequences derived from ramoplanin and/or NRPS gene clusters. Other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophase lambda PL, and T5. In addition, synthetic promoters (U.S. Pat. No. 4,551,433), which do not occur in nature also function in bacterial host cells. In *Streptomyces*, numerous promoters have been described including constitutive promoters, such as ErmE and TcmG (Shen and Hutchinson, (1994) *J. Biol. Chem.* 269: 30726-30733), as well as controllable promoters such as actI and actIII (Pleper et al., (1995) *Nature, vol.* 378: 263-266; Pieper et al., (1995) *J. Am. Chem. Soc.,* 1 17: 11373-11374; and Wiesmann et al., (1995) *Chem. & Biol.* 2: 583-589).

Other regulatory sequences may also be desirable which allow for regulation of expression of the ORFs relative to the growth of the host cell. Regulatory sequences are known to those skill in the art, and examples include those which cause the expression of a gene to be turned on or off in response to a chemical or physical stimulus, including the presence of a regulatory compound. Other type of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

Various ramoplanin ORFs, and/or NRPS clusters or subunits of interest can be cloned into one or more recombinant vectors as individual cassettes, with separate control elements, or under the control of, e.g., a single promoter. The ORFs can include flanking restriction sites to allow for the easy deletion and insertion of other open reading frames so that hybrid synthetic pathways can be generated. The design of such unique restriction sites is known to those of skill in the art and can be accomplished using the techniques described above, such a site-directed mutagenesis and PCR.

Methods of cloning and expressing large nucleic acids such as gene clusters, including NRPS-encoding gene clusters, in cells including *Streptomyces* are well known to those skilled in the art (see, e.g., Stutzman-Engwall and Hutchinson (1989) *Proc. Ntl. Acad. Sci. USA,* 86: 3135-3139: Motamedi and Hutchinson (1987) *Proc. Natl. Acad. Sci. USA,* 84: 4445-4449; Grimm et al. (1994) *Gene,* 151: 1-10; Kao et al. (1994) *Science,* 265: 509-512; and Hopwood et al. (1987) *Meth. Enzymol.,* 153: 116-166). In some examples, nucleic acid sequences of well over 100 kb have been introduced into cells, including prokaryotic cells, using vector-based methods (see for example, Osoegawa et al., (1998) *Genomics,* 52: 1-8; Huang et al., (1996) *Nucl. Acids, Res.,* 24: 4202-4209)

C. Host Cells

The vectors described above can be used to express various protein components of the ramoplanin and/or ramoplanin shunt metabolites, and/or other modified metabolites for subsequent isolation and/or to provide a biological synthesis of one or more desired biomolecules (e.g. ramoplanin and/or a ramoplanin analogue, etc). Where one or more proteins of the ramoplanin biosynthetic gene cluster are expressed (e.g. overexpressed) for subsequent isolation and/or characterization, the proteins are expressed in any prokaryotic or eukaryotic cell suitable for protein expression. In selecting the host, unicellular hosts are selected which are compatible with the selected vector, tolerant of any possible toxic effects of the expressed product, able to secrete the expressed product efficiently if such is desired, able to express the product in the desired conformation, easily scaled up, and having regard to ease of purification of the final product, which may be the expressed polypeptide or the natural product, e.g. an antibiotic, which is a product of the biosynthetic pathway of which the expressed polypeptide is a part. In one preferred embodiment, the proteins are expressed in *E. coli*.

Host cells for the recombinant production of the ramoplanin, ramoplanin metabolites, shunt metabolites, etc. can be derived from any organism with the capability of harboring a recombinant ramoplanin gene cluster and/or subset thereof. Thus, the host cells of the present invention can be derived from either prokaryotic or eucaryotic organisms. Preferred host cells are those of species or strains (e.g. bacterial strains) that naturally express ramoplanin. Suitable host cells include, but are not limited to *Actinomycetes, Actinoplanetes*, and *Streptomycetes, Actinomadura, Micromonospra*, and the like. Particularly preferred host cells include, but are not limited to *Streptomyces globisporus, Streptomyces lividans, Streptomyces coelicolor, Microsmonospora echinospora* spp. *calichenisis, Actionamadura verrucosopora, Micromonospora chersina*, and *Streptomyces carzinostaticus*.

D. Recovery of the Expression Product

Recovery of the expression product (e.g., ramoplanin, ramoplanin analog, ramoplanin biosynthetic pathway polypeptide, etc.) is accomplished according to standard methods well known to those skilled in the art. Thus for example where ramoplanin biosynthetic gene cluster proteins are to be expressed and isolated, the proteins can be expressed with a convenient tag to facilitate isolation (e.g. a $His_6$ tag. Other standard protein purification techniques are suitable and well known to those of skill in the art (see, e.g. (Quadri et al. 1998) *Biochemistry* 37: 1585-1595; Nakano et al. (1992) *Mol. Gen. Genet.* 232: 313-321, etc).

A polypeptide or polypeptide derivative of the invention may be purified by affinity chromatography using as a ligand either an antibody or a compound related to ramoplanin or other lipodepsipeptide which binds to the polypeptide. The antibody is either polyclonal or monoclonal. Purified IgGs are prepared from an antiserum using standard methods (see, e.g., Coligan et al., Current Protocols in Immunology (1994) John Wiley & Sons, Inc., New York, N.Y.). Conventional chromatography supports are described in, e.g., Antibodies: A Laboratory Manual, D. Lane, E. Harlow, Eds. (1988).

Consistent with this aspect of the invention, polypeptide derivatives are provided that are partial sequences of the amino acid sequences of SEQ ID NOS: 2 to 34, partial sequences of polypeptide sequences homologous to the amino acid sequences of SEQ ID NOS: 2 to 34, polypeptides derived from full-length polypeptides by internal deletion, and fusion proteins.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to improve production of ramoplanin or generate novel analogues of the antibiotic or natural products of the lipodepsipeptide class as described herein.

A fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Polynucleotides of 30 to 600 nucleotides encoding partial sequences of sequences homologous to nucleotide sequences of SEQ ID NOS: 2 to 34 are retrieved by PCR amplification using the parameters outlined above and using primers matching the sequences upstream and downstream of the 5' and 3' ends of the fragment to be amplified. The template polynucleotide for such amplification is either the full length polynucleotide homologous to a polynucleotide sequence of SEQ ID NOS: 2 to 34, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: $Tm=4\times(G+C)+2\times(A+T)$. For example, an 18 nucleotide fragment of 50% G+C would have an approximate Tm of 54° C. Short peptides that are fragments of the polypeptide sequences of SEQ IS NOS: 2 to 34 or their homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Where components (e.g. ramoplanin ORFs) are used to synthesize and/or modify various biomolecules (e.g. ramoplanins, ramoplanin analogues, shunt metabolites, or even compounds unrelated to ramoplanin, i.e. biocatalysts) the desired product and/or shunt metabolites(s) are isolated according to standard methods well known to those of skill in the art (see, e.g., Carreras and Khosla (1998) *Biochemistry* 37: 2084-2088, Deutscher (1990) *Methods in Ensymology Volume* 182: *Guide to Protein Purification*, M. Deutscher, ed.

E. Probes

The sequence information provided in the present application enables the design of specific nucleotide probes and primers that are used for identifying and isolating putative lipdepsipeptide-producing microorganisms. Accordingly, an aspect of the invention provides a nucleotide probe or primer having a sequence found in or derived by degeneracy of the genetic code from a sequence shown in the sequence listing.

The term "probe" as used in the present application refers to DNA (preferably single stranded) or RNA molecules (or modifications or combinations thereof) that hybridize under the stringent conditions, as defined above, to nucleic acid molecules of SEQ ID NOS: 1 to 34, or to sequences homologous to those of SEQ ID NOS: 1 to 34, or to their complementary or anti-sense sequences. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of a sequence disclosed in SEQ ID NOS: 1 to 34 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used for identifying and isolating putative lipdepsipeptide-producing microorganisms, as capture or detection probes. Such capture probes are conventionally immobilized on a solid support, directly or indirectly, by covalent means or by passive adsorption. A detection probe is labeled by a detection marker selected from: radioactive isotopes, enzymes such as peroxidase, alkaline phosphatase, enzymes able to hydrolyze a chromogenic or fluorogenic or luminescent substrate, compounds that are chromogenic or fluorogenic or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art. Primers can also be used as probes.

As described herein, the invention also encompasses (i) a reagent comprising a probe of the invention for detecting and/or isolating putative lipdepsipeptide-producing microorganisms; (ii) a method for detecting and/or isolating putative lipdepsipeptide-producing microorganisms, in which DNA or RNA is extracted from the microorganism and denatured, and exposed to a probe of the invention, for example, a capture probe or detection probe or both, under stringent hybridization conditions, such that hybridization is detected; and (iii) a method for detecting and/or isolating putative lipdepsipeptide-producing microorganisms, in which (a) a sample is recovered or derived from the microorganism, (b) DNA is extracted therefrom, (c) the extracted DNA is primed with at least one, and preferably two, primers of the invention and amplified by polymerase chain reaction, and (d) the amplified DNA fragment is produced.

EXAMPLES

The following examples are offered to illustrate, but not to limit the claimed invention.

Example 1

Identification of the Ramoplanin Biosynthetic Locus in *Actinoplanes* sp. ATCC 33076

*Actinoplanes* sp. ATCC 33076 was previously shown to naturally produce ramoplanins, a group of biologically active lipodepsipeptides (U.S. Pat. No. 4,303,646). The genetic locus involved in the production of this compound was not previously identified. *Actinoplanes* sp. ATCC 33076 was obtained from the American Tissue Culture Collection (ATCC) Manassas, Va., and cultured according to standard microbiological techniques (Kieser et al. *Practical Streptomyces Genetics*, John Innes Centre, Norwich Research Part, Colney, Norwich NR4 7UH, England, 2000). Confluent mycelia from oatmeal agar plates were used for the extraction of genomic DNA as previously described (Kieser et al., supra) and the size range of the DNA obtained was assessed on agarose gels by electrical field inversion techniques as described by the manufacturer (FIGE, BioRad). The DNA serves for the preparation of a small size fragment genomic sampling library, i.e. the small-insert library, as well as a large size fragment cluster identification library, i.e. the large-insert library. Both libraries contained DNA fragments generated randomly from genomic DNA and, therefore, they represent the entire genome of *Actinoplanes* sp.

For the generation of the small-insert library, genomic DNA was randomly sheared by sonication. DNA fragments having a size range between 1.5 and 3 kb were fractionated on a agarose gel and isolated using standard molecular biology techniques (Sambrook et al., Molecular Cloning, $2^{nd}$ Ed. Cold Spring Harbor Laboratory Press, 1989). The ends of the obtained DNA fragments were repaired using T4 DNA polymerase (Roche) as described by the supplier. This enzyme creates DNA fragments with blunt ends that can be subsequently cloned into an appropriate vector. The repaired DNA fragments were subcloned into a derivative of pBluescript SK+ vector (Stratagene) which does not allow transcription of cloned DNA fragments. This vector was selected as it contains a convenient polylinker region surrounded by sequences corresponding to universal sequencing primers such as T3, T7, SK, and KS (Stratagene). The unique EcoRV restriction site found in the polylinker region was used as it allows insertion of blunt-end DNA fragments. Ligation of the inserts, use of the ligation products to transform *E. coli* DH10B host, selection for recombinant clones, and isolation of plasmids carrying the *Actinoplanes* sp. genomic DNA fragments were performed using well-known methods (Sambrook et al., supra). The insert size of 1.5 to 3 kb was confirmed by electrophoresis on agarose gels. Using this procedure a library of small size random genomic DNA fragments is generated that is representative of the entire genome of the studied microorganism. The number of individual clones that can be generated is infinite but only a small number is further analyzed to sample the microorganism's genome.

To generate the large-insert library, high molecular weight genomic DNA was partially digested with a frequent cutting restriction enzyme, Sau3A (G|ATC). This enzyme generates random fragments of DNA ranging from the initial undigested size of the DNA to short fragments of which the length is dependent upon the frequency of the enzyme DNA recognition site in the genome and the extent of the DNA digestion. Conditions generating DNA fragments having an average length of ~40 kb were chosen (Sambrook et al., supra). The Sau3A restricted DNA was ligated into the BamHI site of the SuperCos-1 cosmid cloning vector (Stratagene) and packaged into phage particles (Gigapack III XL, Stratagene) as specified by the supplier. *E. coli* strain DH10B was used as host and 864 recombinant clones carrying cosmids were selected and propagated to generate the large-insert library. Considering an average size of 8 Mb for an *actinomycetes* genome and an average size of 35 kb of genomic insert per cosmid in the large insert library, a library of 864 clones represents a 3.78-fold coverage of the microorganism's entire genome. Subsequently, the *Actinoplanes* sp. large-insert library was transferred onto membrane filters (Schleicher & Schnell) as specified by the manufacturer.

The small insert library was analyzed by sequence determination of the cloned genomic DNA inserts. The universal primers KS or T7, referred to as forward (F) primer, were used to initiate polymerization of labeled DNA. Extension of at least 700 bp from the priming site can be routinely achieved using the TF, BDT v2.0 sequencing kit as specified by the supplier (Applied Biosystems). Sequence analysis of the generated fragments (Genomic Sequence Tags, GSTs) was performed using a 3700 ABI capillary electrophoresis DNA sequencer (Applied Biosystems). The average length of the DNA sequence reads was ~700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the proprietary Ecopia natural product biosynthetic gene Decipher™ database using previously described algorithms (Altschul et al., supra). Sequence similarity with known proteins of defined function in the database enables one to make predictions on the function of the partial protein that is encoded by the translated GST.

A total of 882 *Actinoplanes* sp. GSTs were analyzed by sequence comparison. Sequence alignments displaying an E value of at least e-5 were considered as significantly homologous and retained for further evaluation. The E value relates the expected number of chance alignments with an alignment score at least equal to the observed alignment score. An E value of 0.00 indicates a perfect homolog. The E values are calculated as described in Altschul et al. J. Mol. Biol., October 5; 215(3) 403-10. The E value assists in the determination of whether two sequences display sufficient similarity to justify an inference of homology.

GSTs showing similarity to a gene of interest can be at this point selected and used to identify larger segments of genomic DNA including the gene of interest. Ramoplanins produced by *Actinoplanes* sp. belong to the family of nonribosomal polypeptide antibiotics. Nonribosomal polypeptides are synthesized by nonribosomal peptide synthetase (NRPS) enzymes that perform a series of condensations and modifications of amino acids. Many members of this enzymatic class are found in protein databases rendering possible the identification of an unknown NRPS by sequence similarity. Analysis of the *Actinoplanes* sp. GSTs revealed the presence of three GSTs having similarity to known NRPS proteins in the NCBI nonredundant protein database (Table 1). The obtained E values confirm that these GSTs encode partial NRPS sequences. The three NRPS GSTs were selected for the generation of oligonucleotide probes which were then used to identify gene clusters harboring the specific NRPS genes in the large insert library.

TABLE 1

| | Length (bp) | Proposed function | Homology | Probability | Proposed function of protein match |
|---|---|---|---|---|---|
| GST1 | 632 | NRPS | PIR T36248 | $3.00^{E}-20$ | CDA peptide synthetase I in *Streptomyces coelicolor* |
| GST2 | 592 | NRPS | PIR T36248 | $5.00^{E}-28$ | CDA peptide synthetase I in *Streptomyces coelicolor* |
| GST3 | 502 | NRPS | PIR T36180 | $7.00^{E}-31$ | CDA peptide synthetase III in *Streptomyces coelicolor* |

Oligonucleotide probes were designed from the nucleotide sequence of the selected GSTs, radioactively labeled, and hybridized to the large-insert library using standard molecular biology techniques (Sambrook et al., supra, Schleicher & Schnell). Positive clones were identified, cosmid DNA was extracted (Sambrook et al., supra) and entirely sequenced using a shotgun sequencing approach (Fleischmann et al., *Science*, 269:496-512 ). Identification of the original GSTs, used to generate the oligonucleotide probes, within the DNA sequence of the obtained cosmids confirmed that these cosmids indeed carried the gene cluster of interest.

Generated sequences were assembled using the Phred-Phrap algorithm (University of Washington, Seattle, USA) recreating the entire DNA sequence of the cosmid insert. Reiterations of hybridizations of the large-insert library with probes derived from the ends of the original cosmid allow indefinite extension of sequence information on both sides of the original cosmid sequence until the complete sought-after gene cluster is obtained. Application of this method on *Actinoplanes* sp. and use of the above-described NRPS GST probes yielded 6 cosmids. Complete sequence of these cosmids and analysis of the proteins encoded by them undoubtedly demonstrated that the gene cluster obtained was indeed responsible for the production of ramoplanin. Subsequent inspection of the ramoplanin biosynthetic cluster sequence, approximately 88.5 kilo base pairs, revealed the presence of three additional GSTs from the small-insert library, bringing the total number of ramoplanin locus GSTs to six.

Example 2

Genes and Proteins Involved in the Biosynthesis of Ramoplanin

The biological function of the 32 ramoplanin biosynthetic proteins was assessed by computer comparison of each protein with proteins found in the GenBank database of protein sequences (National Center for Biotechnology Information, National Library of Medicine, Bethesda, Md. USA) using the BLASTP algorithm (Altschul et al., 1997, Nucleic Acids Res. Vol. 25, pp. 3389-3402). Significant amino acid sequence homologies found for each protein in the ramoplanin locus are shown in Table 2.

TABLE 2

Proposed functions of the proteins of the ramoplanin biosynthetic pathway based on sequence comparison:

| RF | SEQ ID NO | # aa | proposed function | GenBank accession | probability | % identity | % similarity | proposed function of GenBank match |
|---|---|---|---|---|---|---|---|---|
| 1 | 2 | 333 | unknown; membrane protein | CAB48902 | 5.00E−22 | 27 | 41 | possible membrane protein, unknown function, in *Streptomyces coelicolor* |
| 2 | 3 | 304 | ABC transporter | CAB48901 | 3.00E−55 | 42 | 59 | probable ABC transporter ATP-binding protein from *Streptomyces coelicolor* |
|   |   |   |   | AAF81232 | 7.00E−32 | 31 | 47 | ABC transporter ATP binding protein found in nonactin biosynthetic locus of *Streptomyces griseus* |
|   |   |   |   | AAF12291 | 4.00E−29 | 34 | 51 | ABC transporter, ATP-binding protein from *Deinococcus radiodurans* |
| 3 | 4 | 336 | unknown; membrane protein | CAB48902 | 2.00E−15 | 35 | 50 | possible membrane protein, unknown function, in *Streptomyces coelicolor* |
| 4 | 5 | 283 | oxidoreductase similar to prephenate dehydrogenases | CAA11792 | 2.00E−69 | 53 | 63 | similar to prephenate dehydrogenase; chloroeremomycin biosynthesis in *Amycolatopsis orientalis* |
|   |   |   |   | CAB38592 | 2.00E−67 | 50 | 62 | probable oxidoreductase similar to prephenate dehydrogenase; calcium-dependent antibiotic biosynthesis in *Streptomyces coelicolor* |
|   |   |   |   | AAF67499 | 3.00E−66 | 47 | 64 | putative oxidoreductase protein similar to prephenate dehydrogenase; novobiocin biosynthesis in *Streptomyces spheroides* |
| 5 | 6 | 336 | transcriptional regulator similar to StrR | CAA07385 | 1.00E−74 | 46 | 58 | StrR DNA-binding protein/regulator of 5'-hydroxystreptomycin biosynthesis in *Streptomyces glaucescens*; positive transcriptional regulator of strU, strVW genes |
|   |   |   |   | CAB45047 | 2.00E−74 | 47 | 62 | probable transcriptional regulator in chloroeremomycin biosynthetic locus of *Amycolatopsis orientalis*; similar to other regulators of antibiotic biosynthesis |
|   |   |   |   | CAA68515 | 4.00E−70 | 47 | 60 | putative regulatory protein StrR in streptomycin biosynthetic locus in *Streptomyces griseus* |
|   |   |   |   | AAB66654 | 6.00E−68 | 44 | 59 | SpcR putative transcriptional regulator of spectinomycin biosynthesis in *Streptomyces flavopersicus* |
|   |   |   |   | AAF67500 | 9.00E−58 | 42 | 61 | NovG putative regulatory protein in novobiocin biosynthetic locus of *Streptomyces spheroides* |
| 6 | 7 | 444 | Amino-transferase | CAB38598 | 1.00E−123 | 56 | 67 | possible aminotransferase found in the calcium-dependent antibiotic biosynthetic locus of *Streptomyces coelicolor* |
|   |   |   |   | CAA11790 | 1.00E−101 | 47 | 62 | protein similar to aminotransferase found in the chloroeremomycin biosynthetic locus of *Amycolatopsis orientalis* |
| 7 | 8 | 356 | oxidoreductase similar to glycolate oxidases | CAB38520 | 1.00E−115 | 60 | 70 | putative glycolate oxidase found in calcium-dependent antibiotic biosynthetic locus of *Streptomyces coelicolor* |
|   |   |   |   | AAA34030 | 6.00E−77 | 47 | 62 | spinach glycolate oxidase from *Spinacia oleracea* |
|   |   |   |   | CAB78838 | 2.00E−75 | 45 | 60 | glycolate oxidase-like protein from *Arabidopsis thaliana* |
|   |   |   |   | CAA11762 | 4.00E−75 | 47 | 61 | protein similar to glycolate oxidase in chloroeremomycin biosynthetic locus of *Amycolatopsis orientalis* |
| 8 | 9 | 640 | ABC transporter involved in resistance/transport | CAA11793 | 0 | 55 | 71 | protein similar to mdr/ABC transporter found in chloroeremomycin biosynthetic locus of *Amycolatopsis orientalis* |
|   |   |   |   | AAF67494 | 1.00E−114 | 38 | 57 | NovA ABC transporter in novobiocin biosynthetic locus of *Streptomyces spheroides* |
|   |   |   |   | CAB38879 | 1.00E−78 | 34 | 50 | probable ABC transporter found in the calcium-dependent antibiotic biosynthetic locus of *Streptomyces coelicolor* |
| 9 | 10 | 271 | esterase/hydrolase | CAB38877 | 6.00E−66 | 48 | 63 | probable hydrolase found in the calcium-dependent antibiotic biosynthetic locus of *Streptomyces coelicolor* |
|   |   |   |   | CAA11784 | 9.00E−58 | 44 | 56 | protein similar to haloperoxidase found in chloroeremomycin biosynthetic locus of *Amycolatopsis orientalis* |
|   |   |   |   | CAA71338 | 2.00E−45 | 41 | 54 | putative thioesterase found in streptothricin biosynthetic locus of *Streptomyces* sp. strain F20 |
| 10 | 11 | 529 | unknown | AAB30311 | 2.00E−29 | 41 | 56 | unknown protein found in putative chloramphenicol biosynthetic locus of *Streptomyces venezuelae* |

TABLE 2-continued

Proposed functions of the proteins of the ramoplanin biosynthetic pathway based on sequence comparison:

| RF | SEQ ID NO | # aa | proposed function | GenBank accession | probability | % identity | % similarity | proposed function of GenBank match |
|---|---|---|---|---|---|---|---|---|
| 11 | 12 | 90 | acyl carrier protein | AAA22001 | 6.00E−08 | 33 | 54 | polyketide synthase in Anabaena PCC7120 |
| | | | | CAA98988 | 8.00E−08 | 37 | 57 | polyketide synthase found in the phenolpthiocerol biosynthetic locus of Mycobacterium tuberculosis |
| | | | | AAF62883 | 7.00E−07 | 39 | 55 | type I polyketide synthase found in the epothilone biosynthetic locus of Sorangium cellulosum |
| 12 | 13 | 1051 | nonribosomal peptide synthetase | CAB15186 | 0 | 38 | 55 | nonribosomal peptide synthetase involved in siderophore 2,3-dihydroxybenzoate biosynthesis in Bacillus subtilis |
| | | | | AAD56240 | 0 | 38 | 55 | DhbF peptide synthetase involved in siderophore production in Bacillus subtilis |
| | | | | AAC38442 | 1.00E−179 | 40 | 52 | actinomycin synthetase II peptide synthetase found in the actinomycin biosynthetic locus of Streptomyces chrysomallus |
| 13 | 14 | 6893 | nonribosomal peptide synthetase | AAC80285 | 0 | 36 | 52 | SyrE peptide synthetase found in the syringomycin biosynthetic locus of Pseudomonas syringae |
| | | | | AAC45930 | 0 | 31 | 48 | TycC tyrocidine synthetase 3 found in the tyrocidine biosynthetic locus of Brevibacillus brevis |
| 14 | 15 | 8695 | nonribosomal peptide synthetase | AAC80285 | 0 | 36 | 51 | SyrE peptide synthetase found in the syringomycin biosynthetic locus of Pseudomonas syringae |
| | | | | AAC45930 | 0 | 32 | 49 | TycC tyrocidine synthetase 3 found in the tyrocidine biosynthetic locus of Brevibacillus brevis |
| 15 | 16 | 234 | thioesterase | AAC69333 | 2.00E−30 | 36 | 50 | PikAV thioesterase II found in the methymycin/pikromycin biosynthetic locus of Streptomyces venezuelae |
| | | | | AAC01736 | 6.00E−30 | 34 | 49 | thioesterase found in the rifamycin biosynthetic locus of Amycolatopsis mediterranei |
| | | | | CAA57967 | 2.00E−29 | 39 | 48 | protein with similarity to thioesterases found in the pyochelin biosynthetic locus of Pseudomonas aeruginosa |
| | | | | AAA79279 | 1.00E−28 | 34 | 48 | thioesterase found in the bialaphos biosynthetic locus of Streptomyces hygroscopicus |
| 16 | 17 | 274 | short chain secondary alcohol dehydrogenase/ | CAB54559 | 7.00E−49 | 39 | 58 | Rhodococcus erythropolis LimC carveol dehydrogenase, a nicotinoprotein belonging to the short chain alcohol dehydrogenase/reductase superfamily |
| | | | 3-ketoacyl-acyl carrier protein reductase | CAA15546 | 3.00E−46 | 39 | 54 | hypothetical protein from Mycobacterium tuberculosis, similar to dehydrogenases |
| | | | | AAF64503 | 9.00E−43 | 39 | 53 | cholesterol oxidase from Nocardioides simplex |
| | | | | CAA68181 | 2.00E−38 | 38 | 54 | UcpA protein, belongs to alcohol dehydrogenase/rybitol dehydrogenase family |
| | | | | AAC44307 | 4.00E−36 | 34 | 53 | FabG 3-ketoacyl-acyl carrier protein reductase from Bacillus subtilis |
| | | | | CAA77599 | 1.00E−33 | 36 | 49 | beta ketoacyl reductase in unknown polyketide biosynthetic locus of Streptomyces cinnamonensis |
| 17 | 18 | 891 | threonine-specific adenylate ligase | CAA67248 | 1.00E−143 | 49 | 58 | Pristinamycin I synthase 2 nonribosomal peptide synthetase in the pristinamycin biosynthetic locus of Streptomyces pristinaespiralis |
| | | | | AAC38442 | 1.00E−141 | 49 | 57 | actinomycin synthetase II nonribosomal peptide synthetase in the actinomycin biosynthetic locus of Streptomyces chrysomallus |
| | | | | CAB38518 | 1.00E−138 | 48 | 58 | CDA peptide synthetase I found in the calcium-dependent antibiotic biosynthetic locus of Streptomyces coelicolor |
| 18 | 19 | 187 | unknown | none | | | | |
| 19 | 20 | 415 | transmembrane protein | CAB42730 | 2.00E−82 | 43 | 57 | probable transmembrane protein from Streptomyces coelicolor |
| | | | | CAB02537 | 5.00E−59 | 39 | 50 | probable membrane protein from Mycobacterium tuberculosis |
| | | | | AAF25828 | 2.00E−56 | 35 | 48 | putative transmembrane protein Mycobacterium smegmatis |

TABLE 2-continued

Proposed functions of the proteins of the ramoplanin biosynthetic pathway based on sequence comparison:

| RF | SEQ ID NO | # aa | proposed function | GenBank accession | probability | % identity | % similarity | proposed function of GenBank match |
|---|---|---|---|---|---|---|---|---|
| 20 | 21 | 491 | halogenase/hydroxylase | CAA11780 | 1.00E−180 | 63 | 76 | protein similar to non-heme oxygenase/halogenase found in chloroeremomycin biosynthetic locus of *Amycolatopsis orientalis* |
|  |  |  |  | CAA76550 | 1.00E−178 | 63 | 75 | BhaA protein similar to halogenase, found in the balhimycin biosynthetic locus of *Amycolatopsis mediterranei* |
|  |  |  |  | AAB49297 | 1.00E−176 | 62 | 74 | hypothetical hydroxylase a found in the vancomycin biosynthetic locus of *Amycolatopsis orientalis* |
|  |  |  |  | AAD24884 | 6.00E−37 | 30 | 46 | PltA putative halogenase found in the pyoluteorin biosynthetic locus of *Pseudomonas fluorescens* |
| 21 | 22 | 217 | two-component response regulator | CAB59507 | 9.00E−58 | 52 | 71 | *Streptomyces coelicolor* protein highly similar to various putative two-component response regulators |
|  |  |  |  | CAA22374 | 8.00E−52 | 52 | 66 | probable luxR family response regulator from *Streptomyces coelicolor* |
|  |  |  |  | CAB50960 | 3.00E−51 | 49 | 66 | probable two-component system response regulator from *Streptomyces coelicolor* |
|  |  |  |  | CAB42025 | 3.00E−48 | 49 | 64 | probable two-component system regulator from *Streptomyces coelicolor* |
|  |  |  |  | CAB38597 | 3.00E−38 | 44 | 58 | AbsA2, two component response regulator from *Streptomyces coelicolor*, acts as part of a two component signal transduction system |
| 22 | 23 | 403 | two-component sensory protein kinase | CAB42041 | 1.00E−38 | 37 | 48 | probable two-component system sensor kinase from *Streptomyces coelicolor* |
|  |  |  |  | CAB51250 | 1.00E−34 | 32 | 44 | probable two-component system sensor kinase from *Streptomyces coelicolor* |
|  |  |  |  | CAB89761 | 1.00E−34 | 34 | 42 | probable two-component system sensor kinase from *Streptomyces coelicolor* |
|  |  |  |  | CAB38596 | 3.00E−27 | 31 | 43 | AbsA1, two component sensor kinase from *Streptomyces coelicolor*, acts as part of a two component signal transduction system |
| 23 | 24 | 309 | ABC transporter involved in resistance/transport | CAB48901 | 2.00E−45 | 41 | 55 | probable ABC transporter ATP-binding protein from *Streptomyces coelicolor* |
|  |  |  |  | CAB49966 | 4.00E−28 | 33 | 55 | ATP-binding transport protein from *Pyrococcus abyssi* |
|  |  |  |  | AAF12291 | 9.00E−28 | 38 | 56 | ABC transporter, ATP-binding protein from *Deinococcus radiodurans* |
| 24 | 25 | 553 | acyl-CoA dehydrogenase | AAD45605 | 2.00E−18 | 25 | 44 | isovaleryl-CoA dehydrogenase from *Arabidopsis thaliana* |
|  |  |  |  | CAB55554 | 7.00E−18 | 24 | 43 | isovaleryl-CoA dehydrogenase from *Pisum sativum* |
|  |  |  |  | CAB46799 | 4.00E−16 | 29 | 44 | probable acyl-CoA dehydrogenase from *Streptomyces coelicolor* |
|  |  |  |  | CAA16488 | 9.00E−14 | 29 | 39 | RedW acyl-coa dehydrogenase in the undecylprodigiosin biosynthetic locus of *Streptomyces coelicolor* |
|  |  |  |  | AAF08800 | 3.00E−13 | 23 | 44 | YngJ protein found in the mycosubtilin biosynthetic locus of *Bacillius subtilis* |
| 25 | 26 | 585 | acyl-CoA dehydrogenase | CAB61531 | 2.00E−27 | 26 | 43 | FadE fatty acid acyl-CoA dehydrogenase found in *Streptomyces lividans* |
|  |  |  |  | CAB07077 | 6.00E−22 | 24 | 39 | *Mycobacterium tuberculosis* protein highly similar to acyl-CoA dehydrogenase |
|  |  |  |  | CAA17679 | 2.00E−21 | 26 | 43 | probable Acyl-CoA dehydrogenase found in *Mycobacterium tuberculosis* |
| 26 | 27 | 587 | acyl-CoA ligase | AAG02359 | 1.00E−115 | 45 | 56 | BlmVI peptide synthetase in bleomycin biosynthetic locus of *Streptomyces verticillus* |
|  |  |  |  | AAC44128 | 1.00E−94 | 38 | 53 | Mx1 peptide synthetase B in saframycin biosynthetic locus of *Myxococcus xanthus* |
|  |  |  |  | CAA16183 | 1.00E−85 | 37 | 49 | polyketide synthase found in the undecylprodigiosin biosynthetic locus of *Streptomyces coelicolor* |
|  |  |  |  | CAB05426 | 3.00E−84 | 35 | 51 | Fad29 probable acyl-CoA synthetase found in *Mycobacterium tuberculosis* |
|  |  |  |  | CAA17589 | 2.00E−82 | 36 | 51 | Fad24 probable acyl-CoA synthetase found in *Mycobacterium tuberculosis* |
|  |  |  |  | CAB01395 | 1.00E−81 | 35 | 50 | Fad25 probable acyl-CoA synthetase found in *Mycobacterium tuberculosis* |
|  |  |  |  | AAB52538 | 2.00E−78 | 34 | 50 | acyl-CoA synthase from *Mycobacterium bovis* |
|  |  |  |  | CAB36629 | 4.00E−78 | 35 | 52 | putative acyl-CoA synthase from *Mycobacterium leprae* |
| 27 | 28 | 75 | unknown | CAB38589 | 1.00E−24 | 70 | 80 | small conserved hypothetical protein found in the calcium-dependent antibiotic biosynthetic locus of *Streptomyces coelicolor* |

TABLE 2-continued

Proposed functions of the proteins of the ramoplanin biosynthetic pathway based on sequence comparison:

| RF | SEQ ID NO | # aa | proposed function | GenBank accession | probability | % identity | % similarity | proposed function of GenBank match |
|---|---|---|---|---|---|---|---|---|
|  |  |  |  | CAB08480 | 3.00E−22 | 67 | 77 | MbtH possibly involved in mycobactin synthesis in *Mycobacterium tuberculosis* |
|  |  |  |  | CAA11799 | 3.00E−19 | 74 | 89 | hypothetical protein found in chloroeremomycin biosynthetic locus of *Amycolatopsis orientalis* |
| 28 | 29 | 94 | chorismate mutase-like protein | CAB02002 | 2.00E−15 | 50 | 69 | hypothetical protein in *Mycobacterium tuberculosis* |
|  |  |  |  | CAB82023 | 2.00E−11 | 46 | 59 | hypothetical protein in *Streptomyces coelicolor* |
|  |  |  |  | CAB72783 | 7.00E−03 | 36 | 59 | chorismate mutase\prephenate dehydratase from *Campylobacter jejuni* |
|  |  |  |  | AAC75649 | 6.00E−02 | 30 | 50 | chorismate mutase-T and prephenate dehydrogenase protein from *E. coli* |
| 29 | 30 | 619 | membrane protein | CAB16086 | 2.00E−56 | 28 | 43 | unknown protein in *Bacillius subtilis* |
|  |  |  |  | CAA05568 | 4.00E−34 | 35 | 54 | YkcB unknown protein in *Bacillius subtilis* |
|  |  |  |  | CAB76994 | 0.01 | 26 | 35 | putative integral membrane protein in *Streptomyces coelicolor* |
|  |  |  |  | AAC18892 | 0.049 | 29 | 37 | transmembrane protein from *Streptomyces aureofaciens* |
| 30 | 31 | 355 | 4-hydroxyphenylpyruvate dioxygenase | CAA11761 | 5.00E−87 | 50 | 63 | protein similar to hydroxyphenyl pyruvate dioxygenase found in the chloroeremomycin biosynthetic locus of *Amycolatopsis orientalis* |
|  |  |  |  | CAB38519 | 1.00E−69 | 44 | 54 | probable 4-hydroxyphenylpyruvic acid dioxygenase found in the calcium-dependent antibiotic biosynthetic locus of *Streptomyces coelicolor* |
|  |  |  |  | CAB51008 | 2.00E−49 | 36 | 51 | probable 4-hydroxyphenylpyruvic acid dioxygenase found in *Streptomyces coelicolor* |
|  |  |  |  | AAA50231 | 3.00E−49 | 36 | 50 | 4-hydroxyphenylpyruvic acid dioxygenase from *Streptomyces avermitilis* |
| 31 | 32 | 429 | transmembrane transporter | CAB45049 | 4.00E−81 | 46 | 64 | putative integral membrane ion antiporter found in the chloroeremomycin biosynthetic locus of *Amycolatopsis orientalis* |
|  |  |  |  | BAA16991 | 3.00E−72 | 39 | 56 | sodium/proton antiporter from *Synechocystis* sp. |
|  |  |  |  | CAA23036 | 8.00E−65 | 37 | 57 | putative sodium/protein exchanging protein from *Arabidopsis thaliana* |
|  |  |  |  | AAF26906 | 1.00E−41 | 30 | 48 | protein similar to sodium/proton and drug/proton antiporters found in the epothilone biosynthetic locus of *Sorangium cellulosum* |
| 32 | 33 | 189 | Unknown | CAB72201 | 1.00E−11 | 31 | 41 | hypothetical protein in *Streptomyces coelicolor* |
|  |  |  |  | CAB56690 | 2.00E−08 | 31 | 42 | hypothetical protein in *Streptomyces coelicolor* |
| 33 | 34 | 309 | Unknown, incomplete | none |  |  |  |  |

The correlation between the order of repeated units in most peptide synthetases and the order in which the respective amino acids appear in the peptide product makes it possible to correlate peptides of known structure with putative genes encoding their synthesis, as demonstrated by the identification of the mycobactin biosynthetic gene cluster from the genome of Mycobacterium tuberculosis (Quadri et al., 1998, Chem. Biol. Vol. 5, pp. 631-645). This principle has been used here to assign a biosynthetic role for each repeating unit of the ramoplanin peptide synthetases described in this invention, as diagrammed in FIGS. 2A, B and C. The approximate boundaries, at the amino acid level, of the domains of the repeating units (modules) of each ORF are tabulated in Table 3, wherein C represents a condensation domain, A represents an adenylation domain, T represents a thiolation domain and Te represents a thioesterase domain.

TABLE 3

Approximate boundaries of domains of each moldule at the amino acid level

Orf 12

| Module 1: | C | 1-470 |
|---|---|---|
|  | A | 471-959 |
|  | T | 961-1030 |

TABLE 3-continued

Approximate boundaries of domains of each moldule at the amino acid level

Orf 13

| Module 1: | C | 1-517 |
|---|---|---|
|  | A | 518-990 |
|  | T | 991-1059 |
| Module 2: | C | 1106-1560 |
|  | A | 1561-2052 |
|  | T | 2054-2122 |
| Module 3: | C | 2159-2618 |
|  | A | 2619-3122 |
|  | T | 3123-3191 |
| Module 4: | C | 3237-3697 |
|  | A | 3698-4160 |
|  | T | 4161-4228 |
| Module 5: | C | 4241-4718 |
|  | A | 4719-5192 |
|  | T | 5193-5260 |
| Module 6: | C | 5307-5754 |
|  | T | 5755-5824 |
| Module 7: | C | 5838-6317 |
|  | A | 6318-6804 |
|  | T | 6805-6873 |

TABLE 3-continued

Approximate boundaries of domains of each moldule at the amino acid level

Orf 14

| | | |
|---|---|---|
| Module 1: | C | 1-486 |
| | A | 487-993 |
| | T | 994-1062 |
| Module 2: | C | 1109-1567 |
| | A | 1568-2041 |
| | T | 2042-2110 |
| Module 3: | C | 2122-2602 |
| | A | 2603-3095 |
| | T | 3097-3165 |
| Module 4: | C | 3212-3671 |
| | A | 3672-4135 |
| | T | 4136-4202 |
| Module 5: | C | 4217-4698 |
| | A | 4699-5199 |
| | T | 5200-5268 |
| Module 6: | C | 5317-5776 |
| | A | 5777-6280 |
| | T | 6281-6350 |
| Module 7: | C | 6363-6839 |
| | A | 6840-7343 |
| | T | 7344-7411 |
| Module 8: | C | 7458-7925 |
| | A | 7926-8380 |
| | T | 8381-8449 |
| | Te | 8450-8695 |

A. Formation of the Lipodepsipeptide Core Structure:

Nine proteins, encoded by ORFs 9, 11, 12, 13, 14, 15, 17, 26 and 27 (SEQ ID NOS: 10, 12, 13, 14, 15, 16, 18, 27 and 28), are likely to be involved in the formation of the lipodepsipeptide core structure of ramoplanin. ORFs 11, 12, 13, 14 and 17 (SEQ ID NOS: 12, 13, 14, 15 and 18) show significant similarity to peptide synthetases or peptide synthetase domains. Analysis of the adenylation domains found in these ORFs allows the amino acid that is incorporated by each unit to be identified (see FIG. 3 A and B). The following amino acid specificities are consistent with these comparisons: ORF 12: asparagine (Asn); ORF 13, module 1: 4-hydroxyphenylglycine (HPG); ORF 13, module 2: ornithine (Orn); ORF 13, module 3: threonine (Thr); ORF 13, module 4: HPG; ORF 13, module 5: HPG; ORF 13, module 6 contains no adenylation domain; ORF 13, module 7: phenylalanine (Phe); ORF 14, module 1: Orn; ORF 14, module 2: HPG; ORF 14, module 3: Thr; ORF 14, module 4: HPG; ORF 14, module 5: glycine (Gly); ORF 14, module 6: leucine (Leu); ORF 14, module 7: unspecified; ORF 14, module 8: HPG; ORF 17, threonine (Thr). The numbers and predicted amino acid substrate specificities of the peptide synthetase repeating units are in precise agreement with the structure of the ramoplanin peptide core, providing conclusive evidence that the genetic locus described here is responsible for the biosynthesis of ramoplanin.

The amino acid specificity of adenylation domains may be altered by mutagenesis (Stachelhaus et al., 1999, Chem. Biol. Vol. 6, pp. 493-505; Challis et al., Chem. Biol., 2000, Vol. 7, pp. 211-224) or by swapping domains between peptide synthetases (Stachelhaus et al., 1995, Science Vol. 269, pp. 482-485; Schneider et al., 1998, Mol. Gen. Genet. Vol. 257, pp. 308-318; de Ferra et al., 1998, J. Biol. Chem. Vol. 272, pp. 25304-25309) and thereby generate derivatives of a natural peptide product.

Figure 2A:
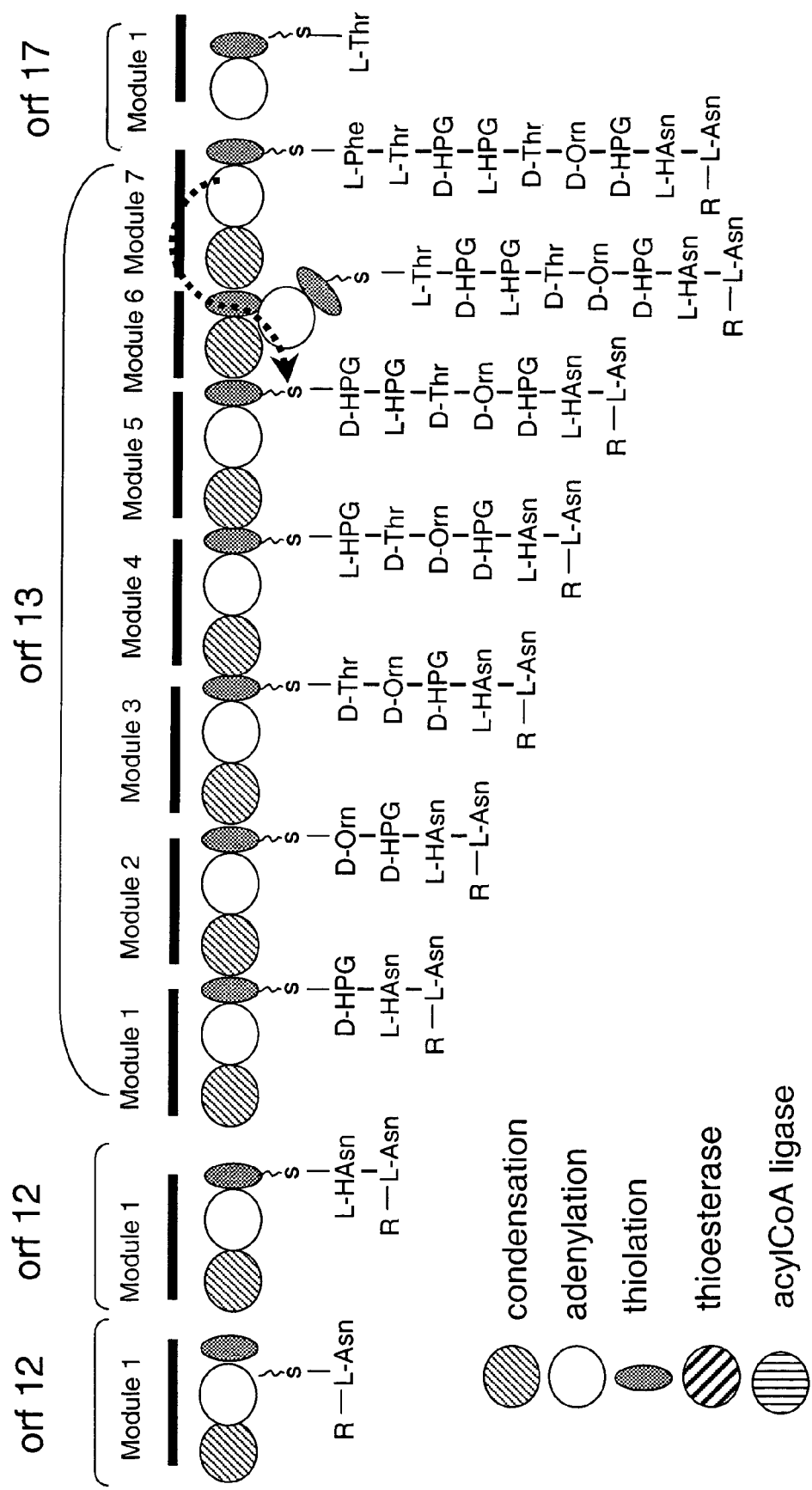
FIG. 2A is a model for the biosynthesis of ramoplanin. The ramoplanin chain is assembled in stepwise fashion through the concerted activities of consecutive modules of the ramoplanin peptide synthetases. Domains in each module are denoted by the circular and oval symbols as indicated. R denotes the fatty acyl group that caps the N-terminus of the first amino acid (Asn) incorporated into the ramoplanin peptide (see FIG. 2B). Note that ORF 12 recognizes Asn and is proposed to incorporate both Asn residues found in the ramoplanin peptide; hydroxylation of the second Asn residue may occur before or after recognition and activation of the amino acid. The thick dotted arrow indicates that the ORF 17 protein interacts with module 6 of the ORF 13 product to catalyze the incorporation of Thr at the appropriate position. The thin dotted line indicates that the side chain hydroxyl group of the beta-hydroxyasparagine residue undergoes nucleophilic attack upon the thioester bond linking the ramoplanin product with module 8 of ORF 14, resulting in the cyclization and release of the peptide product. Abbreviations: HAsn, beta-hydroxyasparagine; other abbreviations are as in the text.
Figure 2A:
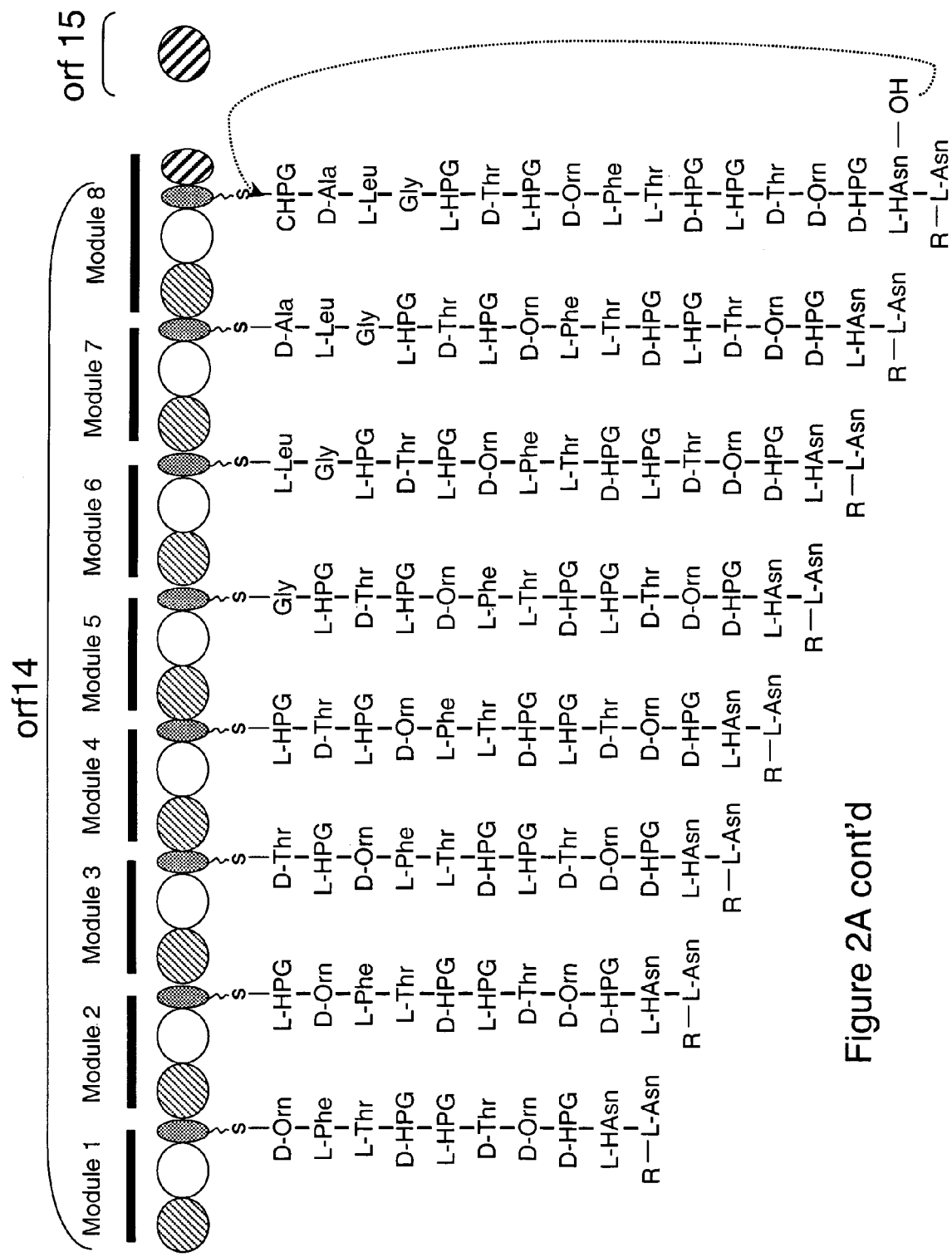

A model for the biosynthesis of the ramoplanin peptide core structure can be built by comparing the specificity and order of the repeating units in the ramoplanin peptide synthetases with the order of the amino acid substituents in ramoplanin (diagrammed in FIG. 2A and C). ORF 12 (SEQ ID NO: 13) contains the only adenylation domain specifying Asn and therefore may catalyze the incorporation of the first two (Asn) amino acid residues into the peptide chain. Subsequent amino acids are incorporated in the precise order in which the respective units occur in the adjacent ORFs 13 and 14 (SEQ ID NOS: 14 and 15). The only exception to the colinearity of peptide synthetase units and the order of incorporation of amino acids into ramoplanin occurs at module 6 of ORF 13 (SEQ ID NO: 14). This module contains condensation and thiolation domains, but is lacking an adenylation domain. The structure of ramoplanin indicates that a Thr must be incorporated into the peptide chain at this position. ORF 17 (SEQ ID NO: 18) encodes an unusual peptide synthetase unit having an adenylation domain that specifies Thr, but lacks a conventional condensation domain. According to the model diagrammed in FIG. 2A, the ORF 17 (SEQ ID NO: 18) protein interacts with module 6 of ORF 13 (SEQ ID NO: 14) and substitutes for the missing adenylation domain of this module, thus catalyzing the incorporation of Thr into the growing ramoplanin peptide precursor at the appropriate position. Such a trans interaction between peptide synthetase units has a precedent in the biosynthesis of the lipodepsipeptide antibiotic syringomycin. In the syringomycin system, the adenylation domain of the SyrB1 protein, which lacks a condensation domain, is proposed to interact with and complement the activity of a SyrE1 peptide synthetase unit that contains a condensation domain but is lacking an adenylation domain (Guenzi et al., 1998, J. Biol. Chem. Vol. 273, pp. 32857-32863).

Figure 2B:
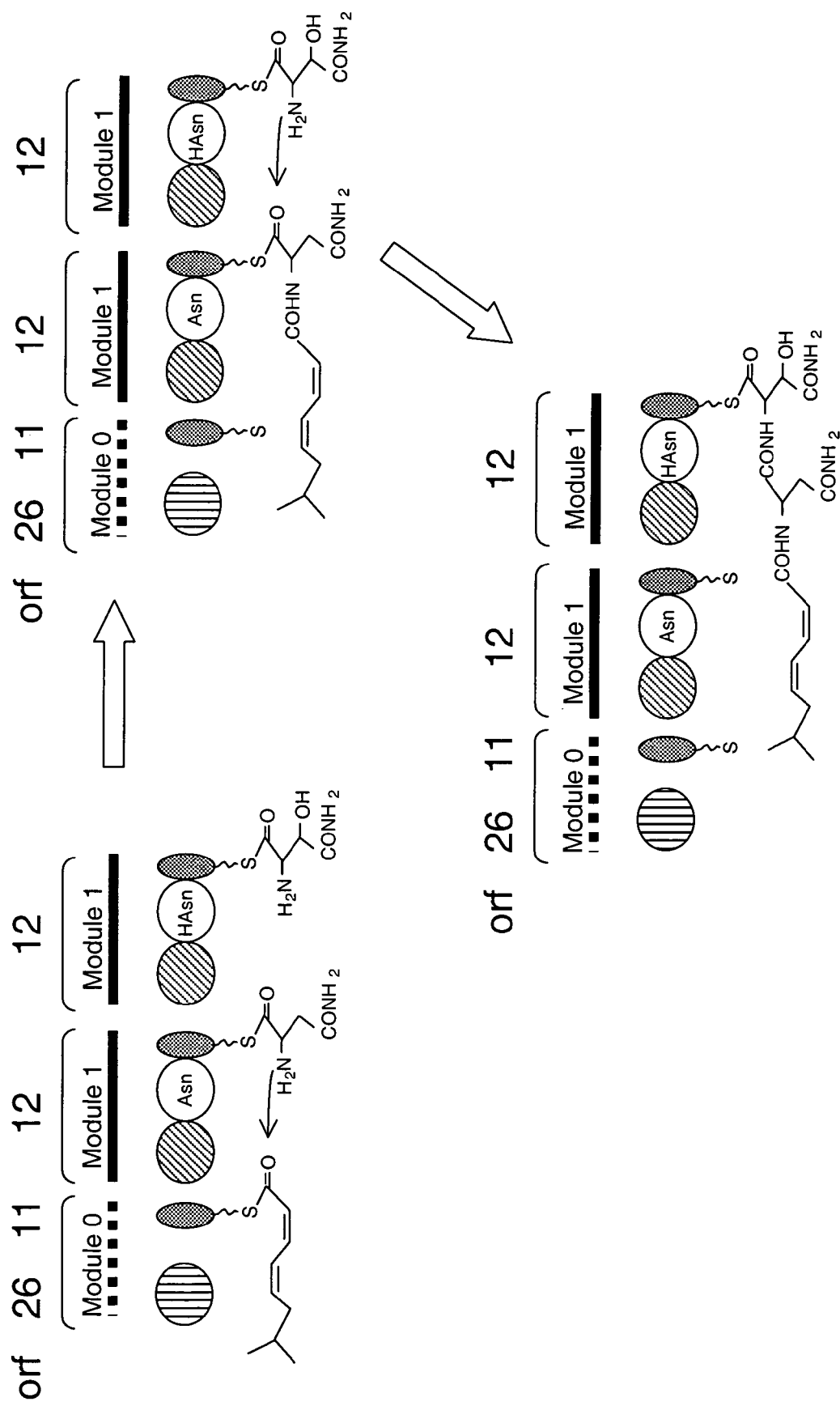
FIG. 2B is a model for the initiation of ramoplanin peptide synthesis using a fatty acid starter group. ORF 11 and ORF 26 are proposed to act coordinately as a starter unit, using a fatty acid group to prime the assembly of the peptide chain. Symbols are as in FIG. 2A.
Figure 2C:
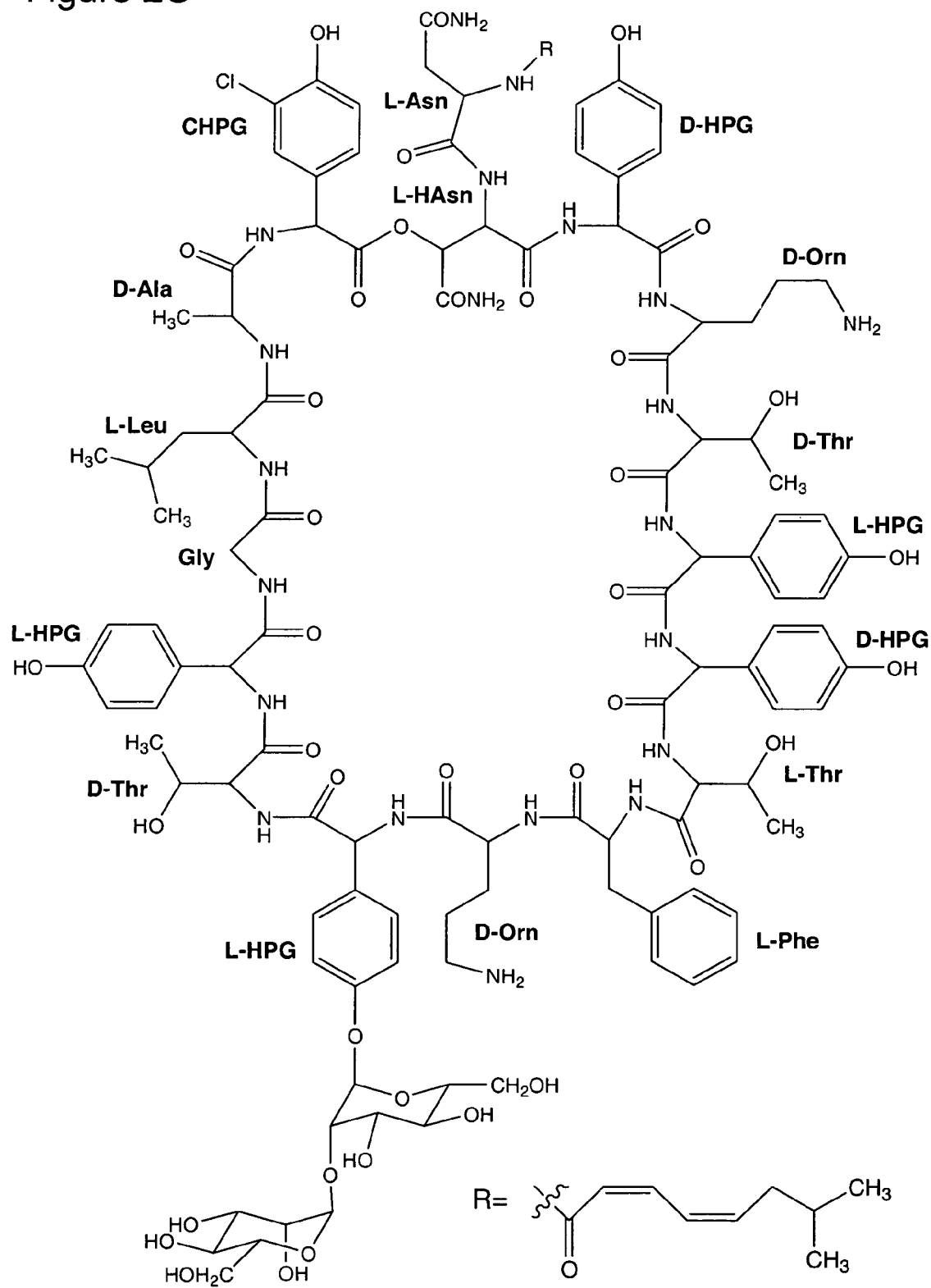
FIG. 2C illustrates the structure of ramoplanin. Shown are the positions of amino acid substituents, as well as an embodiment wherein the acylamide moiety is derived from an eight-carbon fatty acid (R). Alternative fatty acyl chaims may also be incorporated at this position.

The peptide synthetase encoded by ORF 12 (SEQ ID NO: 13) is unusual for a starter unit in having a condensation domain at the N-terminus of the protein. Most peptide synthetase starter units described to date contain adenylation domains at their N-terminus that are responsible for activating the first amino acid (the "starter" amino acid) that is incorporated into the peptide product. In contrast, the ramoplanin starter unit encoded in ORF 12 (SEQ ID NO: 13) has a condensation domain at the N-terminus of the protein, indicating that the initiation of peptide synthesis may occur in an unusual fashion. The N-terminus of the ramoplanin peptide is modified by one of three possible fatty acid groups, suggesting that the construction of the ramoplanin peptide may start with a fatty acid rather than an amino acid. A proposed mechanism of chain initiation using a fatty acid starter group is diagrammed in FIG. 2B. According to this model, the condensation domain at the N-terminus of ORF 12 (SEQ ID NO: 13) catalyzes the linkage of amino acid 1 (Asn) bound to module 1 to a fatty acid bound to the acyl carrier protein encoded by ORF 11 (SEQ ID NO: 12) via amide bond formation, providing an "acyl-N-capped" amino acid intermediate for further chain extension.

ORFs 11 and 26 (SEQ ID NOS: 12 and 27) are proposed to cooperate in the activation and transfer of fatty acid precursors to the ORF 12 (SEQ ID NO: 13) peptide synthetase. ORF 26 (SEQ ID NO: 27) shows similarity to acyl-CoA ligases, proteins of the adenylate-forming superfamily of enzymes that catalyze the activation of fatty acids via an activated adenylate intermediate. ORF 11 (SEQ ID NO: 12) shows similarity to acyl carrier proteins and peptide synthetase thiolation domains that accept activated adenylate intermediates. As diagrammed in FIG. 2B, the activity of these two ORFs may generate activated fatty acid thioesters that serve as the initiating groups for the synthesis of the ramoplanin lipopeptide core structure. ORF 26 (SEQ ID NO: 27) may be replaced or mutated, alone or in combination with the condensation domain of ORF 12 (SEQ ID NO: 13), in order to generate derivatives of ramoplanin having alternative fatty acids.

The final unit in most peptide synthetases contains a special C-terminal thioesterase domain, postulated to be involved in product release. Release of the complete peptide product from the peptide synthetase requires a thioesterase function that is generally found at the C-terminus of the peptide synthetase. ORF 14 (SEQ ID NO: 15) contains a C-terminal thioesterase domain, and may be involved in peptide release and cyclization by catalyzing the formation of the ester bond between the carboxylate goup of the C-terminal HPG and the hydroxyl group of HAsn, resulting in a free cyclic depsipeptide structure. ORF 15 (SEQ ID NO: 16) may also play a role in peptide release and/or cyclization. ORF 15 (SEQ ID NO: 16) shows strong similarity to thioesterases that are frequently found associated with peptide synthetases and are postulated to be involved in the release of peptide products or intermediates and may also be involved in the release and/or cyclization of the ramoplanin peptide. ORF 9 (SEQ ID NO: 10) shows similarity to esterases of the alpha/beta hydrolase fold family and may also be involved in peptide release.

ORF 27 (SEQ ID NO: 28) shows strong similarity to several small conserved proteins encoded by genes that are frequently found to be associated with peptide synthetase genes and are therefore likely to play a role in peptide biosynthesis.

B. Epimerization of L-amino Acids into Corresponding D-amino Acids:

An unexpected feature of the ramoplanin peptide synthetases is the absence of epimerization domains in the repeating units. Epimerization domains catalyze the conversion of L-amino acids into the corresponding D-amino acids. Ramoplanin contains seven D-amino acid units. Most bacterial peptide synthetases that incorporate D-amino acids do so by first recognizing and incorporating the corresponding L-amino acid and subsequently altering the configuration to the D-form through the activity of the epimerization domain. The lack of epimerization domains in the ramoplanin peptide synthetases despite the presence of D-amino acids in the final natural product may be due to specific recognition of D-amino acids by the adenylation domains found in modules 1, 2, 3 and 5 of ORF 13 (SEQ ID NO: 14) and modules 1, 3 and 7 of ORF 14 (SEQ ID NO: 15). The direct recognition and incorporation of D-amino acids by peptide synthetases has been postulated for the eukaryotic cyclosporin and HC toxin peptide synthetases (Weber et al., 1994, Curr. Genet Vol. 26, pp. 120-125; Scott-Craig et al., 1992, J. Biol. Chem. Vol. 267, pp. 26044-26049).

Alternatively, epimerization may be catalyzed by cellular amino acid epimerases/epimerases of primary or secondary metabolism, as has been proposed for the incorporation of D-valine in the gramicidin and tyrocidine systems (Pfeifer et al., 1995, Biochem. Vol. 34, pp. 7450-7459; Stein et al., 1995, Biochem. Vol. 34, pp. 4633-4642).

Yet another explanation is that specialized domains within the NRPSs may have evolved the ability to carry out dual functions. One domain that stands out as a candidate for having such dual functions is the condensation domain. Normally within a typical NRPS module that introduces a D-amino acid into the peptide product, epimerization (E) domains follow the thiolation (T) domain. In terms of linear domain organization on NRPS enzymes condensation (C) domains and epimerization (E) domains can be thought of occupying equivalent positions. That is, in an NRPS with multiple modules that is devoid of E domains, a C domain from any given module is found directly adjacent to the thiolation (T) domain of the upstream module. In addition, C domains and E domains also share a considerable amount of sequence similarity. Several highly conserved core motifs are shared between C and E domains. One particularly important motif that is common to both C and E domains is the histidine motif HHXXXDG (SEQ ID NO: 44) which has been shown by mutagenesis to form part of the active site (Stachelhaus et al.; *Journal of Biological Chemistry* 1998; 273:22773-22781). Thus, the C domains of modules 2, 3, 4 and 6 of OFR 13 (SEQ ID NO:14) and modules 2, 4 and 8 of ORF 14 (SEQ ID NO: 15) may be capable of amino acid epimerization as well as amide bond formation and be responsible for the 7-D-amino acid residues found in ramoplanin.

C. Formation of Fatty-acid Side Chains:

The ramoplanin depsipeptide core structure may carry one of three different medium-chain fatty acids attached to the N-terminus of Asn in position 1, resulting in the three different ramoplanin components A1-A3. Little is known about the biosynthetic origin of the three unsaturated fatty acid precursors, octa-2,4-dienoic acid (a C8 fatty acid) and its analogs 7-methylocta-2,4-dienoic acid (C9) and 8-methylnona-2,4-dienoic acid (C10). These medium-chain fatty acids may be derived from longer chain fatty acids by beta-oxidative degradation. It has been shown that the yields of component A2, carrying the octa-2,4-dienoic acid moiety, can be increased by adding the amino acid leucine to the fermentation medium of the producing organism, indicating that branched-chain amino acids may also serve as biosynthetic precursors to the fatty acid side chains of ramoplanin (European patent EP259780). Three proteins encoded by the ramoplanin locus, namely ORFs 16, 24, 25 (SEQ ID NOS: 17, 25 and 26), show similarity to enzymes associated with fatty acid metabolism and therefore may be involved in the generation of the fatty acid side chains for attachment to the depsipeptide core structure of ramoplanin. ORFs 24 and 25 (SEQ ID NOS: 25 and 26) are highly similar to each other and to flavin-dependent acyl-CoA dehydrogenases, enzymes involved in the degradation of fatty acids and in the degradation of leucine to fatty acid intermediates. These ORFs may channel branched-chain amino acid and fatty acid intermediates into the ramoplanin biosynthetic pathway. In addition, the dehydrogenase activity of ORFs 24 and 25 (SEQ ID NOS: 25 and 26) may be responsible for generating the two double bonds found in the unsaturated fatty acid groups of ramoplanin. ORF 16 (SEQ ID NO: 17) may also be involved in generating the fatty acid group of ramoplanin as it shows strong similarity to 3-oxoacyl-acyl carrier protein reductases, NAD-dependent enzymes of primary metabolism that are also involved in fatty acid degradation.

D. Amino-acid 4-hydroxyphenylglycine (HPG) Synthesis:

Five proteins encoded by the ramoplanin locus, namely ORF 4, ORF 6, ORF 7, ORF 28 and ORF 30 (SEQ ID NOS: 5, 7, 8, 29 and 31), are likely to be involved in synthesizing the unusual amino acid 4-hydroxyphenylglycine (HPG) which serves as a substrate for incorporation into the lipodepsipeptide core structure of ramoplanin. The natural occurrence of HPG in secondary metabolites is relatively infrequent, the best-known examples being nocardicin A; vancomycin, aridicin, chloroeremomycin, teicoplanin and related glycopeptide antibiotics; the calcium-dependent antibiotic (CDA) of *Streptomyces coelicolor*; and ramoplanin. Biochemical studies have indicated that the HPG residues of the antibiotics vancomycin, aridicin, and nocardicin are derived from the common amino acid tyrosine and a pathway for the synthesis of HPG from tyrosine has been proposed (Nicas et al., in Biotechnology of Antibiotics, Marcel Dekker, Inc., 1997, pp. 363-392 and references therein; Chung et al., 1986, J. Antibiotics Vol.1986, pp. 642-651; Hosoda et al., 1977, Agric.

Biol. Chem. Vol. 41, pp. 1007-1012; Hammond et al., 1982, J. Chem. Soc. (Chem. Comm.), Vol. 1982, pp. 344-346). However, analysis of the ORFs encoded by the ramoplanin biosynthetic locus provides evidence for an alternative pathway, as illustrated in FIG. 4. The combined activities of ORF 4, ORF 6, ORF 7, ORF 28 and ORF 30 (SEQ ID NOS: 5, 7, 29, and 31) would allow conversion of intermediates of tyrosine metabolism into the unusual amino acid HPG. Proteins showing similarity to ORFs 4, 6, 7 and 30 (SEQ ID NOS: 5, 7, 8 and 31) can be found in the biosynthetic loci encoding CDA and chloroeremomycin, two natural products that also contain HPG substituents, although the roles of these proteins in the biosynthesis of the respective natural products were not proposed (GenBank accession numbers AL035640, AL035707, and AL035654; van Wageningen et al. 1997, Chem. Biol. Vol. 5, pp. 155-162).

E. Resistance and/or Localization Proteins:

Eight proteins encoded by the ramoplanin locus (ORF 1, ORF 2, ORF 3, ORF 8, ORF 19, ORF 23, ORF 29 and ORF 31) are likely to be membrane-associated proteins that are involved in resistance and/or the subcellular localization of the ramoplanin biosynthetic machinery. ORFs 2, 8, and 23 (SEQ ID NOS: 3, 9 and 24) show similarity to the superfamily of ATP binding cassette transport proteins involved in target-specific secretion and are likely to be involved in the transport of ramoplanin or biosynthetic precursors across the cytoplasmic membrane, providing a possible mechanism for resistance to the toxic effects of the antibiotic or increased production of ramoplanin. ORF 31 (SEQ ID NO: 32) shows similarity to various sodium/proton and drug/proton antiporters and may also provide a means to transport ramoplanin across the cytoplasmic membrane. ORFs 1, 3, 19 and 29 (SEQ ID NOS: 2, 4 and 20) show similarity to various transmembrane proteins of unknown function and may be involved in localizing the ramoplanin biosynthetic machinery to the cytoplasmic membrane in order to provide access to lipid and fatty acid precursors.

F. Proteins Involved in Regulation of Ramoplanin Biosynthesis:

Three proteins encoded by the ramoplanin locus, namely ORF 5, ORF 21, ORF 22 (SEQ ID NOS: 6, 22 and 23), are likely to be involved in the regulation of ramoplanin biosynthesis. ORF 5 (SEQ ID NO: 6) shows similarity to a number of transcriptional regulators of antibiotic biosynthesis. This protein is likely to regulate the transcription of one or more genes in the ramoplanin genetic locus. ORFs 21 and 22 (SEQ ID NOS: 22 and 23) show homology to 2-component signal transduction systems, such as the Abs A1/A2 system involved in the global regulation of antibiotic synthesis of *Streptomyces coelicolor*. These ORFs may act coordinately to regulate the expression of ramoplanin biosynthetic genes and the production of ramoplanin in response to environmental or cellular signals.

G. Chlorination of Terminal HPG Residue:

ORF 20 (SEQ ID NO: 21) shows similarity to halogenases involved in the chlorination of secondary metabolites, including the PrnC halogenase of *Pseudomonas fluorescens* responsible for the chlorination of an aromatic precursor of pyrrolnitrin biosynthesis and a halogenase proposed to be responsible for the chlorination of a tyrosine residue in chloroeremomycin. This protein most likely catalyzes the chlorination of the terminal HPG residue incorporated into the ramoplanin peptide core, generating the 3-chloro-HPG form.

H. Beta-hydroxyasparagine Residue Formation:

As disclosed in U.S. Ser. No. 60/283,296, ORF 10 (SEQ ID NO: 11) is a member of a new family of metal cofactor hydroxylase enzymes. This discovery is very surprising because one would have expected that cytochrome P450 enzymes would be implicated in the beta-hydroxylation reaction requied to generate beta-hydroxyasparagine.

The possibility that a novel mechanism for beta-hydroxylation of amino acid residues may be operative in the biosynthesis of ramoplanin was first suggested by the fact that none of the ORFs encoded by the ramoplanin biosynthetic locus displayed significant amino acid sequence homology to the known cytochrome P450 monooxygenases by BLASTP analysis. ORF 10, ORF 18 and ORF 32 (SEQ ID NOS: 11, 19 and 33) could not initially be assigned a putative role in the biosynthesis of ramoplanin and were considered as candidate asparagine beta-hydroxylases. ORF 10 (SEQ ID NO: 11) shows homology to a protein of unknown function in the bleomycin biosynthetic locus of *Streptomyces verticillus* and to a partial protein of unknown function found in putative chloramphenicol biosynthetic locus of *Streptomyces venezuelae*. Significantly, bleomycin and chloramphenicol also contain a beta-hydroxylated amino acid residue. ORF 18 (SEQ ID NO: 19) shows no similarity to proteins in the GenBank database, while ORF 32 (SEQ ID NO: 33) shows similarity to hypothetical bacterial proteins of unknown function in *Streptomyces coelicolor*. Since enzymes that catalyze hydroxylation reactions commonly use metal cofactors, ORFs 10, 18 and 32 (SEQ ID NOS: 11, 19 and 33) were further analyzed for the presence of amino acid motifs that are associated with the binding of metal cofactors.

FIG. 5 illustrates clustal alignments showing sequence homology between ORF 10 (SEQ ID NO: 11) and various metal ligand motifs. In each of the clustal alignments: (i) a line above the alignment is used to mark strongly conserved positions; (ii) an asterisk "*" indicates positions which have a single, fully conserved residues; (iii) a colon ":" indicates that one of the following strong groups is fully conserved: S, T or A; N, E, Q or K; N, H, Q or K; N, D, E or Q; Q, H, R or K; M, I, L or V; M, I, L or F; H or Y; and F, Y or W; and (iv) a period "." indicates that one of the following weaker groups is fully conserved: C, S or A; A, T or V; S, A or G; S, T, N or K; S, T, P or A; S, G, N or D; S, N, D, E, Q or K; N, D, E, Q, H or K; N, E, Q, H, R or K; F, V, L, I or M: and H, F or Y.

ORF 10 (SEQ ID NO:11) contains two amino acid sequence motifs that are frequently found in enzymes that use metal cofactors. The N-terminal region of ORF 10 (SEQ ID NO: 11) contains a cluster of histidine residues (the His-motif) that shows significant local sequence homology to a conserved histidine motif found in several zinc-binding beta-lactamases. FIG. 5A shows the local amino acid sequence homology between ORF 10 (SEQ ID NO: 11) and a key motif involved in coordinating two zinc molecules in the beta-lactamase superfamily. The alignment depicts amino acids 263 to 318 of ORF 10 (SEQ ID NO: 11), amino acids 42 to 99 of a member of the beta-lactamase superfamily, the L1 metallo-beta-lactamase (1SML) from *Stenotrophomonas maltophilia* for which the crystal structure has been determined (Ullah et al., 1998, *J. Mol. Biol.*, 125-136), and amino acids 12 to 67 of the consensus sequence for pfam00753, i.e. the beta-lactamase superfamily motif (Bateman et al., 2000, *Nucleic Acids Research*, Vol. 28, No.1, 263-266). Highlighted in black are residues demonstrated in the L1 metallo-beta-lactamase to co-ordinate zinc and their counterparts in the other two sequences. X-ray crystal structure analysis demonstrates that the histidine residues in this conserved motif are responsible for binding the zinc metal cofactor (Ullah et al., 1998, *J. Mol. Biol.*, 125-136). The precise alignment and conserved spacing of the amino acid residues in the His-motif of ORF 10 (SEQ ID NO: 11) as compared to the zinc-binding beta-lactamases indicates that ORF 10 (SEQ ID NO: 11) is likely to bind a metal cofactor.

FIG. 5B shows the local amino acid sequence homology between ORF 10 (SEQ ID NO: 11) and a key motif involved in coordinating an iron molecule in cytochrome P450 monooxygenases. The alignment depicts amino acids 405 to 452 of ORF 10 (SEQ ID NO: 11) and amino acids 370 to 421 of the consensus sequence for pfam00067, i.e. the cytochrome P450 motif (Bateman et al., 2000, *Nucleic Acids Research*, Vol. 28, No. 1, 263-266). The region of ORF 10 (SEQ ID NO: 11) in highlight is in relatively good agreement with the Prosite motif PS00086 (Hofmann et al., 1999, *Nucleic Acids Research*, Vol. 27, No. 1, 215-219) required for binding iron. Notably, the least variable positions of this motif are present in ORF10 (SEQ ID NO: 11), i.e. residues Phe-423, Gly-425, Cys-428, and Gly-430). The C-terminal region of ORF 10 (SEQ ID NO: 11) contains a cluster of amino acid residues that shows significant local sequence homology to a motif frequently found in cytochrome P450 monooxygenases (the Cys-motif). This motif includes a cysteine residue that is highly conserved in the cytochrome P450 monooxygenases and that has been shown by X-ray crystal structure analysis to be involved in binding the iron metal cofactor required for catalysis. The Cys-motif of ORF 10 (SEQ ID NO: 11) is likely to contribute to the binding of a metal cofactor. The presence of two amino acid sequence motifs that are found in well-characterized metal-binding enzymes indicates that ORF 10 (SEQ ID NO: 11) is likely to be a metal-binding enzyme. Thus, the ORF 10 (SEQ ID NO: 11) is likely to be responsible for the formation of beta-hydroxyasparagine during the synthesis of ramoplanin.

Example 3

Expression Analysis

A—Acyl Starter Unit Chain Initiation

To investigate the involvement of an acyl starter unit chain in chain initiation of the ramoplanin NRPS system, ORF 11, ORF 12, and ORF 26 (SEQ ID NOS: 12 to 14) were individually PCR-amplified using oligonucleotide primer pairs that introduced convenient restriction enzyme sites at either end of each ORF as well as ten consecutive histidine tags at the N-terminus. These recombinant N-terminal HIS10-tagged ORFs were subcloned into an *E. coli* expression vector and the resulting plasmids were introduced into *E. coli* which were then grown under conditions that lead to high level expression of the recombinant ORFs. Cells were pelleted and disrupted, and the recombinant ORF 11, ORF 12, and ORF 26 (SEQ ID NOS: 12, 13 and 27) proteins were purified by nickel affinity chromatography. The ORF 11 and ORF 26 (SEQ ID NOS: 12 and 27) proteins are readily obtained as soluble protein preparations whereas the solubility of ORF 26 (SEQ ID NO: 27) is more reduced presumably due to its large size.

Based on sequence homology, ORF 11 (SEQ ID NO: 12) is predicted to be an acyl or amino acyl carrier protein. Purified recombinant ORF 11 (SEQ ID NO: 12) protein can be primed to its holo form in vitro using purified Sfp from *Bacillus subtilis* and coenzyme A, as indicated by an increase in mass by MALDI-MS that corresponds to the addition of the 4'-phosphopantetheine moiety of coenzyme A. The fact that recombinant ORF 11 is amenable to this posttranslational modification that converts it from an inactive apo into the active holo form confirms that it is indeed an acyl or amino acyl carrier protein.

The availability of solube recombinant ORF 26 together with solube, holo ORF 11 (described above) provides a means to confirm ORF 26's role in the transfer of the short chain fatty acids onto holo ORF 11. Such an experiment using as substrate the $^{14}$C-radiolabeled long chain fatty acid palmetic acid was inconclusive. These findings are consistent with the hypothesis that ORF 26 is specific for shorter chain fatty acids such as the three 8- to 10-carbon unsaturated fatty acids found in ramoplanins rather than long chain saturated fatty acids such as 16-carbon palmitic acid. Substrate specificity is further examined by synthesis of the fatty acyl groups that are naturally found linked to the amino terminus of the ramoplanin peptide.

B—beta-hydroxyasparagine

To confirm characterization of ORF 10 (SEQ. ID NO: 11) as a beta-hydroxylase and to confirm the role of ORF 10 (SEQ. ID NO: 11.) in hydroxylation of asparagine at the beta position, a recombinant N-terminal His10-tagged ORF 10 *E. coli* expression system was designed as described above for ORFs 11, 12 and 26 (SEQ ID NOS: 12, 13 and 27). Purified recombinant ORF 10 (SEQ ID NO: 11) protein was obtained in a soluble form by nickel affinity chromatography. The fact that the purified recombinant protein does not display the characteristic absorption spectrum of heme-containing enzyme indicates that ORF 10 (SEQ ID NO: 11) is not a P450 enzyme. The ORF 10 (SEQ ID NO: 11) metal-binding motifs mentioned above therefore co-ordinate a non-heme iron or a metal other than iron.

As an alternative source of native ORF 10 (SEQ ID NO: 11), a *Streptomyces* expression system was employed. ORF 10 (SEQ ID NO: 11) was amplified by high fidelity PCR using two specific oligonucleotides, namely primer sequences (5' to 3') N-oligo: CACACAGAATTCACCAGCGC-CACTCGCGCTT (SEQ ID NO:45), and C-oligo: CACA-CATCGATGGGCAACGCCGATCAGCCG (SEQ ID NO:46). This primer pair introduces convenient restriction enzyme sites at either end of the ORF 10 gene but does not introduce any exogenous amino acids. The amplified genes were then subcloned using ClaI and EcoRI restriction enzymes into a *Streptomyces/E. coli* expression shuttle vector, pECO1202. Following confirmation of the cloned sequences, *Streptomyces lividans* TK24 was transformed with this construct. Five independent transformants were selected for further analysis. Cultures were grown for 48 hours in a gyrating 30° C. incubator using 25 ml erlenmeyer flasks containing 5 ml of Tryptic Soy Broth (TSB, Difco). Total RNA was extracted from the cell pellets using the RNeasy kit (Qiagen). The integrity and concentration of the RNA was monitored by agarose gel electrophoresis. Subsequently, reverse transcription was performed using 1 ug total RNA primed with an antisense primer sequence located in the vector just downstream of the stop codon. Following reverse transcription of each sample and appropriate controls, 20 cycles of PCR were performed using the original ORF-specific oligonucleotides, N-oligo and C-oligo. According to the RT-PCR analysis, the five recombinant *S. lividans* clones express relatively high levels of ORF 10-specific mRNA and the size of the RT-PCR product is as expected. FIG. 6 shows the RT-PCR analysis of recombinant *S. lividans* clones expressing ramoplanin ORF 10, wherein is lane 1 is 1 kb DNA ladder; lane 2 is untransformed *S. lividans*; lane 3 is *S. lividans* transformed with empty expression vector; lanes 4-8 are five different *S. lividans* recombinant clones expressing ramoplanin orf 10; lane 9 is an *S. lividans* recombinant clone expressing an unrelated gene; lane 10 is negative control performed without RNA; lane 11 is negative control performed without RT; lane 12 is positive control for PCR using plasmid DNA.

To confirm that these recombinant strains actually produce the expected ORF 10 protein lysates were analyzed by SDS-PAGE. Briefly, cell pellets from the above cultures were resuspended in cold extraction buffer (0.1 M Tris-HCl, pH 7.6, 10 mM $MgCl_2$, 1 mM PMSF) and sonicated four times for 20 sec on ice with 1 min intervals. Soluble proteins were recovered by centrifugation for 10 min at 20,000×g and the total protein concentration was determined using the Bradford reagent (Biorad). Equal amounts of total soluble protein were subjected to 10% SDS-PAGE analysis. Proteins were visualized by staining with coomassie brilliant blue.

As shown in FIG. 7, the four recombinant strains tested contain a significant amount of protein with an apparent mobility of approximately 60 kilodaltons, consistent with the predicted molecular mass of 58916.80 kilodaltons for the ORF 10 protein. FIG. 7 is the SDS-PAGE analysis of recombinant *S. lividans* clones expressing ramoplanin ORF 10 (SEQ ID NO.: 11). The soluble fraction of protein lysates was subjected to 10% SDS-PAGE and stained with coomassie blue. Lane 1 is molecular weight standards with sizes in kilodaltons indicated to the left; lane 2 is untransformed *S. lividans*; lane 3 is *S. lividans* transformed with empty expression vector; lanes 4 to 7 are four different *S. lividans* recombinant clones expressing ramoplanin ORF 10 (SEQ. ID NO.: 11). The approximately 60 kDa ORF 10 gene product is clearly visible in lanes 4 to 7, as indicated by the arrowhead to the right.

It is to be understood that the embodiments described herein are for illustrative purposes only and that various modifications or changes in light thereof will be suggested to persons skilled in the art and are to be included within the spirit and purview of this application and scope of the appended claims. All publications, patents and patent applications and sequences from GenBank and other databases referred to herein are incorporated by reference in their entirety for all purposes.

The invention claimed is:

1. An isolated nucleic acid comprising a polynucleotide which encodes a domain of a ramoplanin nonribosomal peptide synthetase, wherein said ramoplanin nonribosomal peptide synthetase comprises the amino acid sequence of SEQ ID NO: 14, and wherein said domain is condensation domain, an adenylation domain or a thiolation domain.

2. The isolated nucleic acid of claim 1, wherein said domain is a condensation domain of the synthetase of SEQ ID NO:14.

3. The isolated nucleic acid of claim 2, wherein said nucleic acid comprises a coding sequence identical to or complementary to a nucleic acid selected from the group consisting of: nucleotides 19032-20582 of SEQ ID NO:1; nucleotides 22347-23711 of SEQ ID NO:1; nucleotides 25506-26885 of SEQ ID NO:1; nucleotides 28740-30122 of SEQ ID NO:1; nucleotides 31752-33185 of SEQ ID NO:1; nucleotides 34950-36293 of SEQ ID NO:1 and nucleotides 36543-37982 of SEQ ID NO:1.

4. The isolated nucleic acid of claim 1, wherein said domain is an adenylation domain of the synthetase of SEQ ID NO:14.

5. The isolated nucleic acid of claim 4, wherein said nucleic acid comprises a coding sequence identical to or complementary to a nucleic acid selected from the group consisting of: nucleotides 20583-22001 of SEQ ID NO:1; nucleotides 23712-25187 of SEQ ID NO:1; nucleotides 26886-28397 of SEQ ID NO:1; nucleotides 30123-31511 of SEQ ID NO:1; nucleotides 33186-34607 of SEQ ID NO:1; and nucleotides 37983-39443 of SEQ ID NO:1.

6. The isolated nucleic acid of claim 1, wherein said domain is a thiolation domain of the synthetase of SEQ ID NO:14.

7. The isolated nucleic acid of claim 6, wherein said nucleic acid comprises a coding sequence identical to or complementary to a nucleic acid selected from the group consisting of: nucleotides 22002-22208 of SEQ ID NO: 1; nucleotides 25191-25397 of SEQ ID NO:1; nucleotides 28398-28604 of SEQ ID NO:1; nucleotides 31512-31715 of SEQ ID NO:1; nucleotides 34608-34811 of SEQ ID NO:1; nucleotides 36294-36503 of SEQ ID NO:1 and nucleotides 39444-39650 of SEQ ID NO:1.

8. The isolated nucleic acid of claim 1, wherein said polynucleotide encodes a condensation domain comprising an amino acid sequence selected from the group consisting of: amino acids 1-517 of SEQ ID NO: 14; amino acids 1106-1560 of SEQ ID NO: 14; amino acids 2159-2618 of SEQ ID NO: 14; amino acids 3237-3697 of SEQ ID NO: 14; amino acids 4241-4718 of SEQ ID NO: 14; amino acids 5307-5754 of SEQ ID NO: 14; and amino acids 5838-6317 of SEQ ID NO: 14.

9. The isolated nucleic acid of claim 1, wherein said polynucleotide encodes an adenylation domain comprising an amino acid sequence selected from the group consisting of: amino acids 518-990 of SEQ ID NO: 14; amino acids 1561-2052 of SEQ ID NO: 14; amino acids 2619-3122 of SEQ ID NO: 14; amino acids 3698-4160 of SEQ ID NO: 14; amino acids 4719-5192 of SEQ ID NO: 14; and amino acids 6318-6804 of SEQ ID NO: 14.

10. The isolated nucleic acid of claim 1, wherein said polynucleotide encodes a thiolation domain comprising an amino acid sequence selected from the group consisting of: amino acids 991-1059 of SEQ ID NO: 14; amino acids 2054-2122 of SEQ ID NO: 14; amino acids 3123-3191 of SEQ ID NO: 14; amino acids 4161-4228 of SEQ ID NO: 14; amino acids 5193-5260 of SEQ ID NO: 14; amino acids 5755-5824 of SEQ ID NO: 14 and amino acids 6805-6873 of SEQ ID NO: 14.

11. The isolated nucleic acid of claim 1, wherein said nucleic acid comprises (i) nucleotides 19032-39713 of SEQ ID NO: 1, (ii) a polynucleotide fully complementary to nucleotides 19032-39713 of SEQ ID NO: 1, or (iii) a polynucleotide that encodes the amino acid sequence of SEQ ID NO: 14.

12. An expression vector comprising a nucleic acid of claim 1.

13. A host cell transformed with an expression vector of claim 12.

14. A method of preparing a nonribosomal peptide synthetase, comprising transforming a host cell with an expression vector of claim 12, culturing said host cell under conditions such that a nonribosomal peptide synthetase is produced and recovering the nonribosomal peptide synthetase from the cell culture.

15. The isolated nucleic acid of claim 1, comprised in cosmid 008CK (IDAC 190901-1) or cosmid 008CH (IDAC 19090 1-3).

16. An isolated nucleic acid comprising a polynucleotide which encodes a module of a nonribosomal peptide synthetase comprising a domain of the ramoplanin nonribosomal peptide synthetase of SEQ ID NO: 14, wherein said module is selected from the group consisting of (i) module 1, consisting of amino acids 1-1059 of SEQ ID NO:14, (ii) module 2, consisting of amino acids 1106-2122 of SEQ ID NO:14, (iii) module 3, consisting of amino acids 2159-3191 of SEQ ID NO:14, (iv) module 4, consisting of amino acids 3237-4228 of SEQ ID NO:14, (v) module 5, consisting of amino acids 4241-5260 of SEQ ID NO:14, (vi) module 6, consisting of amino acids 5307-5824 of SEQ ID NO:14, and (vii) module 7, consisting of amino acids 5838-6873 of SEQ ID NO:14.

17. The isolated nucleic acid of claim 16, wherein said polynucleotide encodes a module of a nonribosomal peptide synthetase comprising a condensation domain and an adenylation domain of the ramoplanin nonribosomal peptide synthetase of SEQ ID NO: 14.

18. The isolated nucleic acid of claim 16, wherein said polynucleotide encodes a module of a nonribosomal peptide synthetase comprising a condensation domain, an adenylation domain and a thiolation domain of the ramoplanin nonribosomal peptide synthetase of SEQ ID NO: 14.

19. An expression vector comprising a nucleic acid of claim 16.

20. A host cell transformed with an expression vector of claim 19.

21. A method of preparing a nonribosomal peptide synthetase, comprising transforming a host cell with an expression vector of claim 19, culturing said host cell under conditions such that a nonribosomal peptide synthetase is produced and recovering the nonribosomal peptide synthetase from the cell culture.

22. An isolated polynucleotide molecule encoding a polypeptide having at least 95% sequence identity to the amino acid sequence of SEQ ID NO: 14.

23. An expression vector comprising the polynucleotide molecule of claim 22.

24. A host cell transformed with an expression vector of claim 23.

25. A method of preparing a nonribosomal peptide synthetase, comprising culturing the host cell of claim 24 under conditions such that a nonribosomal peptide synthetase is produced and recovering the nonribosomal peptide synthetase from the cell culture.

* * * * *

UNITED STATES PATENT AND TRADEMARK OFFICE
CERTIFICATE OF CORRECTION

PATENT NO. : 7,635,765 B2
APPLICATION NO. : 11/205109
DATED : December 22, 2009
INVENTOR(S) : Farnet et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 165 days.

Signed and Sealed this

Ninth Day of November, 2010

David J. Kappos
*Director of the United States Patent and Trademark Office*